US011733246B2

(12) United States Patent
Agnew et al.

(10) Patent No.: US 11,733,246 B2
(45) Date of Patent: *Aug. 22, 2023

(54) COMPOSITIONS, IMAGING, AND THERAPEUTIC METHODS TARGETING FOLATE RECEPTOR 1 (FOLR1)

(71) Applicant: Indi Molecular, Inc., Los Angeles, CA (US)

(72) Inventors: Heather Dawn Agnew, Culver City, CA (US); Anders Eliasen, Culver City, CA (US); Bert Tsunyin Lai, Culver City, CA (US)

(73) Assignee: INDI MOLECULAR, INC., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,941

(22) Filed: Jan. 12, 2022

(65) Prior Publication Data

US 2022/0229066 A1 Jul. 21, 2022

Related U.S. Application Data

(63) Continuation of application No. PCT/US2021/057877, filed on Nov. 3, 2021.

(60) Provisional application No. 63/256,922, filed on Oct. 18, 2021, provisional application No. 63/109,176, filed on Nov. 3, 2020.

(51) Int. Cl.
*A61K 47/65* (2017.01)
*G01N 33/68* (2006.01)
*C07K 7/06* (2006.01)
*C12N 9/02* (2006.01)
*G01N 33/573* (2006.01)

(52) U.S. Cl.
CPC ......... *G01N 33/6803* (2013.01); *C07K 7/06* (2013.01); *C12N 9/0069* (2013.01); *G01N 33/573* (2013.01); *C12Y 113/11052* (2013.01); *G01N 2333/90241* (2013.01)

(58) Field of Classification Search
CPC .............................. A61K 31/165; A61K 47/65
See application file for complete search history.

(56) References Cited

U.S. PATENT DOCUMENTS

| | | |
|---|---|---|
| 4,899,755 A | 2/1990 | Lauffer |
| 5,021,556 A | 6/1991 | Srinivasan |
| 5,075,099 A | 12/1991 | Srinivasan |
| 5,118,797 A | 6/1992 | Jurisson |
| 5,183,653 A | 2/1993 | Linder |
| 5,364,613 A | 11/1994 | Sieving |
| 5,367,080 A | 11/1994 | Toner |
| 5,387,409 A | 2/1995 | Nunn |
| 5,474,756 A | 12/1995 | Tweedle |
| 5,547,668 A * | 8/1996 | Kranz ............... C07K 16/2809 530/391.1 |
| 5,608,110 A | 3/1997 | Ramalingam |
| 5,656,254 A | 8/1997 | Ramalingam |
| 5,662,885 A | 9/1997 | Pollak |
| 5,665,329 A | 9/1997 | Ramalingam |
| 5,688,487 A | 11/1997 | Linder |
| 5,720,934 A | 2/1998 | Dean |
| 5,780,006 A | 7/1998 | Pollak |
| 5,846,519 A | 12/1998 | Tweedle |
| 5,849,261 A | 12/1998 | Dean |
| 5,879,658 A | 3/1999 | Dean |
| 5,886,142 A | 3/1999 | Thakur |
| 5,976,495 A | 11/1999 | Pollak |
| 6,093,382 A | 7/2000 | Wedeking |
| 6,143,274 A | 11/2000 | Tweedle |
| 6,566,088 B1 | 5/2003 | McKnight |
| 8,710,180 B2 | 4/2014 | Pitram |
| 8,841,083 B2 | 9/2014 | Heath |
| 8,906,830 B2 | 12/2014 | Agnew |
| 9,188,584 B2 | 11/2015 | Agnew |
| 9,221,889 B2 | 12/2015 | Pitram |
| 9,239,332 B2 | 1/2016 | Heath |
| 9,775,912 B2 | 10/2017 | Steiner |
| 9,913,875 B2 | 3/2018 | Farrow |
| 9,920,115 B2 | 3/2018 | Dubridge |
| 10,598,671 B2 | 3/2020 | Heath |
| 11,007,245 B2 | 5/2021 | Farrow |
| 2003/0069395 A1 | 4/2003 | Sato |
| 2006/0153839 A1 | 7/2006 | Mohamed |
| 2007/0202045 A1 | 8/2007 | Dennis |

(Continued)

FOREIGN PATENT DOCUMENTS

| | | |
|---|---|---|
| EP | 2719706 | 4/2014 |
| WO | 1986006605 | 11/1986 |

(Continued)

OTHER PUBLICATIONS

O'Shannessy et al. 2011; Characterization of the human folate receptor alpha via novel antibody-based probes. Oncotarget. 2: 1227-1243.*
Muller et al. 2011; Folic acid conjugates for nuclear imaging of folate receptor-positive cancer. J. Nucl Med 52:1-4.*
Artali, et al., "A molecular dynamics study of human serum albumin binding sites", II Farmaco, 60:485-495 (2005).
Balachandran, et al., "Imaging of ovarian cancer", Applied Radiology, 34(9):19-29 (2005).

(Continued)

*Primary Examiner* — Karen Cochrane Carlson
(74) *Attorney, Agent, or Firm* — Pabst Patent Group LLP

(57) ABSTRACT

The present application provides stable heterobiligands made up of peptide-based FOLR1 ligands and folate (the ligand of FOLR1) and methods of use of the heterobiligands as detection, imaging, diagnostic, and therapeutic agents. The application further provides methods of manufacturing FOLR1 heterobiligands, capture agents, and imaging agents.

30 Claims, 52 Drawing Sheets

Specification includes a Sequence Listing.

(56) References Cited

U.S. PATENT DOCUMENTS

| | | |
|---|---|---|
| 2007/0269422 A1 | 11/2007 | Beirnaert |
| 2010/0009896 A1 | 1/2010 | Agnew |
| 2011/0263515 A1 | 10/2011 | Agnew |
| 2012/0202219 A1 | 8/2012 | Agnew |
| 2012/0252071 A1 | 10/2012 | Greif |
| 2014/0302998 A1 | 10/2014 | Heath |
| 2015/0037334 A1 | 2/2015 | Kufer |
| 2015/0099658 A1 | 4/2015 | Pfeilsticker |
| 2015/0132314 A1 | 5/2015 | Masternak |
| 2015/0344523 A1 | 12/2015 | Deyle |
| 2016/0331800 A1 | 11/2016 | Farrow |
| 2020/0407712 A1 | 12/2020 | Boyd |
| 2022/0211648 A1* | 7/2022 | Agnew .......... A61P 35/00 |

FOREIGN PATENT DOCUMENTS

| | | |
|---|---|---|
| WO | 1991001743 | 2/1991 |
| WO | 1991003200 | 3/1991 |
| WO | 1995003280 | 2/1995 |
| WO | 1995006633 | 3/1995 |
| WO | 1995028179 | 10/1995 |
| WO | 1995028967 | 11/1995 |
| WO | 1996003427 | 2/1996 |
| WO | 1996023526 | 8/1996 |
| WO | 1997036619 | 10/1997 |
| WO | 1998018496 | 5/1998 |
| WO | 1998018497 | 5/1998 |
| WO | 1998046612 | 10/1998 |
| WO | 1998052618 | 11/1998 |
| WO | 1999017809 | 4/1999 |
| WO | 9921576 | 5/1999 |
| WO | 2001045746 | 6/2001 |
| WO | 02083064 | 10/2002 |
| WO | 03006620 | 1/2003 |
| WO | 2004003019 | 1/2004 |
| WO | 2004041865 | 5/2004 |
| WO | 2005097202 | 10/2005 |
| WO | 2005113762 | 12/2005 |
| WO | 2006040153 | 4/2006 |
| WO | 2006122787 | 11/2006 |
| WO | 2007050963 | 5/2007 |
| WO | 2008043821 | 4/2008 |
| WO | 2008043822 | 4/2008 |
| WO | 2009016043 | 2/2009 |
| WO | 2009051555 | 4/2009 |
| WO | 2009105746 | 8/2009 |
| WO | 2009155420 | 12/2009 |
| WO | 2010135431 | 11/2010 |
| WO | 2011057347 | 5/2011 |
| WO | 2011095545 | 8/2011 |
| WO | 2012069654 | 5/2012 |
| WO | 2012106651 | 8/2012 |
| WO | 2012106671 | 8/2012 |
| WO | 2013009869 | 1/2013 |
| WO | 2013033561 | 3/2013 |
| WO | 2013034982 | 3/2013 |
| WO | 2014056813 | 4/2014 |
| WO | 2014074907 | 5/2014 |
| WO | 2014205317 | 12/2014 |
| WO | 2017011769 | 1/2017 |
| WO | 2017176769 | 10/2017 |
| WO | 2018064597 | 4/2018 |
| WO | 2018111580 | 6/2018 |
| WO | 2018170096 | 9/2018 |
| WO | 2018200551 | 11/2018 |
| WO | 2020127224 | 6/2020 |
| WO | 2020127227 | 6/2020 |

OTHER PUBLICATIONS

Bianchi et al., "Vaccination with peptide mimetics of the gp41 prehairpin fusion intermediate yields neutralizing antisera against HIV-1 isolates", PNAS, 107(23): 10655-10660 (2010).

Boersma, "Gaining knowledge of single carbon chains", Theory of condensed matter, Radboud Univ. Nijmegen, 18 pages (2011).

Chan, et al., "Dual-targeting anti-angiogenic cyclic peptides as potential drug leads for cancer therapy", Scientific Reports, 6:35247, 13 pages (2016).

Chattopadhyay, et al., "Techniques to improve the direct ex vivo detection of low frequency antigen-specific CD8+ T cells with peptide-major histocompatibility complex class I tetramers", Cytometry Part A, 73(11): 1001-1009 (2008).

Chauhan, et al. "The Taming of the Cell Penetrating Domain of the HIV Tat: Myths and Realities", J. Control Release, 117(2): 148-162 (2007).

Chen, et al., "Fusion protein linkers: property, design and functionality", Adv. Drug Deliv. Rev., 65(10): 1357-1369 (2013).

Cheong, et al., "A patent review of IDO1 inhibitors for cancer", Expert Opinion on Therapeutic Patents, 28(4):317-330 (2018).

Choksi, et al., "ACD8 DE loop peptide analog prevents graft-versus-host disease in a multiple minor histocompatibility antigen-mismatched bone marrow transplantation model", Biology of Blood and Marrow Transplantation, 10(10):669-680 (2004).

Coppock, et al., "Peptide-based protein capture agents with high affinity, selectivity, and stability as antibody replacements in biodetection assays", Proc. of SPIE, 9107:910711-1 (2014).

Davis, et al., "'Platinum resistant' ovarian cancer: what is it, who to treat and how to measure benefit?", Gynecologic Oncology, 133(3):624-631 (2014).

Dieck, et al., "Development of bispecific molecules for the in situ detection of protein-protein interactions and protein phosphorylation", Cell & Biology, 21:357-368 (2014).

Eiber, et al., "Prostate-Specific Membrane Antigen Ligands for Imaging and Therapy", The Journal of Nuclear Medicine, 58(Supplement 2):67S-76S (2017).

Fisher, et al., "Trivalent Gd-DOTA reagents for modification of proteins", RSC Adv., 5: 96194-96200 (2015).

Fitzer-Attas, et al., "Harnessing Syk family tyrosine kinases as signaling domains for chimeric single chain of the Variable Domain recept", J. Immunol., 160(1):145-154 (1998).

Gao, et al., "Crystal structure of the complex between human CD8alpha(alpha) and HLA-A2", Nature, 387:630-4 (1997).

Gen Bank: AAH25715.1 , "CD8a molecule [Homo sapiens]" retrieved from the internet Jun. 17, 22.

Grunewald, et al., "Targeted Therapies for Ovarian Cancer", Best Practice & Research Clinical Obstetrics & Gynaecology, 41:139-152 (2017).

Handl, et al., "Hitting multiple targets with multimeric ligands", Expert Opin. Ther. Targets, 8(6):565-586 (2004).

Hill, et al., "Constraining Cyclic Peptides to Mimic Protein Structure Motifs", Angewandte Chemie, 53(48):13020-13041 (2014).

Hirai, et al., "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, 9(7): 1956-1967 (2010).

Hudson, et al, "Multiplex epitope mapping using bacterial surface display reveals both linear and conformational epitopes", Scientific Reports, 2(706):1-9 (2012).

Iwata, et al., "A new, convenient method forthe preparation of 4-[18F]fluorobenzyl halides", Applied radiation and Isotopes, 52(1): 87-92 (2000).

Josan, et al., "Cell-specific targeting by heterobivalent ligands", Bioconjug Chem., 22(7): 1270-1279 (2011).

Lai, et al., "Epitope-Targeted Macrocyclic Peptide Ligand with Picomolar Cooperative Binding to Interleukin-17F", Chemistry, 24(15):3760-3767 (2018).

Li, et al., "Identification of the CD8 DE loop as a surface functional epitope. Implications for major histocompatibility complex class I binding and CD8 inhibitor design", Journal of Biological Chemistry, 273(26): 16442-16445 (1998).

Lin, et al., "Inhibition of HIV-1 Tat-mediated transcription by a coumarin derivative, BPRHIV001, through the Akt pathway", Journal of Virology, 85(17): 9114-9126 (2011).

Lindlsey, et al., "The P13K/Akt Pathway: Recent Progress in the Development of ATP-Competitive and Allosteric Akt Kinase Inhibitors", Current Cancer Drug Targets, 8: 7-18 (2008).

Liu, et al., "99mTc-Labeled Small Peptides as Diagnostic Radiopharmaceuticals", Chem. Rev., 99(9):2235-2268 (1999).

(56) References Cited

OTHER PUBLICATIONS

Ma, et al., "A cyclic peptide-polymer probe for the detection of Clostridium botulinum neurotoxin serotype A", Toxicon, 47(8):901-908 (2006).
Mabry, et al., "Engineering of stable bispecific antibodies targeting IL-17 A and IL-23", Protein Engineering, Design & Selection, 23(3):115-127 (2010).
Macraild et al., "Antibody Recognition of Disordered Antigens", Structure 24:148-157, (2016).
Macraild et al., "Conformational Dynamics and Antigenicity in the Disordered Malaria Antigen Merozoite Surface Protein 2", PLOS ONE, 13 pages (2015).
Makrides, et al., "Extended in vivo half-life of human soluble complement receptor type 1 fused to a serum albumin-binding receptor", J. Pharmacol. Exp. Ther., 277(1):534-542 (1996).
Malm, et al., "Engineering of a bispecific affibody molecule towards HER2 and HER3 by addition of an albumin-binding domain allows for affinity purification and in vivo half-life extension", Biotechnol. J., 9(9):1215-1222 (2014).
Mamidyala et al., In situ click chemistry: probing the binding landscapes of biological molecules, Chemical Society Reviews, 39(4):1252-1261 (2010).
Manea, et al., "Antibody Recognition and Conformational Flexibility of a Plaque-Specific-Amyloid Epitope Modulated by Non-native Peptide Flanking Regions", J. Med. Chem., 51(5):1150-1161 (2008).
Matsuura, "Identification of conformational neutralizing epitopes on the capsid protein of canine calicivirus", Journal of General Virology, 82:1695-1702 (2001).
Melenhorst et el., "Detection of low avidity CD8(+) T cell populations with coreceptor-enhanced peptide-major histocompatibility complex class I tetramers", J Immunol Methods, 338(1-2): 31-39 (2008).
Merriam-Webster online definition of "correspond" downloaded Jun. 29, 2020 from internet, https://www.merriam-webster.com/dictionary/correspond (Year: 2020).
Millward, et al., "In situ click chemistry: from small molecule discovery to synthetic antibodies", Integr. Biol (Camb)., 5(1): 87-95 (2013).
Millward, et al., "Iterative in situ click chemistry assembles a branched capture agent and allosteric inhibitor for Akt1", JACS, 133(45):18280-18288 (2011).
Miossec, "Update on interleukin-17: a role in the pathogenesis of inflammatory arthritis and implication for clinical practice", RMD Open, 3(1):e000284 (2017).
Mor, et al., Mimicking the Structure of the V3 Epitope Bound to HIV-1 Neutralizing Antibodies, Biochemistry, 48(15):3288-3303 (2009).
Nag et al., "A chemical epitope-targeting strategy for protein capture agents: the serine 474 epitope of the kinase Akt2", Angewandte Chemie International Edition, 52:13975-13979 (2013).
Pansca, et al., "Structural disorder in eukaryotes", PLoS ONE, www.plosone.org Apr. 1, 2012, 7(4): e34687, 10 pages (2012).
Pfeilsticker, et al., "A cocktail of thermally stable, chemically synthesized capture agents for the efficient detection of anti-gp41 antibodies from human sera", PloS One, 8(10):Article No. e76224, 5 pages (2013).
Saito, et al., "Identification of anti-CD98 antibody mimotopes for inducing antibodies with antitumor activity by mimotope immunization", Cancer Science, 105(4): 396-401 (2014).
Sarbassov, et al., "Phosphorylation and regulation of Akt/PKB by the rictor-mTOR complex", Science, American Association for The Advancement of Science, 307(5712): 1098-1101 (2005).
Scaranti et al., "Exploiting the folate receptor α in oncology", Nature Reviews Clinical Oncology, 17(6):349-359 (2020).
Schweinsberg, et al., "Novel glycated [99mTc(CO)3]-labeled bombesin analogues for improved targeting of gastrin-releasing peptide receptor-positive tumors", Bioconjugate Chem., 19(12):2432-2439 (2008).
Son, et al., "New Cyclic Lipopeptides of the Iturin Class Produced by Saltern-Derived *Bacillus* sp. KCB14S006", Marine Drugs, 14(4): 72 (2016).
Stewart, et al., "Ovarian Cancer: An Integrated Review", Seminars in Oncology Nursing, 35(2):151-156 (2019).
Subramanyam, et al., "Inhibition of Protein Kinase Akt1 by Apoptosis Signal-regulating Kinase-1 (ASK1) is Involved in Apoptotic Inhibition of Regulatory Volume Increase", Journal of Biological Chemistry, 285(9): 6109-6117(2010).
Suzuki, et al., "Preferential Cleavage of a Tripeptide Linkage by Enzymes on Renal Brush Border Membrane to Reduce Renal Radioactivity Levels of Radiolabeled Antibody Fragments", Journal of Medicinal Chemistry., 61(12):5257-5268 (2018).
Tang et al., "Chimeric molecules facilitate the degradation of androgen receptors and repress the growth of LNCaP cells", Asian Journal of Andrology, 11(1): 119-126 (2009).
Tao, et al., "Expression, purification and identification of an immunogenic fragment in the ectodomain of prostate-specific membrane antigen", Experimental and Therapeutic Medicine, 11(3): 747-752 (2016).
Thigpen, "Contemporary phase III clinical trial endpoints in advanced ovarian cancer: assessing the pros and cons of objective response rate, progression-free survival, and overall survival", Gynecologic Oncology, 136(1):121-129 (2015).
Todorova, et al., "Biochemical nature and mapping of PSMA epitopes recognized by human antibodies induces after immunization with gene-based vaccines", Anticancer Research, 25: 4727-4732 (2005).
Torres, et al., "A revolutionary therapeutic approach for psoriasis: bi specific biological agents", Expert Opinion on Investigational Drugs, 25(7): 751-754 (2016).
Wang, et al., "Epitope Mapping Using Phage-Display Random Fragment Libraries", Epitope Mapping Protocols, Methods in Molecular Biology, 524: 315-332 (2009). Abstract Only.
Wang, et al., "Radioligand Therapy of Prostate Cancer with a Long-Lasting Prostate-Specific Membrane Antigen Targeting Agent 90 Y-DOTA-EB-MCG", Bioconjugate Chemistry, 29(7): 2309-2315 (2018).
Wilson, et al., "Reductive amination of [18F]fluorobenzaldehydes: Radiosyntheses of [2-18F]- and [4-18F]fluorodexetimides", Journal of Labeled Compounds and Radiopharmaceuticals, 28(10):1189-1199 (1990).
Wooldridge, et al., "Tricks with tetramers: how to get the most from multimeric peptide-MHC", Immunology, 126:147-164 2009 (2009).
Zhang, et al., "Structure and function of interleukin-17 family cytokines", Protein & Cell, 2(1): 26-40 (2011).
Adams, et al., "Extending the half-life of a fab fragment through generation of a humanized anti-human serum albumin Fv domain: An investigation into the correlation between affinity and serum half-life", MAbs, 8(7):1336-1346 (2016).
Agnew, et al., "Iterative In Situ Click Chemistry Creates Antibody-like Protein-Capture Agents", Angew. Chem. Int. Ed. Engl., 48:4944-4948 (2009).
Agnew, et al., "Protein-Catalyzed Capture Agents", Chemical Reviews, 119(17):9950-9970 (2019).
Alexander, et al., "Intracranial black-blood MR angiography with high-resolution 3D fast spin echo", Magn. Reson. Med., 40(2): 298-310 (1998).
Altschul, et al., "Gapped BLAST and PSI-BLAST: a new generation of protein database search programs", Nucleic Acids Res., 25(17):3389-402 (1997).
Bueno, et al., "The alpha folate receptor is highly activated in malignant pleural mesothelioma", The Journal of Thoracic and Cardiovascular Surgery, 121(2):225-233 (2001).
Charkhchi, et al., "CA125 and Ovarian Cancer: A Comprehensive Review", Cancers, 12(12):3730 (2020).
Claverie, "Information enhancement methods for large scale sequence analysis", Comput. Chem., 17:191-201 (1993).
Cramer, et al., "Crystal structure of a bacterial albumin-binding domain at 1.4 A resolution", FEBS Lett., 581(17):3178-3182 (2007).
Das, et al., "A General Synthetic Approach for Designing Epitope Targeted Macrocyclic Peptide Ligands", Angew. Chemie Int. Ed., 54(45):13219-24 (2015).
Dennis, et al., "Albumin binding as a general strategy for improving the pharmacokinetics of proteins", J. Biol. Chem., 277(38):35035-43 (2002).

(56) References Cited

OTHER PUBLICATIONS

Edelman, et al., "Extracranial carotid arteries: evaluation with "black blood" MR angiography", Radiology, 177:45-50 (1990).
Farrow, et al., "Epitope-Targeting of Tertiary Protein Structure Enables Target-Guided Synthesis of a Potent in Cell Inhibitor of Botulinum Neurotoxin", Angew. Chemie Int. Ed., 54(24):7114-9 (2015).
Food and Drug Administration, "Microdose Radiopharmaceutical Diagnostic Drugs: Nonclinical Study Recommendations Guidance for Industry", retrieved from website < fda.gov/media/107641/ download>, (2018).
Food and Drug Administration, "Oncology Therapeutic Radiopharmaceuticals: Nonclinical Studies and Labeling Recommendations Guidance for Industry" retrieved from website <fda.gov/media/129547/download>, (2019).
Frejd, et al., "Affibody molecules as engineered protein drugs", Exp. Mol. Ed.,49(3):e306, 8 pages (2017).
Goodrich, et al., "A quantitative study of ramped radio frequency, magnetization transfer, and slab thickness in three-dimensional time-of-flight magnetic resonance angiography in a patient population", Invest. Radia., 31:323-32 (1996).
Grindle, et. al., "Validation of high-throughput methods for measuring blood urea nitrogen and urinary albumin concentrations in mice", Comp Med., 56(6):482-6 (2006).
Gu, et al., "CA 125, PET alone, PET-CT, CT and MRI in diagnosing recurrent ovarian carcinoma: a systematic review and meta-analysis", European Journal of Radiology, 71(1):164-174 (2009).
Han, et. al., "Improving outcomes of acute kidney injury using mouse renal progenitor cells alone or in combination with erythropoietin or suramin", Stem Cell Res Ther., 4(3):74 (2013).
International Search Report for PCT application PCTUS2021/057877 dated Feb. 16, 2022.
Jacobs, et al., "Fusion to a highly stable consensus albumin binding domain allows for tunable pharmacokinetics", Protein Eng. Des. Sel., 28(10):385-393 (2015).
Jonsson, et al., "Engineering of a femtomolar affinity binding protein to human serum albumin", Protein Eng., Des. Sel., 21(8):515-527 (2008).
Jouret, et. al., "Nuclear Magnetic Resonance Metabolomic Profiling of Mouse Kidney, Urine and Serum Following Renal Ischemia/ Reperfusion Injury", PLoS One,11(9):e0163021, 14 pages (2016).
Kamen, et al., "Delivery of folates to the cytoplasm of MA104 cells is mediated by a surface membrane receptor that recycles", Journal of Biological Chemistry, 263(27):13602-13609 (1988).
Kossaï, et al., "Ovarian Cancer: A Heterogeneous Disease", Pathobiology, 85(1-2):41-49 (2018).
Kuroki, et al., "Treatment of epithelial ovarian cancer", BMJ, 371:m3773, 20 pages (2020).
Kurtzhals, et al., "Albumin binding of insulins acylated with fatty acids: characterization of the ligand-protein interaction and correlation between binding affinity and timing of the insulin effect in vivo", Biochem. J., 312(Pt 3):725-731 (1995).
Lorusso, et al., "The role of secondary surgery in recurrent ovarian cancer", International Journal of Surgical Oncology, 2012:613980, 6 pages (2012).
Markussen, et al., "Soluble, fatty acid acylated insulins bind to albumin and show protracted action in pigs", Diabetologia, 39(3):281-288 (1996).
Matulonis, et al., "Ovarian cancer", Nature Reviews Disease Primers, 2(1):16061, 48 pages (2016).
Meyers, et al., "Optimal alignments in linear space", Comp Applic. Biol. Sci., 4(1):11-17 (1988).
Muller, et al., "DOTA Conjugate with an Albumin-Binding Entity Enables the First Folic Acid-Targeted 177Lu-Radionuclide Tumor Therapy in Mice", The Journal of Nuclear Medicine, 54(1):124-131 (2013).
Necela, et al., "Folate receptor-α (FOLR1) expression and function in triple negative tumors", PLOS ONE, 10(3):e0122209, 19 pages (2015).
Nunez, et al., "High expression of folate receptor alpha in lung cancer correlates with adenocarcinoma histology and EGFR [corrected] mutation", Journal of Thoracic Oncology, 7(5):833-840 (2012).
O'Shannessy, et al., "Folate receptor alpha expression in lung cancer: diagnostic and prognostic significance", Oncotarget, 3(4):414-425 (2012b).
O'Shannessy, et al., "Folate receptor alpha (FRA) expression in breast cancer: identification of a new molecular subtype and association with triple negative disease", SpringerPlus., 1 (1):22, 9 pages (2012a).
Orlova, et al., "Site-specific radiometal labeling and improved biodistribution using ABY-027, a novel HER2-targeting affibody molecule-albumin-binding domain fusion protein", J. Nucl. Med., 54(6):961-968 (2013).
Poethko, et al., "Two-step methodology for high-yield routine radiohalogenation of peptides: (18)F-labeled RGD and octreotide analogs", The Journal of Nuclear Medicine, 45(5):892-902 (2004).
Rodrigues, et al., "Establishing standards for studying renal function in mice through measurements of body size-adjusted creatinine and urea levels", Biomed Res Int. , 2014:872827, 8 pages (2014).
Roett, et al., "Ovarian cancer: an overview", American Family Physician, 80(6):609-616 (2009).
Schottelius, et al., "First (18)F-labeled tracer suitable for routine clinical imaging of sst receptor-expressing tumors using positron emission tomography", Clinical Cancer Research, 10(11):3593-3606 (2004).
Stork, et al., "A novel tri-functional antibody fusion protein with improved pharmacokinetic properties generated by fusing a bispecific single-chain diabody with an albumin-binding domain from streptococcal protein G", Protein Eng. Des. Sel., 20(11):569-576 (2007).
Wootton, et al., "Statistics of local complexity in amino acid sequences and sequences databases", Comput. Chem., 17(2):149-63 (1993).
Zorzi, et al., "Acylated heptapeptide binds albumin with high affinity and application as tag furnishes long-acting peptides", Nat Commun., 8:16092 (2017).
Zorzi, et al., "Non-covalent albumin-binding ligands for extending the circulating half-life of small biotherapeutics", MedChemComm., 10(7):1068-1081 (2019).

* cited by examiner

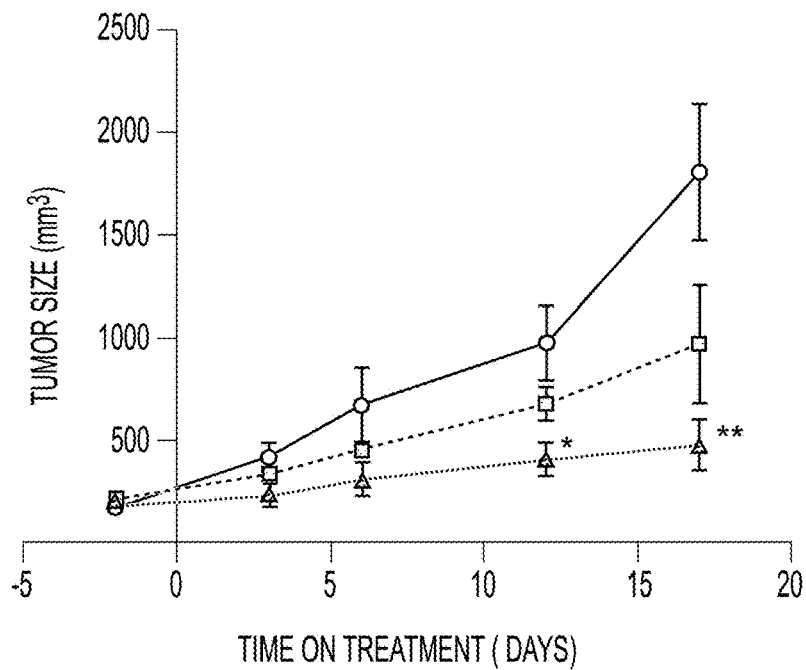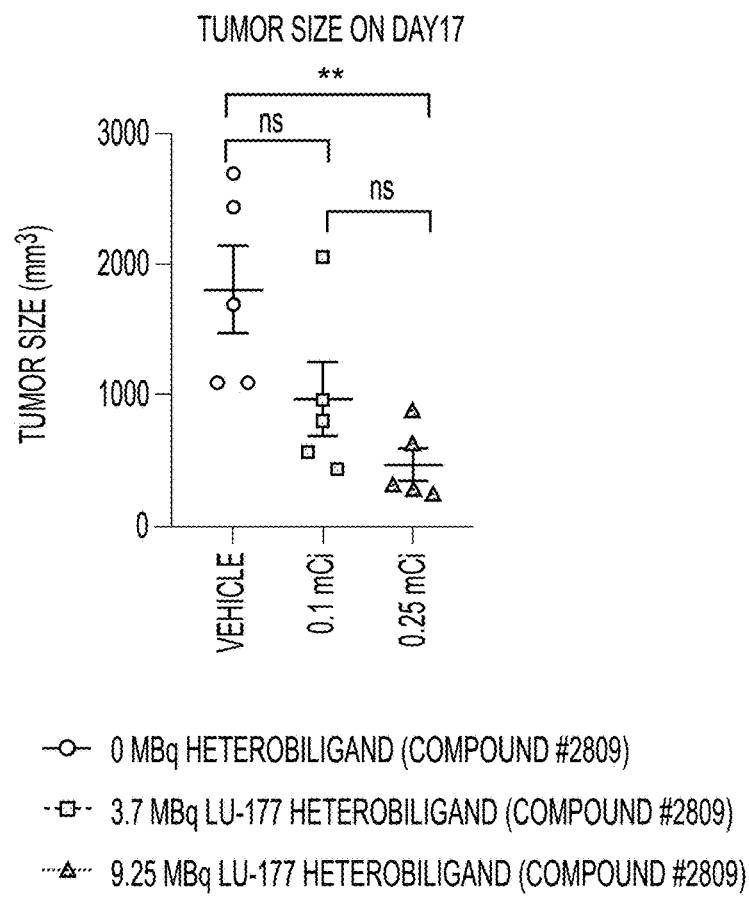
FIG. 20

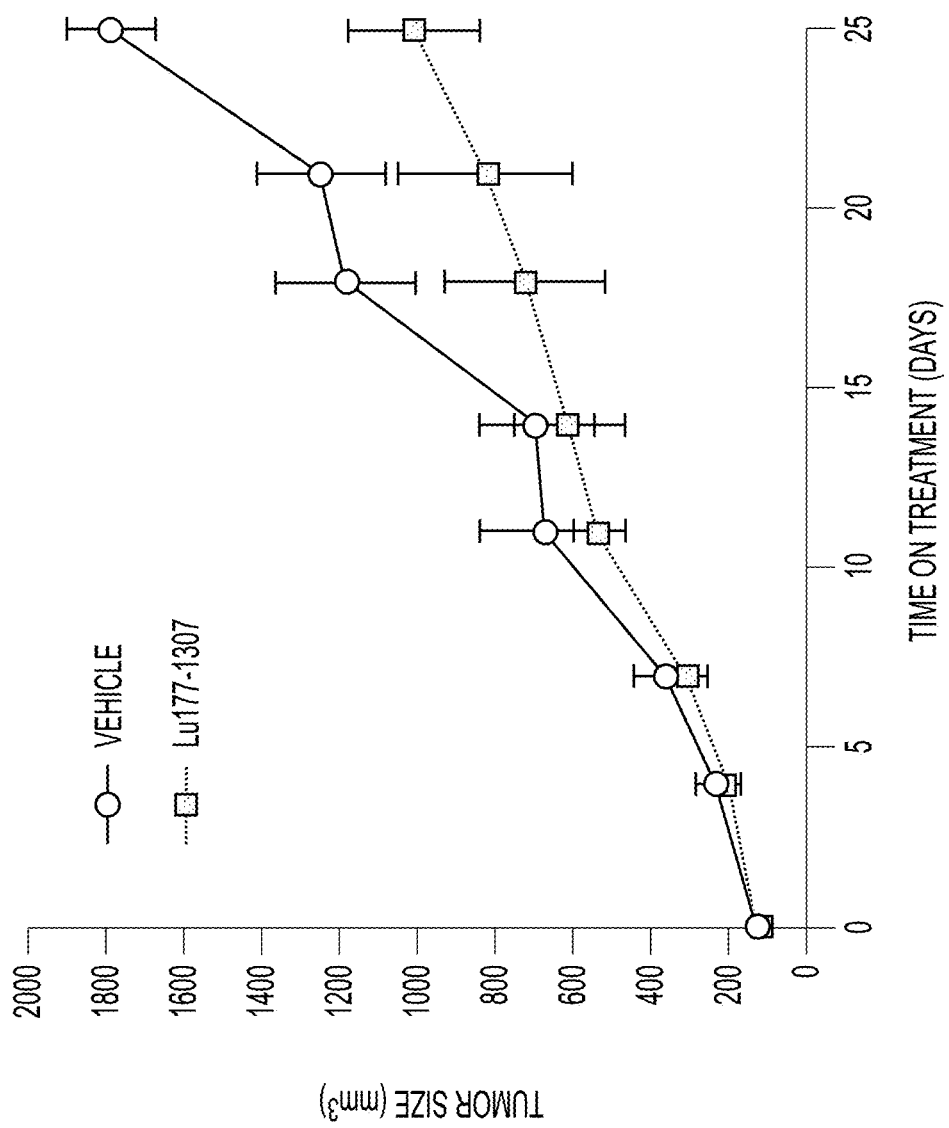

SEQUENCE LISTING

```
<160> NUMBER OF SEQ ID NOS: 36

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110
```

```
Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 2
<211> LENGTH: 255
<212> TYPE: PRT
<213> ORGANISM: Mus musculus

<400> SEQUENCE: 2

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
                20                  25                  30

Asn Val Cys Met Asp Ala Lys His His Lys Glu Lys Pro Gly Pro Glu
            35                  40                  45

Asp Asn Leu His Asp Gln Cys Ser Pro Trp Lys Thr Asn Ser Cys Cys
50                  55                  60

Ser Thr Asn Thr Ser Gln Glu Ala His Lys Asp Ile Ser Tyr Leu Tyr
65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
            115                 120                 125

Asp Val Pro Leu Cys Lys Glu Asp Cys Gln Trp Trp Glu Asp Cys
130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
            195                 200                 205

Gln Met Trp Phe Asp Pro Ala Gln Gly Asn Pro Asn Glu Glu Val Ala
            210                 215                 220
```

```
Arg Phe Tyr Ala Glu Ala Met Ser Gly Ala Gly Phe His Gly Thr Trp
225                 230                 235                 240

Pro Leu Leu Cys Ser Leu Ser Leu Val Leu Leu Trp Val Ile Ser
                245                 250                 255

<210> SEQ ID NO 3
<211> LENGTH: 14
<212> TYPE: PRT
<213> ORGANISM: artificial sequence
<220> FEATURE:
<223> OTHER INFORMATION: Epitope 1

<400> SEQUENCE: 3

His His Lys Glu Lys Pro Gly Pro Glu Asp Lys Leu His Glu
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Epitope 2

<400> SEQUENCE: 4

Gly Pro Trp Ile Gln Gln Val Asp Gln Ser Trp Arg Lys Glu Arg Val
1               5                   10                  15

Leu Asn

<210> SEQ ID NO 5
<211> LENGTH: 20
<212> TYPE: PRT
<213> ORGANISM: Artificial Sequence
<220> FEATURE:
<223> OTHER INFORMATION: Epitope 3

<400> SEQUENCE: 5

Arg Cys Ile Gln Met Trp Phe Asp Pro Ala Gln Gly Asn Pro Asn Glu
1               5                   10                  15

Glu Val Ala Arg
            20

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 6

His Ser His Thr Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 7
```

```
Ser Leu Tyr Tyr Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (2)..(5)

<400> SEQUENCE: 8

Gly His Trp Glu Phe
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 9

Lys Tyr Glu Glu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 10

Leu Thr Asp Trp His
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 11

His Glu Pro Phe Phe
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(1)
<220> FEATURE:
<221> NAME/KEY: D-amino acid
```

```
<222> LOCATION: (3)..(5)

<400> SEQUENCE: 12

Trp Gly Leu His Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 13

Trp Trp Pro Arg Gly
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 14

Asn Asn Tyr Leu
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(4)

<400> SEQUENCE: 15

Thr Trp Ser Trp
1

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 16

Tyr Phe Tyr Thr Trp
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: D-amino acid
<222> LOCATION: (1)..(5)

<400> SEQUENCE: 17

Trp Lys His Glu Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: D-amino acid
<222> LOCATION: (4)..(5)

<400> SEQUENCE: 18

Thr Tyr Gly Glu His
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(2)
<220> FEATURE:
<221> NAME/KEY: D-amino acid
<222> LOCATION: (4)..(5)

<400> SEQUENCE: 19

Ala Asn Gly Glu Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: D-amino acid
<222> LOCATION: (1)..(5)

<400> SEQUENCE: 20

Asp Glu Arg Tyr Thr
1               5

<210> SEQ ID NO 21
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 21

Trp Trp Glu Gln Asp Arg Asp Trp Asp Phe Asp Val Phe Gly Gly Gly
1               5                   10                  15

Thr Pro

<210> SEQ ID NO 22
```

-continued

```
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 22

Trp Trp Glu Leu Asp Arg Asp Trp Asp Phe Asp Val Phe Gly Gly Gly
1               5                   10                  15

Thr Pro

<210> SEQ ID NO 23
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 23

Tyr Trp Trp Glu Arg Arg Asp Trp Asp Phe Asp Val Phe Gly Gly Gly
1               5                   10                  15

Thr Pro

<210> SEQ ID NO 24
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 24

Glu Trp Trp Trp Arg Arg Asp Trp Asp Phe Asp Val Phe Gly Gly Gly
1               5                   10                  15

Thr Pro

<210> SEQ ID NO 25
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 25

Leu Phe Trp Trp Glu Arg Asp Trp Asp Phe Asp Val Phe Gly Gly Gly
1               5                   10                  15

Thr Pro

<210> SEQ ID NO 26
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 26

Lys Trp Trp Glu Ile Arg Asp Trp Asp Phe Asp Val Phe Gly Gly Gly
1               5                   10                  15

Thr Pro Ala Lys Ser Asp Glu
            20

<210> SEQ ID NO 27
<211> LENGTH: 11
<212> TYPE: PRT
<213> ORGANISM: Artificial Sequence
```

```
<220> FEATURE:
<223> OTHER INFORMATION: Synthetic Peptide

<400> SEQUENCE: 27

Asp Ile Cys Leu Pro Arg Trp Gly Cys Leu Trp
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 28

Arg Leu Ile Glu Asp Ile Cys Leu Pro Arg Trp Gly Cys Leu Trp Glu
1               5                   10                  15

Asp Asp

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 29

Met Glu Asp Ile Cys Leu Pro Arg Trp Gly Cys Leu Trp Gly Asp
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 30

Gln Arg Leu Met Glu Asp Ile Cys Leu Pro Arg Trp Gly Cys Leu Trp
1               5                   10                  15

Glu Asp Asp Glu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 31

Gln Gly Leu Ile Gly Asp Ile Cys Leu Pro Arg Trp Gly Cys Leu Trp
1               5                   10                  15

Gly Arg Ser Val
            20

<210> SEQ ID NO 32
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 32

Glu Tyr Glu Lys Glu Tyr Glu
```

<210> SEQ ID NO 33
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 33

```
Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala
        35                  40
```

<210> SEQ ID NO 34
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 34

```
Leu Lys Asn Ala Lys Glu Asp Ala Ile Ala Glu Leu Lys Lys Ala Gly
1               5                   10                  15

Ile Thr Ser Asp Phe Tyr Phe Asn Ala Ile Asn Lys Ala Lys Thr Val
            20                  25                  30

Glu Glu Val Asn Ala Leu Lys Asn Glu Ile Leu Lys Ala
        35                  40                  45
```

<210> SEQ ID NO 35
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 35

```
Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45
```

<210> SEQ ID NO 36
<211> LENGTH: 51
<212> TYPE: PRT
<213> ORGANISM: Artificial Sequence
<220> FEATURE:
<223> OTHER INFORMATION: Synthetic Peptide

<400> SEQUENCE: 36

```
Thr Ile Asp Glu Trp Leu Leu Lys Glu Ala Lys Glu Lys Ala Ile Glu
1               5                   10                  15
```

```
Glu Leu Lys Lys Ala Gly Ile Thr Ser Asp Tyr Tyr Phe Asp Leu Ile
            20                  25                  30
Asn Lys Ala Lys Thr Val Glu Gly Val Asn Ala Leu Lys Asp Glu Ile
        35                  40                  45
Leu Lys Ala
    50
```

COMPOSITIONS, IMAGING, AND THERAPEUTIC METHODS TARGETING FOLATE RECEPTOR 1 (FOLR1)

CROSS-REFERENCE TO RELATED APPLICATIONS

This application is a continuation of International Application No. PCT/US2021/057877 filed Nov. 3, 2021, which claims the benefit of and priority to U.S. Application No. 63/109,176 filed Nov. 3, 2020, and U.S. Application No. 63/256,922 filed Oct. 18, 2021, the contents of which are incorporated by reference in their entirety.

REFERENCE TO SEQUENCE LISTING

The Sequence Listing submitted Jan. 12, 2022, as a text file named "INDI_108_CON_ST25.txt," created on Jan. 11, 2022, and having a size of 14,080 bytes is hereby incorporated by reference.

FIELD OF THE INVENTION

The disclosed invention is generally in the field of folate receptor 1 (FOLR1) and specifically in the area of compositions, imaging, and therapeutic methods relating to targeting of FOLR1.

BACKGROUND OF THE INVENTION

Folate receptor 1 (FOLR1) is a cell membrane protein with significant overexpression in carcinomas. FOLR1 is a 38 kD glycosylphosphatidylinositol (GPI) anchored protein that binds folate with high affinity (less than one nM). FOLR1 is responsible for trafficking folic acid into cells via receptor-mediated endocytosis. The protein is anchored to the cell via a (GPI) attached to the C terminus of FOLR1. The mechanism allows folate to readily be delivered to cells for entrance by receptor-mediated endocytosis. Folate is transferred to an endosomal compartment at low pH.

Folate receptor (FOLR1) is restricted to limited cell types. Normal healthy tissues express very low or undetectable levels of the folate receptor. The exceptions are kidney, choroid plexus, and placenta. Many malignant tissues, including ovarian, breast, bronchial, and brain cancers express significantly elevated levels of FOLR1 receptor. It is estimated that 80% of all ovarian carcinomas overexpress the folate receptor.

FOLR1 is a desirable target for compositions to treat and image malignant tissue.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

Disclosed are compounds, compositions, imaging, therapeutics and methods relating to ligands having affinity for an epitope on folate receptor 1 (FOLR1). In particular, disclosed are heterobiligands comprising a first ligand having affinity for an epitope on folate receptor 1 (FOLR1), a linker, and a second ligand, where the second ligand comprises folate (the ligand of FOLR1), where the linker links the first ligand and the second ligand, where the heterobiligand specifically binds FOLR1, and where the first ligand comprises a 3-10 amino acid sequence of D-amino acids, artificial amino acids, or combinations thereof. FOLR1 comprises an active site to which folate binds. The binding of the folate (second ligand) and the binding of the first ligand to the epitope on FOLR1, provides specific binding to FOLR1.

In some forms, the folate binds the FOLR1 active site. In some forms, the folate

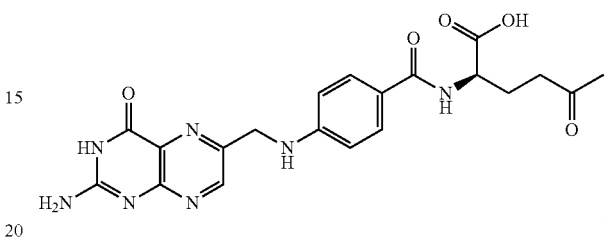

In some forms, the first ligand comprises 5 to 9 amino acids.

In some forms, the epitope comprises the amino acid sequence HHKEKPGPEDKLHE (SEQ ID NO:3), GPWIQQVDQSWRKERVLN (SEQ ID NO:4), or RCIQMWFDPAQGNPNEEVAR (SEQ ID NO:5). In some forms, the epitope comprises the amino acid sequence HHKEKPGPEDKLHE (SEQ ID NO:3). In some forms, the epitope comprises the amino acid sequence GPWIQQVDQSWRKERVLN (SEQ ID NO:4). In some forms, the epitope comprises the amino acid sequence RCIQMWFDPAQGNPNEEVAR (SEQ ID NO:5).

In some forms, the first ligand comprises an amino acid sequence selected from the group consisting of hshta (SEQ ID NO:6), kyeet (SEQ ID NO:9), deryt (SEQ ID NO:20), Ghwef (SEQ ID NO:8), ltdwh (SEQ ID NO:10), hepff (SEQ ID NO:11), wGlhk (SEQ ID NO:12), wwprG (SEQ ID NO:13), nnyl (SEQ ID NO:14), twsw (SEQ ID NO:15), yfytw (SEQ ID NO:16), wkhef (SEQ ID NO:17), tyGeh (SEQ ID NO:18), and anGel (SEQ ID NO:19). In some forms, the first ligand comprises an amino acid sequence hshta (SEQ ID NO:6), kyeet (SEQ ID NO:9), and deryt (SEQ ID NO:20). In some forms, the first ligand comprises an amino acid sequence hshta (SEQ ID NO:6).

In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue. In some forms, the linker is a peptide bond, $PEG_3$, $PEG_3$-Tz, $PEG_3$-Lys, or peptide.

In some forms, the heterobiligand further comprises a reporter moiety. In some forms, the reporter moiety is selected from the group consisting of biotin, copper-DOTA, biotin-$PEG_3$, aminooxyacetate, $^{19}$FB, $^{18}$FB, and FITC-$PEG_3$. In some forms, the reporter moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{11}$C and $^{76}$Br. In some forms, the reporter moiety is $^{18}$F. In some forms, the reporter moiety is coupled to the first ligand, the second ligand, the linker, or the therapeutic moiety. In some forms, the reporter moiety is coupled to the C-terminal end of the first ligand or the N-terminal end of the first ligand.

In some forms, the heterobiligand further comprises a therapeutic moiety. In some forms, the therapeutic moiety is selected from the group consisting of radionuclide-DOTA and radionuclide-NOTA. In some forms, the therapeutic moiety is $^{177}$Lu-DOTA or $^{177}$Lu-NOTA. In some forms, the therapeutic moiety is $^{225}$Ac-DOTA or $^{225}$Ac-NOTA. In some forms, the therapeutic moiety is coupled to the first ligand, the second ligand, the linker, or the reporter moiety. In some forms, the therapeutic moiety is coupled to the C-terminal end of the first ligand or the N-terminal end of the first ligand.

In some forms, the heterobiligand further comprises an albumin binding moiety. In some forms, the albumin binding moiety is 4-methylphenyl butyrate (MPBA) or 4-iodophenyl butyrate (IPBA). In some forms, the albumin binding moiety is coupled to the first ligand, the second ligand, the linker, the reporter moiety, or the therapeutic moiety. In some forms, the albumin binding moiety is coupled to the C-terminal end of the first ligand or the N-terminal end of the first ligand.

In some forms, the heterobiligand comprises a reporter moiety, whereby the heterbiligand is an imaging agent. In some forms, the heterobiligand further comprises a therapeutic moiety, whereby the heterobiligand is a therapeutic and organ protectant.

Also disclosed are compositions comprising any of the disclosed heterobiligands. In some forms, the composition is an imaging agent. In some forms, the heterobiligand further comprises a therapeutic moiety, whereby the composition is a therapeutic and organ protectant.

Also disclosed are methods comprising the disclosed heterobiligand.

Also disclosed are methods of detecting FOLR1 in a biological sample, the method comprising contacting the biological sample with a composition comprising any of the disclosed heterobiligands, wherein the heterobiligand comprises a reporter moiety, and detecting the reporter moiety.

Also disclosed are methods of treating a subject with cancer, the method comprising administering the disclosed composition to the subject, wherein the heterobiligand comprises a therapeutic moiety. In some forms, the subject has cancer cells expressing FOLR1.

In some forms of the method, the composition is an imaging agent. In some forms of the method, the heterobiligand further comprises a therapeutic moiety, whereby the composition is a therapeutic and organ protectant. In some forms of the method, the heterobiligand binds to the tumor and provides a therapeutic effect, thereby decreasing the size of the tumor.

In some forms of the method, the heterobiligand cleaves to deliver a therapeutic to the tumor. In some forms, the cleaved heterobiligand is protective to an organ. In some forms, the organ is the kidney.

In some forms, the therapeutic moiety is selected from the group consisting of radionuclide-DOTA and radionuclide-NOTA. In some forms, the therapeutic moiety is $^{177}$Lu-DOTA or $^{177}$Lu-NOTA. In some forms, the therapeutic moiety is $^{225}$Ac-DOTA or $^{225}$Ac-NOTA.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 17A is tumor in mouse 4. FIG. 17B is tumor in mouse 6. FIG. 17C is kidney in mouse 4. FIG. 17D is kidney in mouse 6. FIG. 17E is tumor/muscle in mouse 4. FIG. 17F is tumor/muscle in mouse 6.

FIG. 20 are graphs of tumors over time under treatment with different radionuclide doses delivered via heterobiligands.

FIGS. 33A-33C are graphs of tumor size over days of treatment for OVCAR3 xenografts treated with Lu177-#2809 (FIG. 33A), for OVCAR3 xenografts treated with Lu177-#1307 (FIG. 33B), and for OVCAR3 xenografts treated with Lu177-#6305 (FIG. 33C).

FIG. 37A used 0 MBq of $^{177}$Lu-7327. FIG. 37B used 9.25 MBq of $^{177}$Lu-7327. FIG. 37C used 14.8 MBq of $^{177}$Lu-7327. FIG. 37D used 29.6 MBq of $^{177}$Lu-7327.

DETAILED DESCRIPTION OF THE INVENTION

Figure 1:
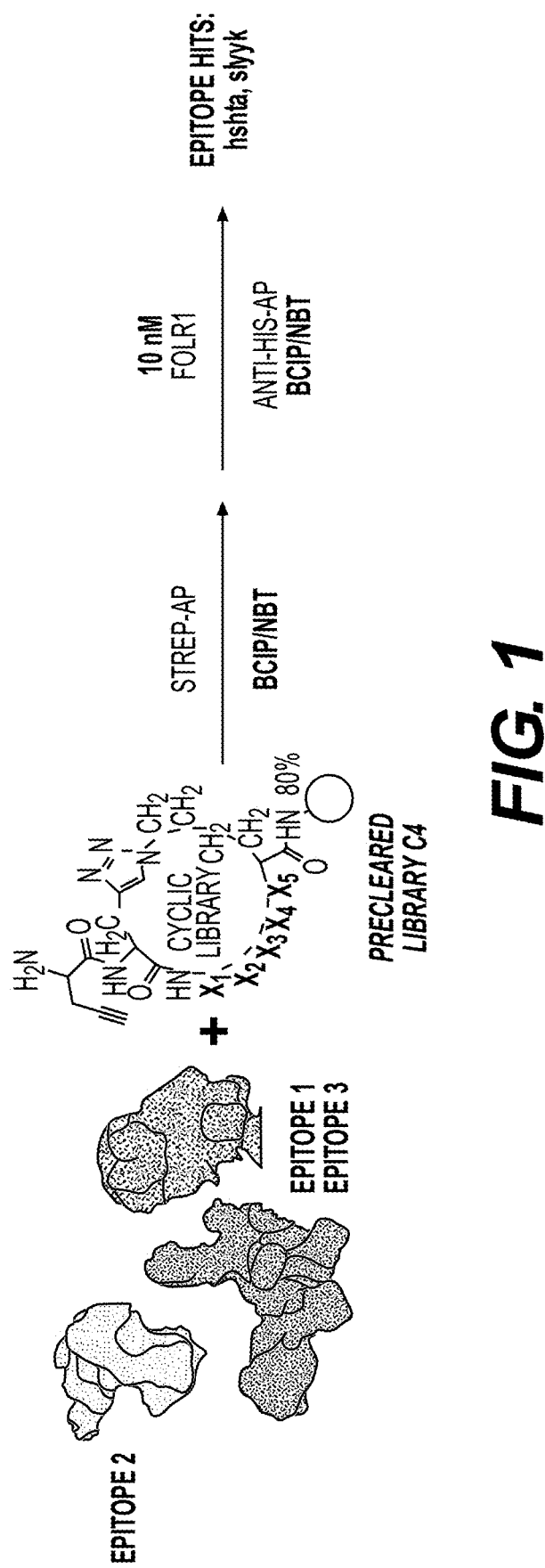
FIG. 1 is a diagram of an example of screening for PCC ligands of FOLR1 using synthetic epitopes (SynEps).

The disclosed method and compositions can be understood more readily by reference to the following detailed description of particular embodiments and the Examples included therein and to the Figures and their previous and following description.

Folate receptor (FOLR1) is restricted to limited cell types. Normal healthy tissues express very low or undetectable levels of the folate receptor. The exceptions are kidney, choroid plexus, and placenta. Many malignant tissues, including ovarian, breast, bronchial, and brain cancers express significantly elevated levels of FOLR1 receptor. It is estimated that 80% of all ovarian carcinomas overexpress the folate receptor.

Covalent conjugation of small molecules and proteins to folic acid does not prevent folic acid conjugates from binding to the folate receptor. Composition conjugates that bind FOLR1 can readily be delivered to and can enter cells by receptor-mediated endocytosis.

FOLR1 is a desirable target for compositions to treat and image malignant tissue.

The disclosed heterobiligands—folate linked to a receptor-specific ligand—can be used to detect, image, and treat targeted cancers. Some example heterobiligands display cooperative binding that yields very high EC50s compared to native folate. The disclosed heterobiligands are designed based on medicinal chemistry principles to diminish off target binding and alter pharmacokinetics for specific applications, such as imaging and therapy.

We developed a PCC that has the dual purpose of binding to a tumor that expresses FOLR1, providing an imaging marker for a tumor that expresses FOLR1. The PCC binds to the tumor with a secondary therapeutic activity. Epitope-targeted macrocyclic peptide ligands against FOLR1 were identified using protein catalyzed capture agent (PCC) technology and was joined with a folate (the ligand of FOLR1) via a linker to form heterobiligands useful for binding, detection and imaging FOLR1.

Epitope-targeted macrocyclic peptide ligands against FOLR1 were identified using PCC technology and were further developed as in vivo positron emission tomography (PET) imaging agents and FOLR1 heterobiligands. Three human FOLR1 epitopes have been designed and screened against one-bead-one-compound (OBOC) peptide libraries. Two epitopes are located at or near the active site, while the third epitope is situated on the protein surface. Epitope-targeted macrocyclic peptide ligands were identified against FOLR1.

Epitope-targeted macrocyclic peptide ligands against FOLR1 were developed by in situ click screening of one-bead-one-compound (OBOC) peptide libraries. Screens were performed against human FOLR1 epitopes that show high homology with mouse FOLR1 epitopes. These ligands were designed to bind to specific synthetic epitopes of FOLR1 similar to the method of developing monoclonal antibodies (mAbs). Cyclic peptides have an ability to display protein-like epitopes with restricted conformational flexibility and thus often display enhanced bioavailability, increased stability towards metabolic degradation, and superior binding affinities as compared to their linear counterparts.

In some forms, the peptide library is composed of exclusively D-amino acids and artificial amino acids.

Two biligand strategies are pursued to achieve low nM to pM binding. Biligands can be developed by attaching an epitope-targeted PCC macrocycle to a folate anchor. This approach takes advantage of the specific binding of folate. Biligands are developed by joining together pairs of two epitope-targeted PCC macrocyclic peptide ligands using a chemical linker to promote cell penetration. Cell penetration and cellular activity studies of ligands and biligands are pursued with input from medicinal chemistry. The optimized, cell-penetrant PCCs display specific binding and in vivo pharmacokinetics compatible with imaging FOLR1 in vivo using fluorine-18 PET. Separately, the PCCs are investigated as novel therapeutic compounds.

A. Definitions

In some forms, the term "FOLR1" as used herein refers to human FOLR1. In some forms, FOLR1 comprises one of the following amino acid sequence or an amino acid sequence substantially identical to it.

```
1. Human FOLR1 protein
                                    (SEQ ID NO: 1)
         10         20         30
MAQRMTTQLL LLLVWVAVVG EAQTRIAWAR 40         50         60
TELLNVCMNA KHHKEKPGPE DKLHEQCRPW 70         80         90
RKNACCSTNT SQEAHKDVSY LYRFNWNHCG 100        110        120
EMAPACKRHF IQDTCLYECS PNLGPWIQQV 130        140        150
DQSWRKERVL NVPLCKEDCE QWWEDCRTSY 160        170        180
TCKSNWHKGW NWTSGFNKCA VGAACQPFHF 190        200        210
YFPTPTVLCN EIWTHSYKVS NYSRGSGRCI 220        230        240
QMWFDPAQGN PNEEVARFYA AAMSGAGPWA

250
AWPFLLSLAL

MLLWLLS

2. Mouse FOLR1 protein
                                    (SEQ ID NO: 2)
         10         20         30
MAHLMTVQLL LLVMWMAECA QSRATRARTE 40         50         60
LLNVCMDAKH HKEKPGPEDN LHDQCSPWKT 70         80         90
NSCCSTNTSQ EAHKDISYLY RFNWNHCGTM 100        110        120
TSECKRHFIQ DTCLYECSPN LGPWIQQVDQ 130        140        150
SWRKERILDV PLCKEDCQQW WEDCQSSFTC 160        170        180
KSNWHKGWNW SSGHNECPVG ASCHPFTFYF 190        200        210
PTSAALCEEI WSHSYKLSNY SRGSGRCIQM 220        230        240
WFDPAQGNPN EEVARFYAEA MSGAGFHGTW

250
PLLCSLSLVL LWVIS
```

As used herein, the term "mammal" includes humans and both domestic animals such as laboratory animals and household pets (e.g., cats, dogs, swine, cattle, sheep, goats, horses, rabbits), and non-domestic animals such as wildlife and the like.

The term "capture agent" as used herein refers to a composition that comprises one or more target-binding moieties, or ligands which specifically binds to a target protein via those target-binding moieties. Each target-binding moiety exhibits binding affinity for the target protein, either individually or in combination with other target-binding moieties. In some forms, each target-binding moiety binds to the target protein via one or more non-covalent interactions, including for example hydrogen bonds, hydrophobic interactions, and van der Waals interactions. A capture agent can comprise one or more organic molecules, including for example polypeptides, peptides, polynucleotides, and other non-polymeric molecules. In some aspects, a capture agent is a protein catalyzed capture agent. In some forms, capture agents comprising one or more peptide ligands that specifically bind FOLR1 are also referred to as epitope-targeted macrocyclic peptide ligands against FOLR1.

Reference to "capture agents" further refers to pharmaceutically acceptable salts thereof. "Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The capture agents described herein, or their pharmaceutically acceptable salts, may contain one or more asymmetric centers and may thus give rise to enantiomers, diastereomers, and other stereoisomeric forms that can be defined, in terms of absolute stereochemistry, as (R) or (S) or, as (D) or (L) for amino acids. The disclosed compositions and methods are meant to include all such possible isomers, as well as their racemic and optically pure forms. Optically active (+) and (−), (R) and (S), or (D) and (L) isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G."

A "stereoisomer" refers to a compound made up of the same atoms bonded by the same bonds but having different three-dimensional structures, which are not interchangeable. The disclosed compositions and methods contemplate various stereoisomers and mixtures thereof and include "enantiomers," which refers to two stereoisomers whose molecules are non-superimposable mirror images of one another.

A "tautomer" refers to a proton shift from one atom of a molecule to another atom of the same molecule. The disclosed compositions and methods include tautomers of any said compounds.

The term "epitope" as used herein refers to a distinct molecular surface of a protein (e.g., FOLR1). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid Amino acids can be referred to herein by either their commonly known three letter symbols or by the one-letter symbols recommended by the IUPAC-IUB Biochemical Nomenclature Commission.

The term "artificial amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The artificial amino acid can be a close analog of one of the twenty natural amino acids, or it can introduce a completely new functionality and chemistry, as long as the hydrophobicity of the artificial amino acid is either equivalent to or greater than that of the natural amino acid. The artificial amino acid can either replace an existing amino acid in a protein (substitution), or be an addition to the wild type sequence (insertion). The incorporation of artificial amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-19}$ M or even lower.

The term "$K_D$" as used herein refers to the dissociation equilibrium constant of a particular capture agent-antigen interaction.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

The term "imaging agent" refers to capture agents that have been labeled for detection. In some forms, imaging agents are isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to a pharmacologically important site of action. Certain isotopically-labelled disclosed imaging agents, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, can afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy. Isotopically-labeled imaging agents can generally be prepared by conventional techniques known to those skilled in the art or by processes analogous to those described in the Examples as set out below using an appropriate isotopically-labeled reagent in place of the non-labeled reagent previously employed.

The present disclosure is also meant to encompass the in vivo metabolic products of the disclosed imaging agents. Such products can result from, for example, the oxidation, reduction, hydrolysis, amidation, esterification, and the like of the administered compound, primarily due to enzymatic processes. Accordingly, disclosed are compounds produced by a process comprising administering a compound as disclosed to a mammal for a period of time sufficient to yield a metabolic product thereof. Such products are typically identified by administering a radiolabeled the disclosed compounds in a detectable dose to an animal, such as rat, mouse, guinea pig, monkey, or to human, allowing sufficient time for metabolism to occur, and isolating its conversion products from the urine, blood or other biological samples.

A "pharmaceutical composition" refers to a formulation of a compound as disclosed and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refers to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed capture agent can vary according to factors such as the disease state, age, sex, and weight of the individual, and the ability of the capture agent to elicit a desired response in the individual.

The term "stable" as used herein with regard to a capture agent, protein catalyzed capture agent, or pharmaceutical formulation thereof refers to the agent or formulation retaining structural and functional integrity for a sufficient period of time to be utilized in the methods described herein.

The term "synthetic" as used herein with regard to a protein catalyzed capture agent refers to the capture agent having been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which can be homopolymeric tracts, short-period repeats, or regions enriched in one or more amino acids. Such low-complexity regions can be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity can be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci.

4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

B. Development of FOLR1 Capture Agents

Antibodies are currently the default detection agent for use in diagnostic and therapeutic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the "best fit" inhibitor from these library components by selectively promoting 1,3-dipolar cycloaddition between the acetylene and azide groups to form a triazole linkage (the "click" reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (U.S. Publication No. 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand can be identified by screening the protein against a large ($>10^6$ element) one-bead-one-compound (OBOC) peptide library, where the peptides themselves can be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

C. FOLR1 Capture Agents

In one aspect, provided herein is a stable, synthetic capture agent that specifically binds FOLR1, wherein the capture agent comprises one or more "anchor" ligands (also referred to as simply "ligands" herein), a linker, and one or more additional ligands, and wherein the ligands selectively bind FOLR1. These are referred to herein as capture agents.

Ligands are target-binding moieties (also referred to as binding molecules, specific binding molecules, target-binding molecules, binding moieties, and specific binding moieties).

In some forms, two separate ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D = K_{D1} \times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

A capture agent having two ligands can be referred to as a biligand capture agent, or just as a biligand. Where the two ligands have different character, such as a peptide ligand and a small molecule ligand, the biligand capture agent can be referred to as a heterobiligand, or just as a heterobiligand.

A capture agent having three ligands can be referred to as a triligand capture agent, or just as a triligand. Where two or three of the ligands have different character, such as two peptide ligands and one small molecule ligand, the triligand capture agent can be referred to as a heterotriligand, or just as a heterotriligand.

In some forms, a ligand comprises one or more polypeptides or peptides. In some forms, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted 1,2,3-triazole. In some forms, the ligand comprises a peptide comprising D-amino acids and artificial amino acids.

In some forms, the ligands are linked to one another via a covalent linkage through a linker. In some forms, the ligand and linker are linked to one another via an amide bond or a 1,4-disubstituted-1,2,3-triazole linkage as shown below:

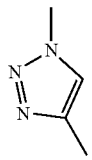

1,4-disubstituted-1,2,3-triazole linkage.

In those forms where the ligands and linker are linked to one another via a 1,4-disubstituted-1,2,3-triazole linkage, the 1,4-disubstituted-1,2,3-triazole linkage can be formed by Cu-Catalyzed Azide/Alkyne Cycloaddition (CuAAC).

In some forms, the ligands and linker are linked to one another by a Tz4 linkage having the following structure:

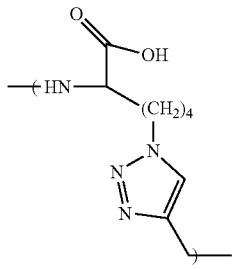

In some forms, the ligands and linker are linked to one another by a Tz5 linkage having the following structure:

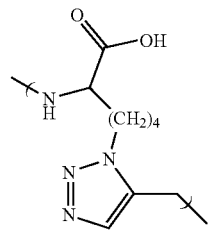

In those forms wherein one or more of the ligands and linker are linked to one another via amide bonds, the amide bond can be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In some forms, the capture agents provided herein are stable across a range of reaction conditions and/or storage times. A capture agent that is "stable" as used herein maintains the ability to specifically bind to a target protein. In some forms, the capture agents provided herein are more stable than an antibody binding to the same target protein under one or more reaction and/or storage conditions. For example, in some forms the capture agents provided herein are more resistant to proteolytic degradation than an antibody binding to the same target protein.

In some forms, the capture agents provided herein have a shelf-life of greater than six months, meaning that they are stable in storage for greater than six months. In some forms, the capture agents have a shelf-life of one year or greater, two years or greater, or more than three years. In some forms, the capture agents are stored as a lyophilized powder. In some forms, the capture agents provided herein have a longer shelf-life than an antibody binding to the same target protein.

In some forms, the capture agents provided herein are stable at temperatures ranging from about −80° to about 120° C. In some forms, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In some forms, the capture agents provided herein are stable across a wider range of temperatures than an antibody binding to the same target protein, and/or remain stable at a specific temperature for a longer time period than an antibody binding to the same target protein.

In some forms, the FOLR1 capture agents provided herein are stable at a pH range from about 3.0 to about 8.0. In some forms, the range is about 4.0 to about 7.0. In some forms, the range is about 7.0 to about 8.0.

In some forms, the FOLR1 capture agents provided herein are stable in human serum for more than 12 hours. In some forms, the capture agents are stable in human serum for more than 18 hours, more than 24 hours, more than 36 hours, or more than 48 hours. In some forms, the capture agents provided herein are stable for a longer period of time in human serum than an antibody binding to the same target protein. In some forms, the capture agents are stable as a powder for two months at a temperature of about 60° C.

In some forms, the FOLR1 capture agents provided herein can comprise one or more detection labels, including for example biotin, copper-1,4,7,10-tetraazacyclododecane-1,4, 7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I, $^{67}$Ga, $^{111}$In and $^{99m}$Tc, or other radiolabeled products that can include gamma emitters, proton emitters, positron emitters, tritium, or covered tags detectable by other methods (i.e., gadolinium) among others. In some forms, the detection label is $^{18}$F. The capture agents can be used as diagnostic agents.

In some forms, the FOLR1 capture agents provided herein can be modified to obtain a desired chemical or biological activity. Examples of desired chemical or biological activities include, without limitation, improved solubility, stability, bioavailability, detectability, or reactivity. Examples of specific modifications that can be introduced to a capture agent include, but are not limited to, cyclizing the capture agent through formation of a disulfide bond; modifying the capture agent with other functional groups or molecules. Similarly, a capture agent can be synthesized to bind to non-canonical or non-biological epitopes on proteins, thereby increasing their versatility. In some forms, the capture agent can be modified by modifying the synthesis blocks of the target-binding moieties before the coupling reaction.

In some forms, the FOLR1 capture agents provided herein are stable across a wide range of temperatures, pH values, storage times, storage conditions, and reaction conditions, and in some forms the imaging agents are more stable than a comparable antibody or biologic. In some forms, the capture agents are stable in storage as a lyophilized powder. In some forms, the capture agents are stable in storage at a temperature of about −80° C. to about 60° C. In some forms, the capture agents are stable at room temperature. In some forms, the capture agents are stable in human serum for at least 24 hours. In some forms, the capture agents are stable at a pH in the range of about 3 to about 12. In some forms, the capture agents are stable as a powder for two months at a temperature of about 60° C.

As shown in the Example, tuning of heterobiligand capture agents can enhance, for example, binding to the target, in vivo half-life, and combinations of these. For example, incorporation of unnatural or modified amino acids can increase binding. Deletion of amino acids in a hit peptide ligand can increase, for example, binding to the target (deletions can also decrease these properties). Related to these, substitution of amino acids can increase, for example, binding to the target. Alanine scanning of hit peptides is useful for identify amino acids that can be modified without reducing binding or other properties.

The length and composition of linkers can be tuned to optimize, for example, binding to the target, in vivo half-life, and combinations of these. For example, in addition to PEG linkers, all carbon (e.g., alkyl) linkers, linkers with mixtures of PEG and alkyl, peptide linkers, linkers with mixtures of PEG and peptides (amino acids), linkers with mixtures of alkyl and peptides (amino acids), and mixtures of PEG, alkyl, and amino acids can be used. In particular, inclusion of an alkyl on the end of the linker that couples to the folate (or inclusion of an alkyl tail on the folate for coupling to the linker) is useful for tuning the heterobiligand.

Methylation of amines in heterobiligands, preferably in the peptide ligand, but also in the linker, can increase cell penetration. Addition of a cell penetrating peptide sequence in the heterobiligand can increase cell penetration. Lipidating groups can be added to the heterobiligand, such as in the peptide ligand or in the linker, to increase lipophilicity of the heterobiligand. The closure (cyclization) of the peptide ligand can be accomplished using different chemistries and different groups. For example, triazole linkages can be used.

Combinations of these modifications (tunings) can be used to increase or modulate these effects.

In some forms, the compound is a cyclic peptide having the following structure (I):

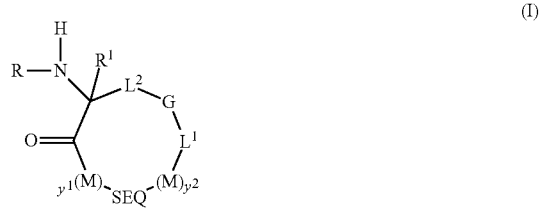

or a salt, tautomer, prodrug or stereoisomer thereof, wherein:
$L^1$ and $L^2$ are each individually a bond or an optionally substituted linker moiety, wherein each linker moiety optionally comprises a linkage to the NEP cleavage site and the first component, a linkage to the first component, a linkage to a ligand, a linkage to a reporter moiety, a linkage to an albumin binding moiety, a linkage to a peptide ligand, or combinations thereof;
G is a triazole, a carbon-carbon double bond or an amide;
M is methionine;
R is H or an optionally substituted linker moiety, wherein each linker moiety optionally comprises a linkage to the NEP cleavage site and the first component, a linkage to the first component, a linkage to a ligand, a linkage to a reporter moiety, a linkage to an albumin binding moiety, a linkage to a peptide ligand, or combinations thereof;
$R^1$ is H or $C_1$-$C_6$ alkyl;
$Y^1$ and $Y^2$ are each individually 0 or 1; and
SEQ is an amino acid sequence comprising from 2 to 20 amino acids selected from natural and non-natural amino acids.

In some forms, $L^1$ is —C(HR$^2$)— wherein $R^2$ is H, —R$^5$-L$^3$-A$^1$, —R$^5$—C(═O)-L$^3$-A$^1$, —R$^5$-A$^2$-L$^3$-A$^1$, —R$^5$—C(═O)-A$^2$-L$^3$-A$^1$, —R$^5$-L$^3$(-A$^2$)-A$^1$, or —R$^5$—C(═O)-L$^3$(-A$^2$)-A$^1$, where —R$^5$ is absent, —C(═O)—NH—, or —CH$_2$—C(═O)—NH—, where L$^3$ is a linker moiety, and where A$^1$ and A$^2$ independently comprise the NEP cleavage site and the first component, the first component, a linkage to a ligand, a reporter moiety, an albumin binding moiety, a peptide ligand, a linker moiety, or combinations thereof. In some forms, A$^1$ and A$^2$ independently further comprise -L$^4$-, wherein -L$^4$- is a linker moiety.

In some forms, $L^2$ is —C(HR$^4$)—, wherein $R^4$ is H, —R$^6$-L$^5$-A$^3$, —R$^6$—C(═O)-L$^5$-A$^3$, —R$^6$-A$^4$-L$^5$-A$^3$, —R$^6$—C(═O)-A$^4$-L$^5$-A$^3$, —R$^6$-L$^5$(-A$^4$)-A$^3$, or —R$^6$—C(═O)-L$^5$(-A$^4$)-A$^3$, where —R$^6$ is absent, —C(═O)—NH—, or —CH$_2$—C(═O)—NH—, where L$^5$ is a linker moiety, and where A$^3$ and A$^4$ independently comprise the NEP cleavage site and the first component, the first component, a linkage to a ligand, a reporter moiety, an albumin binding moiety, a peptide ligand, a linker moiety, or combinations thereof. In some forms, A$^3$ and A$^4$ independently further comprise -L$^6$-, wherein -L$^6$- is a linker moiety.

In some forms, R is H, -L$^7$-A$^5$, —C(═O)-L$^7$-A$^5$, -A$^6$-L$^7$-A$^5$, —C(═O)-A$^6$L$^7$-A$^5$, -L$^7$(-A$^6$)-A$^5$, or —C(═O)-L$^7$(-A$^6$)-A$^5$, where L$^7$ is a linker moiety and A$^5$ and A$^6$ independently comprise the NEP cleavage site and the first component, the first component, a linkage to a ligand, a reporter moiety, an albumin binding moiety, a peptide ligand, a linker moiety, or combinations thereof. In some forms, $A^5$ and $A^6$ independently further comprise -$L^8$-, wherein -$L^8$- is a linker moiety.

In some forms, $L^1$ is —C(H$R^2$)—, wherein $R^2$ is H, —$R^5$-$L^3$-$A^1$, —$R^5$—C(=O)-$L^3$-$A^1$, —$R^5$-$A^2$-$L^3$-$A^1$, —$R^5$—C(=O)-$A^2$-$L^3$-$A^1$, —$R^5$-$L^3$(-$A^2$)-$A^1$, or —$R^5$—C(=O)-$L^3$(-$A^2$)-$A^1$, where —$R^5$ is absent, —C(=O)—NH—, or —CH$_2$—C(=O)—NH—, where $L^3$ is a linker moiety, and where $A^1$ and $A^2$ independently are the NEP cleavage site and the first component, the first component, a linkage to a ligand, a reporter moiety, an albumin binding moiety, a peptide ligand, a linker moiety, or combinations thereof. In some forms, $A^1$ and $A^2$ independently further comprise -$L^4$-, wherein -$L^4$- is a linker moiety.

In some forms, $L^2$ is —C(H$R^4$)—, wherein $R^4$ is H, —$R^6$-$L^5$-$A^3$, —$R^6$—C(=O)-$L^5$-$A^3$, —$R^6$-$A^4$-$L^5$-$A^3$, —$R^6$—C(=O)-$A^4$-$L^5$-$A^3$, —$R^6$-$L^5$(-$A^4$)-$A^3$, or —$R^6$—C(=O)-$L^5$(-$A^4$)-$A^3$, where —$R^6$ is absent, —C(=O)—NH—, or —CH$_2$—C(=O)—NH—, where $L^5$ is a linker moiety, and where $A^3$ and $A^4$ independently are the NEP cleavage site and the first component, the first component, a linkage to a ligand, a reporter moiety, an albumin binding moiety, a peptide ligand, a linker moiety, or combinations thereof. In some forms, $A^3$ and $A^4$ independently further comprise -$L^6$-, wherein -$L^6$- is a linker moiety.

In some forms, R is H, -$L^7$-$A^5$, —C(=O)-$L^7$-$A^5$, -$A^6$-$L^7$-$A^5$, —C(=O)-$A^6$-$L^7$-$A^5$, -$L^7$(-$A^6$)-$A^5$, or —C(=O)-$L^7$(-$A^6$)-$A^5$, where $L^7$ is a linker moiety and $A^5$ and $A^6$ independently are the NEP cleavage site and the first component, the first component, a linkage to a ligand, a reporter moiety, an albumin binding moiety, a peptide ligand, a linker moiety, or combinations thereof. In some forms, $A^5$ and $A^6$ independently further comprise -$L^8$-, wherein -$L^8$- is a linker moiety.

In some forms, one or more of $A^1$, $A^2$, $A^3$, $A^4$, $A^5$, and $A^6$ individually and independently comprise a combination of one or more of the following: the NEP cleavage site and the first component, the first component, a linkage to a ligand, a reporter moiety, an albumin binding moiety, and a peptide ligand.

A preferred set of amino acids from which the amino acids of SEQ can be selected (Set 1) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

Another preferred set of amino acids from which the amino acids of SEQ can be selected (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation).

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

In some forms, G is a triazole. Such triazoles may be derived by reaction of an alkyne and azide on a precursor acyclic peptide.

In some forms, G is a carbon-carbon double bond. In some forms, these peptides are obtained by reactions of two carbon-carbon double bonds (alkenes) present in an acyclic precursor. Such reactions can be carried out using Grubbs metathesis chemistry, which is well-known to those of skill in the art.

In some forms of the foregoing, the cyclic peptide has one of the following structures (Ia) or (Ib):

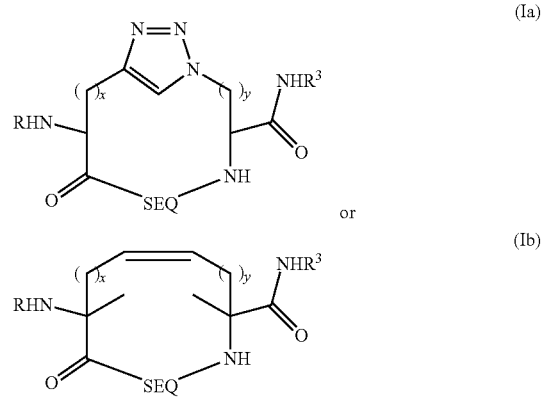

wherein:

$R^3$ is H, -$L^3$-$A^1$, —C(=O)-$L^3$-$A^1$, -$A^2$-$L^3$-$A^1$, —C(=O)-$A^2$-$L^3$-$A^1$, -$L^3$(-$A^2$)-$A^1$, or —C(=O)-$L^3$(-$A^2$)-$A^1$, where $L^3$ is a linker moiety and $A^1$ and $A^2$ independently comprise the NEP cleavage site and the first component, the first component, a linkage to a ligand, a reporter moiety, an albumin binding moiety, a peptide ligand, a linker moiety, or combinations thereof; and x and y are each independently an integer from 1 to 8.

In some forms, $A^1$ and $A^2$ independently further comprise -$L^4$-, wherein -$L^4$- is a linker moiety.

In some forms, $R^3$ is H, -$L^3$-$A^1$, —C(=O)-$L^3$-$A^1$, -$A^2$-$L^3$-$A^1$, —C(=O)-$A^2$-$L^3$-$A^1$, -$L^3$(-$A^2$)-$A^1$, or —C(=O)-$L^3$(-$A^2$)-$A^1$, where $L^3$ is a linker moiety and $A^1$ and $A^2$ independently are the NEP cleavage site and the first component, the first component, a linkage to a ligand, a reporter moiety, an albumin binding moiety, a peptide ligand, a linker moiety, or combinations thereof. In some forms, $A^1$ and $A^2$ independently further include -$L^4$-, wherein -$L^4$- is a linker moiety.

In some forms of the compounds of structure (Ia) and (Ib), x is 1. In some forms, x is 2. In some forms, x is 3. In some forms, x is 4. In some forms, x is 5. In some forms, x is 6. In some forms, x is 7. In some forms, x is 8.

In some forms of the compounds of structure (Ia) and (Ib), y is 1. In some forms, y is 2. In some forms, y is 3. In some forms, y is 4. In some forms, y is 5. In some forms, y is 6. In some forms, y is 7. In some forms, y is 8.

In some forms, R is H, -$L^7$-$A^5$, —C(=O)-$L^7$-$A^5$, -$A^6$-$L^7$-$A^5$, —C(=O)-$A^6$-$L^7$-$A^5$, -$L^7$(-$A^6$)-$A^5$, or —C(=O)-$L^7$(-$A^6$)-$A^5$, where $L^7$ is a linker moiety and $A^5$ and $A^6$ independently comprise the NEP cleavage site and the first component, the first component, a linkage to a ligand, a reporter moiety, an albumin binding moiety, a peptide ligand, a linker moiety, or combinations thereof. In some forms, $A^5$ and $A^6$ independently further comprise -$L^8$-, wherein -$L^8$- is a linker moiety.

In some forms, R is H, -$L^7$-$A^5$, —C(=O)-$L^7$-$A^5$, -$A^6$-$L^7$-$A^5$, —C(=O)-$A^6$-$L^7$-$A^5$, -$L^7$(-$A^6$)-$A^5$, or —C(=O)-$L^7$(-$A^6$)-$A^5$, where $L^7$ is a linker moiety and $A^5$ and $A^6$ independently are the NEP cleavage site and the first component, the first component, a linkage to a ligand, a reporter moiety, an albumin binding moiety, a peptide ligand, a linker moiety, or combinations thereof. In some forms, $A^5$ and $A^6$ independently further include -$L^8$-, wherein -$L^8$- is a linker moiety.

In some forms the cyclic peptide is biligand capture agent, and $A^1$, $A^2$, $A^3$, $A^4$, $A^5$, and/or $A^6$ is a bond to a peptide ligand, for example a linear peptide ligand or a cyclic peptide ligand. In some forms, the peptide ligand further comprises a second peptide ligand, and the cyclic peptide is thus a tri-ligand capture agent.

The structure of the "linker moieties" (e.g., $L^3$, $L^4$, $L^5$, $L^6$, $L^7$, and $L^8$) are not particularly limited. For example, in some forms, linkers comprising ethylene glycol of various lengths (e.g., 1-10 glycol repeating units, e.g., about 5-7) can be used. Ethylene diamine linkers can also be employed alone or in combination with other moieties (e.g., ethylene glycol). Linker moieties comprising triazole (e.g., resulting from reaction of an alkyne and azide) are also useful.

In some forms, $y^1$ and $y^2$ are each 0.

In some forms, the cyclic peptide has one of the following structures:

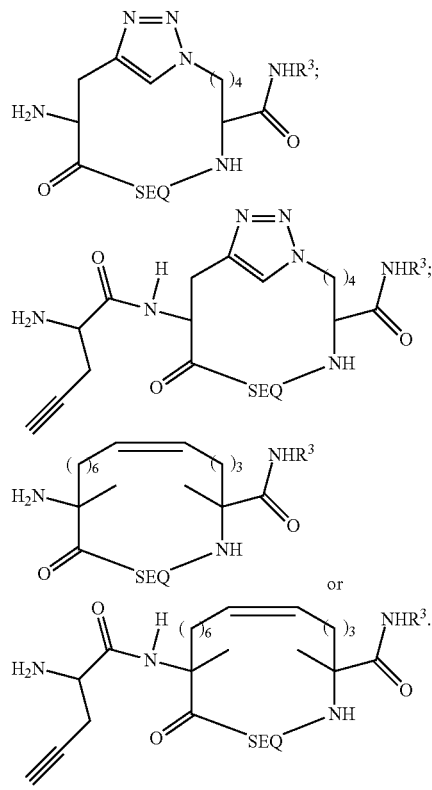

For example, in some forms SEQ comprises from 2 to 9 amino acids. In some forms, SEQ comprises from 5 to 7 amino acids.

In some forms, SEQ comprise natural amino acids. In some forms, SEQ comprises non-natural amino acids. In some forms, SEQ comprises natural and non-natural amino acids.

In some forms, the amino acids are selected from D and L stereoisomers of Ala, Gly, Leu, Ile, Val, Phe, Trp, Arg, His, Lys, Asp, Glu, Asn, Gln, Ser, Thr, Tyr and Pro. In some forms, the amino acids are selected from D and L stereoisomers of Ala, Gly, Leu, Val, Phe, Trp, Arg, His, Lys, Asp, Glu, Asn, Ser, Thr, Tyr and Pro. In some forms, the amino acids are selected from CyA, Gly, FP, MT, MeOPyr, PhF, Asn, Ser, Thr, His, Lys, Arg, Glu, BPhA, N-Me-a, and Pro (Set 1). In some forms, the amino acids are selected from CyA, Gly, FP, MT, Thz, PhF, Phe, Asn, Ser, Thr, His, Lys, Arg, Glu, N-Me-a, and Pro (Set 2). In some forms, the amino acids are selected from CyA, Gly, FP, MT, MeOPyr, Thz, PhF, Phe, Asn, Ser, Thr, His, Lys, Arg, Glu, BPhA, N-Me-a, and Pro (Set 3).

The amino acids in SEQ are selected to have affinity for the desired target, including allosteric binding sites such as protein epitopes.

Compositions comprising any of the foregoing compounds or cyclic peptides and a pharmaceutically acceptable carrier are also provided. In some forms, a library comprising a plurality of the forgoing compounds or cyclic peptides is provided.

In some forms, the compounds or cyclic peptides (also referred to herein as capture agents) provided herein have a shelf-life of greater than six months, meaning that they are stable in storage for greater than six months. In some forms, the capture agents have a shelf-life of one year or greater, two years or greater, or more than three years. In some forms, the capture agents are stored as a lyophilized powder.

In some forms, the capture agents provided herein have a longer shelf-life than a biologic binding to the same target protein.

In some forms, the capture agents provided herein are stable at temperatures ranging from about −80° C. to about 120° C. In some forms, the capture agents are stable within a temperature range of −80° C. to −40° C.; −40° C. to −20° C.; −20° C. to 0° C.; 0° C. to 20° C.; 20° C. to 40° C.; 40° C. to 60° C.; 60° C. to 80° C.; and/or 80° C. to 120° C. In some forms, the capture agents provided herein are stable across a wider range of temperatures than a biologic binding to the same target protein, and/or remain stable at a specific temperature for a longer time period than a biologic binding to the same target protein.

In some forms, the pH of a capture agent provided herein is in the range of about 3.0 to about 12.0. In some forms, the pH of the capture agent is in the range of about 5.0 to about 9.0. The pH of a capture agent may be adjusted to a physiologically compatible range using methods known in the art. For example, in some forms the pH of the capture agent may be adjusted to the range of about 6.5 to about 8.5.

In some forms, the capture agents provided herein are stable in blood serum for more than 12 hours. In some forms, the capture agents are stable in blood serum for more than 18 hours, more than 24 hours, more than 36 hours, more than 48 hours, or more than 96 hours. In some forms, the capture agents provided herein are stable for a longer period of time in blood serum than a biologic binding to the same target protein.

In some forms, the capture agents provided herein may comprise one or more reporter moieties (detection labels), including for example biotin, copper-1,4,7,10-tetraazacyclododecane-1,4,7,10-tetraaceticacid (copper-DOTA), desferrioxamine B (DFO), a ligand for radiolabeling with $^{68}$Ga, or other radiolabeled products that may include gamma emitters, proton emitters, positron emitters, tritium, or covered tags detectable by other methods (i.e., gadolinium) among others.

In some forms, the capture agents provided herein comprise one or more reporter moieties. In some forms, the reporter moiety is copper-DOTA. In some forms, the reporter moiety is selected from $^{64}$Cu DOTA, $^{68}$Ga DOTA, $^{18}$F, $^{64}$Cu, $^{89}$Zr, $^{124}$I, $^{86}$Y, $^{94m}$Tc, $^{110m}$In, $^{11}$C and $^{76}$Br. In some forms, the reporter moiety is selected from $^{123}$I, $^{131}$I, $^{67}$Ga, $^{111}$In and $^{99m}$Tc. In some forms, the reporter moiety is a fluorescent label.

In some forms, the cyclic peptide comprises a linkage to a reporter moiety, the reporter moiety selected from polyethylene glycol (PEG), biotin, thiol and fluorophores. For example, in some forms the fluorophores are selected from FAM, FITC, Cy5, TRITC, TAMRA.

Table 8 provides reporter moieties useful in various different applications of the compounds or cyclic peptides. Other useful reporter moieties can be derived by one of skill in the art.

TABLE 8

Reporter Moieties

| Application | Reporter |
|---|---|
| ELISA: microtiter plate | Biotin |
| ELISA: lateral flow test | Biotin |
| Immunoprecipitation (and other bead-based assays) | Biotin, thiol |
| Dot blot | Biotin |
| Cell-based assay | Biotin, fluorophore |
| IHC | Biotin, fluorophore |
| In vivo imaging: PET | Radioisotopes including $^{18}$F, $^{68}$Ga, $^{64}$Cu, $^{89}$Zr, $^{124}$I |
| In vivo imaging: SPECT | Radioisotopes including $^{111}$In, $^{90}$Y, $^{99m}$Tc, $^{177}$Lu |
| In vivo imaging: MR | Gd$^{3+}$ |

In some forms, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In some forms, the capture agent may be modified by modifying the synthesis blocks of the target-binding moieties before the coupling reaction.

Provided herein are pharmaceutical formulations comprising one or more of the capture agents provided herein. In some forms, these pharmaceutical formulations comprise one or more pharmaceutically acceptable carriers, excipients, or diluents. These carriers, excipients, or diluents may be selected based on the intended use and/or route of administration of the formulation.

Provided herein are kits comprising one or more of the capture agents disclosed herein. In some forms, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

It is understood that any form or instance of the peptides, as set forth above, and any specific substituent set forth herein for a R, R$^1$, L$^1$, L$^2$, G, M, Y$^1$ Y$^2$ or SEQ group in the peptides, as set forth above, may be independently combined with other forms and/or substituents of the peptides to form embodiments not specifically set forth above. In addition, in the event that a list of substituents is listed for any particular variable in a particular embodiment and/or claim, it is understood that each individual substituent may be deleted from the particular embodiment and/or claim and that the remaining list of substituents will be considered to be within the scope of the disclosed subject matter.

For the purposes of administration, the disclosed peptides may be administered as a raw chemical or may be formulated as pharmaceutical compositions. Pharmaceutical compositions of the disclosed subject matter can comprise a peptide of structure (I) and a pharmaceutically acceptable carrier, diluent or excipient. The peptide of structure (I) is present in the composition in an amount which is effective to treat a particular disease or condition of interest—that is, and preferably with acceptable toxicity to the patient. Activity of compounds of the peptides can be determined by one skilled in the art, for example, as described in the Examples. Appropriate concentrations and dosages can be readily determined by one skilled in the art.

Administration of the disclosed compounds, or their pharmaceutically acceptable salts, in pure form or in an appropriate pharmaceutical composition, can be carried out via any of the accepted modes of administration of agents for serving similar utilities. The disclosed pharmaceutical compositions can be prepared by combining a compound as disclosed with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. The term parenteral as used herein includes subcutaneous injections, intravenous, intramuscular, intrasternal injection, intratumoral, or infusion techniques. The disclosed pharmaceutical compositions can be formulated so as to allow the active ingredients contained therein to be bioavailable upon administration of the composition to a patient. Compositions that will be administered to a subject or patient take the form of one or more dosage units. Actual methods of preparing dosage forms are known, or will be apparent, to those skilled in this art; for example, see Remington: The Science and Practice of Pharmacy, current edition (Philadelphia College of Pharmacy and Science). The composition to be administered will, in any event, contain a therapeutically effective amount of a disclosed compound, or a pharmaceutically acceptable salt thereof, for treatment of a disease or condition of interest in accordance with the description herein.

A pharmaceutical composition as disclosed may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

The pharmaceutical composition may be in the form of a liquid, for example, a solution, emulsion or suspension. The liquid may be for delivery by injection. When intended for injection, one or more of a surfactant, preservative, wetting agent, dispersing agent, suspending agent, buffer, stabilizer and isotonic agent may be included.

The disclosed liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A disclosed liquid pharmaceutical composition intended for parenteral administration should contain an amount of a disclosed compound such that a suitable dosage will be obtained.

The pharmaceutical compositions may be prepared by methodology well known in the pharmaceutical art. For example, a pharmaceutical composition intended to be administered by injection can be prepared by combining a compound with sterile, distilled water so as to form a solution. A surfactant may be added to facilitate the formation of a homogeneous solution or suspension. Surfactants are compounds that non-covalently interact with the compound so as to facilitate dissolution or homogeneous suspension of the compound in the aqueous delivery system.

The disclosed compounds, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

The disclosed compounds, or pharmaceutically acceptable derivatives thereof, may also be administered simultaneously with, prior to, or after administration of one or more other therapeutic agents. Such combination therapy includes administration of a single pharmaceutical dosage formulation which contains a compound and one or more additional active agents, as well as administration of the compound and each active agent in its own separate pharmaceutical dosage formulation. For example, a compound and the other active agent can be administered to the patient together in a single dosage composition or each agent administered in separate dosage formulations. Where separate dosage formulations are used, the compounds and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds may not possess pharmacological activity as such, they may be administered to a mammal and thereafter metabolized in the body to form the intended compounds which are pharmacologically active. Such derivatives may therefore be described as "prodrugs." All prodrugs of the disclosed compounds are specifically contemplated.

Furthermore, all of the disclosed compounds that exist in free base or acid form can be converted to their pharmaceutically acceptable salts by treatment with the appropriate inorganic or organic base or acid by methods known to one skilled in the art. Salts of the compounds can be converted to their free base or acid form by standard techniques.

The disclosed peptides can be prepared by procedures known to those of skill in the art. For example, the peptides can be prepared using standard solid-phase peptide synthesis techniques, and modifications thereof. Modified amino acids may be employed to incorporate amino acids comprising alkyne and/or azide moieties and/or alkene moieties useful for cyclization. Methods for cyclizing the peptides using azide/alkyne chemistry and Grubbs metathesis chemistry are well-known in the art. Such methods are described in more detail in the examples.

It is understood that one skilled in the art may be able to make these compounds by similar methods or by combining other methods known to one skilled in the art. It is also understood that one skilled in the art would be able to make, in a similar manner as described below, other peptides not specifically illustrated in the examples below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

D. Identification of Capture Agents

Disclosed are methods for identification of cyclic peptides that are useful as capture agents for various targets. In general, the methods employ cyclic peptides, such as any of the cyclic peptides described herein, in methods for identification of mono-, bi- and/or tri-ligand capture agents. Higher order capture agents (tetra, penta, and the like) are also specifically contemplated.

In general, any methods employing the compounds or cyclic peptides described herein are specifically contemplated. For example, disclosed a method for identifying a target binding compound (e.g., a protein capture agent) is provided, the method comprising
(a) providing a peptide library comprising a plurality of cyclic peptides comprising:
  (i) a sequence region comprising amino and carboxy termini and a variable peptide sequence of two to twenty amino acids selected from natural and non-natural amino acids; and
  (ii) a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.
(b) contacting the peptide library with a target or a truncated analogue thereof, the target or truncated analogue thereof comprising a binding site and optionally an alkyne, azide or reporter moiety or combinations thereof;
(c) identifying a peptide library member with affinity for the binding site In some forms, a method for identifying a target binding compound (e.g., a protein capture agent) is provided, the method comprising:
(a) providing a first peptide library comprising a plurality of first peptide library members, the first peptide library members optionally comprising an alkyne, azide or reporter moiety or combinations thereof;
(b) contacting the first peptide library with a target or a truncated analogue thereof, the target or truncated analogue thereof comprising a first binding site and optionally an alkyne, azide or reporter moiety or combinations thereof;
(c) identifying a first peptide library member with affinity for the first binding site and optionally modifying the first peptide library member to include an alkyne or azide moiety;
and optionally:
(d) providing a second peptide library comprising a plurality of second peptide library members, the second peptide library members comprising an azide or alkyne or both;
(e) contacting the second peptide library with a composition comprising the target or truncated analogue thereof and the first peptide library member of step C;
(f) forming a triazole-linked conjugate between the first peptide library member of step C and a second peptide library member, the second peptide library member having affinity for a second binding site on the target or truncated analogue thereof,
wherein the first peptide library, the second peptide library, or both, comprise cyclic peptides comprising:
  (i) a sequence region comprising amino and carboxy termini and a variable peptide sequence of two to twenty amino acids selected from natural and non-natural amino acids; and
  (ii) a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

A preferred set of amino acids from which the amino acids of SEQ can be selected contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), and 4-Phenyl Phenylalanine (PhF) (hydrophobic side chain—aromatic); Asn, Ser, Thr (polar side chain—neutral); His, Lys, Arg, Glu (polar side chain charged); and β-Phenylalanine (BPhA), N-Methyl d-alanine (N-Me-a), and Pro (conformational perturbation).

Another preferred set of amino acids from which the amino acids of SEQ can be selected (Set 2) contains Cyclopropyl Alanine (CyA) and Gly (hydrophobic side chain—aliphatic); 4-Fluorophenyl Alanine (FP), Methyl Tryptophan (MT), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and N-Methyl d-alanine (N-Me-a), and Pro (conformational perturbation).

Another preferred set of amino acids from which the amino acids of SEQ can be selected (Set 3) contains Cyclopropyl Alanine (CyA) and Gly (hydrophobic side chain—aliphatic); 4-Fluorophenyl Alanine (FP), Methyl Tryptophan (MT), 2-Methoxy Pyridylalanine (MeOPyr), Thiazolyl Alanine (Thz), 4-Phenyl Phenylalanine (PhF), and Phe (hydrophobic side chain—aromatic); Asn, Ser, Thr (polar side chain—neutral); His, Lys, Arg, Glu (polar side chain—charged); and β-Phenylalanine (BPhA), N-Methyl d-alanine (N-Me-a), and Pro (conformational perturbation).

E. Methods of Making/Screening Capture Agents

Provided herein in some forms are methods of screening target-binding moieties and/or making imaging agents that comprise these target-binding moieties. Methods for screening target-binding moieties and/or making imaging agents that comprise these target-binding moieties can also be found in International Publication Nos. WO 2012/106671, WO 2013/033561, WO 2013/009869 and WO 2014/074907, each of which is incorporated by reference, herein, in their entireties.

For developing a set of PCC binders against a target protein, first one or more PCCs that bind an epitope on the target protein are identified. Optionally, one or more different PCCs binding to a second epitope are identified. Additional PCCs that bind to a third, fourth, etc., epitope can be useful as well. The epitope targeted PCC method teaches that this can be accomplished by screening peptide libraries against synthetic epitopes (SynEps). A SynEp is a polypeptide that has the sequence of the naturally occurring target epitope, except that one position contains an artificial amino acid that presents an azide or acetylene chemical group, called a click handle. The SynEp is further modified to contain an assay handle, such as a biotin group, at the N- or C-terminus. The screening procedure can be done using any procedure disclosed herein or known in the art. By screening, one identifies at least one unique peptide binder to each of at least two epitopes on the target. Those peptide binders are validated via carrying out binding assays against the full protein target as well as against the SynEps. For those binding assays, the SynEps are prepared with the naturally occurring residue in place of the click handle.

Ideally, the different regions of the target protein to which the different ligands bind will be relatively close together (a few nanometers or less) in the tertiary protein structure. For even a single SynEp, a screen can produce PCCs that bind to two different sites. During the SynEp screening steps, PCCs that bind to the N-terminal side of the epitope or the C-terminal side can both be identified.

Once the epitope targeted PCCs are identified, there are several methods for selecting a linker.

In a first method, if the folded structure of the protein is known, and if the PCCs bind to that folded structure, then one can use that information, plus knowledge of which PCCs bind to which epitopes, to estimate an optimal linker length. Analysis of the binding arrangement, together with the structure of the protein from, for example, the Protein Data Bank, permits an estimate of the length of an optimized linker. Such an estimate can narrow down the choice of candidate linkers to a very small number. One example might be to use such a length estimate to select one or two length-matched polyethylene glycol oligomers for testing. The best linker is the one that brings the biligand affinity closest to that a fully cooperative binder.

In a second method, if the folded structure of the protein is not known, or if the protein simply does not have a well-defined folded structure, then one uses as much information as is available to determine the composition of a library of candidate linker molecules. That library is then screened to identify a best linker.

In a third method, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In some forms, linkers can include polyethylene glycol (PEG), alkane, alkene, triazole, amide, or peptides.

F. In Vitro

For detection of FOLR1 in solution, a binding or capture agent as described herein can be detectably labeled (with a reporter moiety) to form an imaging agent, then contacted with the solution, and thereafter formation of a complex between the imaging agent and the FOLR1 target can be detected. As an example, a fluorescently labeled imaging agent can be used for in vitro FOLR1 detection assays, wherein the imaging agent is added to a solution to be tested for FOLR1 under conditions allowing binding to occur. The complex between the fluorescently labeled imaging agent and the FOLR1 target can be detected and quantified by, for example, measuring the increased fluorescence polarization arising from the complex-bound peptide relative to that of the free peptide.

Alternatively, a sandwich-type "ELISA" assay can be used, wherein a imaging agent is immobilized on a solid support such as a plastic tube or well, then the solution suspected of containing FOLR1 is contacted with the immobilized binding moiety, non-binding materials are washed away, and complexed polypeptide is detected using a suitable detection reagent for recognizing FOLR1.

For detection or purification of soluble FOLR1 from a solution, imaging agents as disclosed can be immobilized on a solid substrate such as a chromatographic support or other matrix material, then the immobilized binder can be loaded or contacted with the solution under conditions suitable for formation of an imaging agent/FOLR1 complex. The non-binding portion of the solution can be removed and the complex can be detected, for example, using an anti-FOLR1 antibody, or an anti-binding polypeptide antibody, or the FOLR1 can be released from the binding moiety at appropriate elution conditions.

G. In Vivo Diagnostic Imaging

A particularly preferred use for the disclosed imaging agents is for creating visually readable images of FOLR1 or FOLR1-expressing cells in a biological fluid, such as, for example, in human serum. The FOLR1 imaging agents disclosed herein can be conjugated to a label appropriate for diagnostic detection. Preferably, an imaging agent exhibiting much greater specificity for FOLR1 than for other serum proteins is conjugated or linked to a label appropriate for the detection methodology to be employed. For example, the imaging agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In some forms, rather than directly labeling an imaging agent with a reporter moiety (e.g., a detectable label or radiotherapeutic construct), one or more of the disclosed peptides or constructs can be conjugated with for example, avidin, biotin, or an antibody or antibody fragment that will bind the reporter moiety.

1. Magnetic Resonance Imaging

The FOLR1 imaging agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolysis of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetradecane-1,4,7,10-tetraacetic acid (DOTA), 1-substituted 1,4, 7, -tricarboxymethyl-1,4,7,10-teraazacyclododecane (DO3A), ethylenediaminetetraacetic acid (EDTA), and 1,4, 8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)- ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N"-tris(2,3-dihydroxybenzoyl)-tricatecholate (LICAM); and 1,3,5-N,N',N"-tris(2,3-dihydroxybenzoyl)aminomethylbenzene (MECAM). A preferred chelator is DTPA, and the use of DO3A is particularly preferred. Examples of representative chelators and chelating groups that can be used in the disclosed compositions and methods are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present disclosure, the chelator of the MRI contrast agent is coupled to the FOLR1 imaging agent. The positioning of the chelate should be selected so as not to interfere with the binding affinity or specificity of the FOLR1 imaging agent. The chelate also can be attached anywhere on the imaging agent.

In general, the FOLR1 imaging agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the FOLR1 binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and diols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the disclosed imaging reagents. Depending on their location within the linker, such biodegradable functionalities can include ester, double ester, amide, phosphoester, ether, acetal, and ketal functionalities.

In general, known methods can be used to couple the metal chelate and the FOLR1 imaging agent using such linkers (WO 95/28967, WO 98/18496, WO 98/18497 and discussion therein). The FOLR1 binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between FOLR1-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging FOLR1-expressing tissues, such as tumors, intravenous or intraarterial administration is preferred. For MRI, it is contemplated that the subject will receive a dosage of contrast agent sufficient to enhance the MR signal at the site FOLR1 expression by at least 10%. After injection with the FOLR1 imaging agent containing MRI reagent, the patient is scanned in the MRI machine to determine the location of any sites of FOLR1 expression. In therapeutic settings, upon identification of a site of FOLR1 expression (e.g., fluid or tissue), an anti-cancer agent (e.g., FOLR1 heterobiligands coupled to an anti-cancer agent) can be immediately administered, if necessary, and the patient can be subsequently scanned to visualize viral load.

2. Nuclear Imaging (Radionuclide Imaging) and Radiotherapy

The disclosed FOLR1 imaging agents can be conjugated with a radionuclide reporter appropriate for scintigraphy, SPECT, or PET imaging and/or with a radionuclide appropriate for radiotherapy. Constructs in which the FOLR1 imaging agents are conjugated with both a chelator for a radionuclide useful for diagnostic imaging and a chelator useful for radiotherapy are specifically contemplated.

For use as a PET agent a disclosed imaging agent can be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The disclosed binding moieties can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{225}$Ac, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Tb, $^{166}$Dy, $^{166}$Ho, $^{175}$Yb, $^{177}$Lu, $^{225}$Ac, $^{186/188}$Re, and $^{199}$Au. $^{99m}$Tc is useful for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to FOLR1 imaging agents for diagnostic imaging.

The metal radionuclides can be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the FOLR1 imaging agent via a linker, as described previously, and then directly labeled with the radioactive metal of choice (see, WO 98/52618, U.S. Pat. Nos. 5,879,658, and 5,849,261).

FOLR1 imaging agents comprising $^{18}$F, 4-[$^{18}$F]fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the disclosed reagents, the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a disclosed reagent to be labeled and a sufficient amount of reducing agent to label the reagent with $^{99m}$Tc. Alternatively, the complex can be formed by reacting a disclosed peptide conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful with the disclosed compositions and methods are included the alkali metal salts such as the sodium salt, or ammonium salts or lower alkyl ammonium salts.

Preparation of the disclosed complexes where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOCl_4](AsPh4)$, $ReOCl_3(PPh_3)_2$ and as $ReO_2(pyridine)_4^+$, where Ph is phenyl and Bu is n-butyl. Other rhenium reagents capable of forming a rhenium complex also can be used.

Also disclosed are radioactively labeled PET, SPECT, or scintigraphic imaging agents that have a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled FOLR1 imaging agent can provide 10-20 mCi. After injection of the radionuclide-labeled FOLR1 imaging agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the disclosed radiotherapeutic compounds are known to those skilled in the art. The compounds can be administered using many methods including, but not limited to, a single or multiple IV or IP injections, using a quantity of radioactivity that is sufficient to cause damage or ablation of the targeted FOLR1-expressing tissue, but not so much that substantive damage is caused to non-target (normal tissue). The quantity and dose required is different for different constructs, depending on the energy and half-life of the isotope used, the degree of uptake and clearance of the agent from the body and the mass of the FOLR1-expressing tissue. In general, doses can range from a single dose of about 30-50 mCi to a cumulative dose of up to about 3 Ci.

The disclosed radiotherapeutic compositions can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentisic acid and the like.

Also disclosed are single or multi-vial kits that contain all of the components needed to prepare the disclosed complexes, other than the radionuclide.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γcyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the disclosed complexes are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an FOLR1 imaging agent. In some forms, 4-[$^{18}$F]fluorobenzaldehyde ($^{18}$FB) is conjugated onto an imaging agent bearing an aminooxy moiety, resulting in oxime formation. In some forms, [$^{18}$F] fluorobenzaldehyde is conjugated onto an imaging agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled imaging agents can also be prepared from imaging agents possessing thiosemicarbazide moieties under conditions that promote formation of a thiosemicarbazone, or by use of a $^{18}$F-labeled aldehyde bisulfite addition complex.

The above methods are particularly amenable to the labeling of imaging agents, e.g., the imaging agents described herein, which can be modified during synthesis to contain a nucleophilic hydroxylamine, thiosemicarbazide or hydrazine (or acyl hydrazide) moiety that can be used to react with the labeled aldehyde. The methods can be used for any imaging agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step can be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 can also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde can be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water can be added to a mixture of Kryptofix and $K_2CO_3$. Anhydrous acetonitrile can be added and the solution is evaporated in a heating block under a stream of argon. Additional portions of acetonitrile can be added and evaporated to completely dry the sample. The 4-trimethylammoniumbenzaldehyde triflate can be dissolved in DMSO and added to the dried F-18. The solution can then be heated in the heating block. The solution can be cooled briefly, diluted with water and filtered through a Waters®. Oasis HLB LP extraction cartridge. The cartridge can be washed with 9:1 water:acetonitrile and water to remove unbound $^{18}$F and unreacted 4-trimethylammoniumbenzaldehyde triflate. The 4-[$^{18}$F]fluorobenzaldehyde can then be eluted from the cartridge with methanol in fractions.

H. Therapeutic Applications

Provided herein in some forms are methods of using the FOLR1 capture agents disclosed herein to identify, detect, quantify, and/or separate FOLR1 in a biological sample. In some forms, these methods utilize an immunoassay, with the capture agent replacing an antibody or its equivalent. In some forms, the immunoassay can be a Western blot, pull-down assay, dot blot, or ELISA.

A biological sample for use in the methods provided herein can be selected from the group consisting of organs, tissue, bodily fluids, and cells. Where the biological sample is a bodily fluid, the fluid can be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in some forms are methods of using the FOLR1 imaging agents disclosed herein to diagnose and/or classify (e.g., stage) a condition associated with FOLR1 expression. In some forms, the methods comprise (a) obtaining a biological sample from a subject; (b) measuring the presence or absence of FOLR1 in the sample with the FOLR1 imaging agent; (c) comparing the levels of FOLR1 to a predetermined control range for FOLR1; and (d) diagnosing a condition associated with FOLR1 expression based on the difference between FOLR1 levels in the biological sample and the predetermined control.

In some forms, the FOLR1 capture agents disclosed herein are used as a mutant specific targeted therapeutic. In some forms, the FOLR1 capture agent is administered alone without delivering DNA, a radiopharmaceutical or another active agent.

The FOLR1 capture agents described herein also can be used to target genetic material to FOLR1 expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In some forms, the disclosed capture agents are utilized in gene therapy. In some forms, genetic material, or one or more delivery vehicles containing genetic material can be conjugated to one or more FOLR1 capture agents of this disclosure and administered to a patient.

Therapeutic agents and the FOLR1 capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and FOLR1 binding polypeptide can be coexpressed from the same synthetic gene, created using recombinant DNA techniques, as described above. The coding sequence for the FOLR1 binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the FOLR1 binding polypeptide. A particular advantage of this general approach is that concatamerization of multiple, tandemly arranged FOLR1 capture agents is possible, thereby increasing the number and concentration of FOLR1 binding sites associated with each therapeutic protein. In this manner, FOLR1 binding avidity is increased, which would be expected to improve the efficacy of the recombinant therapeutic fusion protein.

A residue of a monomer unit or moiety refers to the portion of the monomer or moiety that is the resulting product of the monomer unit or moiety in a particular reaction scheme or subsequent formulation or chemical product, regardless of whether the portion of the monomer or moiety is actually obtained from the monomer unit or moiety. Thus, an ethylene glycol residue in a polyester refers to one or more —$OCH_2CH_2O$— units in the polyester, regardless of whether ethylene glycol was used to prepare the polyester. Similarly, an amino acid residue in a peptide refers to one or more —CO—CHR—NH— moieties in the polyester, regardless of whether the residue is obtained by reacting the amino acid to obtain the peptide.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. Peptide as used herein includes oligomers of amino acids and small and large peptides, including polypeptides.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist." One that decreases, or prevents, a known activity is an "antagonist."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

Single dose biodistribution and dosimetry studies of radioactive compounds in OVCAR3 (FOLR+) tumor implanted female NSG mice can be used to guide dose selection for human treatment. To identify any ligand-related toxicities, a general toxicology study with multiple doses of the cold compound can be conducted in immunocompetent female CD-1 mice. The FDA guidance for industry "*Oncology Therapeutic Radiopharmaceuticals: Nonclinical Studies and Labeling Recommendations*" and "*Microdose Radiopharmaceutical Diagnostic Drugs: Nonclinical Study Recommendations*" provide descriptions of the design of the biodistribution and dosimetry and toxicology studies (FDA 2019, Oncology Therapeutic Radiopharmaceuticals: Nonclinical Studies and Labeling Recommendations, Guidance for Industry. website fda.gov/media/129547/download; FDA 2018, Microdose Radiopharmaceutical Diagnostic Drugs: Nonclinical Study Recommendations, Guidance for Industry. web site fda.gov/media/107641/download). In such studies, radioactivity can be evaluated in organs at defined sampling intervals for a period of 10 days post-administration (n=5 per group). Organs can be collected and weighed, and the radioactivity measured using a gamma counter to enable generation of time-integrated activity curves. The activity time curve in these organs can be used to estimate the percent administered activity (% ID), residence time, and time-integrated activity in human organs.

Consistent with the dosing schedule used for studying nonclinical therapy response, mice can receive three doses of the cold compound administered at 20-day intervals by IV injection (41 days dosing phase with 14 days recovery). Toxicology can be evaluated by measuring body weights, food consumption, clinical pathology (hematology and clinical chemistry once prior to necropsy), necropsy, organ weights, and histopathology. The control groups will receive only the carrier solution.

Based on the therapy response studies of Indi $^{177}$Lu-7327 performed in OVCAR3 tumor-bearing NSG mice, the human equivalent dose should satisfy microdose administration criteria. Thus, GLP toxicology studies can use a mass dose that is in excess of 100× the maximum estimated mass dose of the Indi $^{177}$Lu-7327 that would be injected into a human subject. It can also be demonstrated that this large multiple of the estimated human dose does not induce adverse effects in the experimental animals. For example, a 41-day GLP toxicology study can be performed in which immunocompetent female CD-1 mice will receive three doses every 20 days by IV administration with 14 days recovery after the third dose. A 20-day interval between doses was chosen based on the nonclinical MTD and therapy response data. The rationale for selecting female CD-1 mice was to use mice with a functioning immune system that are frequently used in research on toxicology.

The dosing schedule for Indi $^{177}$Lu-7327 can be based upon rodent-derived data as well as $^{177}$Lu targeted therapies that have been studied in the clinic, including LUTATHERA® and $^{177}$Lu-PSMA-617. Nonclinical studies of Indi $^{177}$Lu-7327 established that three treatments of Indi $^{177}$Lu-7327 were tolerated by female NSG mice at radioactive doses up to 111 MBq. Studies examining the anti-tumor activity of Indi $^{177}$Lu-7327 in OVCAR3 (FOLR+) human tumor implanted female NSG mice demonstrated that repeated treatment with the construct resulted in FOLR-dependent tumor growth control at radioactive doses of 29.6 and 74 MBq.

Indi $^{177}$Lu-7327 is useful for the treatment of patients with epithelial ovarian, fallopian tube, or primary peritoneal cancers that are platinum-resistant and FOLR positive. Ovarian cancer is a serious and life-threatening disease, and it has become the fifth most common cause of cancer-related death in women and the gynecological malignancy with the highest lethality responsible for 14,000 deaths in the US every year (Grunewald and Ledermann, *Best Practice & Research Clinical Obstetrics & Gynaecology*. 2017; 41:139-152; Stewart et al., *Seminars in Oncology Nursing*. 2019; 35(2):151-156; Kuroki and Guntupalli, *BMJ*. 2020; 371: m3773). The term ovarian cancer can be used to encompass cancers originating in the ovaries, fallopian tubes, and peritoneum (Stewart et al., *Seminars in Oncology Nursing*. 2019; 35(2):151-156). Ovarian cancer is commonly referred to as "the silent killer" because over 80% of cases are diagnosed at advanced stages of the disease due to the non-specific and subtle clinical presentation (Stewart et al., *Seminars in Oncology Nursing*. 2019; 35(2):151-156; Kuroki and Guntupalli, *BMJ*. 2020; 371:m3773). The high mortality is directly related to the late diagnosis, with 5-year survival rates of as low as 25% in metastatic cases (Kuroki and Guntupalli, *BMJ*. 2020; 371:m3773). Ovarian cancer patients, especially those who become platinum-resistant, experience a significant unmet medical need. They are commonly treated with primary cytoreductive surgery or debulking surgery, followed by four to six cycles of IV platinum/taxane combination chemotherapy (Matulonis et al., *Nature Reviews Disease Primers*. 2016; 2(1):16061; Roett and Evans, *American Family Physician*. 2009; 80(6): 609-616; Kossaï et al., *Pathobiology*. 2018; 85(1-2):41-49). Unfortunately, after an initial disease-free interval following treatment, approximately 70-80% of women relapse (Lorusso et al., *International Journal of Surgical Oncology*. 2012; 2012:613980). Women who relapse have a high likelihood of becoming platinum-resistant, at which point their cancer is not considered curable and second line therapy is focused on palliative treatment to improve the patient's quality of life and extend median survival beyond the 12 months generally observed post-recurrence (Davis et al., *Gynecologic Oncology*. 2014; 133(3):624-631). The development of novel therapies that can address this unmet medical need is essential.

Post-treatment, the levels of CA-125 can be monitored as a predictive biomarker to monitor progression and recurrence of ovarian cancer. The occurrence of certain clinical events (such as a significant decrease in performance status, or bowel obstruction) in conjunction with marked increases in CA-125 levels has been considered progression in ovarian cancer patients. The levels of the historical biomarker CA-125 are elevated in 92% of patients with advanced disease and 50% of patients with early disease (Charkhchi et al., *Cancers*. 2020; 12(12):3730). A response in ovarian cancer patients according to CA-125 can be considered to have occurred if there is at least a 50% reduction in CA-125 levels from a pretreatment or baseline sample. This response should be maintained and confirmed for at least 28 days.

Preferably, CA-125 can be used in patients who have a baseline sample at least twice the upper limit of normal and within 2 weeks prior to starting treatment. Therefore, CA-125 measurements should include 2 weeks pre-treatment, at intervals of 2-4 weeks during treatment, and at intervals of 2-3 months during follow-up. It has been reported that, compared to RECIST, CA-125 levels are more objective and less likely to incur measurement error (Thigpen J T. *Gynecologic Oncology*. 2015; 136(1):121-129). The levels of CA-125 become especially important in recurrent patients, since most of these patients have elevated levels of CA-125 but not all have measurable disease by RECIST. Therefore, response assessment following the CA-125 criteria above is superior to RECIST in predicting survival in patients receiving second-line chemotherapy for recurrent ovarian cancer.

Indi $^{177}$Lu-7327 is useful for the therapy of patients with epithelial ovarian, fallopian tube or primary peritoneal cancers that are platinum-resistant and FOLR positive. Completed nonclinical studies include in vitro binding and enzymatic cleavage, stability in human and mouse plasma, and in vivo proof of concept studies. Planned studies include biodistribution and dosimetry of Indi $^{177}$Lu-7327 and toxicology of Indi 7327, including the cGMP manufacturing of the peptide precursor and radiopharmaceutical preparation.

Indi $^{177}$Lu-7327 can be used to treat a variety of other cancers including TNBC, mesothelioma, and NSCLC. Folate receptor alpha has been reported to be highly expressed in 72% of malignant mesotheliomas (Bueno et al., *The Journal of Thoracic and Cardiovascular Surgery*. 2001; 121(2):225-233). High expression of folate receptor alpha in NSCLC compared with normal bronchial epithelium indicate that this protein can be a target for NSCLC, particularly in lung adenocarcinomas (Nunez et al., *Journal of Thoracic Oncology*. 2012; 7(5):833-840). Findings by O'Shannessy et al. that 74% of lung adenocarcinomas were positive for folate receptor alpha expression and only 13% of squamous cell carcinomas were FOLR positive (p<0.0001) can be used in selecting patients with NSCLC for folate receptor-targeted therapy (O'Shannessy et al., *Oncotarget*. 2012; 3(4): 414-425). In Her2(−) metastatic breast cancer, O'Shannessy et al. further showed that folate receptor alpha was expressed in 86% of TNBC patients (O'Shannessy et al., *SpringerPlus*. 2012; 1(1):22). Depletion of FOLR in overexpressing TNBC cell lines by RNA-interference resulted in growth inhibition, whereas FOLR overexpression promoted folate uptake and provided a selective growth advantage in low folate conditions indicating that folate receptor-targeted therapy can be used for patients with triple negative cancers with high FOLR expression (Necela et al., *PLOS ONE*. 2015; 10(3):e0122209).

I. Albumin Binding Moieties

In some forms, the disclosed molecules, compounds and compositions (e.g., heterobiligand, FOLR1 binding compositions) can include one or more albumin-binding molecules or moieties. Such albumin-binding molecules or moieties can provide for altered pharmacodynamics of a molecule of interest (e.g., the disclosed heterobiligand), such as alteration of tissue uptake, penetration, or diffusion; enhanced efficacy; and increased half-life. For example, the serum half-life of a therapeutic, prophylactic or diagnostic molecule of interest can be increased by linking the molecule of interest to a serum albumin-binding moiety and administering the molecule/serum albumin-binding moiety to a subject. The resulting conjugate will associate with circulating serum albumin and will remain in the serum longer than if the molecule of interest were administered in the absence of a serum albumin-binding moiety.

Thus, in particular forms, albumin-binding molecules or moieties are used to increase the half-life and overall stability of a therapeutic, prophylactic or diagnostic compound that is administered to or enters the circulatory system of a subject. In such methods, an albumin-binding moiety is used to link a therapeutic, prophylactic or diagnostic compound to a serum albumin found in the blood of an individual who will receive the compound. The albumin-binding moiety can be covalently or non-covalently linked, coupled or associated to a selected compound at a site that keeps the albumin-binding site of the moiety intact and still capable of binding to a serum albumin, without compromising the desired diagnostic, prophylactic or therapeutic activity of the compound. In this way, the albumin-binding moiety serves as a linker molecule to link the therapeutic, prophylactic or diagnostic compound of interest to a serum albumin circulating in the blood. This is expected to be particularly useful in increasing the circulating half-life and/or overall stability of compounds that are normally subject to an undesirably rapid rate of degradation or clearance from circulation. Increasing the half-life or overall stability of a compound in the circulatory system is likely to reduce the number and/or size of doses that must be administered to an individual to obtain a desired effect.

Exemplary albumin-binding molecules or moieties that can be used include, without limitation, fatty acids and derivatives thereof, small molecules, peptides, and proteins. See Zorzi A., et al., MedChemComm., 10(7):1068-1081 (2019), which is hereby incorporated by reference in its entirety, and which provides a review of albumin-binding ligands and their use in extending the circulating half-life of therapeutics.

Albumin acts as the key lipid delivery vehicle for tissues, binding up to seven molecules of long fatty acids simultaneously. Short- to medium-length fatty acids (6 to 12 carbons) bind albumin with affinities between 0.5 and 60 µM, while the longest ones (14 to 18 carbons) have 10-fold higher affinities (below 50 nM). This ability of serum albumin to bind fatty acids with a high affinity has inspired the use of post-translational acylation as a safe and effective platform for prolonging the half-life and the mode of action of peptides and small proteins. For example, acylation of insulin with saturated fatty acids containing 10-16 carbon atoms produces insulin with affinity for albumin (Kurtzhals P., et al., *Biochem. J.*, 312:725-731 (1995); Markussen, J., et al., Diabetologia, 39:281-288 (1996)). Approved drugs relying on derivatization with albumin-binding fatty acids to prolong half-life include, LEVEMIR® (insulin detemir), TRESIBA® (insulin degludec), VICTOZA® (liraglutide), and OZEMPIC® (semaglutide). Thus, in some forms, fatty acids (e.g., myristic acid, lauric acid, or palmitic acid) and derivatives thereof, including those used in the aforementioned approved drugs can be used as albumin-binding molecules or moieties.

In addition to fatty acids, serum albumin can bind numerous small organic molecules by exploiting two major structurally dissimilar binding sites, known as Sudlow sites I and II. Site I, also known as the warfarin-azapropazone binding site, usually accommodates dicarboxylic acids and/or bulky heterocycles carrying a central negative charge, whereas site II, also known as the benzodiazepine binding site, can discriminate ligands based on their size and stereoselectivity. Because of their ability to non-covalently bind serum albumin, several organic moieties that are structurally similar to exogenous drugs (e.g., warfarin, ibuprofen and diazepam) and dye molecules (e.g., Evans blue) have also been used. Non-limiting examples of suitable albumin-binding small organic molecules include, 4-methylphenyl butyric acid (4-MPBA), 4-iodophenyl butyric acid (IPBA), naphthalene acyl sulfonamide moieties; diphenylcyclohexanol phosphate ester moieties; 9-fluorenylmethoxycarbonyl (Fmoc) moieties and derivatives (e.g., Fmoc linked to a 16-sulfanylhexadecanoic acid through a maleimide group); dicoumarol derivatives with a maleimide group; Evans blue derivatives with a maleimide group; divalent diflunisal-indomethacin moiety linked through a γGlu-Lys dipeptide coupled to a unit of 8-amino-3,6-dioxaoctanoic acid (O2Oc) (also referred to as Diflunisal-γGlu-Lys(±O2Oc)-indomethacin); lithocholic acid coupled to a γGlu linker; 6-(4-(4-iodophenyl)butanamido)hexanoate otherwise named AlbuTag; A083/B134; A083/B321; A077/B286; and A099/B344. See Zorzi A., et al., 2019; Table 1 and FIG. 2.

Additionally, an increasing number of peptides have been used as albumin-binding molecules. In contrast to small chemical moieties, albumin-binding peptides or proteins can easily be fused to any protein or peptide of interest, either recombinantly or chemically during solid-phase synthesis. Thus, in some forms, the albumin-binding molecule/moiety can be a peptide or protein.

Suitable albumin-binding peptides or proteins and methods of use thereof are known in the art, including those described in Patent Application Publication Nos. U.S. 2003/0069395, U.S. 2007/0269422, U.S. 2007/0202045, U.S. 2015/0037334, WO 1991/001743, WO 2001/045746, WO 2011/095545, WO 2012/069654, and U.S. Pat. Nos. 9,775,912 and 9,920,115, which are hereby incorporated by reference in the entirety, and in particular, for their description of compounds, peptides, epitopes, targets, and methods. Peptides that specifically bind to serum albumin, and that thereby can extend the in vivo half-life of other molecules linked/coupled to them, include variants of bacterial albumin-binding domains (see e.g., WO 2005/097202 and WO 2009/016043), small peptides (e.g., Dennis, M. S., et al., J. Biol. Chem., 277(3):35035-43 (2002) and WO 2001/045746), and fragments of immunoglobulins (see e.g., WO 2008/043822, WO 2004/003019, WO 2008/043821, WO 2006/040153, WO 2006/122787, and WO 2004/041865).

Suitable exemplary albumin-binding peptides/proteins include, without limitation, peptides or proteins containing one or more of the following amino acid sequences: WWEQDRDWDFDVFGGGTP (referred to as 89D03; SEQ ID NO:21), WWELDRDWDFDVFGGGTP (SEQ ID NO:22), YWWERRDWDFDVFGGGTP (SEQ ID NO:23), EWWWRRDWDFDVFGGGTP (SEQ ID NO:24), LFWWERDWDFDVFGGGTP (SEQ ID NO:25), and KWWEIRDWDFDVFGGGTPAKSDE (SEQ ID NO:26), all of which are known to bind tightly ($K_D \leq 20$ nM) to human serum albumin (see WO 2011/095545). Additional examples include peptides having the core amino acid sequence DICLPRWGCLW (SEQ ID NO:27), proteins or peptides including this core sequence (e.g., RLIEDICLPRWGCLWEDD (SEQ ID NO:28), MEDICLPRWGCLWGD (SEQ ID NO:29), QRLMEDICLPRWGCLWEDDE (SEQ ID NO:30), and QGLIGDICLPRWGCLWGRSV (SEQ ID NO:31)), and an acylated heptapeptide, named F-tag, which contains a fatty acid (palmitic acid) combined with a short linear peptide, EYEKEYE (SEQ ID NO:32) (Zorzi A., et al., Nat Commun., 8:16092 (2017)).

Additionally, a number of naturally occurring protein domains from bacteria are known to bind albumin Called albumin-binding domains (ABDs), these domains have a molecular weight of ~6 kDa, fold into a three-helix bundle domain, and interact with serum albumin primarily along one face of the bundle (Makrides S C., et al., J. Pharmacol. Exp. Ther., 277:534-542 (1996); Lejon et al., 2004; Cramer J F., et al., FEBS Lett., 581:3178-3182 (2007)). One such domain, a fragment of protein G from Streptococcus strain GI48, which binds to human serum albumin with an affinity of 1 nM (GI48-GA), has been widely used to extend the serum half-life of proteins. Fusion to this domain has been shown to extend the half-life of soluble complement receptor type 1 (Makrides et al., 1996), a bispecific antibody (Stork R., et al., Protein Eng. Des. Sel., 20:569-576 (2007)), and Affibody scaffold molecules (Orlova A., et al., J. Nucl. Med., 54; 961-968 (2013); Malm M., et al., Biotechnol. J., 9:1215-1222 (2014)). Thus in some forms, suitable albumin-binding molecules or moieties include ABDs and derivatives or variants thereof, non-limiting examples of which include, GI48-GA (LAEAKVLANRELDKYGVSDYYKNLINNAKTVEGVKALIDEILAA; SEQ ID NO:33), ALB8-GA (LKNAKEDAIAELKKAGITSDFYFNAINKAKTVEEVNALKNEILKA; SEQ ID NO:34), ABD035 (Jonsson A., et al., Protein Eng., Des. Sel., 21(8):515-527 (2008)), ABD094 (Frejd F Y. and Kim K T., Exp. Mol. Med., 49(3):e306 (2017)), ABDCon (LKEAKEKAIEELKKAGITSDYYFDLINKAKTVEGVNALKDEILKA; SEQ ID NO:35), and ABDCon12 (TIDEWLLKEAKEKAIEELKKAGITSDYYFDLINKAKTVEGVNALKDEILKA; SEQ ID NO:36). Other suitable ABDs and derivatives or variants thereof, including albumin-binding designed ankyrin repeat proteins (DARPins®), S. solfataricus Sso7d derived ABDs, single domain antibodies (dAbs) also known as AlbudAbs, and stable variable domain of the heavy-chain-only (VHH) antibodies (Nanobodies®), are described in Jacobs S A., et al., Protein Eng. Des. Sel., 28(10):385-393 (2015) and Zorzi A., et al., MedChemComm., 10(7):1068-1081 (2019).

Other albumin-binding proteins suitable for used in accordance with the disclosed methods and compositions include anti-albumin antibodies and fragments thereof, such as the humanized anti-human serum albumin antibody, CA645, which binds to albumin across multiple species with similar affinity (Protein Data Bank (PDB) accession code: 5FUZ; see also Adams R., et al, MAbs, 8(7):1336-1346 (2016)).

The one or more albumin-binding molecules or moieties may be linked, coupled, conjugated, or otherwise associated to a molecule of interest such as a therapeutic, prophylactic or diagnostic compound covalently or non-covalently. In some forms, more than one albumin-binding molecules or moieties can be used (e.g., two or more of the same or different albumin-binding moieties, optionally arranged in tandem and/or separated by linkers). A variety of methods for linking molecules together are known in the art. Such linkages include hydrophobic interactions, van der Waals forces, and ionic linkages. Useful covalent linkages include, but are not limited, to peptide linkages, disulfide linkages, maleimide linkages, ester linkages, and ether linkages. For example, an amino group of the side chain of a lysine residue present in an albumin-binding moiety may be used to covalently link the albumin-binding moiety to another peptide/protein via condensation to form a peptide bond.

In some forms, a fusion polypeptide containing the albumin-binding moiety and peptide/protein of interest may be synthesized directly using an automated peptide synthesizer or using any of the various standard recombinant DNA methods known in the art for producing fusion proteins. For example, a nucleic acid encoding peptide-based albumin-binding moiety can be operably linked to a nucleic acid encoding a peptide or protein of interest, optionally via a linker domain. The linker domain encompasses any group of molecules that provides a spatial bridge between the albumin-binding moiety and the compound of interest. The linker domain can be of variable length and makeup. In some forms, the linker domain preferably allows for the albumin-binding moiety and/or the peptide or protein of interest to bind, substantially free of steric and/or conformational restrictions to the respective target molecule.

Depending on the type of linkage and its method of production, a peptide/protein based albumin-binding moiety may be joined via its N- or C-terminus to the N- or C-terminus of a peptide or protein of interest. In some forms, when the albumin-binding molecules or moieties are peptides or proteins, the peptides or proteins can be linear or cyclized. Cyclization can be achieved by the formation, for example, of a disulfide bond or a lactam bond between a first and a second residue capable of forming a disulfide bond, such as cysteine.

Whatever means is used to link the albumin-binding moiety to another molecule of interest, the desired final product is preferably a compound in which there has been no significant loss of the desired characteristics of each of the component molecules. Particularly, in the case of the albumin-binding moiety component, there is preferably no significant reduction in the ability to bind serum albumin. In some preferred forms, linkage of an albumin-binding moiety with another molecule of interest results in enhanced properties, such as enhanced detectability, increased serum half-life, enhanced solubility, or enhanced therapeutic, prophylactic, or diagnostic efficacy.

The disclosed compositions and methods can be further understood through the following numbered paragraphs.

1. A heterobiligand comprising a first ligand having affinity for an epitope on folate receptor 1 (FOLR1), a linker, and a second ligand, wherein the second ligand comprises a folate, wherein the linker links the first ligand and the second ligand, wherein the heterobiligand specifically binds FOLR1, wherein FOLR1 comprises an active site, wherein the first ligand comprises a 3-10 amino acid sequence of D-amino acids, artificial amino acids, or combinations thereof, and wherein the folate binds the FOLR1 active site.
2. The heterobiligand of paragraph 1, wherein the folate binds the FOLR1 active site.
3. The heterobiligand of paragraph 1 or 2, wherein the folate is

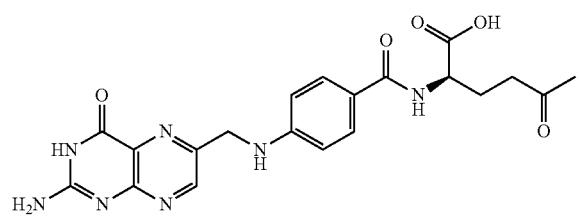

4. The heterobiligand of any one of paragraphs 1-3, wherein the first ligand comprises 5 to 9 amino acids.
5. The heterobiligand of any one of paragraphs 1-4, wherein the epitope comprises the amino acid sequence HHKEKPGPEDKLHE (SEQ ID NO:3), GPWIQQVDQSWRKERVLN (SEQ ID NO:4), or RCIQMWFDPAQGNPNEEVAR (SEQ ID NO:5).
6. The heterobiligand of any one of paragraphs 1-5, wherein the epitope comprises the amino acid sequence HHKEKPGPEDKLHE (SEQ ID NO:3).
7. The heterobiligand of any one of paragraphs 1-5, wherein the epitope comprises the amino acid sequence GPWIQQVDQSWRKERVLN (SEQ ID NO:4).
8. The heterobiligand of any one of paragraphs 1-5, wherein the epitope comprises the amino acid sequence RCIQMWFDPAQGNPNEEVAR (SEQ ID NO:5).
9. The heterobiligand of any one of paragraphs 1-8, wherein the first ligand comprises an amino acid sequence selected from the group consisting of hshta (SEQ ID NO:6), kyeet (SEQ ID NO:9), deryt (SEQ ID NO:20), Ghwef (SEQ ID NO:8), ltdwh (SEQ ID NO:10), hepff (SEQ ID NO:11), wGlhk (SEQ ID NO:12), wwprG (SEQ ID NO:13), nnyl (SEQ ID NO:14), twsw (SEQ ID NO:15), yfytw (SEQ ID NO:16), wkhef (SEQ ID NO:17), tyGeh (SEQ ID NO:18), and anGel (SEQ ID NO:19).
10. The heterobiligand of any one of paragraphs 1-8, wherein the first ligand comprises an amino acid sequence hshta (SEQ ID NO:6), kyeet (SEQ ID NO:9), and deryt (SEQ ID NO:20).
11. The heterobiligand of any one of paragraphs 1-8, wherein the first ligand comprises an amino acid sequence hshta (SEQ ID NO:6).
12. The heterobiligand of any one of paragraphs 1-11, wherein the first ligand comprises a 1,4-substituted-1,2,3-triazole residue (Tz4) or a 1,5-substituted-1,2,3-triazole residue (Tz5).
13. The heterobiligand of any one of paragraphs 1-11, wherein the triazole residue is a 1,4-substituted-1,2,3-triazole (Tz4) residue.
14. The heterobiligand of any one of paragraphs 1-13, wherein the linker is a peptide bond, $PEG_3$, $PEG_3$-Tz, $PEG_3$-Lys, or peptide.
15. The heterobiligand of any one of paragraphs 1-14, wherein the heterobiligand further comprises a reporter moiety.
16. The heterobiligand of paragraph 15, wherein the reporter moiety is selected from the group consisting of biotin, copper-DOTA, biotin-$PEG_3$, aminooxyacetate, $^{19}$FB, $^{18}$FB, and FITC-$PEG_3$.
17. The heterobiligand of paragraph 15, wherein the reporter moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr $^{124}$I, $^{86}$Y, $^{94m}$Tc, $^{110m}$In, $^{11}$C and $^{76}$Br.
18. The heterobiligand of paragraph 15, wherein the reporter moiety is $^{18}$F.
19. The heterobiligand of any one of paragraphs 1-18, wherein the heterobiligand further comprises a therapeutic moiety.
20. The heterobiligand of paragraph 19, wherein the therapeutic moiety is selected from the group consisting of radionuclide-DOTA and radionuclide-NOTA.
21. The heterobiligand of paragraph 19, wherein the therapeutic moiety is $^{177}$Lu-DOTA or $^{177}$Lu-NOTA.
22. The method of paragraph 19, wherein the therapeutic moiety is $^{225}$Ac-DOTA or $^{225}$Ac-NOTA.
23. The heterobiligand of any one of paragraphs 15-22, wherein the reporter moiety is coupled to the first ligand, the second ligand, the linker, or the therapeutic moiety.
24. The heterobiligand of paragraph 23, wherein the reporter moiety is coupled to the C-terminal end of the first ligand or the N-terminal end of the first ligand.

25. The heterobiligand of any one of paragraphs 19-24, wherein the therapeutic moiety is coupled to the first ligand, the second ligand, the linker, or the reporter moiety.
26. The heterobiligand of paragraph 25, wherein the therapeutic moiety is coupled to the C-terminal end of the first ligand or the N-terminal end of the first ligand.
27. The heterobiligand of any one of paragraphs 1-26 further comprising an albumin binding moiety.
28. The heterobiligand of paragraph 27, wherein the albumin binding moiety is 4-methylphenyl butyrate (MPBA) or 4-iodophenyl butyrate (IPBA).
29. The heterobiligand of paragraph 27 or 28, wherein the albumin binding moiety is coupled to the first ligand, the second ligand, the linker, the reporter moiety, or the therapeutic moiety.
30. The heterobiligand of paragraph 29, wherein the albumin binding moiety is coupled to the C-terminal end of the first ligand or the N-terminal end of the first ligand.
31. The heterobiligand of any one of paragraphs 1-30, wherein the heterobiligand comprises a reporter moiety, whereby the heterbiligand is an imaging agent.
32. The heterobiligand of paragraph 31, wherein the heterobiligand further comprises a therapeutic moiety, whereby the heterobiligand is a therapeutic and organ protectant.
33. A composition comprising the heterobiligand of any one of paragraphs 1-32.
34. A method of detecting FOLR1 in a tumor the method comprising contacting the tumor with the composition of paragraph 33, wherein the heterobiligand comprises a reporter moiety, and detecting the reporter moiety.
35. The method of paragraph 34, wherein the composition is an imaging agent.
36. The method of paragraph 35, wherein the heterobiligand further comprises a therapeutic moiety, whereby the composition is a therapeutic and organ protectant.
37. The method of any one of paragraphs 34-36, wherein the heterobiligand binds to the tumor and provides a therapeutic effect, thereby decreasing the size of the tumor.
38. The method of paragraph 37, wherein the heterobiligand cleaves to deliver a therapeutic to the tumor.
39. The method of paragraph 38, wherein the cleaved heterobiligand is protective to an organ.
40. The method of paragraph 39, wherein the organ is the kidney.
41. A method of treating a subject with cancer, the method comprising administering the composition of paragraph 33 to the subject, wherein the heterobiligand comprises a therapeutic moiety.
42. The method of paragraph 41, wherein the therapeutic moiety is selected from the group consisting of radionuclide-DOTA and radionuclide-NOTA.
43. The method of paragraph 42, wherein the therapeutic moiety is $^{177}$Lu-DOTA or $^{177}$Lu-NOTA.
44. The method of paragraph 42, wherein the therapeutic moiety is $^{225}$Ac-DOTA or $^{225}$Ac-NOTA.
45. The method of any one of paragraphs 41-44, wherein the subject has cancer cells expressing FOLR1.

EXAMPLES

Example 1: Analysis of Heterobiligands Having Different Combinations of Components Materials and Methods
Library Synthesis Screens were performed using a triazole-cyclized OBOC library of the form $H_2N$-Pra-(Pra-$X_1X_2X_3X_4X_5$-Az4)-Met-TG, where TG=TentaGel® S $NH_2$ resin (S 30 902, Rapp Polymere), $X_i$=one of sixteen D-amino acids (D-Ala, D-Arg, D-Asn, D-Asp, D-Glu, Gly, D-His, D-Leu, D-Lys, D-Phe, D-Pro, D-Ser, D-Thr, D-Trp, D-Tyr, D-Val), Pra=L-propargylglycine, and ( )=triazole cyclization via flanking Pra and Az4 (=L-azidolysine) residues. An encoded cyclic peptide library (ECPL) was created where 20% of the peptide on each bead is a linear tag for MALDI-TOF/TOF sequencing, while 80% remains the cyclic peptide for ligand discovery. The OBOC library was synthesized using Fmoc-based solid-phase synthesis on a Titan 357 automated peptide synthesizer (AAPPTEC). When synthesizing the ECPL, methionine was first coupled to the TentaGel beads as a cyanogen bromide (CNBr)-selective cleavage handle. Then, Az4 and the 5-residue variable region were coupled via the split-and-mix technique, respectively. A mixture of 80:20 Pra/Gly (mol/mol) was subsequently coupled onto the resins. Then, Cu(I) was added to cyclize the Pra-coupled peptide with the Az4, while the Gly-terminated peptides remained linear for MALDI-TOF/TOF sequencing. Finally, Pra was coupled onto the N-terminus of the library as a click handle for screening. Global side chain deprotection was achieved by treating the library for 2 h with 92.5% TFA, 2.5% $H_2O$, 2.5% TIS (triisopropylsilane), and 2.5% DODT (3,6-dioxa-1,8-octanedithiol). The library resin was then neutralized with 1-methyl-2-pyrrolidinone (NMP), and washed thoroughly with NMP (5×), water (5×), methanol (MeOH, 5×), and methylene chloride (DCM, 5×), and then dried under vacuum before equilibrating in the screening buffer.

Screening a Macrocycle Library Against FOLR1 Epitopes-Library C4

Macrocyclic peptide ligands were identified by screening the library against a cocktail of three FOLR1 epitopes using the following steps: 1) pre-clear and anti-screens to eliminate non-specific binders, 2) a product screen to identify hits resulting from FOLR1 epitope-templated in situ click chemistry, and 3) target screens against His-tagged FOLR1 human recombinant protein to identify peptides that bind to the protein as well as the epitope.

Epitopes 1, 2, and 3 were selected due to their close proximity to the FOLR1 active site. The short distance between these epitopes and the active site enabled the attachment of folate ligand to macrocycle hits to yield heterobiligands.

Pre-clear. Swelled library beads (500 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. In 5 mL Blocking Buffer, 1:1000 Atto565-labeled Streptavidin-Alkaline Phosphatase and 1:10,000 Atto565-labeled Anti-6×His tag antibody [HIS-1] (Alkaline Phosphatase-conjugated) were added to the beads and incubated with gentle shaking at room temperature for 1 h. The beads were subsequently washed with Blocking Buffer (3×1 mM) and TBST (25 mM Tris-HCl, 150 mM NaCl, pH 7.6+0.05% Tween-20) (6×3 mM). Automated sorting was performed on a Union Biometrica BioSorter based on the red signal and object size. The brightest, most non-selective beads were eliminated as background binders (approx. 25% of total). The remaining clear beads were collected and stripped with 0.1 M glycine pH 2.8 buffer for 15 mM, washed six times with water, and incubated in TBST overnight.

Anti-screen. Beads remaining from the pre-clear were incubated in Blocking Buffer for 2 h, then subjected to anti-screening against 50 nM His-tagged CD8α human recombinant protein (10980-H08H, SinoBiological) in Blocking Buffer for 1 h at room temperature. The beads were washed five times with Blocking Buffer and then incubated with 1:10,000 Anti-6×His tag antibody [HIS-1] (Alkaline Phosphatase-conjugated) (ab49746, Abcam) in Blocking Buffer for 1 h at room temperature. The beads were subsequently washed with Blocking Buffer (3×1 min), TBST (3×3 min), TBS (3×3 mM), then Alkaline Phosphatase buffer (100 mM Tris-HCl, 150 mM NaCl, 1 mM $MgCl_2$, pH 9) buffer (3×1 min). Binding was visualized by incubating the beads in the presence of 5-bromo-4-chloro-3-indolyl phosphate/nitro blue tetrazolium (BCIP/NBT) substrate (S3771, Promega). Purple beads indicated background binders and were removed by pipet and discarded. The remaining clear beads were collected and stripped with 0.1 M glycine pH 2.8 buffer for 15 min, washed ten times with water, and incubated in NMP overnight to decolorize.

Beads were washed with water ten times and TBS three times. Anti-screening was then repeated against 50 nM His-tagged PSMA human recombinant protein (15877-H07H, SinoBiological) using the same protocol as above.

Target screen with 50 nM His-tagged FOLR1 protein. Beads remaining from the anti-screen were washed with water ten times and TBS three times. Beads were incubated in Blocking Buffer for 2 h, then subjected to screening against 50 nM His-tagged FOLR1 human recombinant protein (11241-H08H, SinoBiological) in Blocking Buffer for 1 h at room temperature. The beads were washed three times with Blocking Buffer and then incubated with 1:10,000 Anti-6×His tag antibody [HIS-1] (Alkaline Phosphatase-conjugated) (ab49746, Abcam) in Blocking Buffer for 1 h at room temperature. The beads were subsequently washed with Blocking Buffer (5×3 min), TBST (3×3 min), TBS (3×3 min), then Alkaline Phosphatase buffer (pH 9) buffer (3×1 min). Binding was visualized by incubating the beads in the presence of BCIP/NBT substrate (S3771, Promega). Hundreds of purple hit beads bound to FOLR1 protein were selected by pipet. Hits were treated with 0.1 M glycine pH 2.8 buffer for 15 min to remove bound proteins, washed ten times with water, and incubated in NMP overnight to decolorize.

Product screen with FOLR1 epitopes. Hit beads selected in the target screen were washed with water ten times and PBST (0.05% Tween-20 in PBS) three times. They were re-swelled in PBST overnight. Beads were then incubated with a cocktail of three epitopes—50 μM FOLR1 epitope 1 (Biotin-$PEG_3$-HHKEKP[Az4]PEDKLHE; SEQ ID NO:3), 50 μM FOLR1 epitope 2 (Biotin-$PEG_3$-GPWIQQVDQ[Az4]WRKERVLN; SEQ ID NO:4), and 50 μM FOLR1 epitope 3 (Biotin-$PEG_3$-R[S]IQMWFDPA[Az4]GNPNE-EVAR; SEQ ID NO:5)—in PBST at 25° C. overnight to allow for an in situ click reaction to occur. The beads were washed with 3% DMSO in PBST (5×3 min) and Blocking Buffer (3×1 min) and re-blocked with Blocking Buffer for 2 h. A 1:1000 dilution of Streptavidin-Alkaline Phosphatase (V5591, Promega) in 5 mL Blocking Buffer was added for 1 h to detect the presence of FOLR1 epitope clicked to beads. The beads were subsequently washed with Blocking Buffer (5×3 min), TBST (3×3 min), TBS (3×3 min), then Alkaline Phosphatase (pH 9) buffer (3×1 min). After this, the beads were developed with BCIP/NBT as outlined in the target screen. Purple epitope-conjugated hit beads were selected by pipet. These 63 hits were treated with 0.1 M glycine pH 2.8 buffer for 15 min to remove attached streptavidin, washed ten times with water, and incubated in NMP overnight to decolorize.

Target screen with 10 nM His-tagged FOLR1 protein. The 63 hits obtained from the product screen were washed with water ten times and TBS three times. They were then transferred to Corning® 8162 Costar® Spin-X® centrifuge tube filters (cellulose acetate membrane) and incubated with Blocking Buffer at 4° C. overnight. Beads were rinsed three times with Blocking Buffer and then incubated with 10 nM His-tagged FOLR1 human recombinant protein (11241-H08H, SinoBiological) in Blocking Buffer for 1 h at room temperature. The beads were washed three times with Blocking Buffer and then incubated with 1:10,000 Anti-6×His tag antibody [HIS-1] (Alkaline Phosphatase-conjugated) (ab49746, Abcam) in Blocking Buffer for 1 h at room temperature. The beads were subsequently washed with PBST (3×3 min) and PBS (3×3 min) and rinsed once with Alkaline Phosphatase (pH 9) buffer (centrifuging at 7000 rpm for each wash). After this, the beads were developed with BCIP/NBT. Purple hit beads bound to FOLR1 protein were selected by pipet and saved. Of the 63 product hits isolated for the FOLR1 epitopes, 2 beads were purple indicating strong binding to both FOLR1 epitope and protein. The 2 target hits were treated with 0.1 M glycine pH 2.8 buffer for 15 min to remove bound proteins, washed ten times with water, and incubated in NMP overnight to decolorize. The hits were finally washed with water ten times to prepare for sequencing analysis.

Heterobiligands Via In Situ Click Screening-Library D1

Folate-PCC heterobiligands were templated by screening the library and biotinylated azido-folate anchor against FOLR1 protein using the following steps: 1) pre-clear and anti-screen to eliminate non-specific binders, and 2) in situ click screen with biotinylated azido-folate anchor and FOLR1 protein to identify heterobiligand hits resulting from protein-templated in situ click chemistry.

Pre-clear. Swelled library beads (500 mg) were blocked overnight with 2% DMSO in PBST. They were then incubated with 1 μM biotinylated azido-folate anchor (Folate-$PEG_3$-Az4-$PEG_3$-Biotin) in 8 mL of 2% DMSO in PBST at 25° C. overnight. The library/anchor complex was washed with 2% DMSO in PBST (2×1 min), PBST (3×1 min), and 1% BSA in PBST (3×1 min), then blocked overnight with 1% BSA in PBST at 25° C. Binding was detected by incubating the beads in 1% BSA in PBST with 1:1000 Atto565-labeled Streptavidin-Alkaline Phosphatase and 1:10,000 Atto565-labeled Anti-6×His tag antibody [HIS-1] (Alkaline Phosphatase-conjugated) with gentle shaking for 1 h. The beads were subsequently washed with 1% BSA in PBST (3×1 min) and PBST (6×3 min). Automated sorting was then performed on a Union Biometrica BioSorter based on the red signal and object size. The brightest, most non-selective beads were eliminated as background binders. The remaining clear beads were collected and stripped with 0.1 M glycine pH 2.8 buffer (3×5 min), washed five times with water, and incubated in NMP for 1 h to decolorize.

Anti-screen. Beads remaining from the pre-clear were washed with water ten times and 1% BSA in PBST (3×3 min). Beads were incubated with 1% BSA in PBST at 4° C. overnight, then subjected to anti-screening against 50 nM His-tagged PSMA human recombinant protein (15877-H07H, SinoBiological) in 1% BSA in PBST for 1 h at room temperature. The beads were washed with 1% BSA in PBST (5×3 min) and then incubated with 1:10,000 Anti-6×His tag antibody [HIS-1] (Alkaline Phosphatase-conjugated) (ab49746, Abcam) and 1:1000 Streptavidin-Alkaline Phosphatase (V5591, Promega) in 1% BSA in PBST for 1 h at room temperature. The beads were subsequently washed with 1% BSA in PBST (3×5 min), PBST (3×3 min), PBS (3×3 min), then Alkaline Phosphatase buffer (pH 9) buffer (3×1 min). Binding was visualized by incubating the beads in the presence of BCIP/NBT substrate (S3771, Promega). Purple beads indicated background binders and were removed by pipet and discarded. The remaining clear beads were collected and stripped with 0.1 M glycine pH 2.8 buffer (3×5 min), washed ten times with water, incubated in NMP for 1 h to decolorize, and washed ten times with water.

In situ click screen with biotinylated azido-folate anchor and FOLR1 protein. Library beads were treated with biotinylated azido-folate anchor and FOLR1 protein under conditions promoting protein-templated in situ click chemistry between ligands. Here, the clear beads from the anti-screen were first blocked with 2% DMSO in PBST. Biotinylated azido-folate anchor (100 nM) and 1 nM FOLR1 human recombinant protein (11241-H08H, SinoBiological) were mixed in 10 mL of 2% DMSO in PBST overnight at 4° C. in a conical tube. The PBST was then drained from the beads and the 10 mL of anchor/FOLR1 solution was added to the beads and incubated for 4 h at 25° C. under rotation. The library/anchor/protein complex was washed with PBST (5×1 min) and 1% BSA in PBST (3×1 min), then blocked with 1% BSA in PBST for 30 min at 25° C. A 1:1000 dilution of Streptavidin-Alkaline Phosphatase (V5591, Promega) in 1% BSA in PBST (10 mL) was added for 1 h to detect the presence of biotinylated azido-folate anchor clicked to beads. The beads were subsequently washed with 1% BSA in PBST (3×5 min), PBST (3×3 min), PBS (3×3 min), then Alkaline Phosphatase (pH 9) buffer (3×). After this, the beads were developed with BCIP/NBT as outlined above. Purple heterobiligand-linked hit beads were selected by pipet. These 9 hits were treated with 0.1 M glycine pH 2.8 buffer (3×5 min) to remove attached streptavidin, washed ten times with water, incubated in NMP for 1 h to decolorize, and washed ten times with water to prepare for sequencing analysis.

Heterobiligands Via In Situ Click Screening-Library D2

Screens for additional heterobiligands were completed following the above protocol, except that:

Biotinylated azido-folate anchor (500 nM) and 5 nM FOLR1 human recombinant protein (11241-H08H, SinoBiological) were used.

The library/anchor/protein complex was washed with PBST (5×1 min), 0.1 M glycine pH 2.8 buffer (2×5 min), PBST (5×1 min), and 1% BSA in PBST (3×1 min), then blocked with 1% BSA in PBST before detection with Streptavidin-Alkaline Phosphatase.

Purple heterobiligand-linked hit beads were selected by pipet. These 4 hits were treated with 0.1 M glycine pH 2.8 buffer (3×5 min) to remove attached streptavidin, washed ten times with water, incubated in NMP for 1 h to decolorize, and washed ten times with water to prepare for sequencing analysis.

Sequencing Cyclic Peptide Hits by MALDI-TOF/TOF

Peptides on hit beads were selectively cleaved from the resin using CNBr and sequenced by MALDI-MS/MS.

Cleavage of hit peptides from single beads with CNBr. Each hit bead was transferred in pure water (10 μL) to a single well of a 96-well conical-bottom polypropylene microplate. After addition of CNBr (10 μL, 0.50 M in 0.2 N HCl solution) to each well, the plate was purged with argon and then placed under microwave for 1 mM. Acidic aq. CNBr results in methionine-specific cleavage at the C-terminus, resulting in cleavage of the cyclic and linear peptides from the beads. The resulting solution was concentrated under centrifugal vacuum for 2 hours at 45° C.

Sequencing of peptides cleaved from single beads by MALDI-MS and MS/MS. To each sample was added α-cyano-4-hydroxycinnamic acid (CHCA) (0.5 μL, 5 mg/mL matrix solution in acetonitrile/water (70:30) containing 0.1% TFA (v/v)). The mixture was taken up to be spotted onto a 384-well MALDI plate, which was allowed to stand for 15 mM to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each linear peptide in LIFT™ mode. BioTools™ was used to assign the sequence based on analysis of the MS/MS spectra.

Peptide Synthesis

The peptides were synthesized using standard SPPS Fmoc chemistry. CTC resin was loaded with Fmoc-Lys(Dde)-OH. Each subsequent amino acid coupling was achieved using the amino acid (3.0 equiv), HBTU coupling reagent (2.85 equiv.), DIPEA (6.0 equiv.) in DMF. DOTA was installed by deprotecting the Dde protecting group (2% hydrazine in DMF) followed by coupling DOTA (3×tBu). The peptide was cleaved from the resin and precipitated using cold isopropyl ether. The crude peptides were purified by preparative-HPLC.

Fluorine-18 Radiochemistry

Heterobiligands were synthesized as aminooxy conjugates using Fmoc solid-phase peptide synthesis. The aminooxy linker was appended on the side chain of the C-terminal lysine. After acidic resin cleavage and deprotection of the side chains, heterobiligands were purified by $C_{18}$ HPLC. Purity and mass were confirmed before entering into the labeling reaction.

Fluorine-18 labeling of heterobiligands. 4-[$^{18}$F]fluorobenzaldehyde ([$^{18}$F]FBA) in methanol (MeOH) was obtained from the UCLA Crump Institute for Molecular Imaging. The $^{18}$F-fluorobenzaldehyde oxime was prepared by reacting the aminooxy-conjugated heterobiligand (5 mM in 50% MeOH and 50% potassium dihydrogen phosphate solution with phosphoric acid pH 3) with [$^{18}$F]FBA for 7 mM at room temperature (reaction volume=70 μL). The [$^{18}$F]FBA-labeled heterobiligand was purified from the reaction mixture by C18 HPLC and then co-injected with reference standard to confirm its identity. The solvent was evaporated from the purified fraction, and the dried product was dissolved in phosphate-buffered saline (PBS) prior to mouse injection.

Gallium-68 and Lutetium-177 Radiochemistry

Heterobiligands were synthesized as DOTA conjugates using Fmoc solid-phase peptide synthesis. The DOTA chelator was appended on the side chain of the C-terminal lysine. After acidic resin cleavage and deprotection of the side chains, heterobiligands were purified by $C_{18}$ HPLC. Purity and mass were confirmed before entering into the labeling reaction.

Gallium-68 labeling of heterobiligands. $^{68}$GaCl$_3$ was obtained from the UCLA Biomedical Cyclotron Facility. The DOTA-conjugated heterobiligand and $^{68}$GaCl$_3$ (1:1) were reacted for 5 min at 90° C. in buffer comprised of 1.5 mL NaCl and 0.5 mL of 0.1 M NaOAc pH 4. The efficiency was >95% according to HPLC, and the product was diluted with PBS prior to mouse injection.

Lutetium-177 labeling of heterobiligands. $^{177}$LuCl$_3$ in 0.05 M HCl was obtained from the Missouri University Research Reactor (MURR). A specific activity of 0.2 mCi of $^{177}$Lu was added per nmol of DOTA conjugated heterobiligand. The solution was warmed to 95° C. for 15 minutes in 0.4 M sodium acetate buffer (pH 4.5). Conversion was 100% according to both radioTLC and HPLC, and purity was confirmed to be 100% on HPLC. The undiluted product in 0.4 M sodium acetate buffer (pH 4.5) was used directly or formulated in buffered saline.

Mice—Tumor Imaging and Therapeutic Studies

Female, 7-week-old NSG mice were housed under pathogen-free conditions. Water and food were provided ad libitum. To create mice with FOLR1+ ovarian xenograft tumors, mice were injected subcutaneously with OVCAR3 cells (1×10$^7$ cells per mouse) resuspended in 50% Matrigel in PBS into the shoulder region. Tumor growth was monitored by caliper measurements. OVCAR3 is a human ovarian adenocarcinoma known to over-express FOLR1.

In vivo $^{18}$F PET/CT Imaging $^{18}$F positron emission tomography (PET) imaging was used to study in vivo biodistribution of heterobiligands in OVCAR3 tumor bearing mice. 40-60 μCi of [$^{18}$F]-BA-labeled heterobiligand was administered intravenously (i.v.) via the tail vein of each mouse. Dynamic PET imaging was performed from 0-1 h, followed by acquisition of static PET images at 2 h and 4 h post-injection. CT scans were acquired for anatomical reference. Imaging was performed on a GENISYS$^8$ microPET/CT small animal scanner. The PET signal was quantitated by three-dimensional region of interest (ROI) analysis and represented as percent injected dose (% ID) vs. time (min) for major organs including tumor, liver, heart, lung, bladder, and kidney.

In Vivo $^{68}$Ga PET/CT Imaging $^{68}$Ga PET imaging was used to study in vivo biodistribution of heterobiligands in non-tumor bearing (healthy) mice and OVCAR3 tumor bearing mice. 100-200 μCi of [$^{68}$Ga]DOTA-labeled heterobiligand was administered intravenously (i.v.) via the tail vein of each mouse. Dynamic PET imaging was performed from 0-1 h, followed by acquisition of static PET images at 2 h and 4 h post-injection. CT scans were acquired for anatomical reference. Imaging was performed on an Inveon microPET/CT small animal scanner. The PET signal was quantitated by three-dimensional ROI analysis and represented as percent injected dose (% ID) vs. time (mM) for major organs including tumor, liver, heart, lung, bladder, and kidney.

$^{177}$Lu FOLR1 Therapy

OVCAR3 tumor bearing mice were used to study FOLR1-directed radioligand therapy (RLT) for treatment of ovarian cancer. Animals were administered a single dose of heterobiligand (vehicle control) or 111, 37, 18.5, 9.25, or 3.7 MBq [$^{177}$Lu]DOTA-labeled heterobiligand. Mice received the dose intravenously (i.v.) via the tail vein. To monitor the effect of the RLT, tumor size measurements were taken twice weekly and body weights were measured.

At endpoint, mice were sacrificed and plasma and tissues (tumor, kidney, liver, lung, muscle) were collected. Plasma samples were assayed for urea and creatinine biomarkers indicative of nephrotoxicity. Tissue samples were fixed in 10% buffered formalin, transferred to 70% ethanol, and embedded in paraffin for immunohistochemistry.

Plasma Stability

Plasma was thawed in a 37° C. water bath. Residual clots were removed via centrifugation at 4000 rpm for 5 minutes. The pH of the plasma was adjusted to 7.4 if required. Test articles were diluted to 100 μM by diluting a 1 mM working solution (in DMSO) with 45% methanol in water. To 98 μL of plasma was added 2 μL of the 100 μM solution, resulting in 2 μM final concentration of the test article. Samples were incubated at 37° C. in a water bath. At the indicated time points (0, 10, 30, 60, 120 minutes) 100 μL of 4% H$_3$PO$_4$ was added followed by 800 μL of stop solution (200 ng/mL tolbutamide and 200 ng/mL labetalol in 100% acetonitrile). The samples were centrifuged and the plasma protein-free supernatant (100 μL) was subjected to LC-MS/MS analysis.

Plasma Protein Binding

HTD 96 a/b regenerated cellulose membrane strips with mass cutoff of 12-14 kDa were soaked in ultra-pure water at room temperature for 1 hour. Each swelled membrane was then soaked in 20:80 ethanol:water for 20 minutes.

Just prior to the experiment, the membranes were re-soaked in ultra-pure water. Plasma was prepared by thawing under cold water. The plasma was centrifuged to remove any clots and pH was adjusted to 7.0-8.0. Test articles and control compounds were diluted to 2 μM. The dialysis device was loaded by transferring 150 μL of the test article (in triplicate) to the donor side. The dialysis device was placed in a humidified incubator at 37° C. with 5% CO$_2$ in a shaking platform that rotated slowly for 4 hours. After incubation, 50 μL of the supernatant was taken from both sides and analyzed by LC-MS/MS.

Results

Folate receptor 1 (FOLR1) is a cell membrane protein with significant overexpression in carcinomas (most notably ovarian and breast cancers). FOLR1 is responsible for trafficking folic acid into cells via receptor-mediated endocytosis. The protein is anchored to the cell via a glycosylphosphatidylinositol (GPI) attached to the C terminus of FOLR1. FOLR1 is overexpressed in approximately 80% of ovarian cancers. Other organs have very low FOLR1 expression with the exception of the kidney to facilitate folate resorption. Prior FOLR1 therapeutic strategies have relied on a modified folate conjugated to a standard-of-care chemotherapeutic. Efficacy was no better that standard-of-care chemotherapeutic arm. The example heterobiligands—folate linked to a receptor-specific ligand—can use a theranostic platform to image and treat cancer using radioisotopes. Some example heterobiligands display cooperative binding that yields very high EC50s compared to native folate. The heterobiligands can be modified based on medicinal chemistry principles to diminish off target binding and alter pharmacokinetics for specific applications, such as imaging or therapy. $^{177}$Lu provides predictable tumor killing while limiting bystander injury.

The extracellular domain of FOLR1 is 234 amino acids (M1-S234) and is glycosylated at N69, N161, and N201. S234 is coupled to glycosylphosphatidylinositol (GPI). The FOLR1 monomer coordinates (PDB: 4LRH) were minimized and equilibrated using periodic boundary conditions employing Particle Mesh Ewald electrostatics. The monomer was solvated in a water box with at least 10 water molecules separating the protein and unit cell wall. The system was warmed to 310° K, minimized for 1000 steps, and equilibrated for 1000 ps. The minimized monomer has a solvent accessible surface of 11,279.917 Å$^2$.

Pocket analysis was undertaken to identify cavities present on the FOLR1 surface. The modeling software fPocket was used to calculate the volumes of putative pockets. Pockets large enough to accommodate protein catalyzed capture agents (PCCs) are located adjacent to the active site (itself a large rigid cavity). This information informed the epitope design and click handle placement.

Epitope 1 is H20-H33 of FOLR1 (HHKEKPGPEDKLHE; SEQ ID NO:3). Epitope 1 is composed of a largely unstructured loop near the N terminus of the protein. This epitope has high solvent exposure (1141.512 Å$^2$) and a low net charge (−1). The RMSD of the side chains and backbone (average equilibrated backbone RMSD 0.794 (0.175); average equilibrated total RMSD 1.450 (0.272)) suggests that this portion of the protein is flexible. Glycine-26 was selected as the Az4 substitution. The epitope 1 molecule used for catalyzed selection with G26 substituted with Az4 is biotin-PEG3-HHKEKP[G→Az4]PEDKLHE (SEQ ID NO:3). The structure is shown below.

Epitope 2 is G92-N109 of FOLR1 (GPWIQQVDQSWRKERVLN; SEQ ID NO:4). Epitope 2 is an epitope that is located adjacent to the active site. It was realized that the ability to attach folic acid itself to any ligand identified from this screen would further increase potency and selectivity of the final heterobiligand. While many constituent amino acids are charged, the overall epitope has only a +1 net charge. The RMSD of this epitope (average equilibrated backbone RMSD 0.576 (0.103); average equilibrated total RMSD 0.882 (0.150)) suggests that this region is flexible. Epitope 2 has a solvent accessible surface of 976.372 Å$^2$. Serine-101 was selected as the Az4 substitution. The epitope 2 molecule used for catalyzed selection with S101 substituted with Az4 is biotin-PEG3-GPWIQQVDQ[S→Az$_4$]WRKERVLN (SEQ ID NO:4). The structure is shown below.

Epitope 3 is R186-R205 of FOLR1 (RCIQMWFDPAQGNPNEEVAR; SEQ ID NO:5). Epitope 3 is a contiguous sequence near the C terminus of the protein. The epitope is made up of an alpha helix connected to an unstructured loop. Epitope 3 has a solvent accessible surface of 1029.471 Å$^2$ and a net charge of −1. The average equilibrated backbone RMSD is 1.085 (0.205) and the average equilibrated total RMSD is 1.548 (0.207). Glutamine-196 was selected for Az4 substitution. The epitope 3 molecule used for catalyzed selection with Q196 substituted with Az4 is biotin-PEG3-R[C→S]IQMWFDPA[→Az$_4$]GNPNEEVAR (SEQ ID NO:5). The structure is shown below.

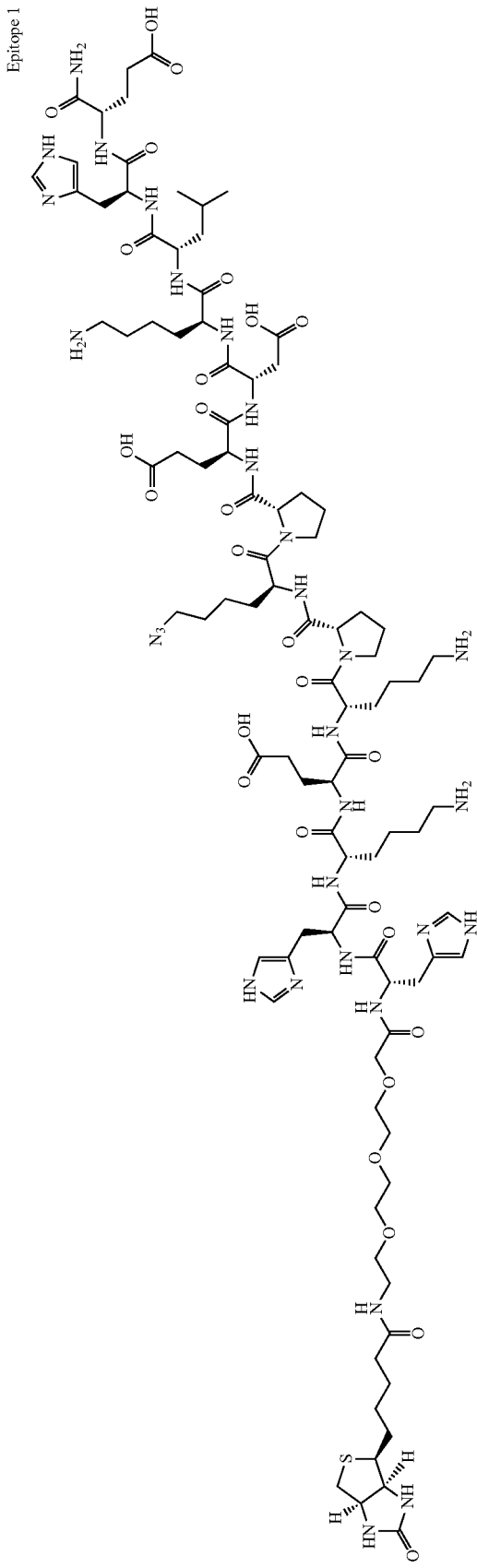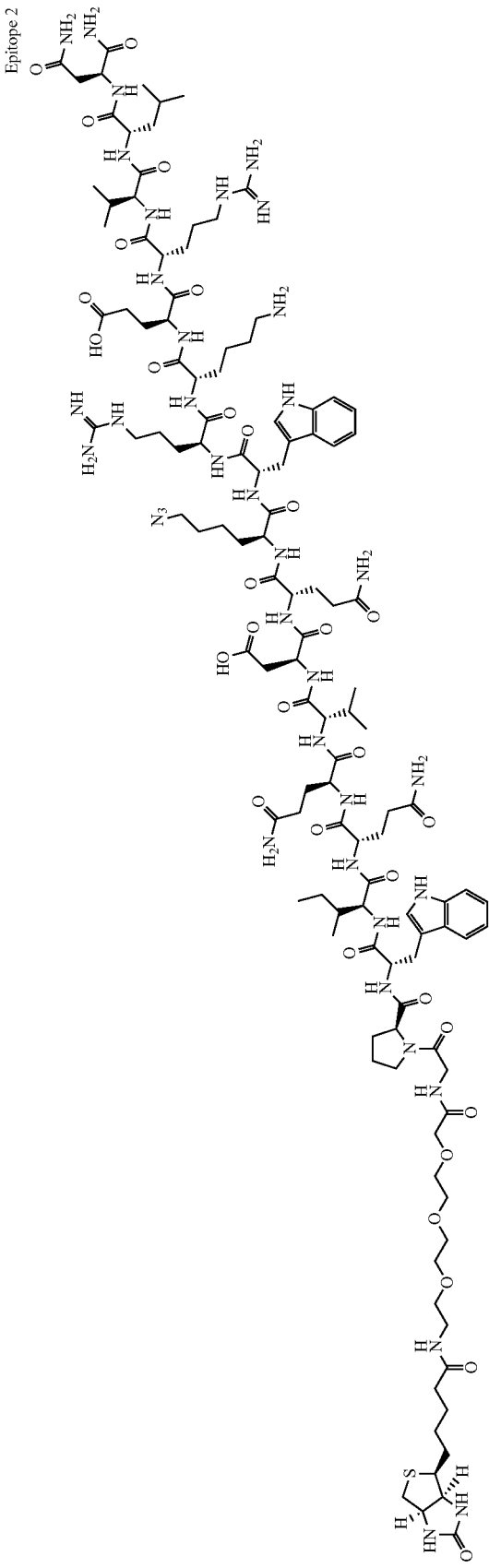

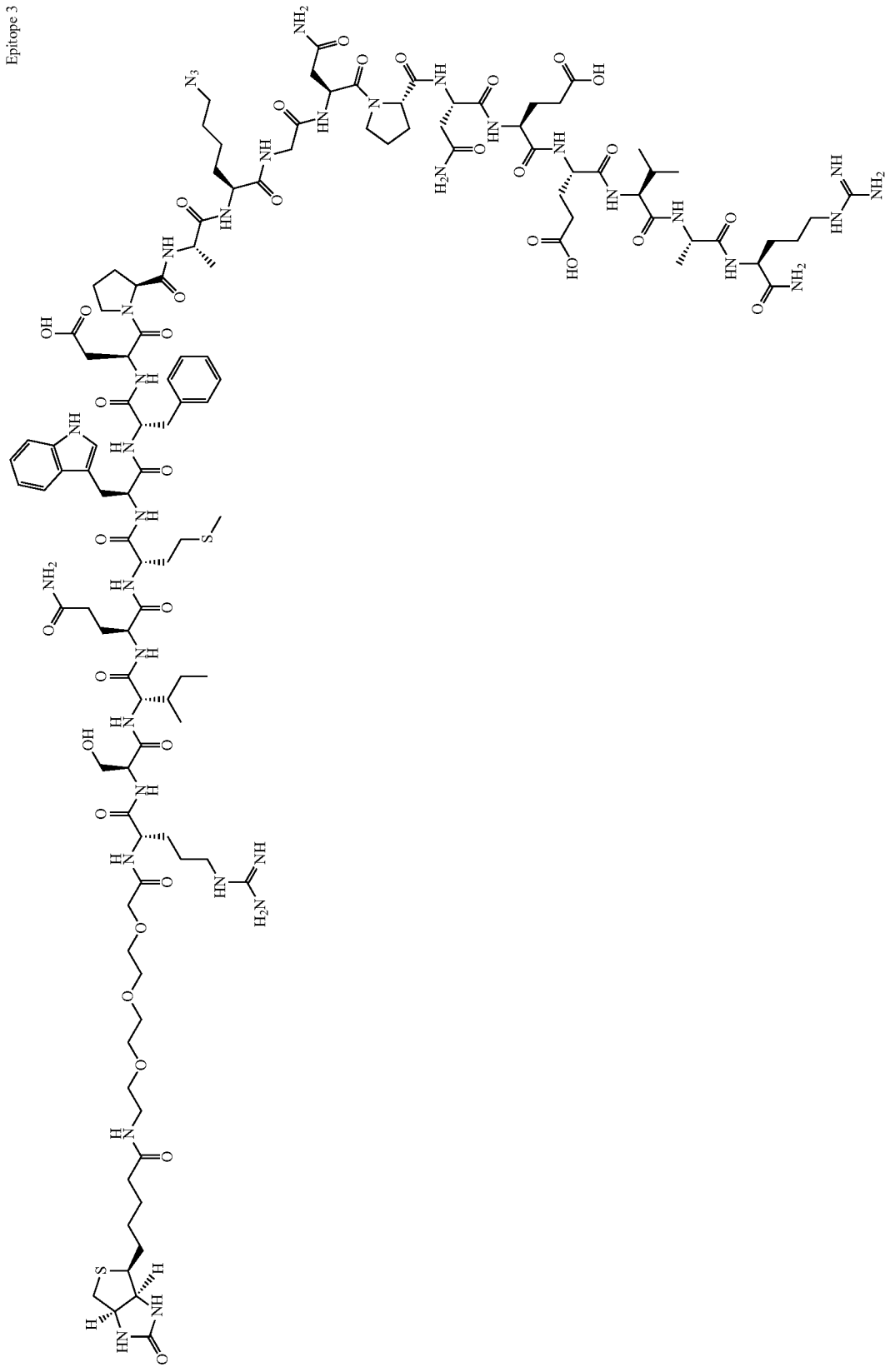

FOLR1 is small enough to allow heterobiligand preparation regardless of which epitope is targeted. Screens were performed using a triazole-cyclized OBOC library of the form $H_2N\text{-Pra-}(Pra\text{-}X_1X_2X_3X_4X_5\text{-Az4})\text{-Met-TG}$, where TG=TentaGel® S $NH_2$ resin (S 30 902, Rapp Polymere), $X_i$=one of sixteen D-amino acids, Pra=L-propargylglycine, and ( )=triazole cyclization via flanking Pra and Az4 (=L-azidolysine) residues. An encoded cyclic peptide library (ECPL) was created where 20% of the peptide on each bead is a linear tag for MALDI-TOF/TOF sequencing, while 80% remains the cyclic peptide for ligand discovery.

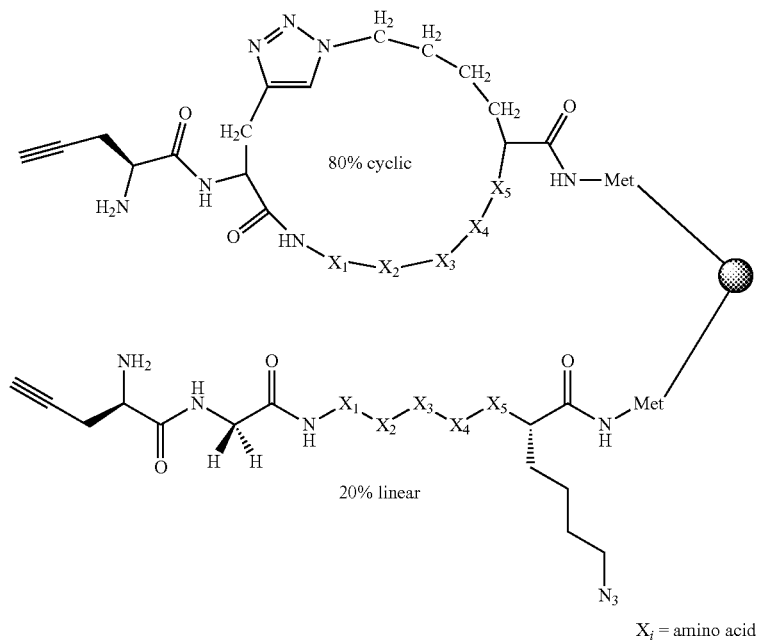

$X_i$ = amino acid

Figure 2:
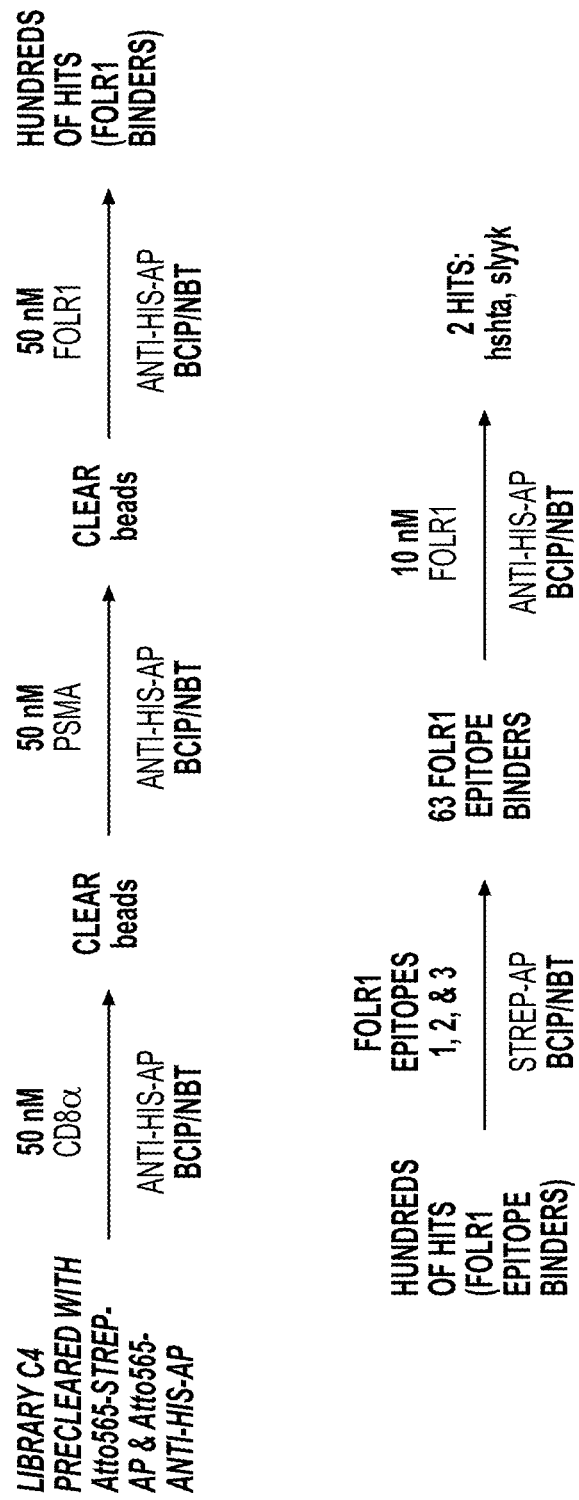
FIG. 2 is a diagram of an example of screening for PCC ligands of FOLR1 using synthetic epitopes (SynEps).

Macrocyclic peptide ligands were identified by screening the library against a cocktail of three FOLR1 epitopes (FIG. 1) using the following steps: (1) pre-clear and anti-screens to eliminate non-specific binders, (2) a product screen to identify hits resulting from FOLR1 epitope-templated in situ click chemistry, and (3) target screens against His-tagged FOLR1 human recombinant protein to identify peptides that bind to the protein as well as the epitope (FIG. 2). Two hits were isolated with strong binding to both FOLR1 epitope and protein: hshta (SEQ ID NO:6) and slyyk (SEQ ID NO:7).

Figure 3:
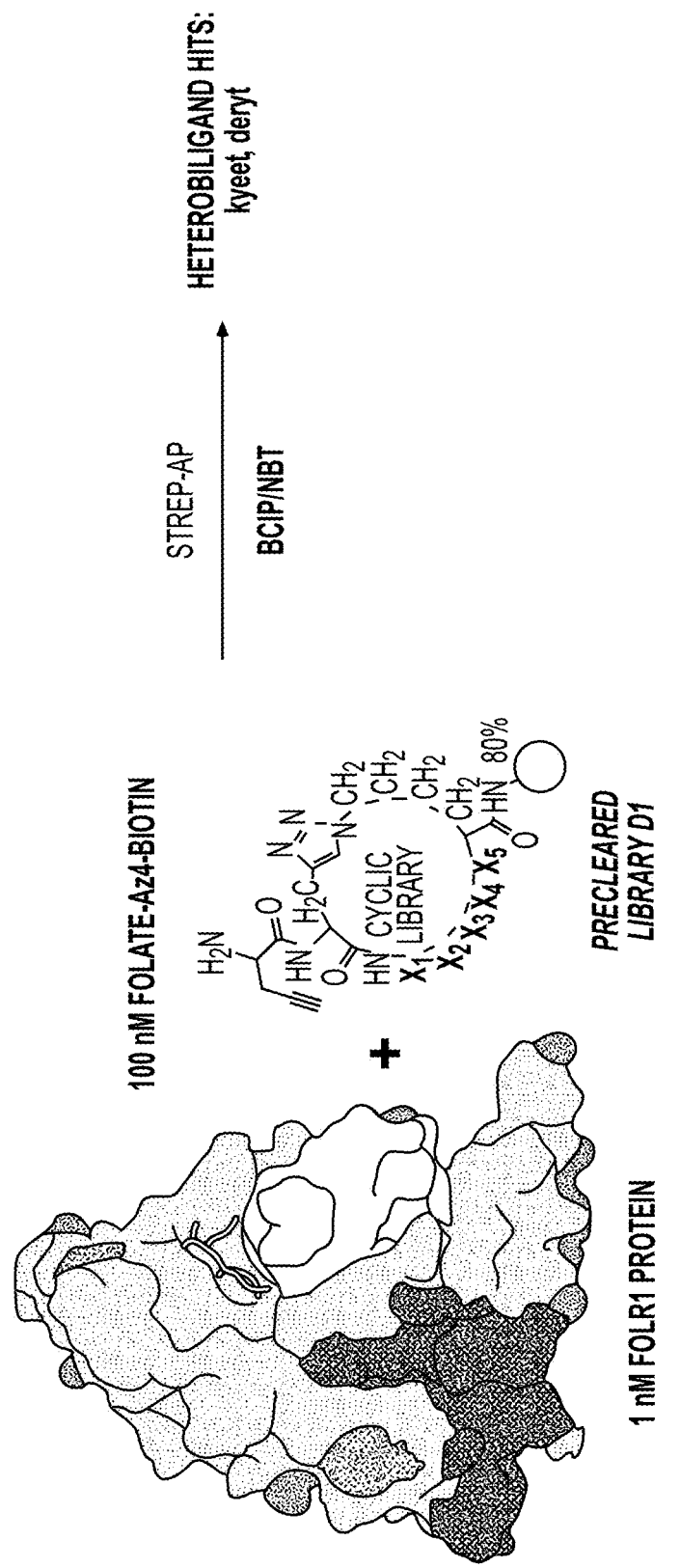
FIG. 3 is a diagram of an example of screening for PCC ligands of FOLR1 using FOLR1 and a folate-Az4-biotin.
Figure 4:
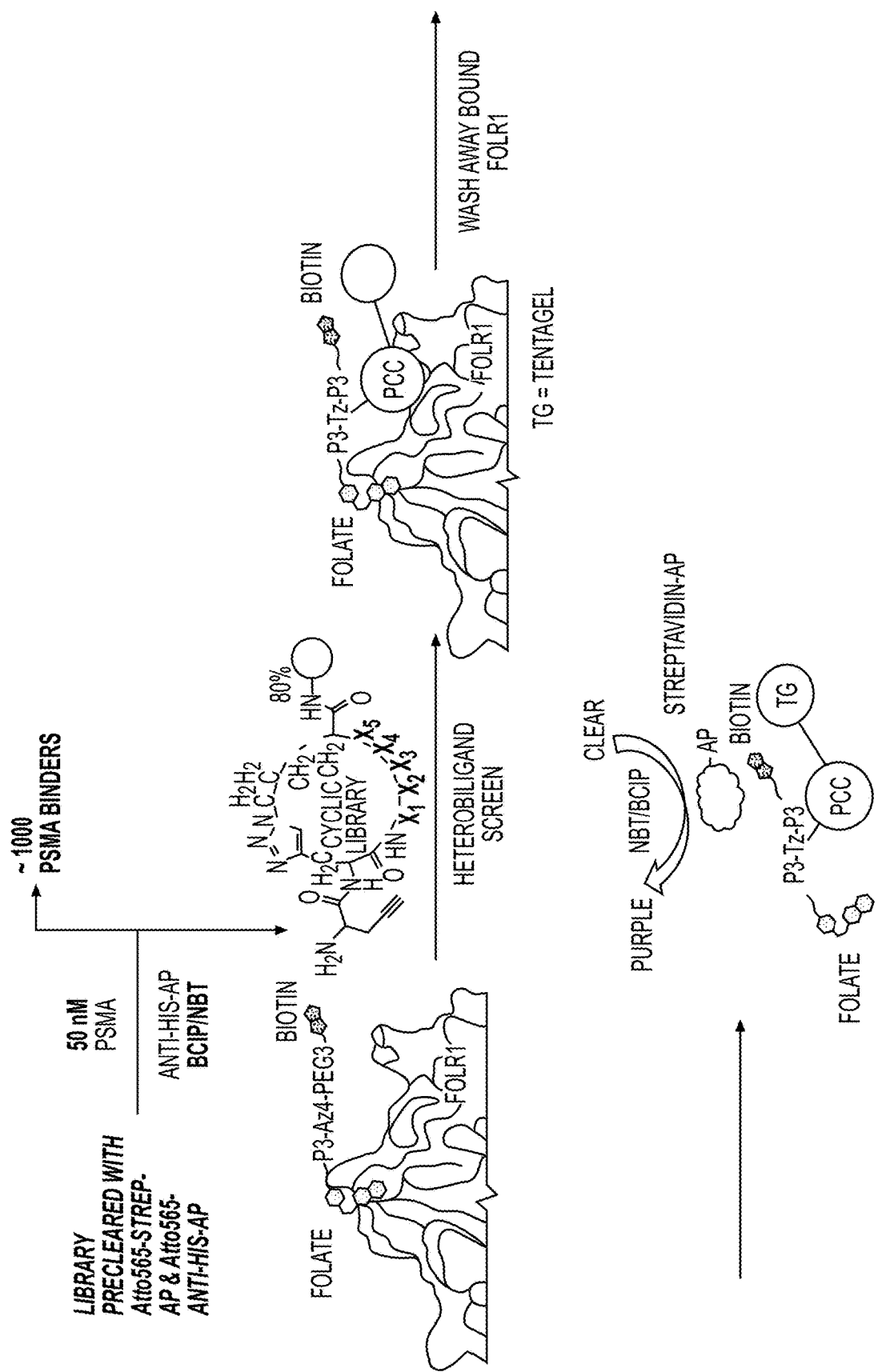
FIG. 4 is a diagram of an example of screening for PCC ligands of FOLR1 using FOLR1 and a folate-Az4-biotin.

Heterobiligands were also developed via in situ click screening (FIG. 3). FOLR1 is a GPI-anchored cell surface protein that binds to folate ligand with high affinity ($K_D \neq 1$ nM). The FOLR1 protein provides a template for selectively promoting the azide-alkyne cycloaddition between folate ligand and library peptide. Folate-PCC heterobiligands were templated by screening the library and biotinylated azido-folate anchor against FOLR1 protein using the following steps: (1) pre-clear and anti-screen to eliminate non-specific binders, and (2) in situ click screen with biotinylated azido-folate anchor and FOLR1 protein to identify heterobiligand hits resulting from protein-templated in situ click chemistry (FIG. 4). Two forms of folate anchor were used and were based on the fact that folate conjugates typically incorporate a PEG3 linker at the Glu side chain.

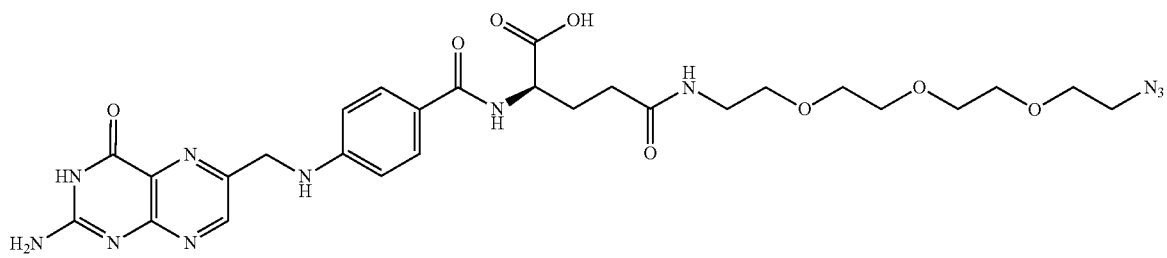

Azido-folate anchor

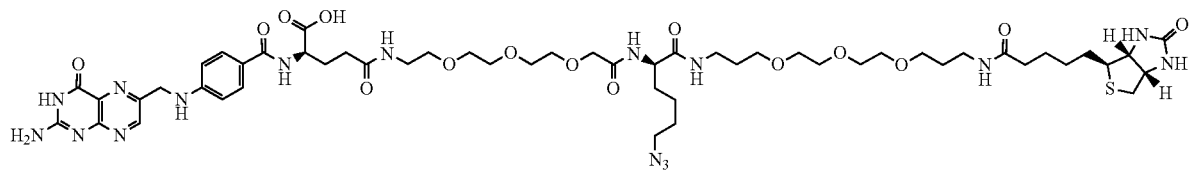

Biotinylated Azido-folate anchor

The short distance between FOLR1 epitope and the active site enabled the attachment of folate ligand to macrocycle hits to yield heterobiligands. The general structure of the heterobiligands is shown below, with the folate on the left, the peptide ligand on the right, and the linker in the middle.

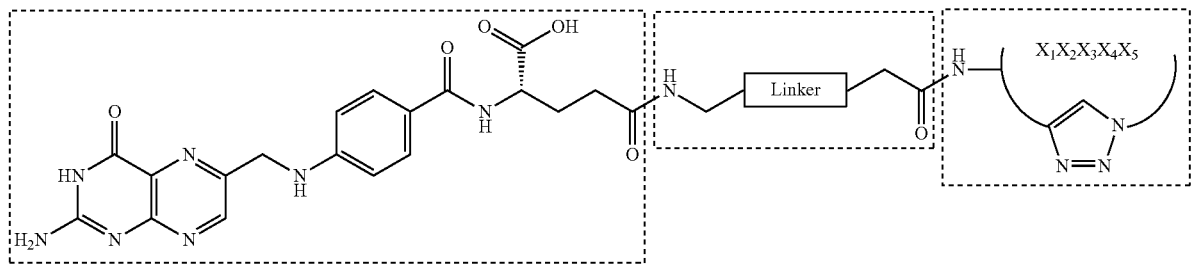

Nine heterobiligand hits were found when the library was screened against 100 nM biotinylated azido-folate anchor and 1 nM FOLR1 protein (Library D1). Ghwef (SEQ ID NO:8), kyeet (SEQ ID NO:9), ltdwh (SEQ ID NO:10), hepff (SEQ ID NO:11), wGlhk (SEQ ID NO:12), wwprG (SEQ ID NO:13), nnyl (SEQ ID NO:14), twsw (SEQ ID NO:15), and yfytw (SEQ ID NO:16). Another four heterobiligand hits were found when the library was screened against 500 nM biotinylated azido-folate anchor and 5 nM FOLR1 protein (Library D2). wkhef (SEQ ID NO:17), tyGeh (SEQ ID NO:18), anGel (SEQ ID NO:19), and deryt (SEQ ID NO:20).

Two forms of heterobiligand were produced using the strong ligand hits. Tz heterobiligands were produced using ligands hshta (SEQ ID NO:6), kyeet (SEQ ID NO:9), and deryt (SEQ ID NO:20) and are characterized by a PEG linker, a Tz attachment of the ligand to the linker, and biotin attached to the N-terminus of the ligand. Tz heterobiligands had the general structure:

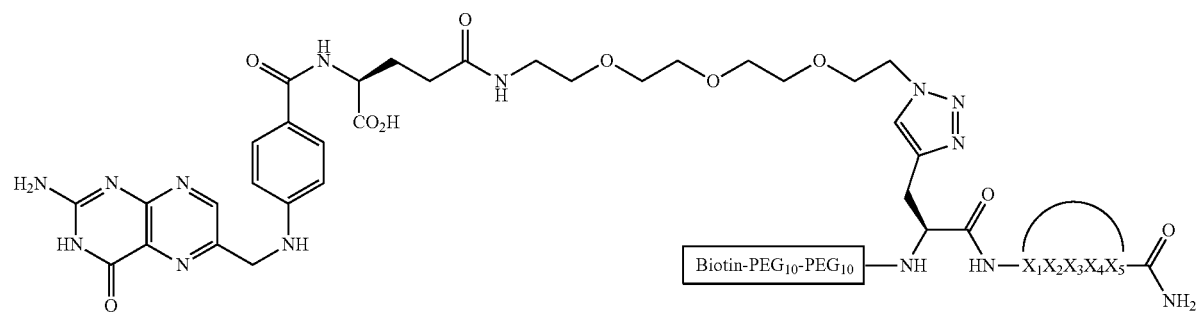

NTerm heterobiligands were produced using the ligand hshta (SEQ ID NO:6) and are characterized by direct attachment of the N-terminus of the ligand to the folate and biotin attached to the C-terminus of the ligand. NTerm heterobiligands have the general structure:
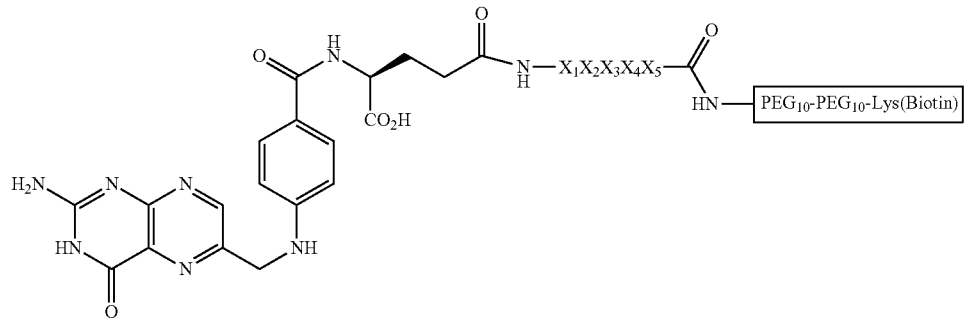
The specific structures of the tested PCCs and heterobiligands are shown below.

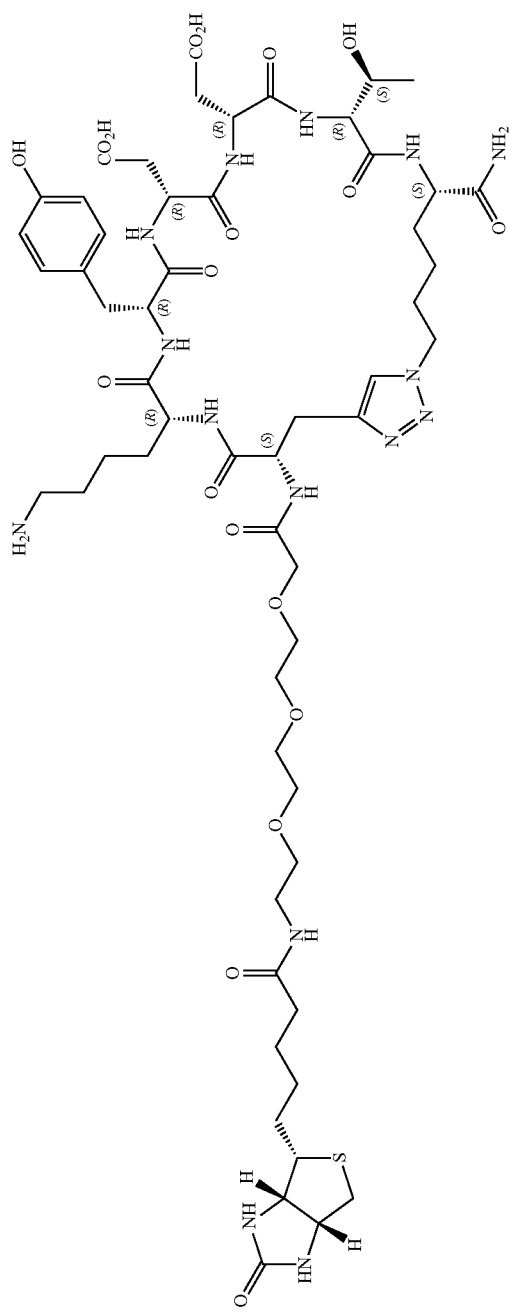
Bio-PEG3-kyeet (SEQ ID NO:9)

Figure 5:
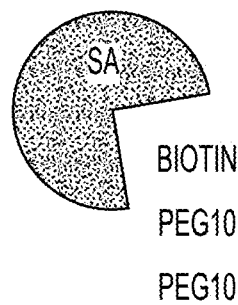
FIG. 5 is a diagram of ELISA assay of FOLR1 binding of heterobiligands.

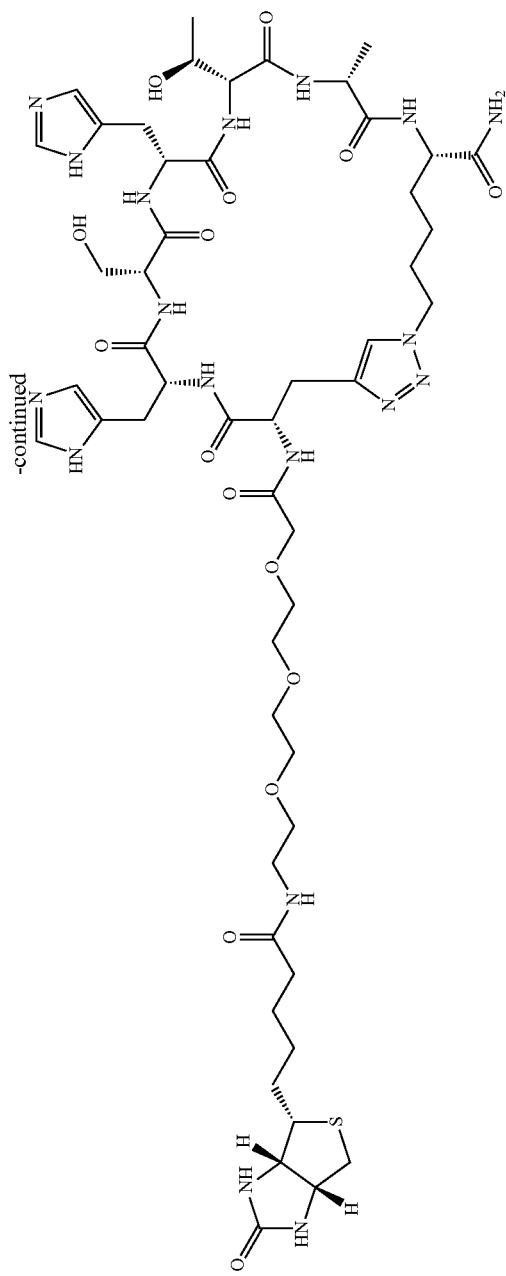
Bio-PEG3-hshta (SEQ ID NO:6)
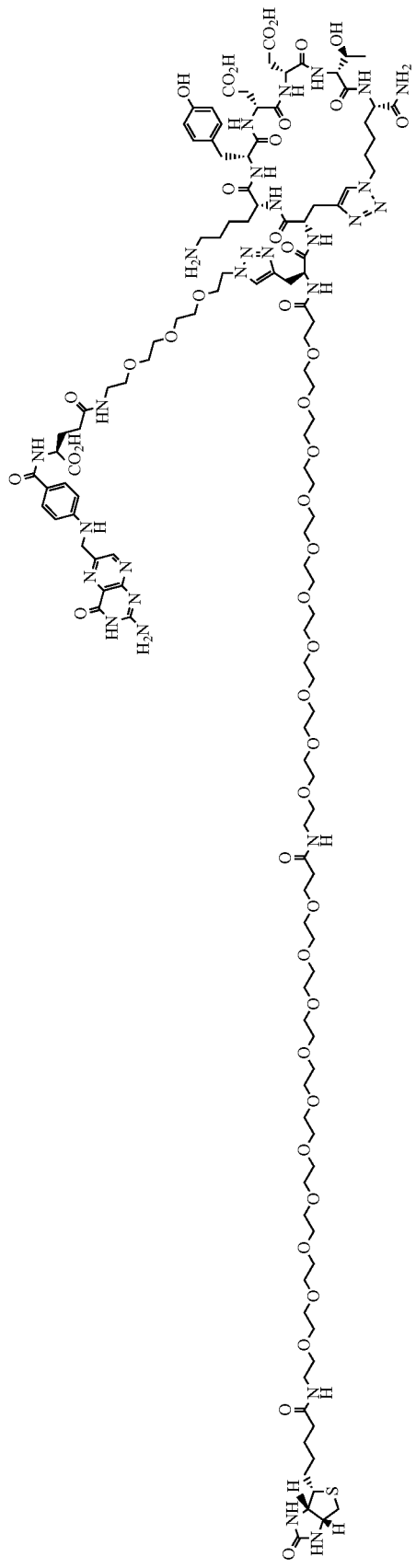
Folate-kyeet (SEQ ID NO:9) Tz heterobiligand -continued
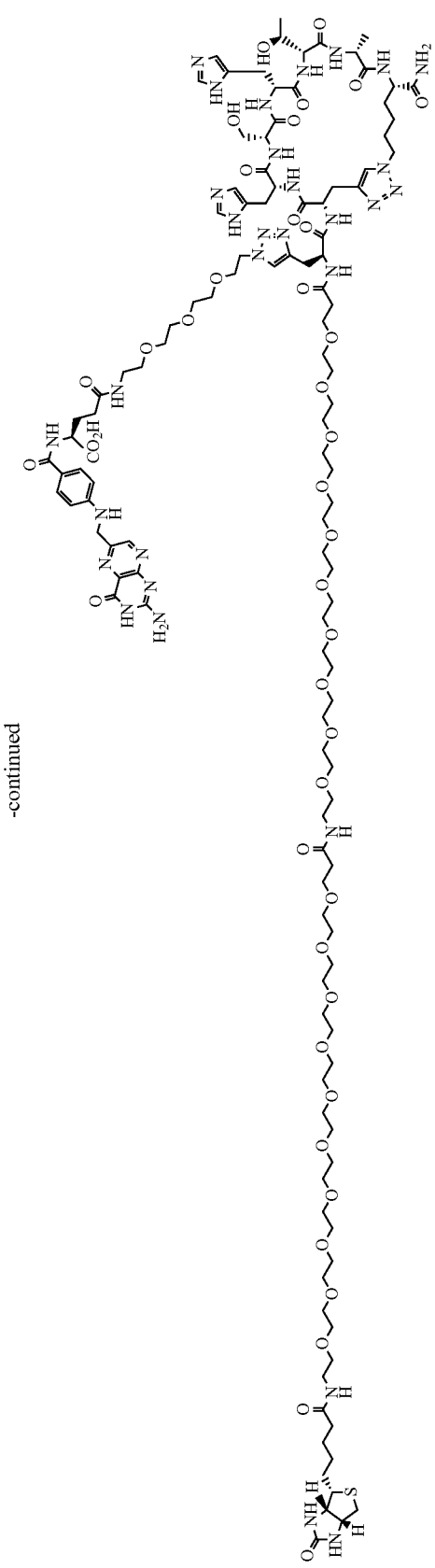
Folate-hshta (SEQ ID NO:6) Tz heterobiligand
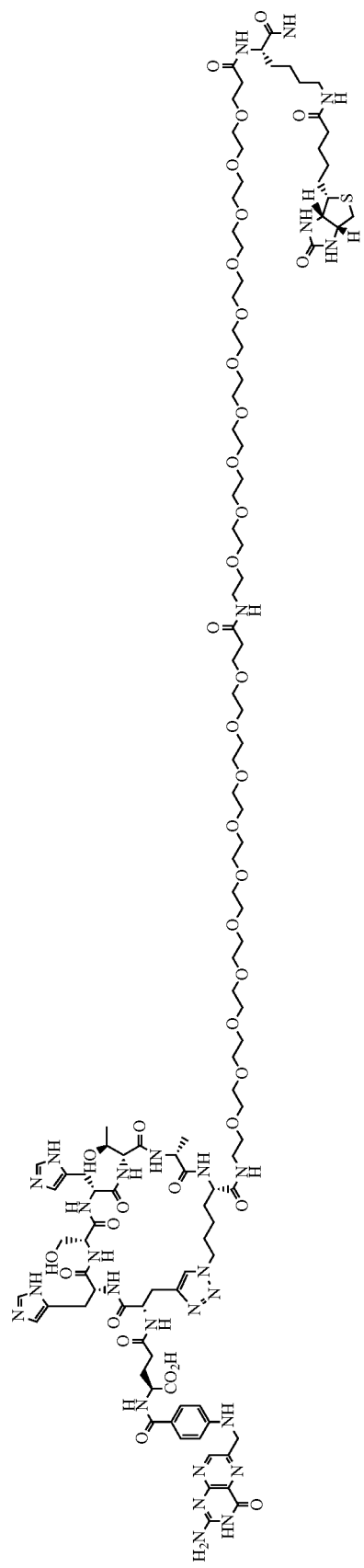
Folate-hshta (SEQ ID NO:6) NTerm heterobiligand Following the identification of promising hits, the compounds were evaluated by ELISA (FIG. 5). Tested alone, kyeet (SEQ ID NO:9) demonstrated only minimal binding affinity for FOLR1 ($EC_{50}$>10,000 nM). However, once conjugated to folic acid, the heterobiligand is a highly potent FOLR1 binder ($EC_{50}$=0.149 nM). This is over an order of magnitude greater than folic acid alone ($EC_{50}$=2.8 nM).

A second PCC with sequence hshta (SEQ ID NO:6) was also evaluated in an analogous workflow. Alone, hshta (SEQ ID NO:6) bound to FOLR1 with an $EC_{50}$ of 3917 nM. Attaching the natural ligand increased the affinity to sub-nanomolar levels. Two heterobiligand constructs were tested, one with folic acid attached to the PCC via click reaction (Tz heterobiligand) and the other attached directly to the N-terminus of the peptide (NTerm heterobiligand). Both constructs were superior to folic acid alone ($EC_{50}$=2.3 nM), with the NTerm heterobiligand (EC50=0.065 nM) outperforming the Tz construct (EC50=0.107 nM).

Figure 6:
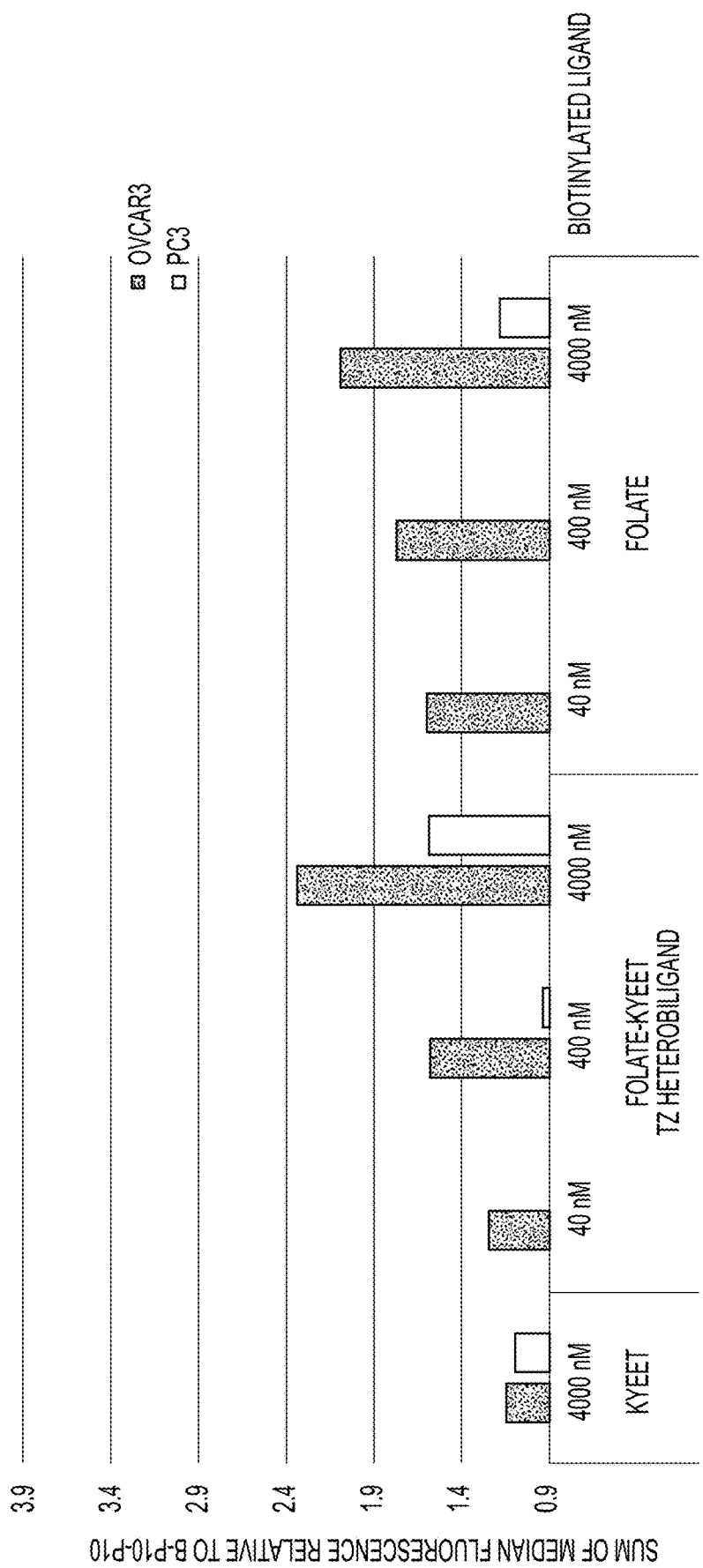
FIG. 6 is a graph binding of ligands and heterobiligands to FOLR1+ and FOLR1− cells assessed by flow cytometry.
Figure 7:
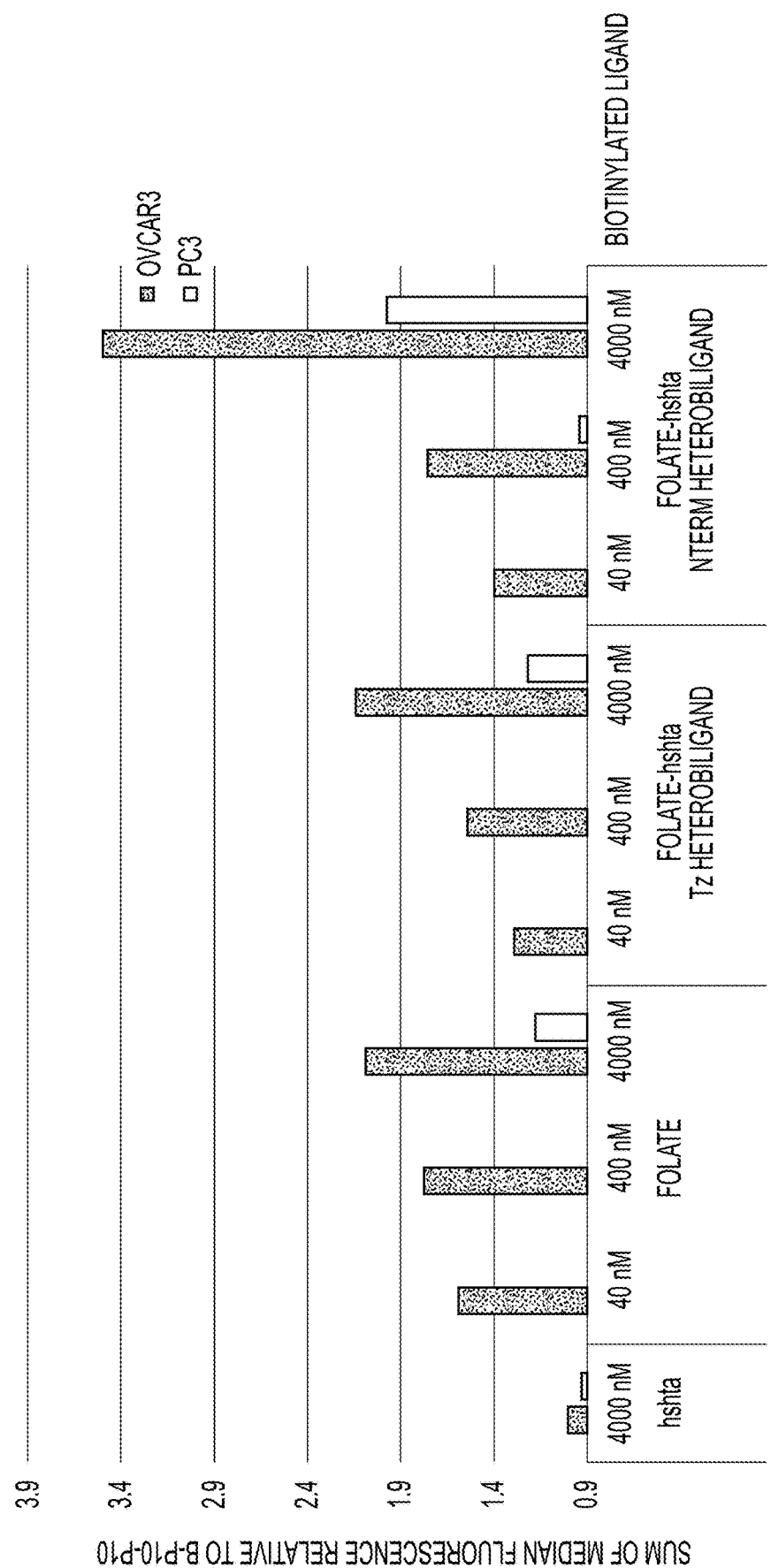
FIG. 7 is a graph binding of ligands and heterobiligands to FOLR1+ and FOLR1− cells assessed by flow cytometry.

Both the kyeet (SEQ ID NO:9) and hshta (SEQ ID NO:6)-derived biligands were tested by flow cytometry for binding to FOLR1 (+) and FOLR1 (−) cell lines (FIGS. 6 and 7). The human ovarian adenocarcinoma-derived cell line OVCAR3 has robust FOLR1 expression and was selected as the FOLR1 (+) cell line. The human prostate adenocarcinoma-derived cell line PC-3 was selected as a FOLR1 (−) cell line. Alone, kyeet (SEQ ID NO:9) showed slight binding selectivity for FOLR1 (+) cells over FOLR1 (−) cells (FIG. 6). The heterobiligand construct containing folic acid conjugated to kyeet demonstrated high selectivity for FOLR1 (+) cells in a dose-dependent manner Virtually complete selectivity was observed at 40 nM of the test article.

The alternative PCC hshta (SEQ ID NO:6) alone demonstrated higher selectivity for FOLR1 than kyeet (SEQ ID NO:9). While both the Tz and NTerm heterobiligands containing folic acid conjugated to hshta (SEQ ID NO:6) demonstrated high selectivity for FOLR1 (+) cells, the NTerm construct was superior (FIG. 7). The selectivity of the best performing folate-hshta (SEQ ID NO:6) NTerm heterobiligand was superior to a commercially available FOLR1 antibody. Non-specific PC3 signal can be titrated away while maintaining OVCAR3 binding at low test concentrations.

To optimize the distance and physicochemical properties of the linker connecting folic acid to the PCC hshta (SEQ ID NO:6), a small linker screen was undertaken. Rather than direct linkage of the PCC to folate, linkers of PEG7, Pro, and Gly were used. Increasing the spacer distance or adding peptidic character were detrimental to the heterobiligand when profiled by ELISA. This trend was also reflected in a cellular context: the parent compound with direct attachment of folic acid to the N-terminus of the peptide was optimal. The folate-deryt (SEQ ID NO:20) heterobiligand also shows good binding affinity against FOLR1 ($EC_{50}$=0.28 nM).

| Folate-hshta Nterm | Ec50 = 0.18 nM |
| Folate-deryt | Ec50 = 0.28 nM |
| Folate-PEG7-hshta | Ec50 = 1.0 nM |
| Folate-Pro-hshta | Ec50 = 0.9 nM |
| Folate-Gly-hshta | Ec50 = 0.9 nM |

Figure 8:
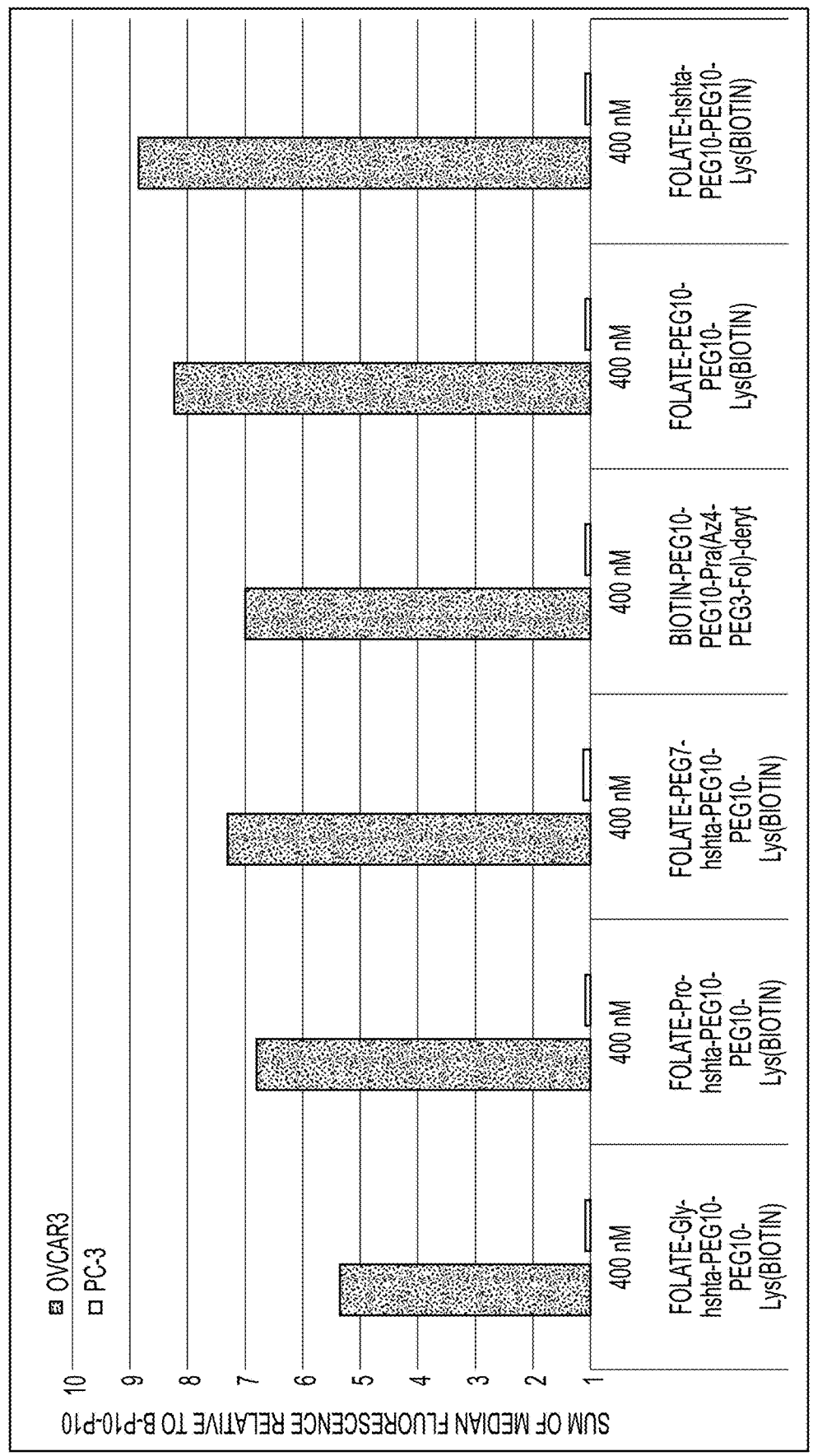
FIG. 8 is a graph binding of heterobiligands with different linkers to FOLR1+ and FOLR1− cells assessed by flow cytometry.

These varied linker heterobiligands were also tested by flow cytometry against OVCAR3 FOLR1+ and PC3 FOLR1− cells FIG. 8). Similar to ELISA, our lead heterobiligand demonstrates the best binding against OVCAR3 FOLR1+ cells. All compounds show little to no binding of PC3 FOLR1− cells. The specific structures of the tested heterobiligands are shown below.

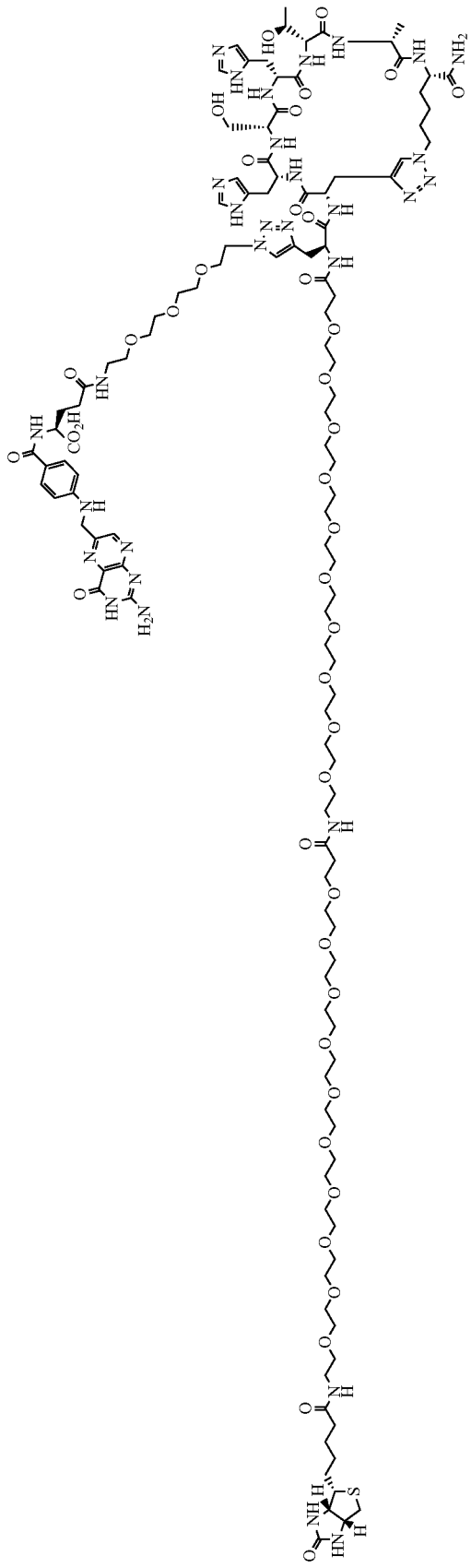

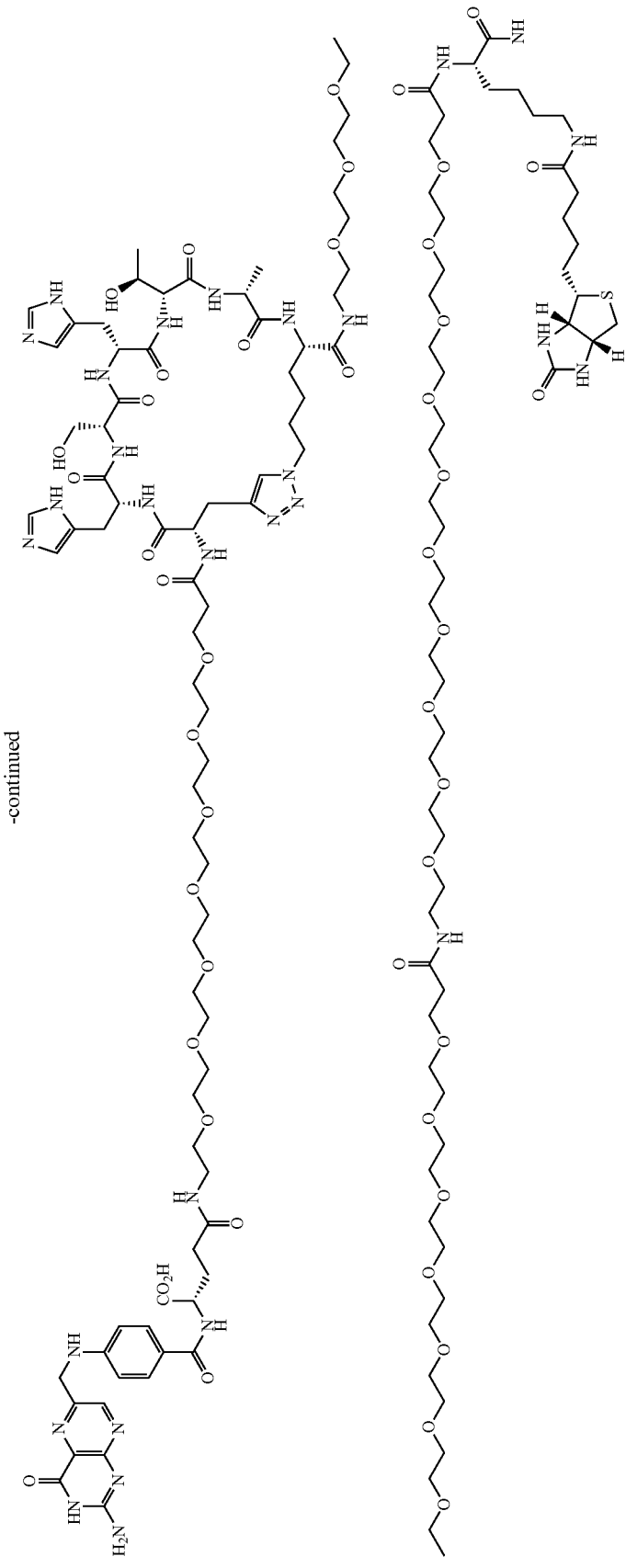
Folate-PEG7-hshta (SEQ ID NO:6) (folate-PEG7-hshta-PEG10-PEG10-Lys(Biotin))

-continued
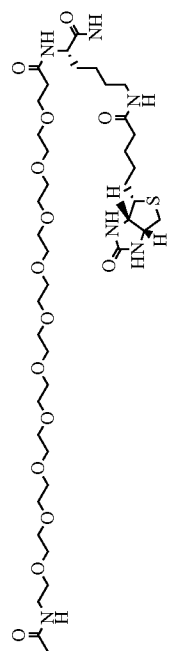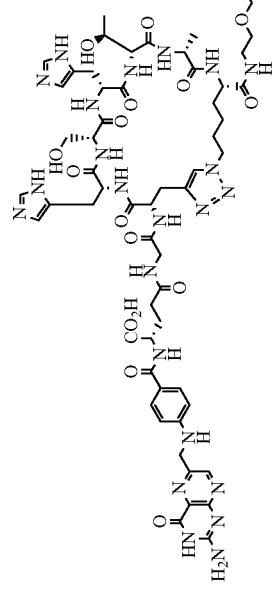
Folate-Gly-hshta (SEQ ID NO:6) (folate-Gly-hshta-PEG10-PEG10-Lys(Biotin))
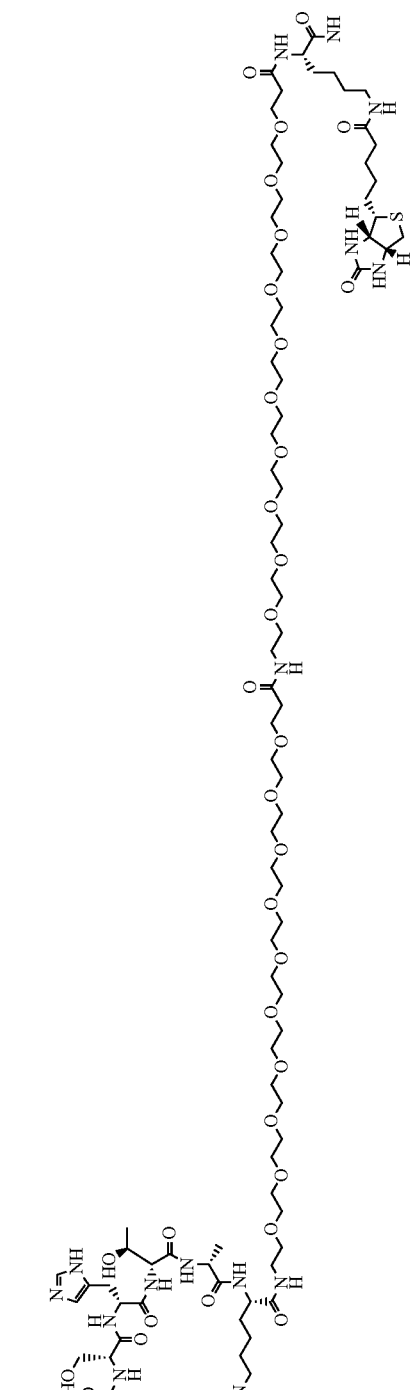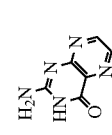
Folate-Pro-hshta (SEQ ID NO:6) (folate-d-Pro-hshta-PEG10-PEG10-Lys(Biotin))

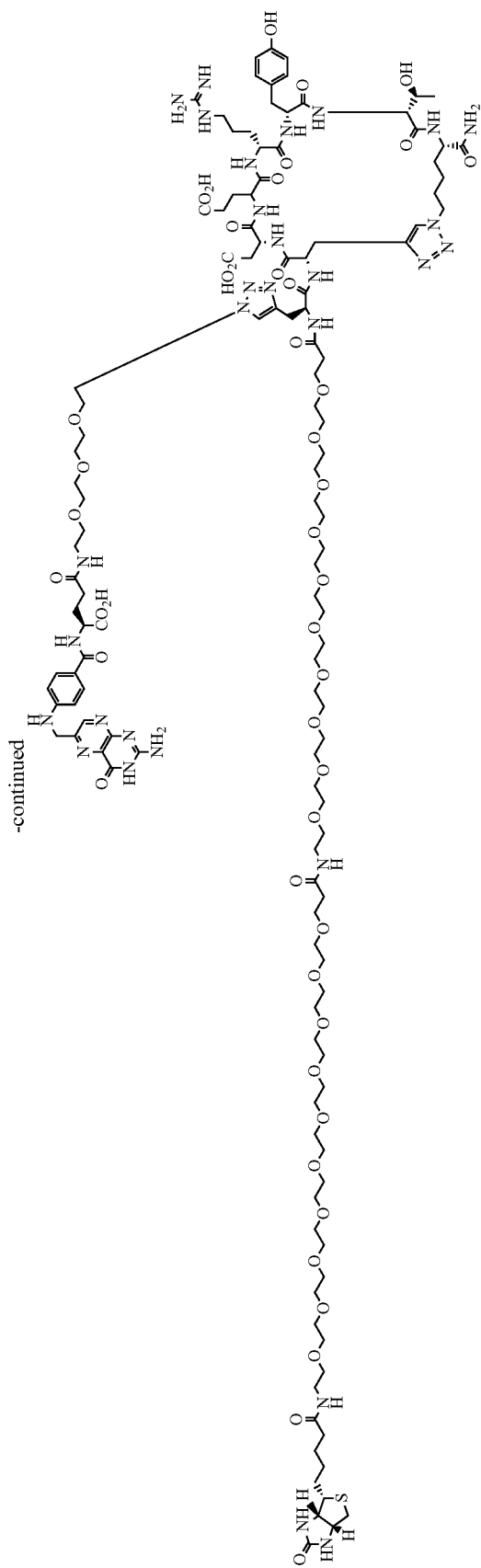
Folate-deryt (SEQ ID NO:20) (Bio-PEG10-PEG10-Pra(Az4-PEG3-Folate)-deryt)

A competition experiment was conducted to further understand the binding kinetics of the lead heterobiligand (folate-hshta (SEQ ID NO:6) Nterm heterobiligand). The natural ligand folic acid was doped into the Nterm heterobiligand dilution series at increasing concentrations to identify a concentration of folic acid that would worsen the apparent affinity of the heterobiligand for FOLR1. At concentrations of folic acid from 0 to 500 nM the binding affinity of the heterobiligand is virtually unchanged. Higher concentration of folic acid (greater than 500 nM) can partially compete away the heterobiligand.

Figure 9:
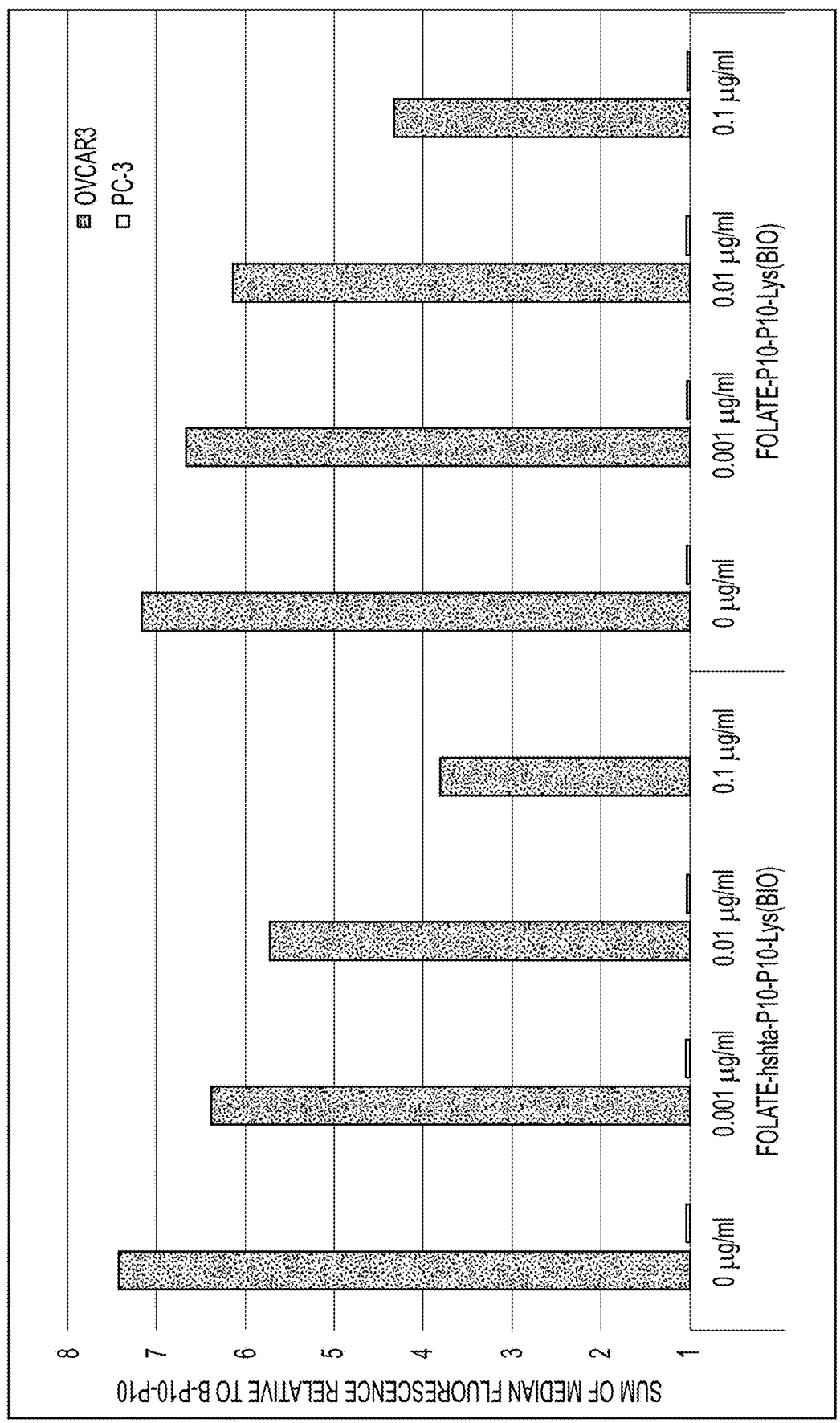
FIG. 9 is a graph binding of different concentrations of heterobiligands to FOLR1+ and FOLR1− cells assessed by flow cytometry.

Competition at the cellular level was also probed. Biotinylated heterobiligand or biotinylated folic acid was incubated with OVCAR3 or PC-3 cells (FIG. 9). At increasing levels of exogenous folic acid, the heterobiligand was more resilient to folic acid displacement than biotinylated folic acid. The heterobiligand and biotinylated folic acid maintained high selectivity for FOLR1 (+) cells. An inverse trend of increased binding of the ligands with the reduction of free folic acid was observed. The percentage of OVCAR3 cells binding to biotinylated heterobiligand was reduced from 76.6% (no folate) to 57% (0.1 µg/mL folate).

Figure 10:
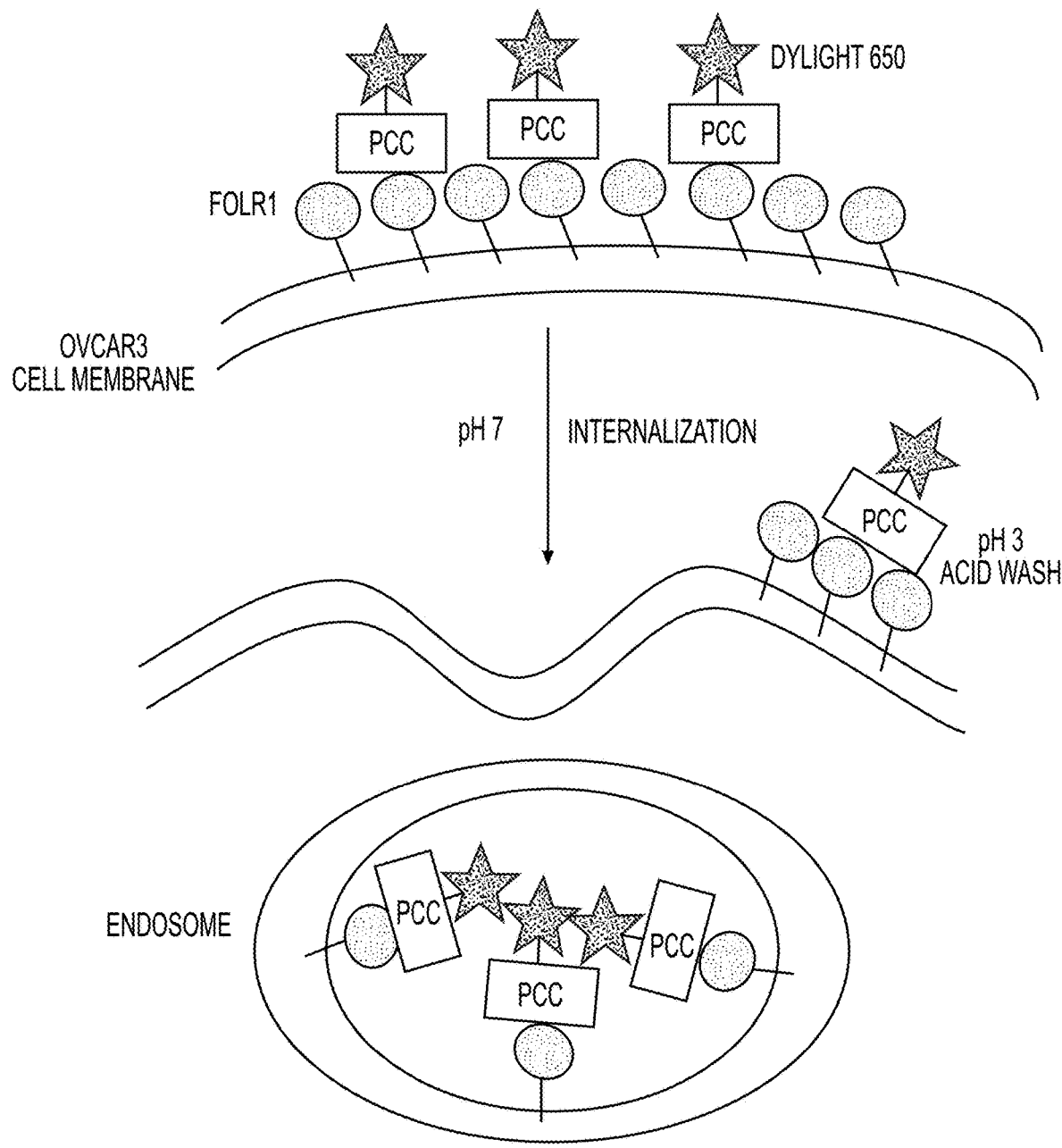
FIG. 10 is a diagram of an assay for assessing cell internalization FOLR1 heterobiligands.

The folate-hshta (SEQ ID NO:6) Nterm heterobiligand was also evaluated in cell penetration imaging assays (FIG. 10). OVCAR3 and PC-3 cells were incubated with the test article at 37° C. for 1 hour. Flow cytometry analysis of the resulting treated cells indicated strong binding to FOLR1 (+) cells. To understand the proportion bound to the surface but not internalized, the cells were briefly washed with acid to liberate the non-internalized peptide. Following acid treatment, the percentage of positively stained cells decreases modestly from 73.4% to 54.2%. This suggests that a larger portion of the positive staining is the result of internalization and not cell surface binding.

To further understand intracellular trafficking of the Nterm heterobiligand, these dye-labeled compounds were imaged by fluorescence microscopy. The cells were counterstained with BioTracker 490, which stains membranes, and Rab5a+, an endosomal stain. The heterobiligand labeled with DyLight 650 demonstrated internalization with clear preference for early endosomes. This colocalization with the endosomal dye suggests receptor-mediated endocytosis. Low levels of DyLight650 was detected within PC-3 (FOLR1−) cells. Taken together, internalization of the heterobiligand appears to be receptor driven and selective for FOLR1 (+) cells.

Further evaluation of the folate-hshta (SEQ ID NO:6) Nterm heterobiligand depended on cross reactivity with mouse recombinant FOLR1 (rMuFOLR1). The heterobiligand binds to both species' variants of FOLR1 with high affinity. This observation was expected given the high homology between the two variants (approximately 92%).

| | | |
|---|---|---|
| Folate-hshta Nterm | Mouse FOLR1 | Ec50 = 0.33 nM |
| Folate-hshta Nterm | Human FOLR1 | Ec50 = 0.35 nM |
| Biotinylated Folate | Mouse FOLR1 | Ec50 = 0.46 nM |
| Biotinylated Folate | Human FOLR1 | Ec50 = 0.82 nM |
| Biotinylated hshta | Mouse FOLR1 | Ec50 = 2100 nM |
| Biotinylated hshta | Human FOLR1 | Ec50 = 3400 nM |
| Biotinylated Folate | Mouse FOLR1 | Ec50 = 0.60 nM |
| Biotinylated Folate | Human FOLR1 | Ec50 = 0.89 nM |
| Biotin | Mouse FOLR1 | |
| Biotin | Human FOLR1 | |

Figure 11:
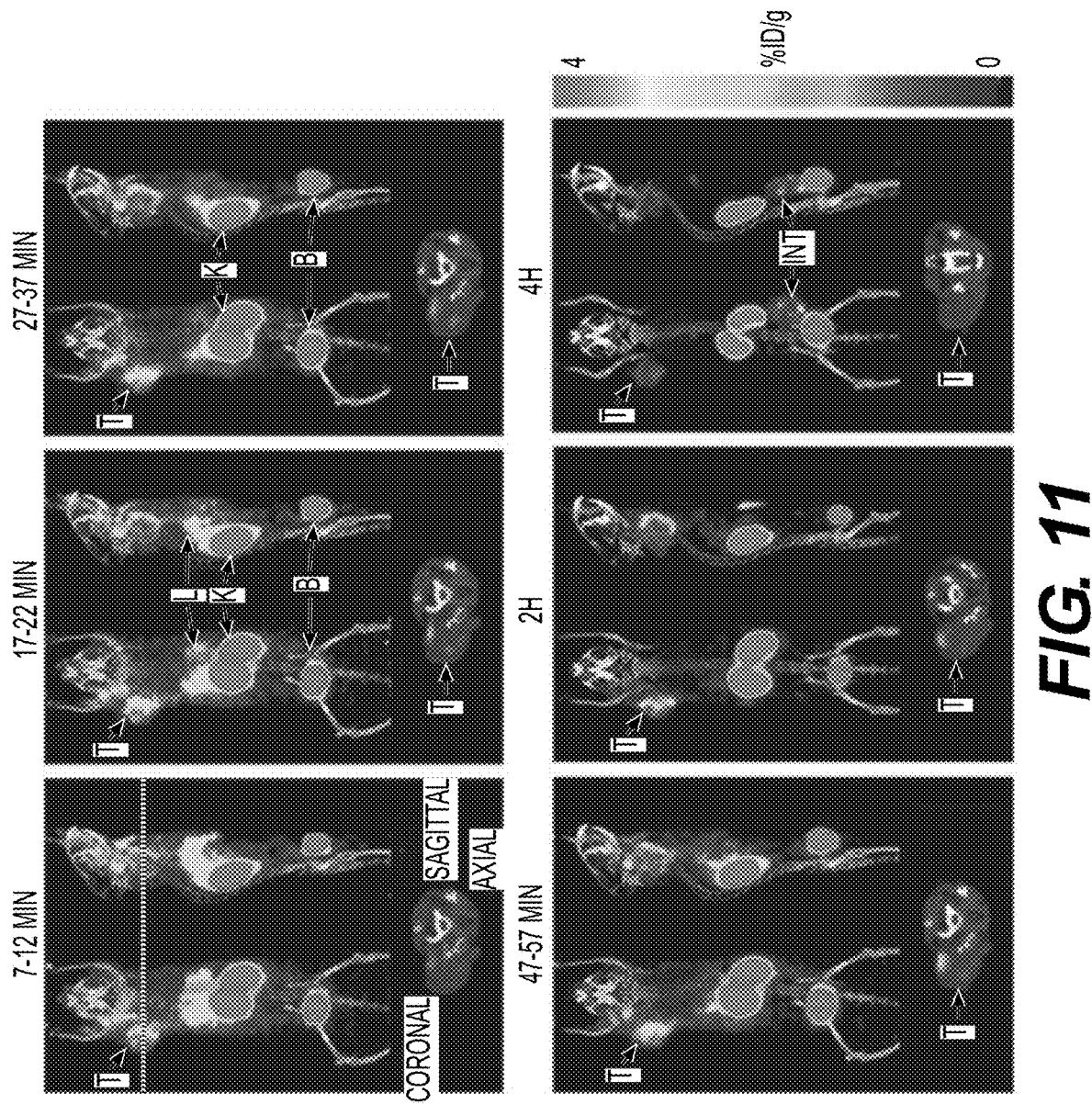
FIG. 11 is PET imaging data for an $^{18}$F-labeled heterobiligand detected in a tumor-bearing mouse over time. T, tumor; L, liver; K, kidney; B, bladder; Int, intestine.
Figure 12:
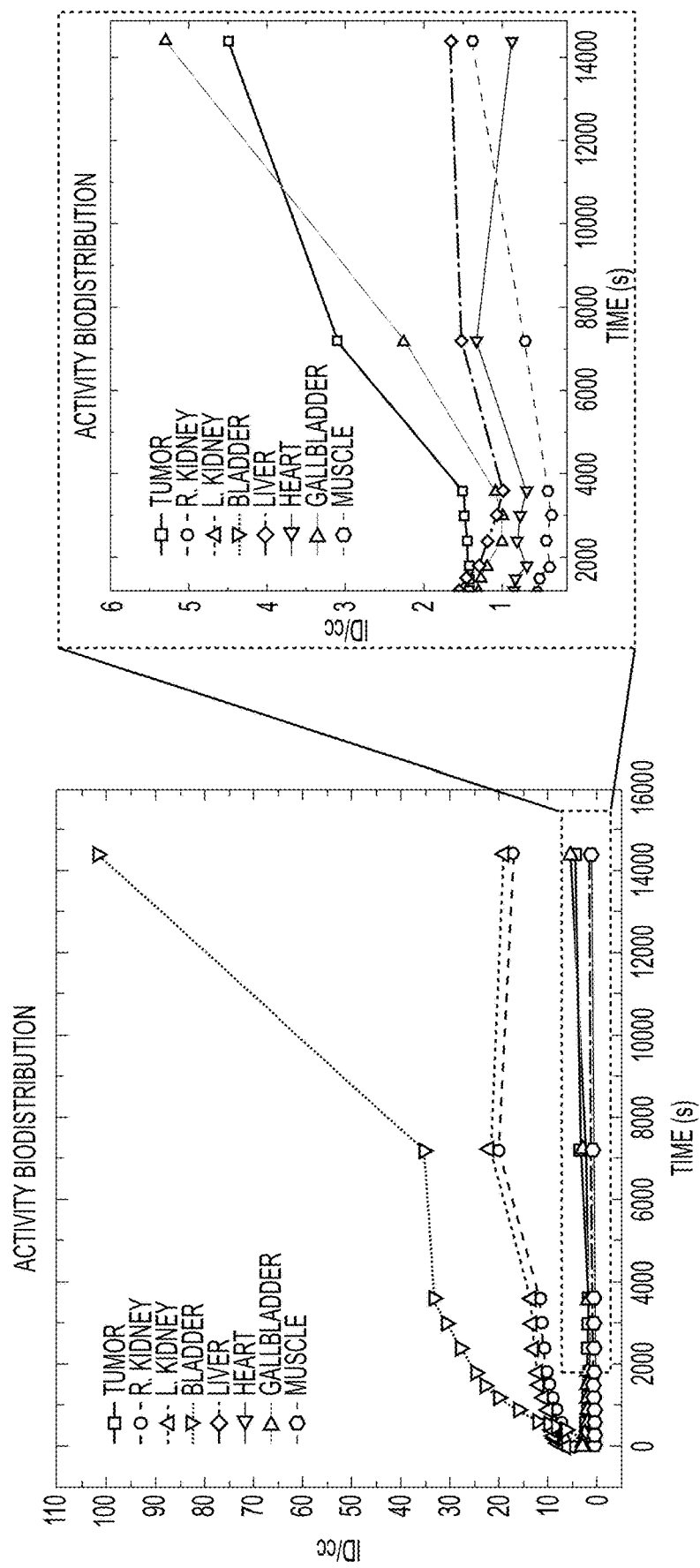
FIG. 12 is the time-course biodistribution analysis to quantify the uptake of an $^{18}$F heterobiligand in a tumor-bearing mouse.
Figure 13:
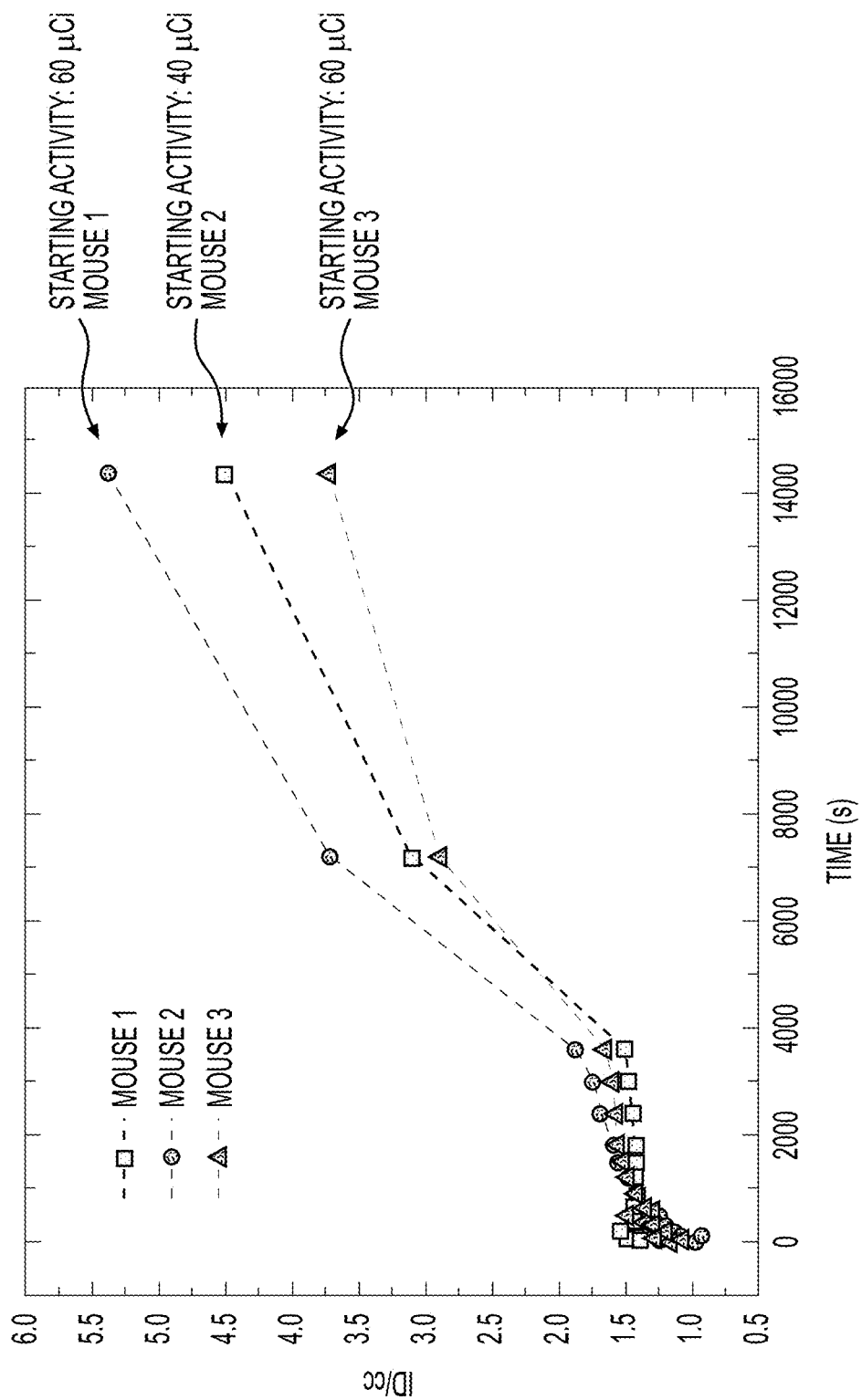
FIG. 13 is a cross trial comparison of three mice showing radiotracer accumulation in the tumor.

NSG mice were engrafted with OVCAR3 cells subcutaneously. Once the tumor had reached around 0.8 cm diameter, they were treated with parenteral $^{18}$F-labeled folate-hshta (SEQ ID NO:6) Nterm heterobiligand and evaluated by PET/CT imaging $^{18}$F PET/CT imaging scans were performed at 0-1 h (dynamic), 2 h (static), and 4 h (static). All time points measured out to 4 hours exhibited substantial tumor uptake of the radiotracer (FIG. 11). Absorption of the radiotracer by highly perfused organs including the lungs indicate systemic circulation of the compound. Compound clearance is driven at the very early timepoints by a combination of hepatic and renal excretion. Over time, clearance is exclusively renal with retention of the compound in the tumor, and kidney. Accumulation in the mouse kidney is not surprising given the high expression of FOLR1 in this organ and the demonstrated cross reactivity of the heterobiligand with muFOLR1. The time-course biodistribution of $^{18}$F-labeled folate-hshta (SEQ ID NO:6) Nterm heterobiligand was calculated to quantify the uptake in major organs including the tumor (FIG. 12). Accumulation of $^{18}$F-labeled folate-hshta (SEQ ID NO:6) Nterm heterobiligand is observed in the tumor with ~4% of the injected dose/cc at 4 h post injection. A cross trial comparison of three mice shows radiotracer accumulation in the tumor ranging from 3.5% and 5.5% of the injected dose/cc at 4 h post injection (FIG. 13).

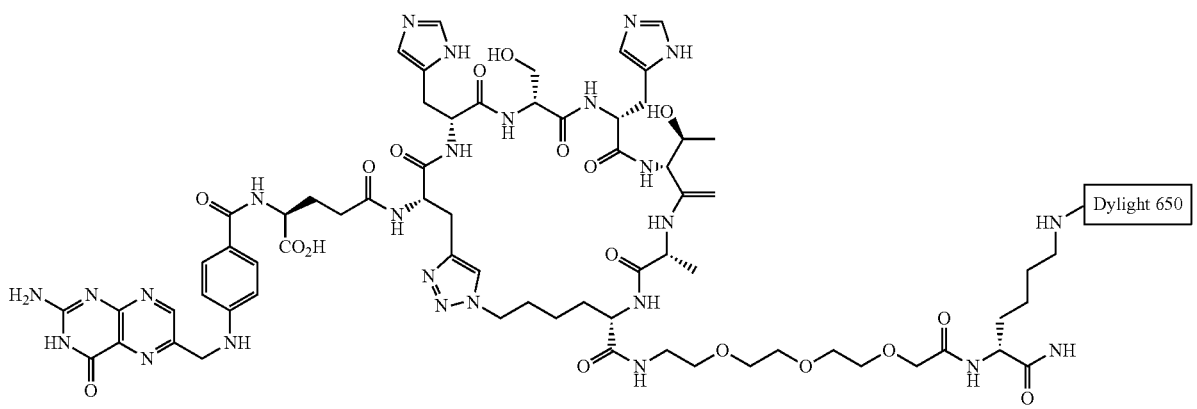 [SMILES: C=C1N[C@H](C)C(=O)N[C@H](C(=O)NCCOCCOCCOCC(=O)N[C@H](CCCCNC)C(N)=O)CCCCn2cc(nn2)C[C@H](NC(=O)CC[C@H](NC(=O)c2ccc(NCc3cnc4nc(N)[nH]c(=O)c4n3)cc2)C(=O)O)C(=O)N[C@H](Cc2cnc[nH]2)C(=O)N[C@H](CO)C(=O)N[C@H](Cc2cnc[nH]2)C(=O)N[C@@H]1[C@H](C)O]

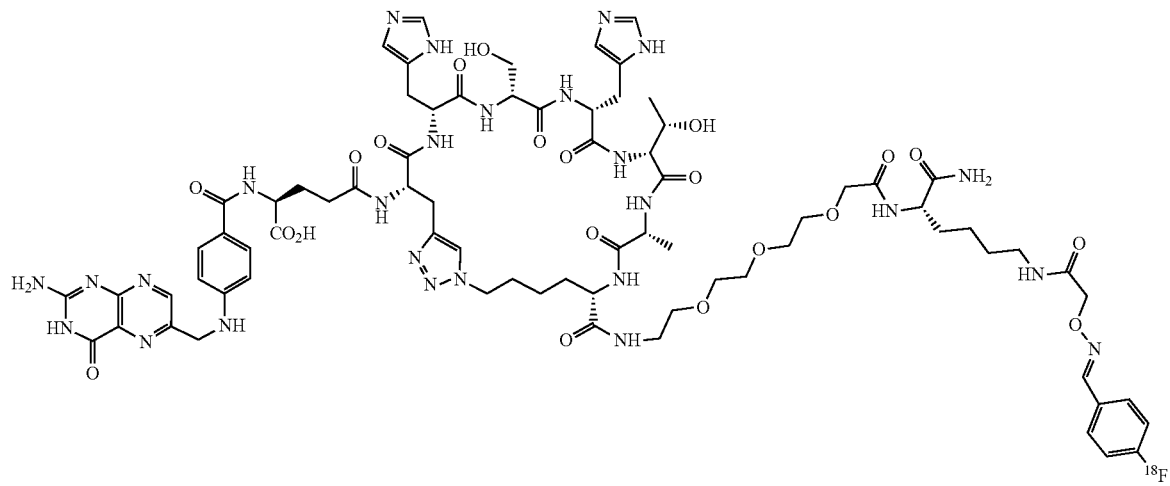

$^{18}$F-labeled folate-hshta (SEQ ID NO:6) Nterm heterobiligand (folate-hshta-PEG3-Lys(FBA))

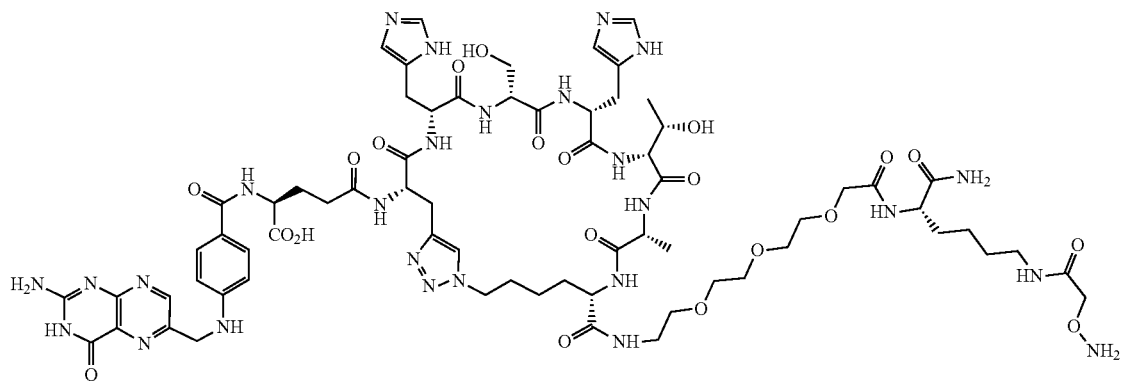

folate-hshta (SEQ ID NO:6) Nterm heterobiligand (folate-hshta-PEG3-Lys(AO))

A biotin-labeled albumin binding heterobiligand was synthesized to verify the heterobiligand binds to FOLR1 with acceptable affinity and to confirm albumin binding. A biotin-labeled heterobiligand was also synthesized to verify the DOTA does not interfere with binding.

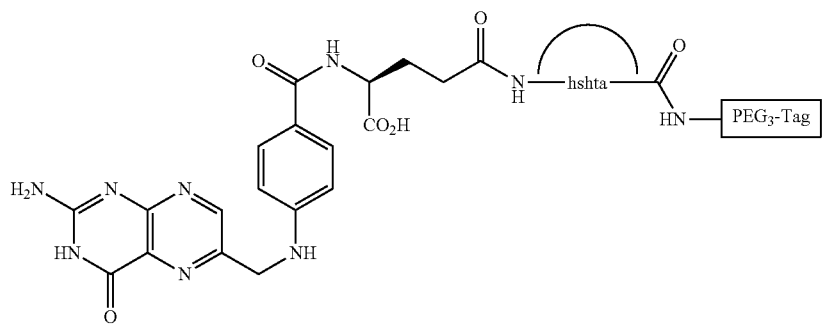

where Tag=Lys(4-MPBA)-PEG10-PEG10-Lys(Biotin) for albumin binder and Lys(DOTA)-PEG10-PEG10-Lys(Biotin) for chelate.

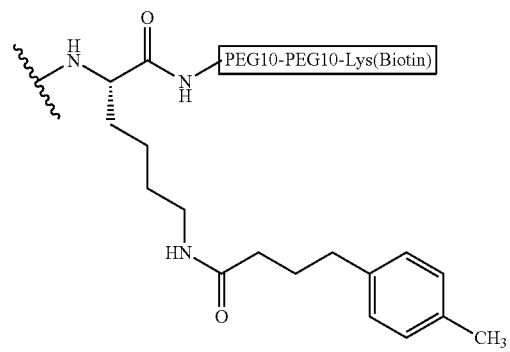

Lys(4-MPBA)-PEG10-PEG10-Lys(Biotin) for albumin binder

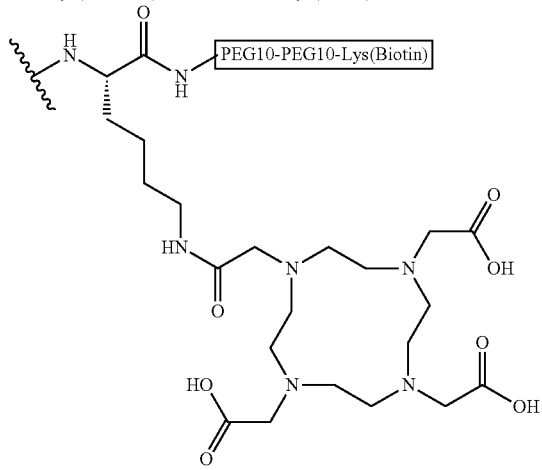

Lys(DOTA)-PEG10-PEG10-Lys(Biotin)

Figure 14:
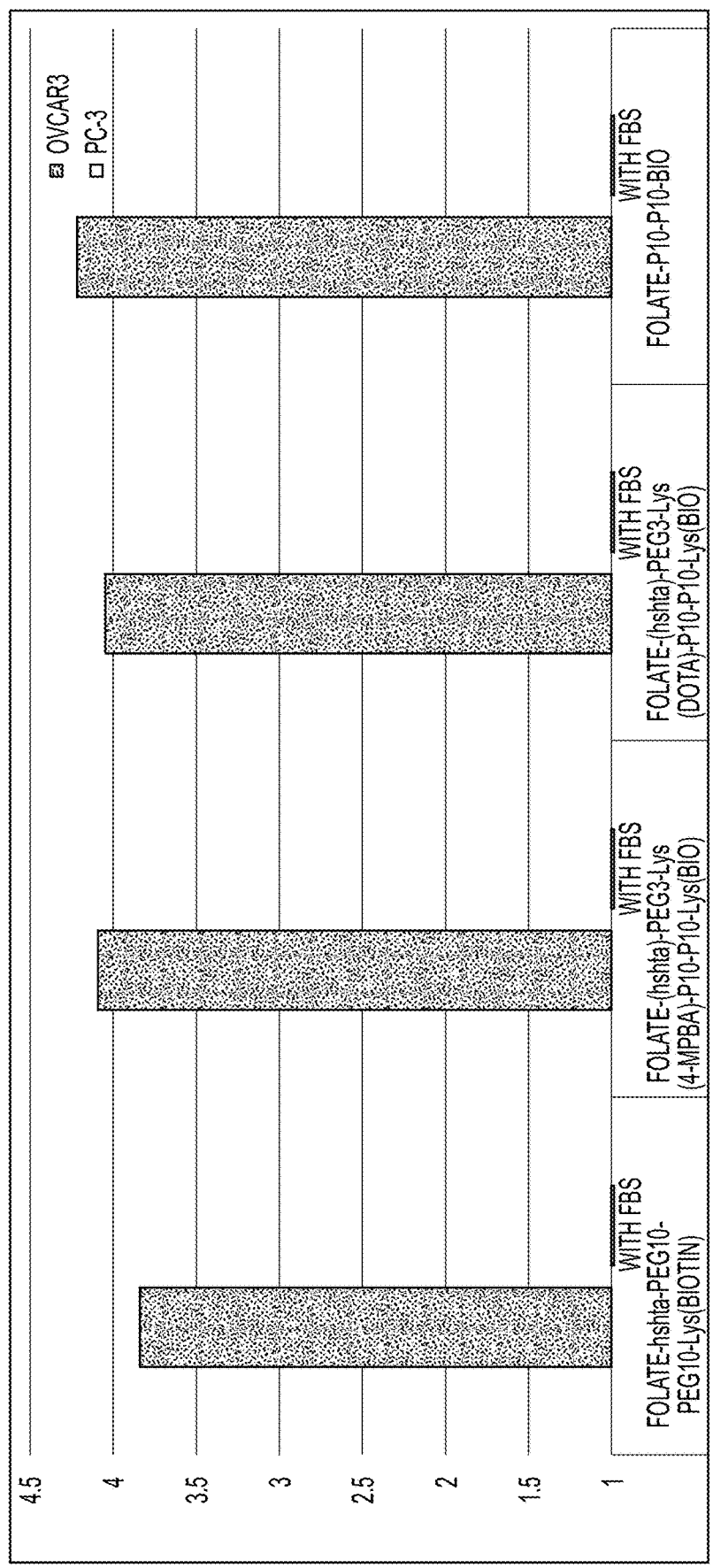
FIG. 14 is a graph binding of heterobiligands with DOTA, MPBA, or both to FOLR1+ and FOLR1− cells assessed by flow cytometry.

Increasing the serum-bound fraction of the peptide may decrease first pass removal of the heterobiligand, and drive compound retention of tumor over kidney. Constructs bearing the known albumin binder 4-methylphenyl butyric acid (4-MPBA) were synthesized. These compounds were evaluated in vitro to verify binding fidelity to FOLR1. The modified heterobiligands were incubated at 400 nM with OVCAR3 and PC-3 cells for 20 minutes at 37° C. in complete media containing 20% FBS. They both bind to OVCAR3 FOLR1+ cells with similar binding affinities as the original heterobiligand studied (FIG. 14). Gratifyingly, the addition of the albumin binding moiety does not impact binding to the target. Similar activity of these heterobiligands is anticipated in vivo.

|  | $EC_{50}$ |
|---|---|
| Folate-hshta | 0.065 nM |
| Folate-hshta-MPBA | 0.110 nM |
| Folate-hshta-DOTA | 0.098 nM |
| Folate | 2.3 nM |

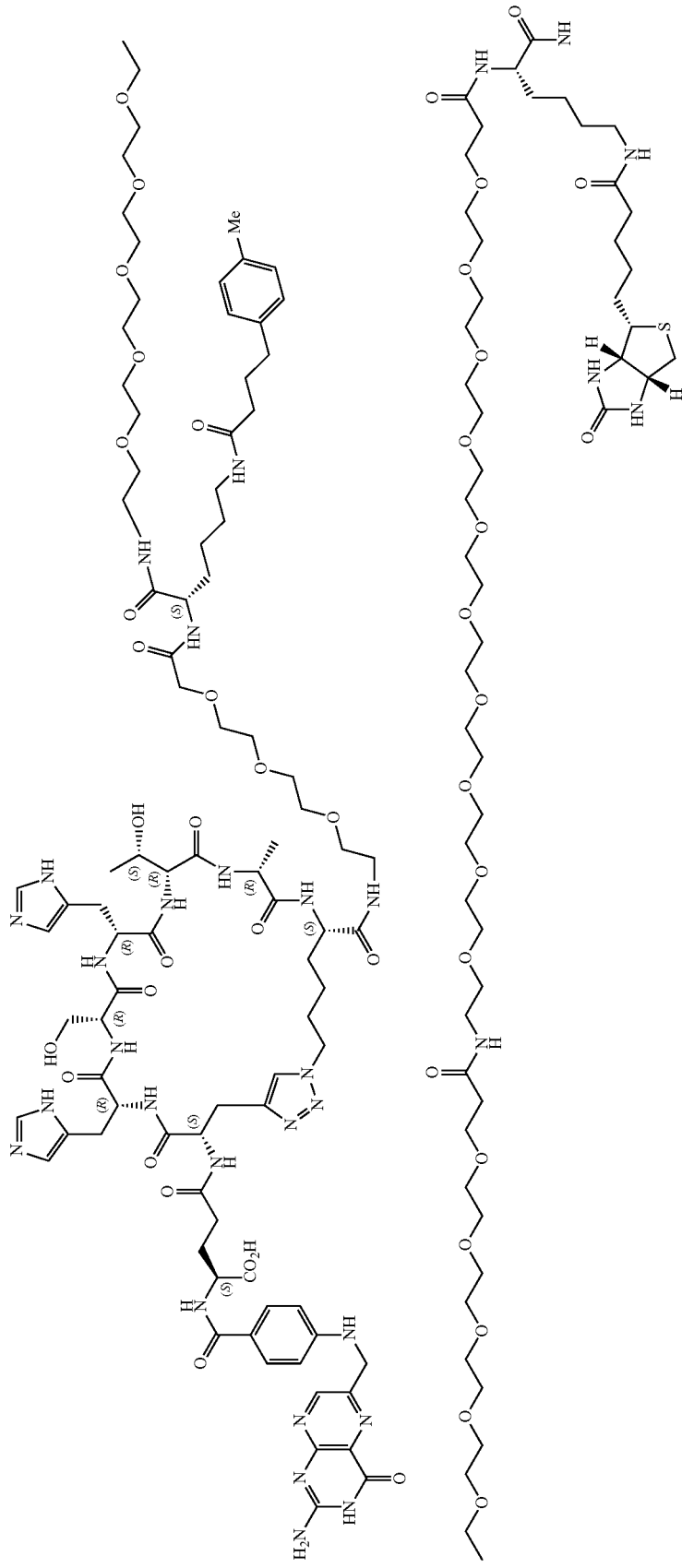
Folate-hshta-MPBA (SEQ ID NO:6)

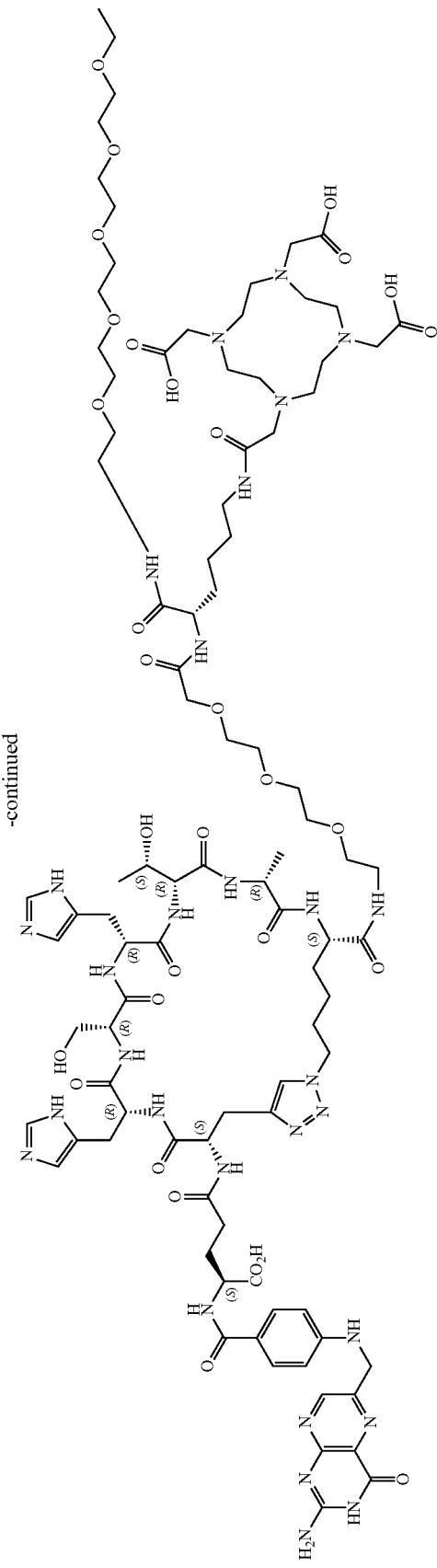
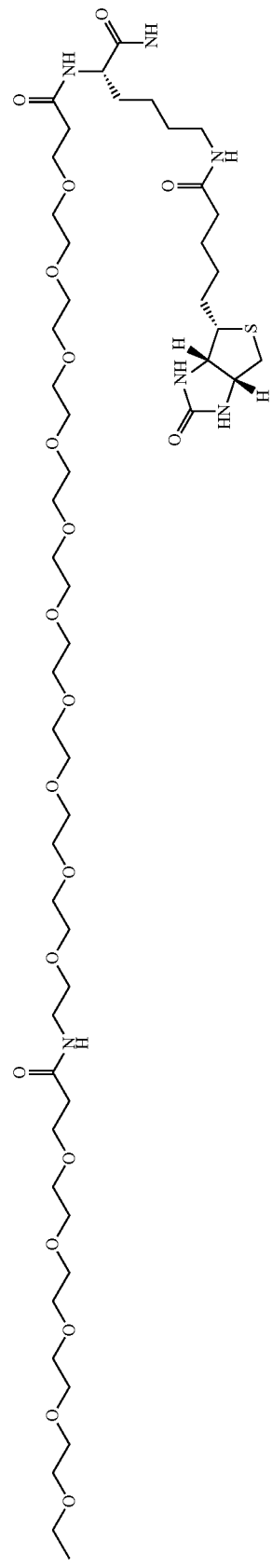
Folate-hshta-DOTA (SEQ ID NO:6)

Figure 15:
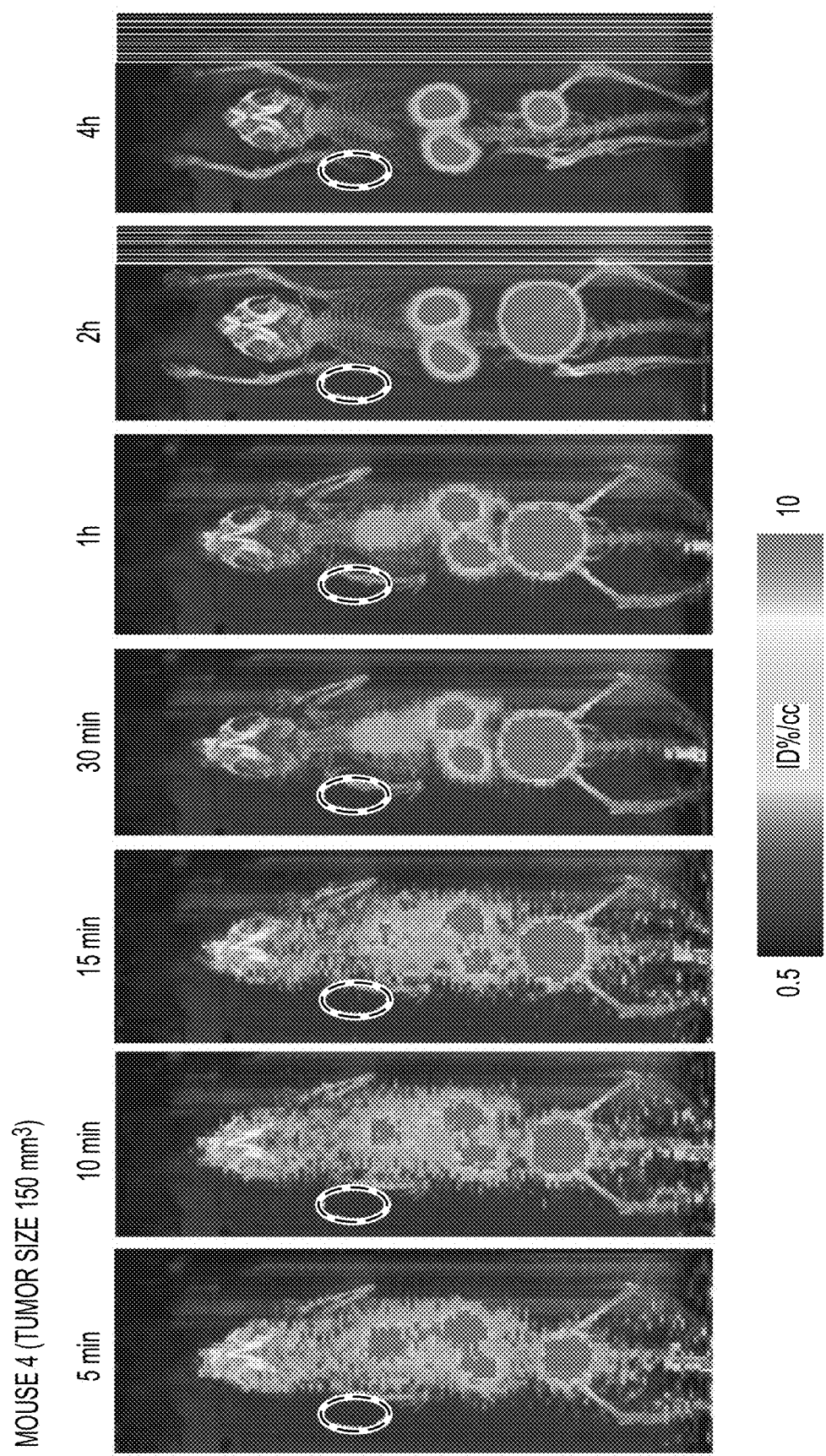
FIG. 15 is PET imaging data for a $^{68}$Ga-labeled heterobiligand detected in a mouse over time at early tumor size.
Figure 16:
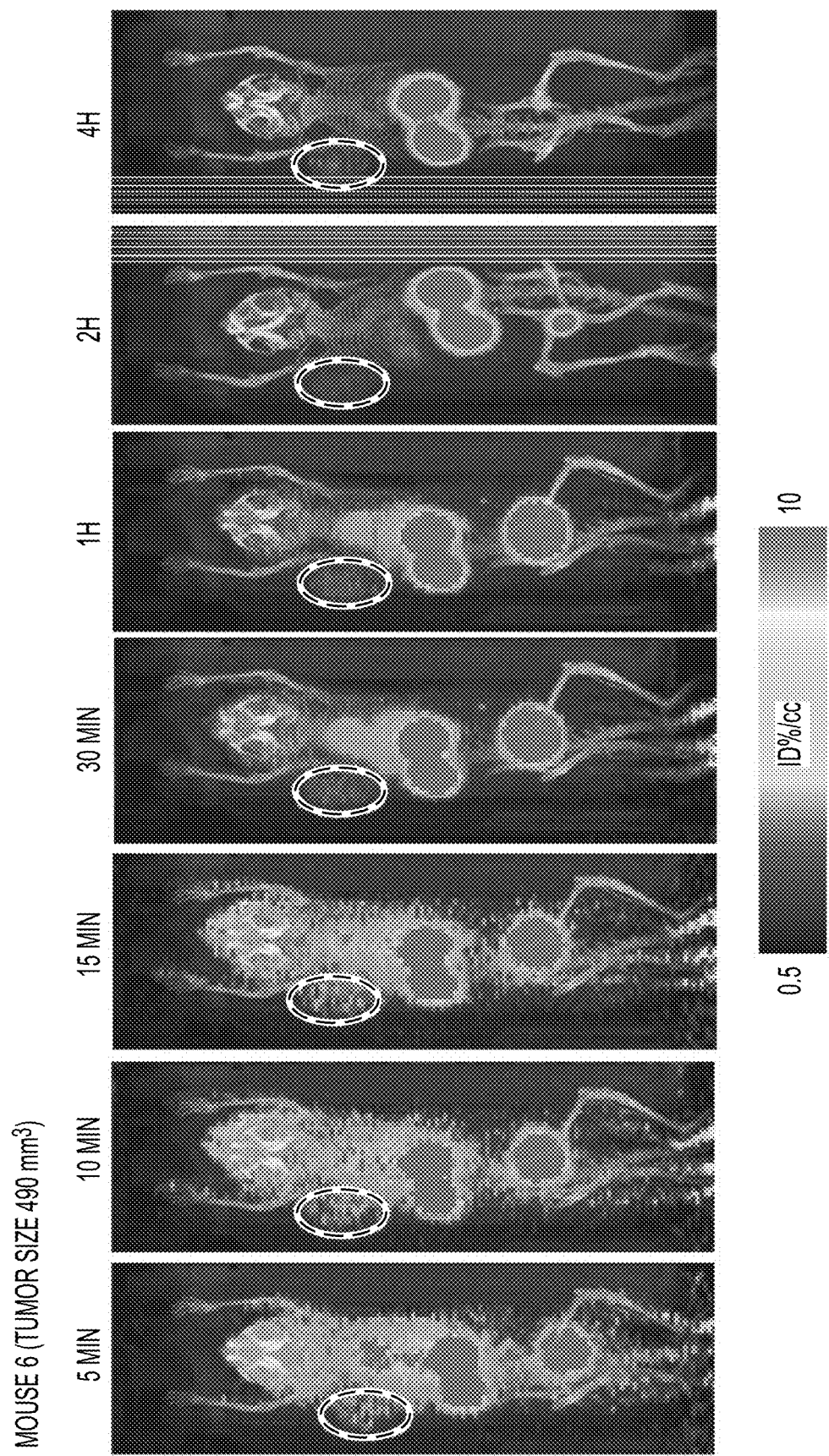
FIG. 16 is PET imaging data for a $^{68}$Ga-labeled heterobiligand detected in a mouse over time at larger tumor size.
Figure 17A:
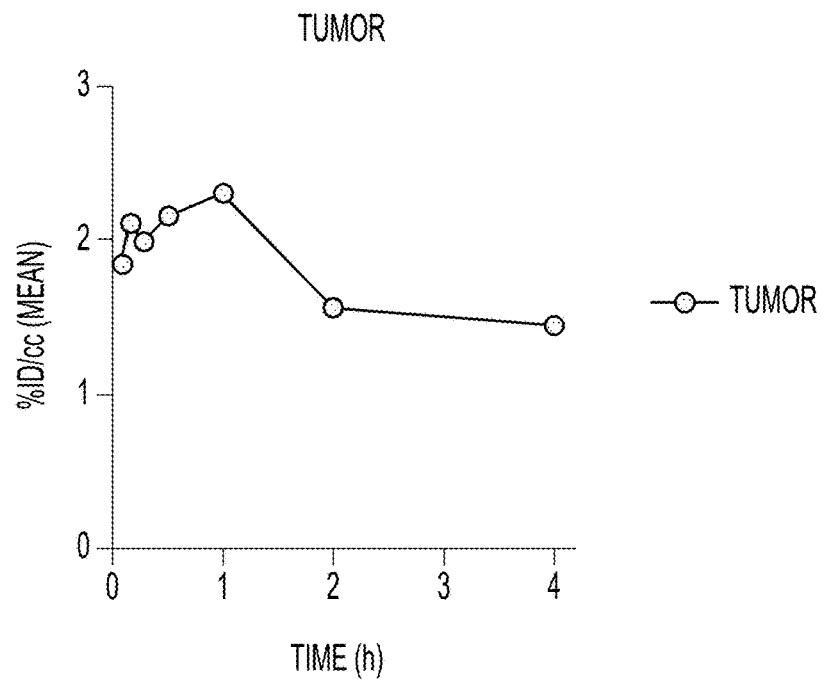
FIGS. 17A-17F are graphs of $^{68}$Ga-labeled heterobiligand over time in various tissues of two mice: mouse 4, with a tumor size of 150 mm$^3$, and mouse 6, with a tumor size of 490 mm3.
Figure 17B:
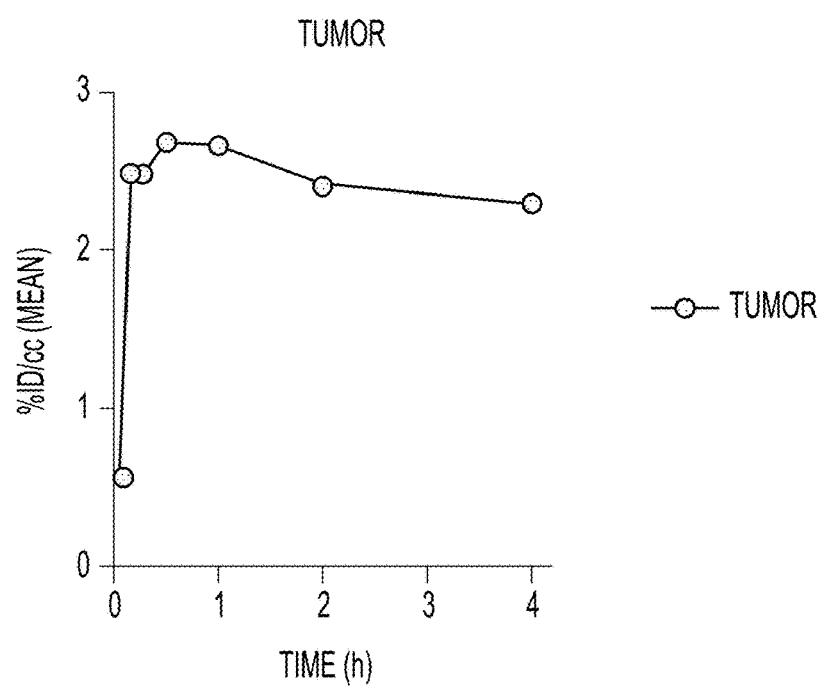
Figure 17C:
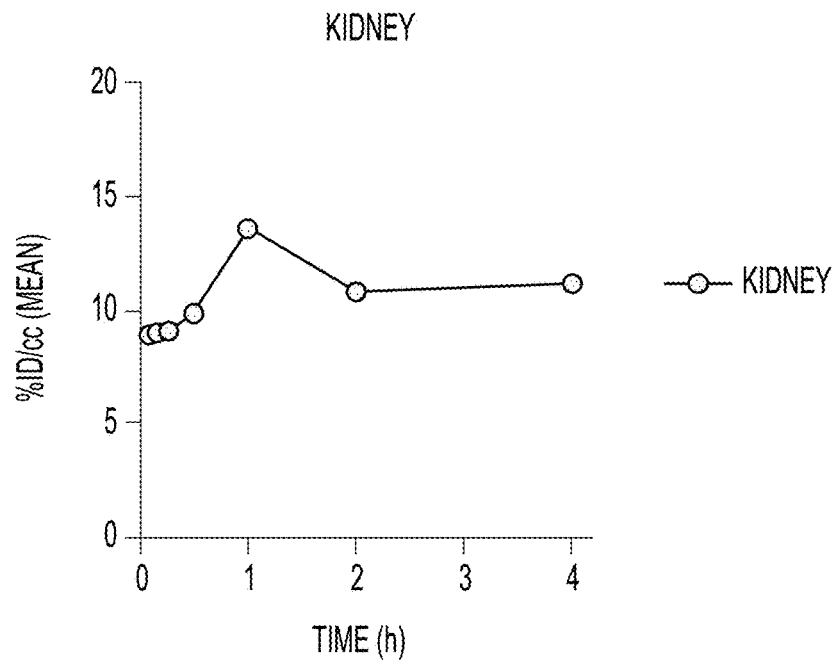
Figure 17D:
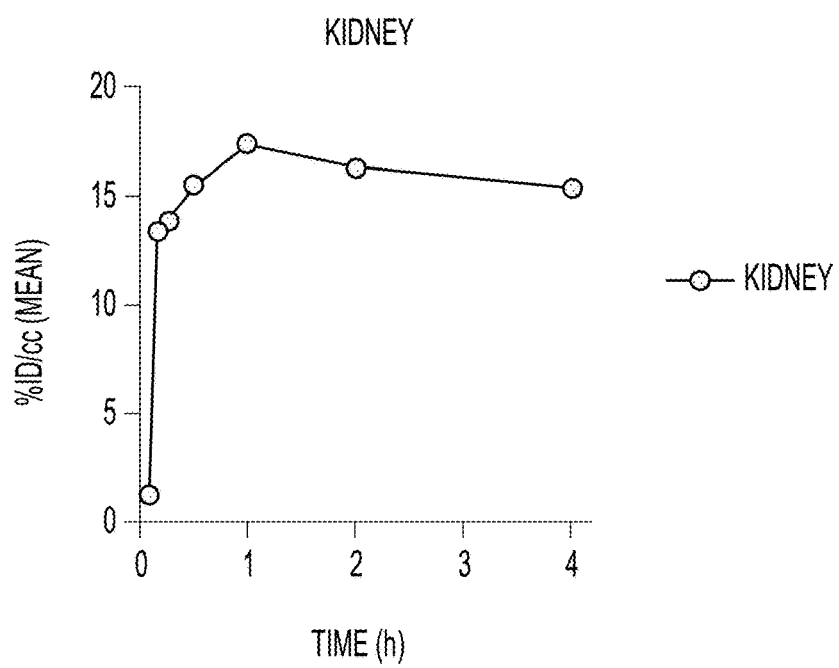
Figure 17E:
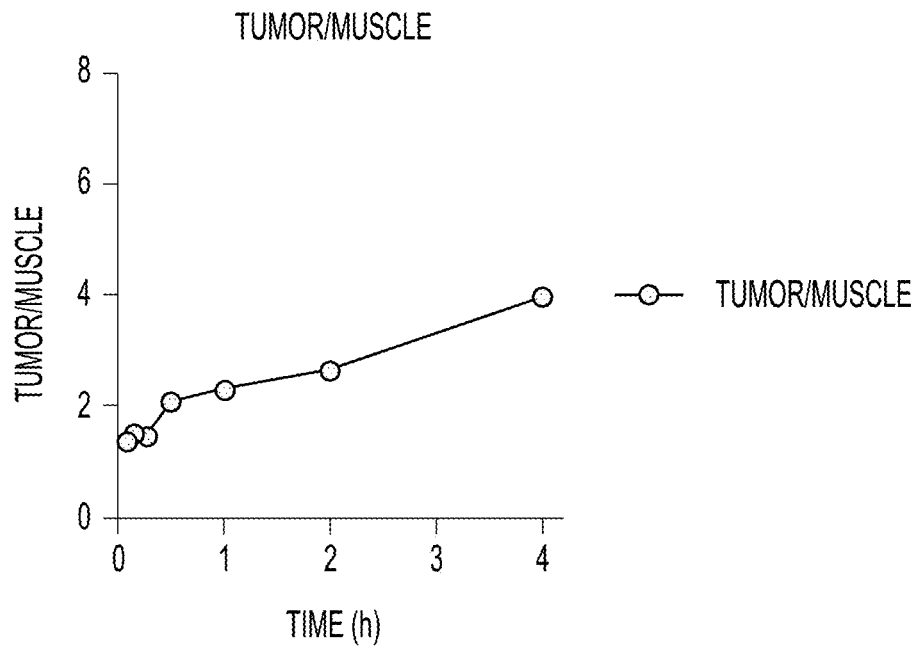
Figure 17F:
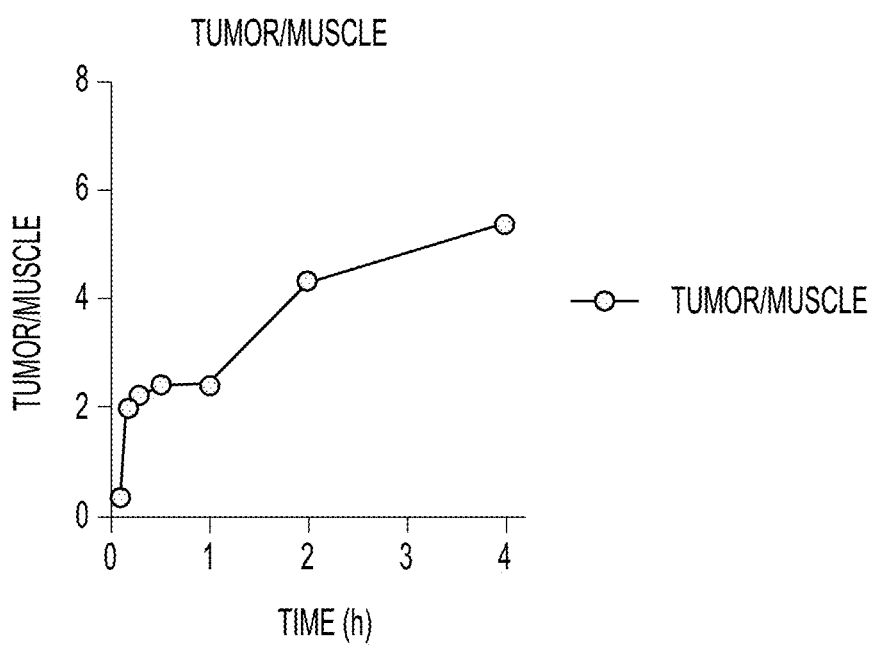
Figure 17G:
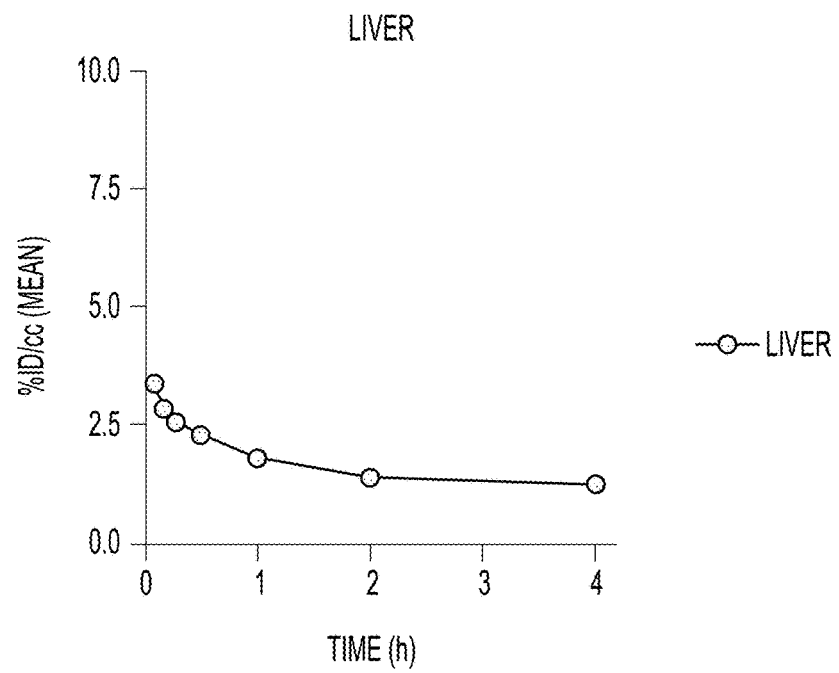
FIG. 17G is liver in mouse 4.
Figure 17H:
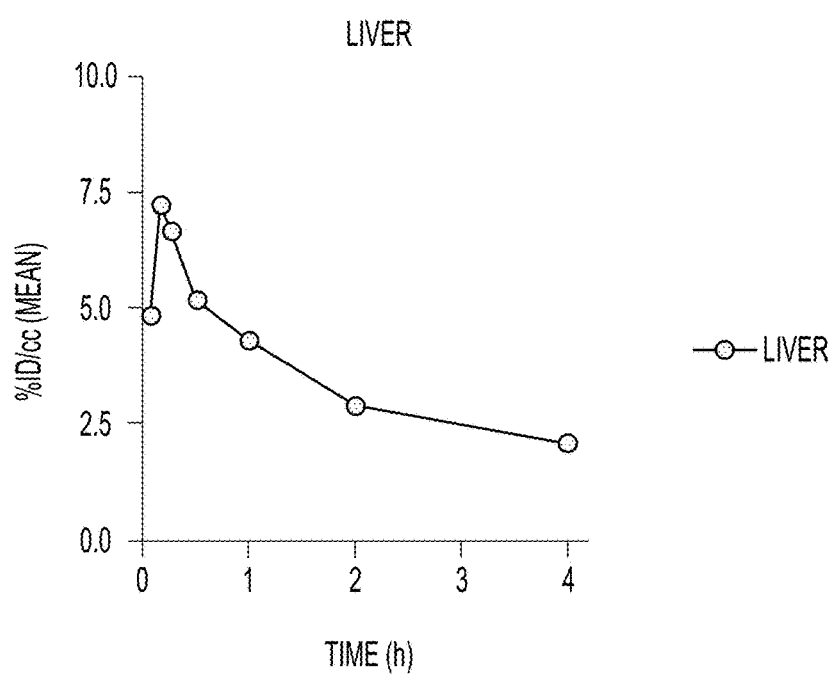
FIG. 17H is liver in mouse 6.
Figure 17I:
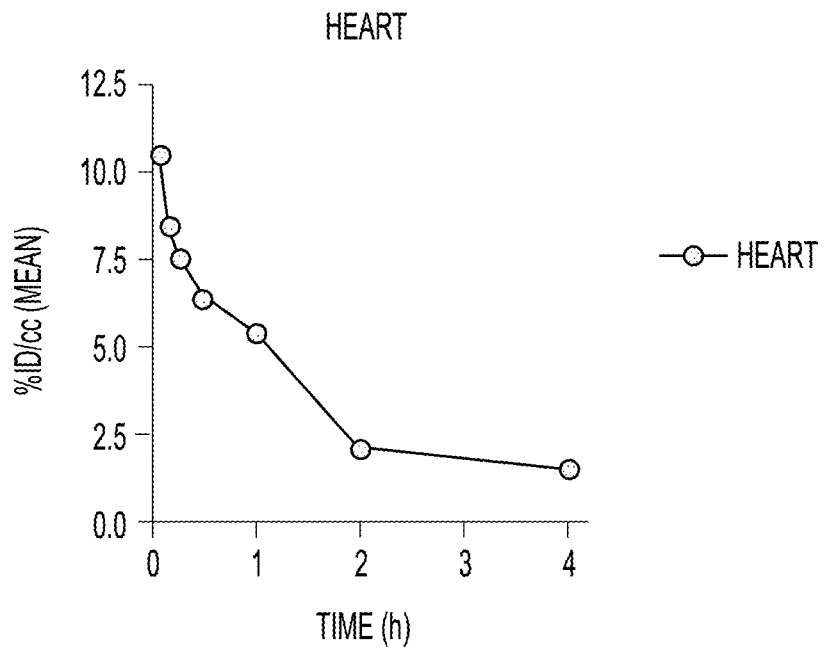
FIG. 17I is heart in mouse 4.
Figure 17J:
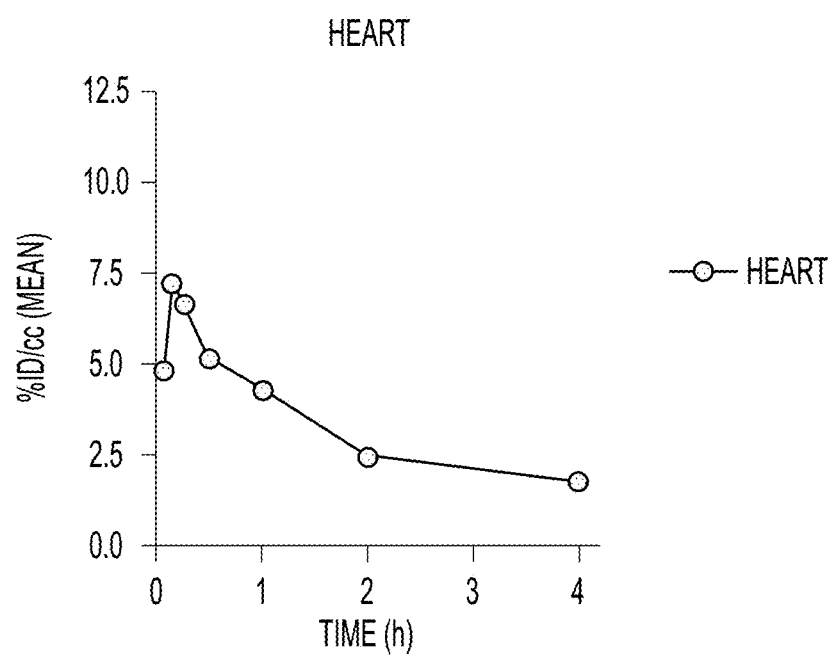
FIG. 17J is heart in mouse 6.
Figure 17K:
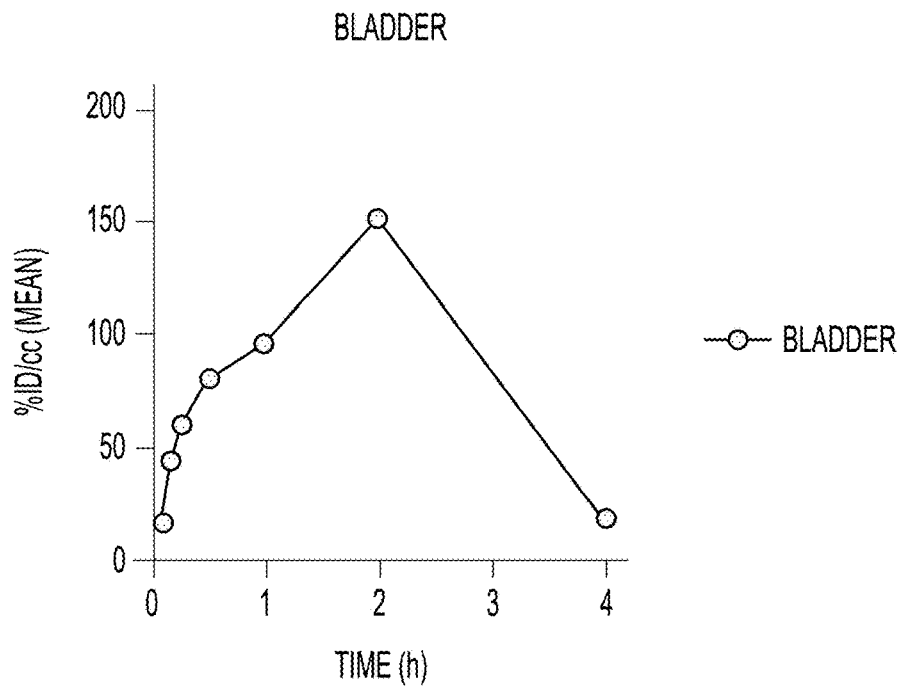
FIG. 17K is bladder in mouse 4.
Figure 17L:
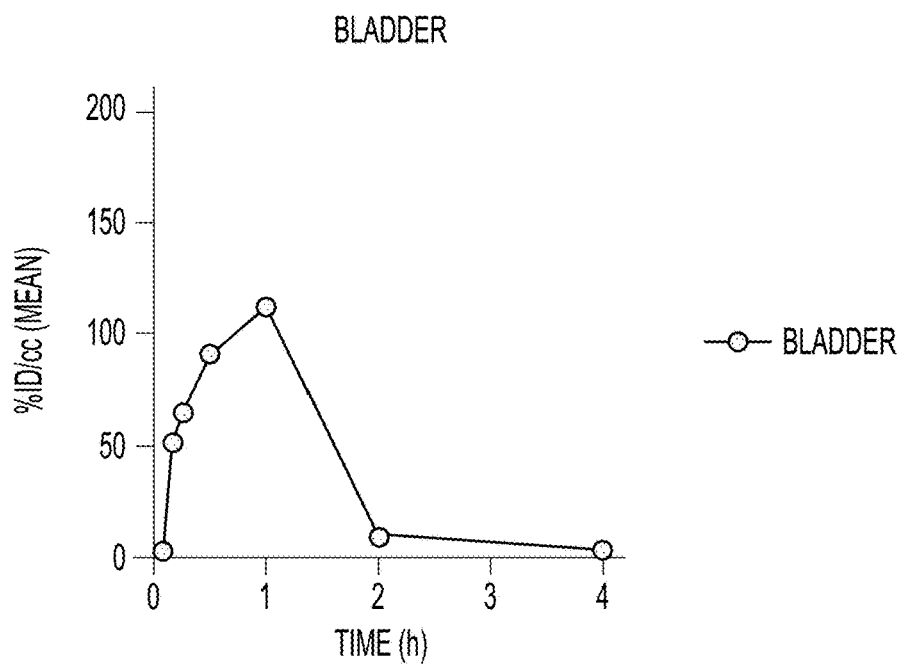
FIG. 17L is bladder in mouse 6.
Figure 18:
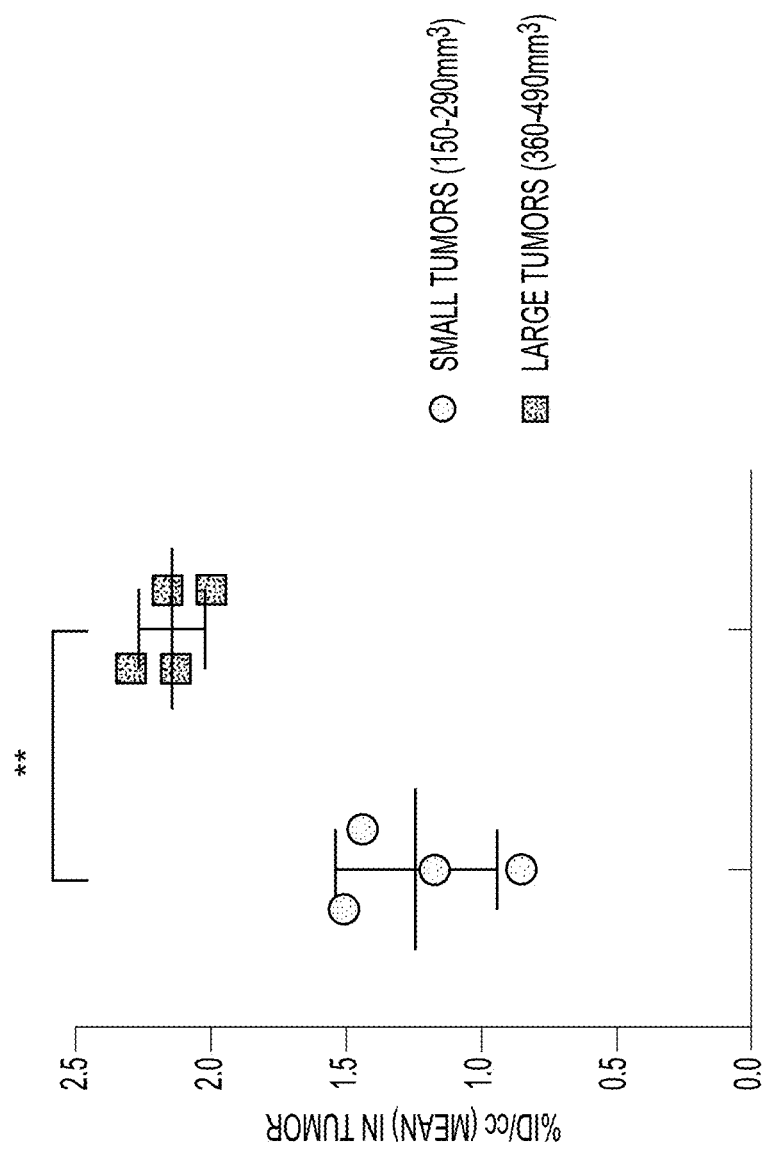
FIG. 18 is a graph of the accumulation of heterobiligand in large tumors compared to smaller tumors.

Evaluation of a folate-hshta (SEQ ID NO:6) Nterm heterobiligand bearing both an albumin binder and DOTA chelator in PET was a priority, given that DOTA can accommodate both $^{68}$Ga for imaging and $^{177}$Lu for radiotherapy. A 200 µCi dose of $^{68}$Ga-labeled folate-hshta-PEG3-Lys(MPBA)-Lys(DOTA) (SEQ ID NO:6) (compound #2809) was injected i.v. via tail vein in an NSG mouse bearing s.c. human OVCAR3 (FOLR1+) tumor. $^{68}$Ga PET/CT imaging scans were performed at 0-1 h (dynamic), 2 h (static), and 4 h (static). Images for mouse 4 are shown in FIG. 15 (tumor size 150 mm³), and images for mouse 6 are shown in FIG. 16 (tumor size 490 mm³). Kidneys are the major organ of elimination. The time-course biodistribution of $^{68}$Ga-labeled folate-hshta-PEG3-Lys(MPBA)-Lys(DOTA) (SEQ ID NO:6) (compound #2809) was calculated to quantify the uptake in major organs including the tumor (FIG. 17). At early tumor sizes (150 mm³), low decay-corrected dose accumulation is observed in the tumor (~1.4% of the injected dose/cc at 4 h post injection) (FIGS. 17A and 17B). Like the $^{18}$F-labeled peptide, however, renal clearance is the preferred excretion pathway (FIGS. 17C and 17D). Larger tumors (490 mm³) were also evaluated with the $^{68}$Ga-chelated PET probe. In these larger models, higher accumulation within the tumor was observed (~2.2% of the injected dose/cc at 4 h post injection) (FIGS. 17A and 17B). Tumor to muscle ratio data indicate that the radiotracer provides sufficient measurable PET signal to identify tumor delineated from background tissue (FIGS. 17E and 17F). Clearance of activity from the liver (FIGS. 17G and 17H) and heart (FIGS. 17I and 17J) is observed over time with elimination through the bladder (FIGS. 17K and 17L). Probe accumulation in tumor is significantly associated with tumor size (FIG. 18; data collected at the 4 h time point are used because they are most relevant to the therapeutic effects).

For use in imaging and targeted therapy additional forms of the lead heterobiligand were produced. The parent compound, including DOTA for chelating a radionuclide (X) is:

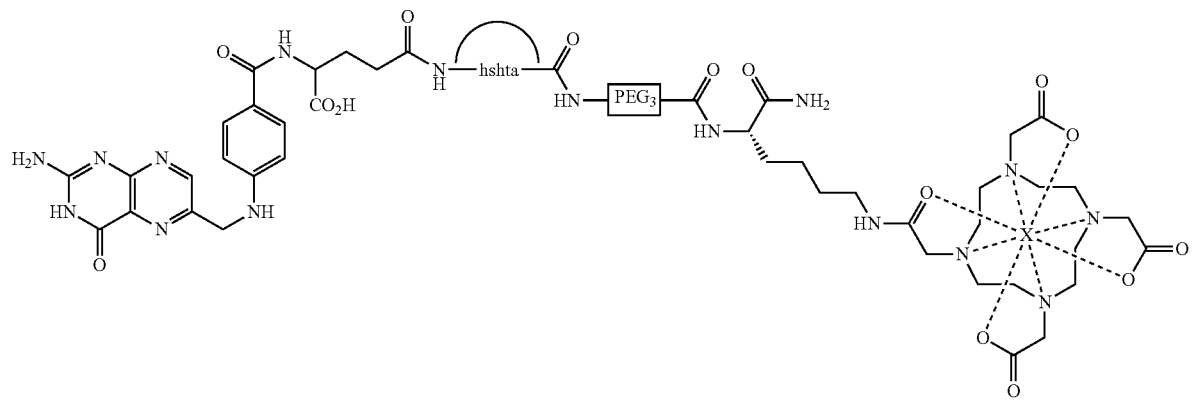

Folate-hshta-PEG3-Lys(DOTA) (SEQ ID NO:6)

To this an albumin binding moiety (MPBA) was added:

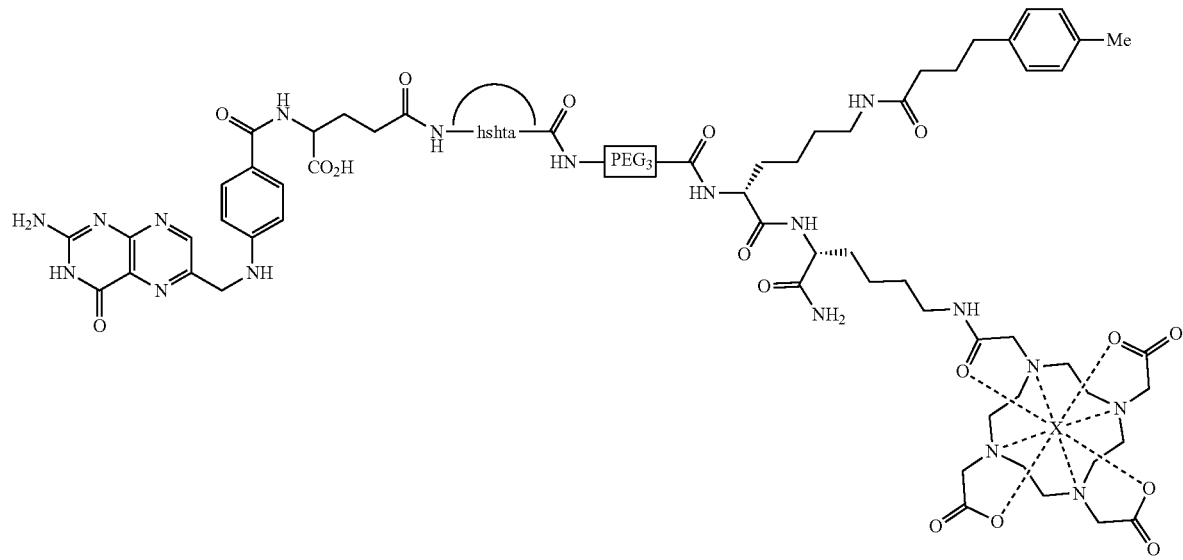

Folate-hshta-PEG3-Lys(MPBA)-Lys(DOTA) (SEQ ID NO:6)
compound #2809

As an alternative, a GFK linker, susceptible to brush border cleavage, was added between the DOTA and the heterobiligand:

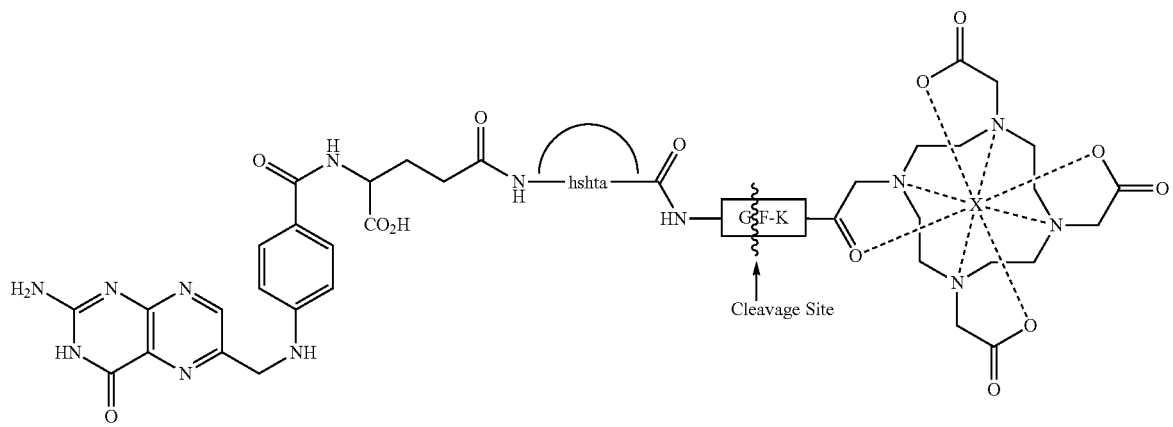

Folate-hshta-PEG3-Lys(MPBA)-Lys(DOTA) (SEQ ID NO:6)

As another alternative, both modifications (albumin binding moiety and brush border cleavage linker) can be included in the same heterobiligand construct (e.g., Folate-hshta-Lys(MPBA)-Gly-Phe-Lys(DOTA) (SEQ ID NO:6), not shown).

With data suggesting targeted tumor retention, a therapeutic study was initiated by engrafting NSG mice with OVCAR3 cells. The engraftment was allowed to expand until palpable tumor sizes ranging in size from 218-384 mm$^3$ were detected. Animals were split into groups in a dose rangefinding experiment receiving 111 MBq, 37 MBq, 18.5 MBq, 9.25 MBq, 3.7 MBq, or 0 MBq radiotracer dose in the form of Folate-hshta-PEG3-Lys(MPBA)-Lys(DOTA) (SEQ ID NO:6) (compound #2809) with $^{177}$Lu chelated (Table 1) Animals receiving the peptide alone with no $^{177}$Lu chelated (0 MBq dose) experienced increasing tumor volume until the study endpoints were met at day 25. Gratifyingly, no observable compound-related adverse events were detected in this 0 MBq dose cohort. Animals treated with the three highest doses (111 MBq, 37 MBq, and 18.5 MBq) displayed adverse events that were dose proportional. These observed effects were consistant with radiation overdosing. The two lowest radio-doses (9.25 MBq and 3.7 MBq) were well tolerated. Mice receiving these dosing regimes demonstrated significant tumor reduction proportional to the dose received. From this study, it was determined that doses of 9.25 MBq and 3.7 MBq are well tolerated and efficacious.

The best response was observed using 9.25 MBq Lu-177 Heterobiligand (compound #2809). Imaging and treatment feasibility was achieved with the same basic PCC construct, thus confirming that the PCC platform can perform theranostically.

TABLE 1

Therapeutic Dose Finding Study in OVCAR3 Ovarian Cancer Xenograft Model

| $^{177}$Lu dose | DOTA-Heterobiligand Albumin binder conjugate | Comments |
| --- | --- | --- |
| 3 mCi (111 MBq) | 3 mice | 2 mice died on day 4 |
|  |  | 1 mouse died on day 5 |
| 1 mCi (37 MBq) | 2 mice | 2 mice died on day 10 |
| 0.5 mCi (18.5 MBq) | 2 mice | 1 mouse died on day 10 |
|  |  | 1 mouse died on day 13 |
| 0.25 mCi (9.25 MBq) | 2 mice | Sacrificed on day 24 |
| 0.1 mCi (3.7 MBq) | 2 mice | Sacrificed on day 24 |
| 0 | 3 mice | Sacrificed on day 24 |

Figure 19:
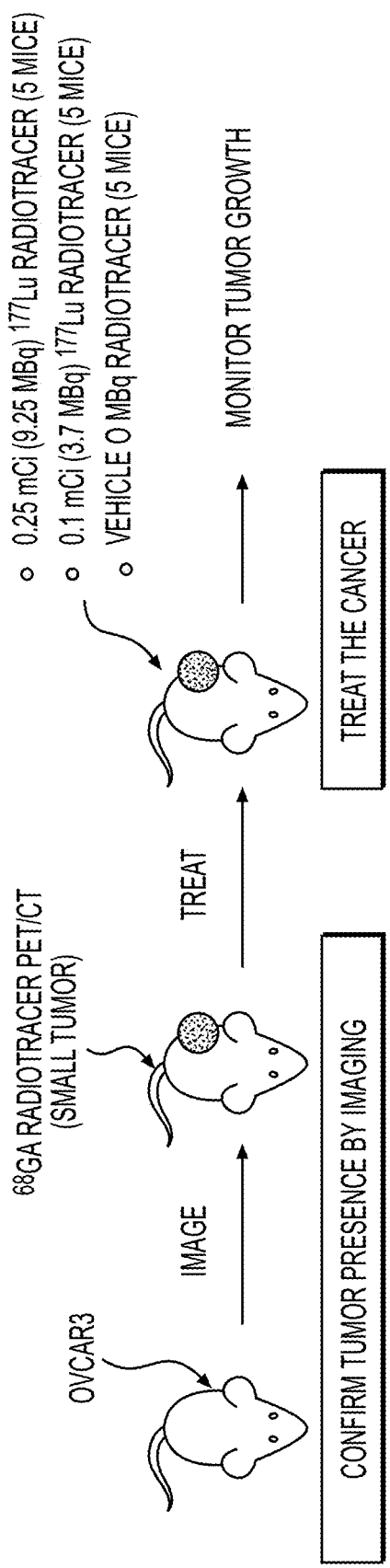
FIG. 19 is a diagram of the combination of tumor imaging and tumor treatment using the same heterobiligand loaded with an imaging radionuclide or a therapeutic radionuclide, respectively.

The identical folate-hshta (SEQ ID NO:6) Nterm heterobiligand bearing both an albumin binder and DOTA chelator is amenable to both $^{68}$Ga chelation for imaging or $^{177}$Lu chelation for radiotherapy (FIG. 19). Doses for this repeat experiment were derived from the tolerability study, with treatment cohorts receiving either 9.25 MBq (high dose) or 3.7 MBq (low dose). The two radiotracer doses and the control dose (peptide only with no $^{177}$Lu) were well tolerated, recapitulating the results of the rangefinding study out to 17 days. Over the course of the experiment, a clear differential in tumor growth was observed for both doses compared to the unabated control cohort (FIG. 20). The response was dose-dependent, with the highest dose exhibiting the largest tumor growth suppression (FIG. 20).

Subjecting the DOTA-containing heterobiligands to $^{177}$LuCl$_3$ at 95° C. for 15 minutes in 0.4 M sodium acetate buffer (pH 4.5) provided the chelated adduct in high yields. No further optimization of the labeling conditions was required. Both folate-hshta-PEG3-Lys(DOTA) and folate-hshta-PEG3-Lys(MPBA)-Lys(DOTA) (SEQ ID NO:6) (compound #2809) were successfully labeled with Lu-177 (100% conversion verified by both radioTLC and HPLC). Purity was confirmed to be 100% on HPLC. For mouse injection, the undiluted product in 0.4 M sodium acetate buffer (pH 4.5) was used directly or formulated in buffered saline.

The gallium labeling conditions were optimized using Ga(NO$_3$)$_3$. The chelation was found to be rapid and efficient, with near quantitative conversion observed after 5 minutes at 90° C. and pH 4. Heating the reaction allowed for nearly 100% conversion of starting material (MW: 1927 m/z) into the gallium chelated product (MW: 1994 m/z) in under 5 min. Analytical HPLC data show the retention time shift from ~24.5 min (starting material) to ~25.1 min (product). HPLC conditions: 150×4.6 mm C18 column; 2-20% B, 60 min gradient; 25 µL injection volume.

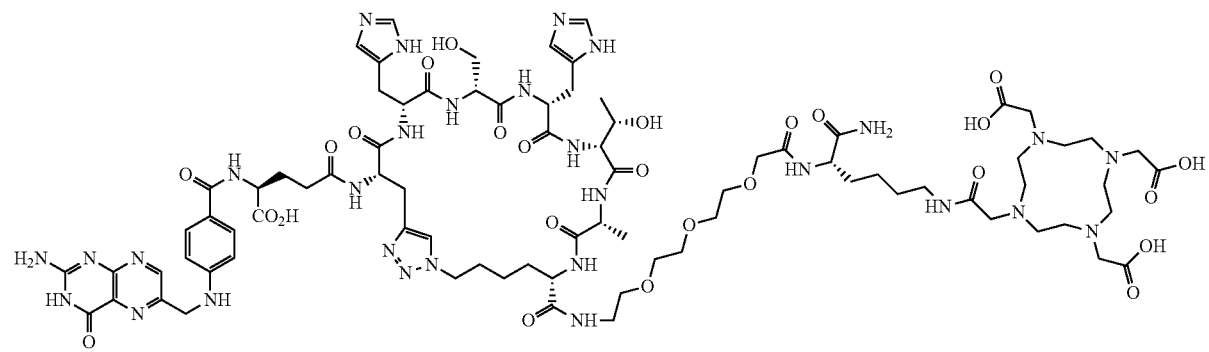

Folate-hshta-PEG3-Lys(DOTA) (SEQ ID NO:6)

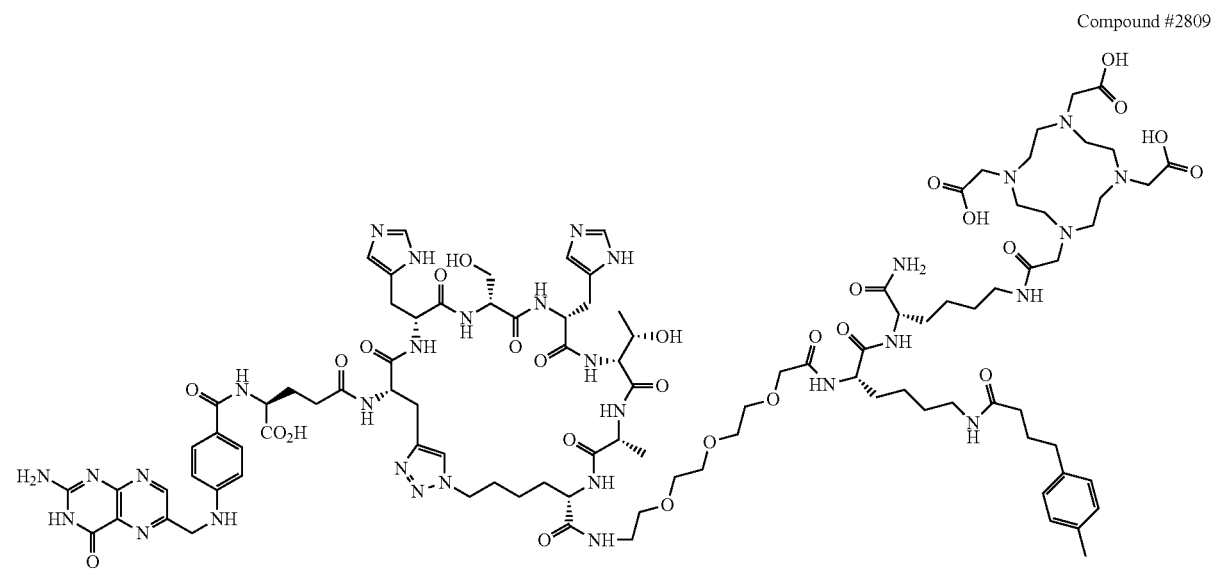

Compound #2809

Folate-hshta-PEG3-Lys(MPBA)-Lys(DOTA) (SEQ ID NO:6)

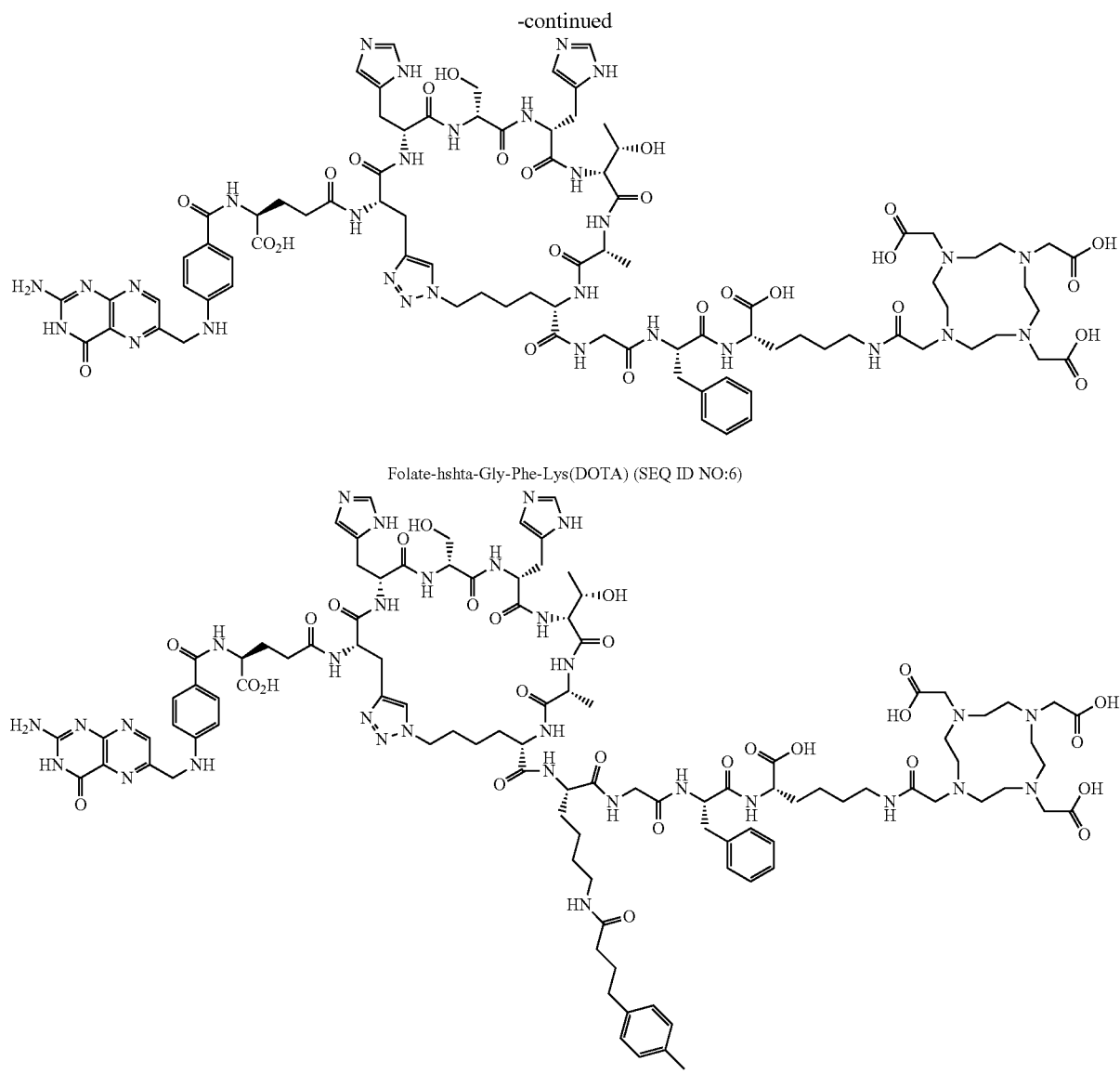

Folate-hshta-Gly-Phe-Lys(DOTA) (SEQ ID NO:6)

Folate-hshta-Lys(MPBA)-Gly-Phe-Lys(DOTA) (SEQ ID NO:6)

Figure 21:
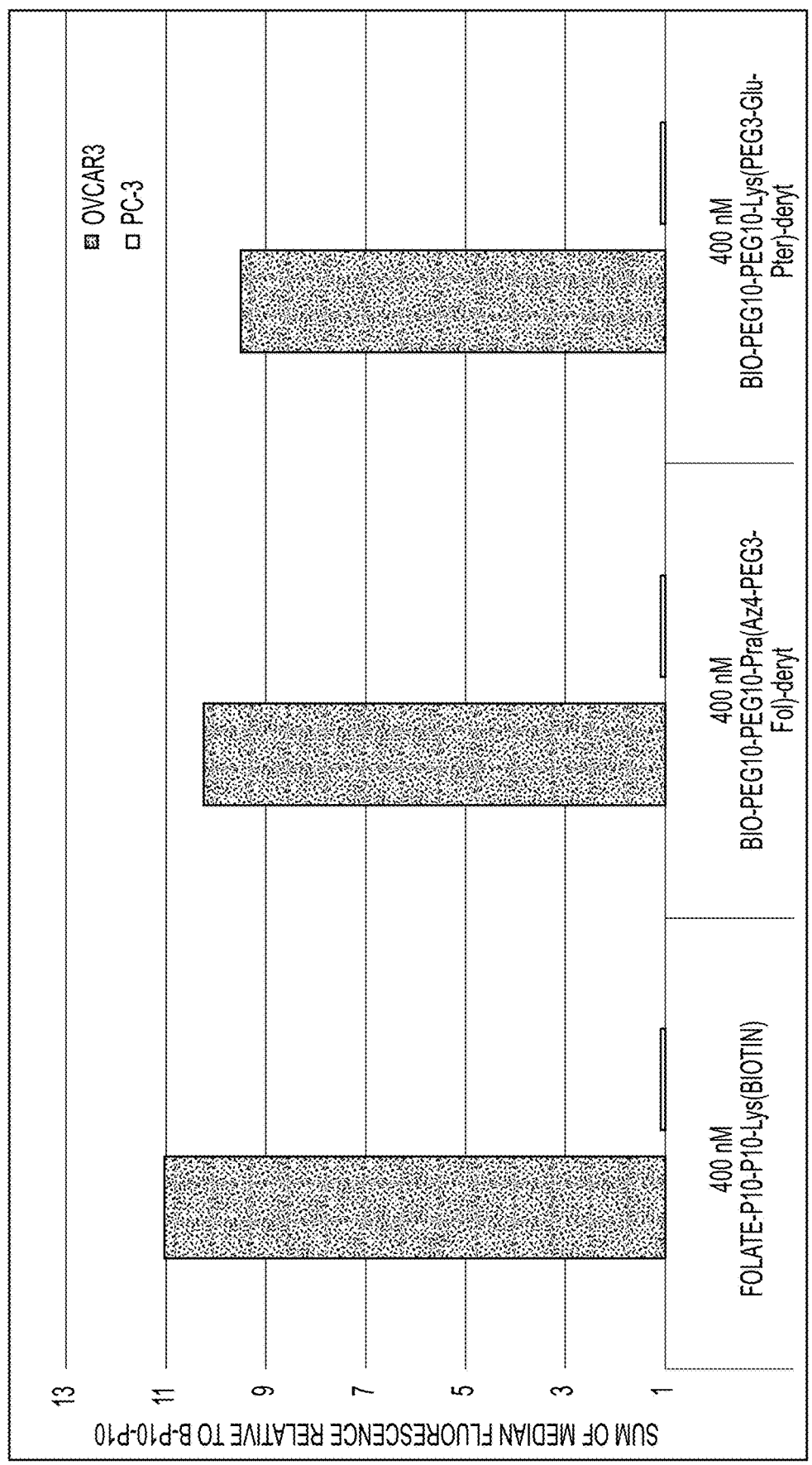
FIG. 21 is a graph binding of ligands and heterobiligands to FOLR1+ and FOLR1− cells assessed by flow cytometry.

Utilizing an azido-folate anchor to template heterobiligands, an additional hit was profiled. This heterobiligand, based on the PCC deryt (SEQ ID NO:20), demonstrated high binding affinity by ELISA and excellent selectivity for FOLR1 (+) cells (FIG. 21). Cells were incubated for 20 min at 37° C. in TC incubator with 400 nM of compound.

| | |
|---|---|
| Lys (PEG3 -Folate)-deryt | $EC_{50}$ = 0.16 nM |
| Pra(Az4-PEG3-folate)-deryt | $EC_{50}$ = 0.27 nM |

-continued

| | |
|---|---|
| Folate | $EC_{50}$ = 2.3 nM |
| deryt | $EC_{50}$ = 10 μM |

Two versions of the folate-deryt (SEQ ID NO:20) heterobiligand were synthesized. The first construct, utilizing a Tz linker, mimics the attachment structure from the in situ click screen. A second construct, utilizing a lysine in place of the Tz linker, maintains the correct distance between folic acid and the PCC but replaces the triazole with an amide bond.

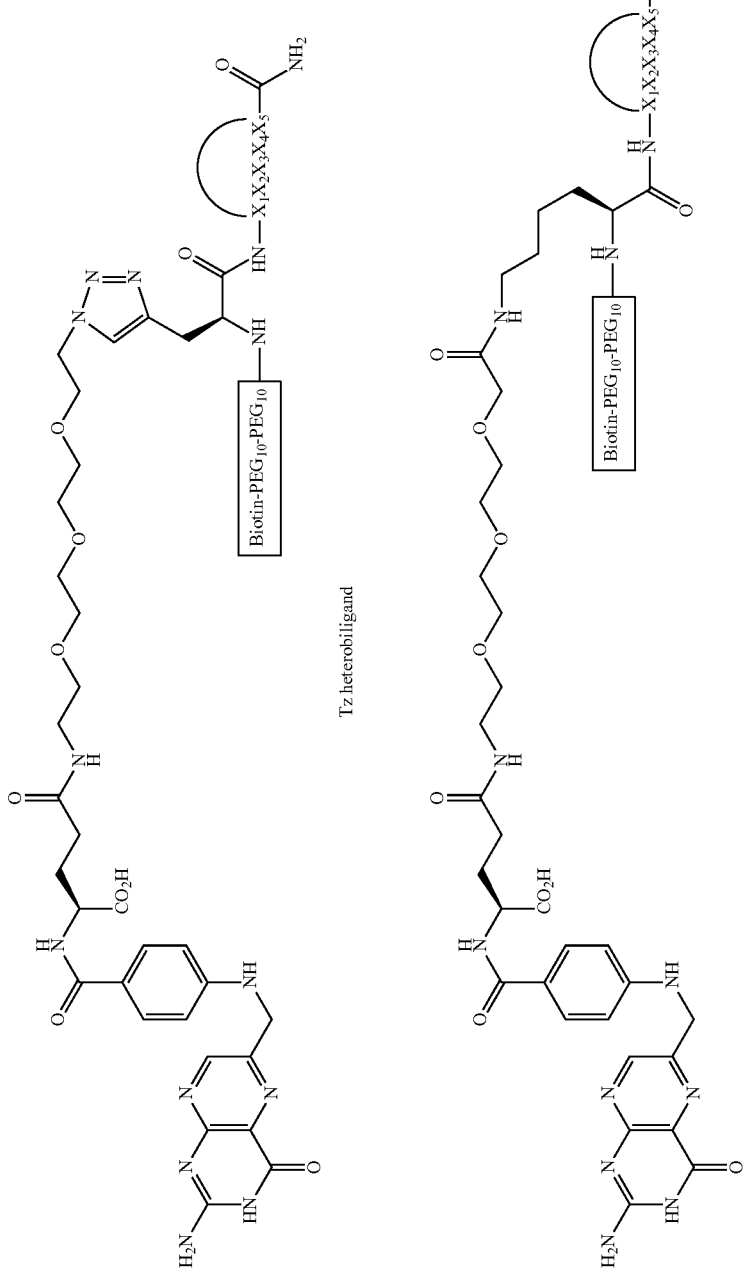

-continued
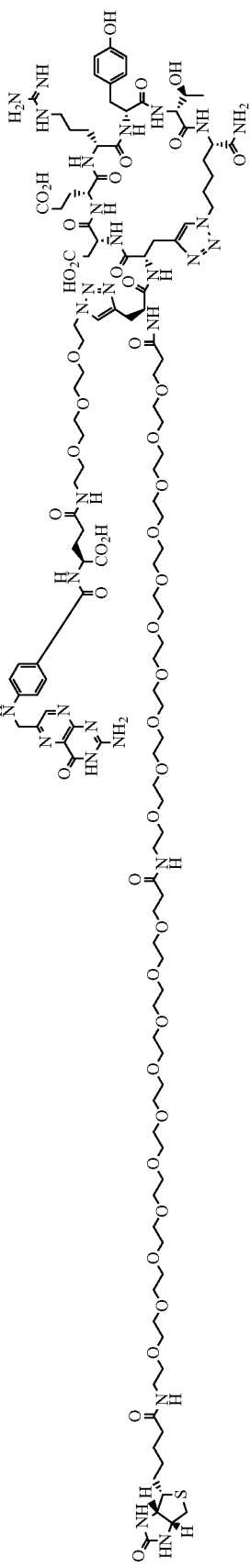
Pra(Az4-PEG3-folate)-deryt (Bio-PEG10-PEG10-Pra(Az4-PEG3-Folate)-deryt)
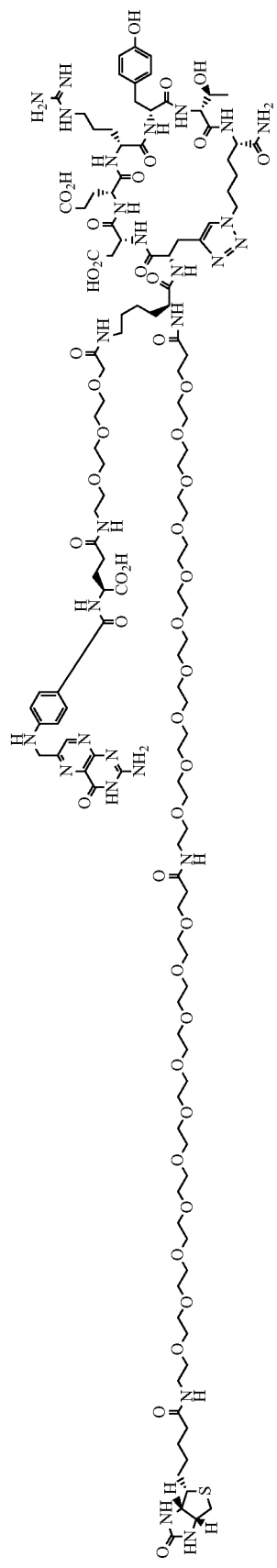
Lys(PEG3-Folate)-deryt (Bio-PEG10-PEG10-Lys(PEG3-Folate)-deryt)

Further experiments were used to determine that the addition of an improved albumin binder and brush border linker would attenuate the high kidney signal we observed in $^{68}$Ga imaging experiment described above. As described above, compound #2809 (folate-hshta-PEG3-Lys(MPBA)-Lys(DOTA) (SEQ ID NO:6)) was tested in tumor bearing NSG mice. This compound contains the folate-PCC heterobiligand with the albumin binder 4-methylphenyl butyric acid (MPBA) and DOTA chelator connected via PEG3.

Figure 22:
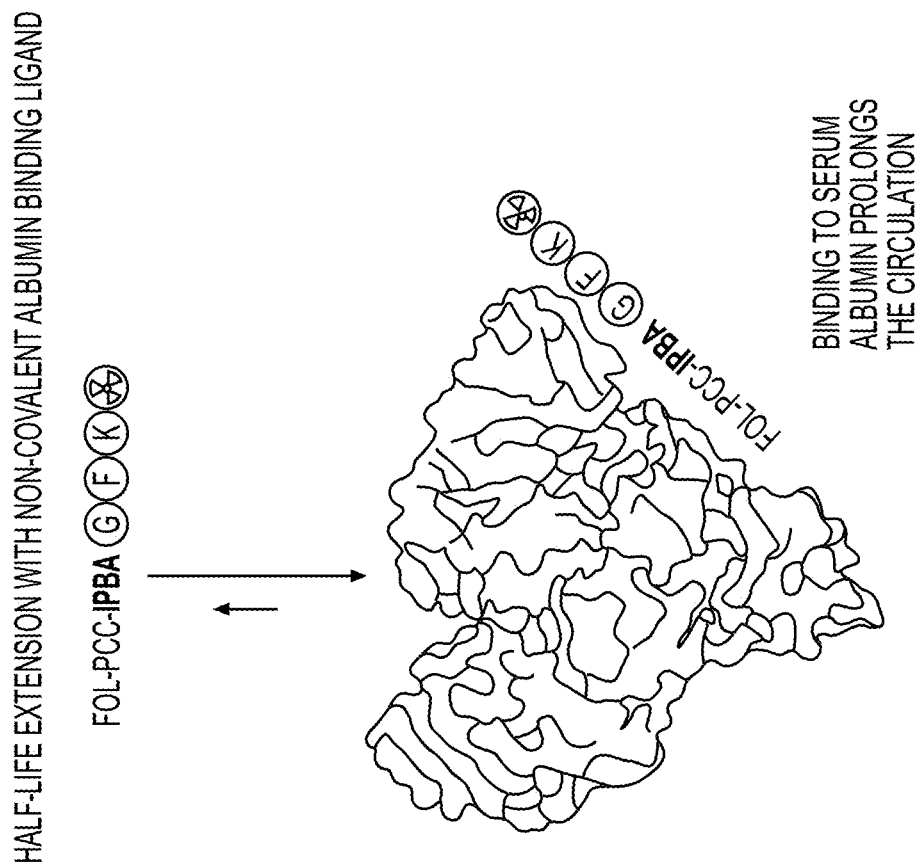
FIG. 22 is a diagram showing half-life extension of compounds by albumin binding.

A new compound (#1307; folate-hshta-Lys(IPBA)-Gly-Phe-Lys(DOTA) (SEQ ID NO:6)) contains the identical FOLR1 binding motif with the addition of a superior albumin binder 4-iodophenyl butyric acid (IPBA). IPBA has a high affinity for albumin, a large component of mammalian serum. By binding to albumin, the heterobiligand-albumin complex is shielded from the kidney's filtering system. The bound and unbound equilibrium allows for the serum-free fraction to participate in FOLR1(+) tumor binding (FIG. 22).

In addition to the albumin binder, a brush border cleavable linker Gly-L-Phe-L-Lys was employed to connect the DOTA chelator. This allows enzymes in the kidney to cleave off the radionuclide-chelator complex which is eliminated through the bladder.

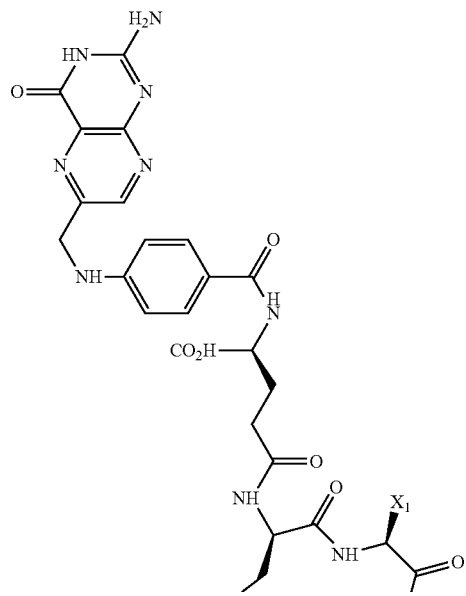

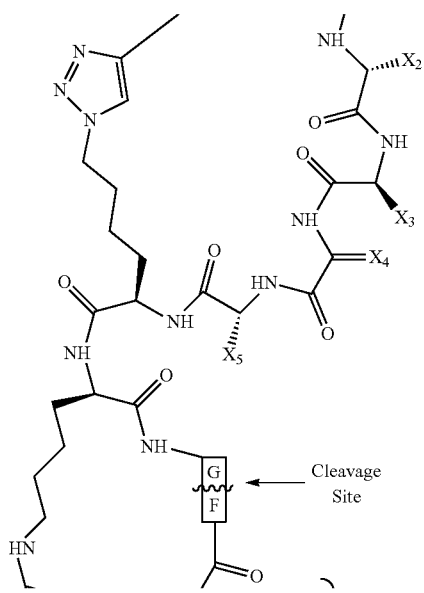

-continued
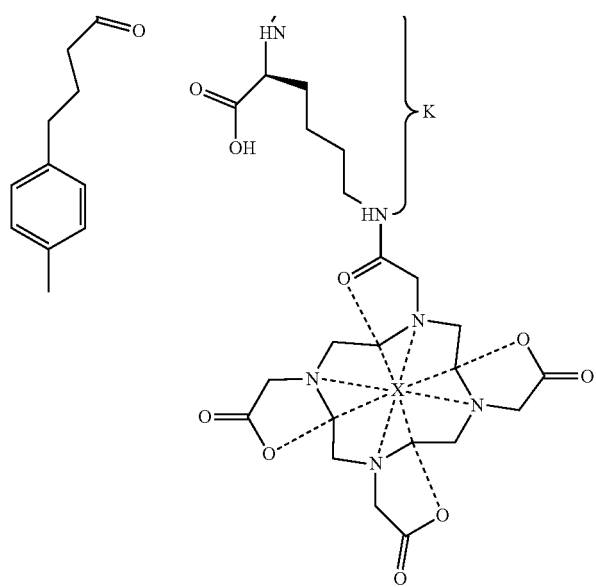
Folate-xxxxx-Lys(IPBA)-Gly-Phe-Lys(DOTA)
Generic compound #1307
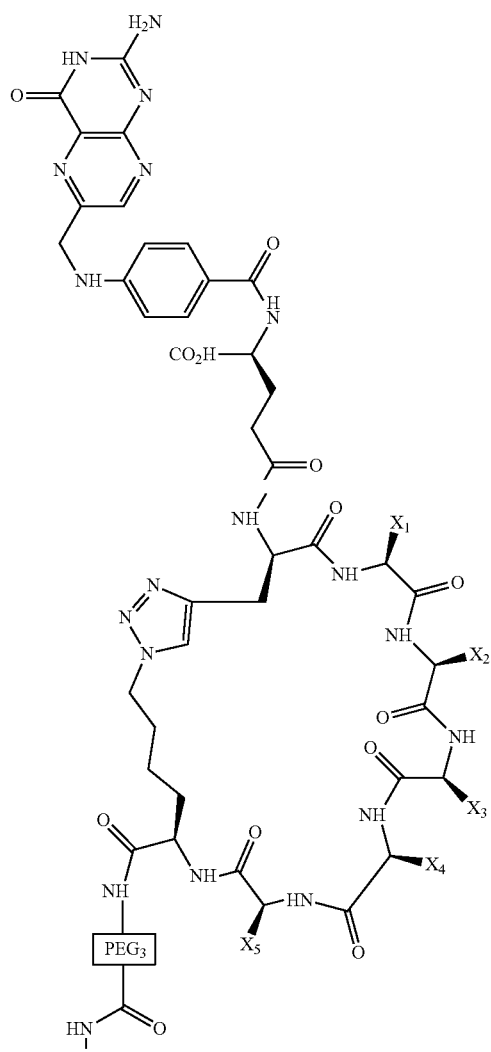

-continued
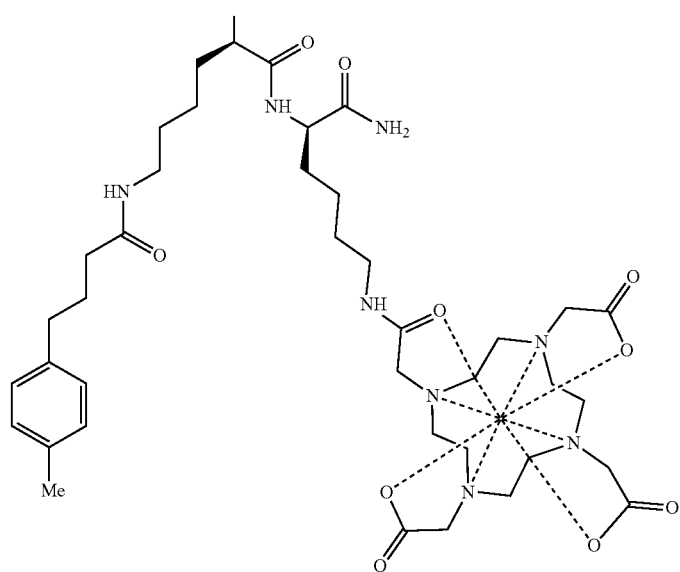
Folate-xxxxx-PEG3-Lys(MPBA)-Lys(DOTA)
Generic compound #2809
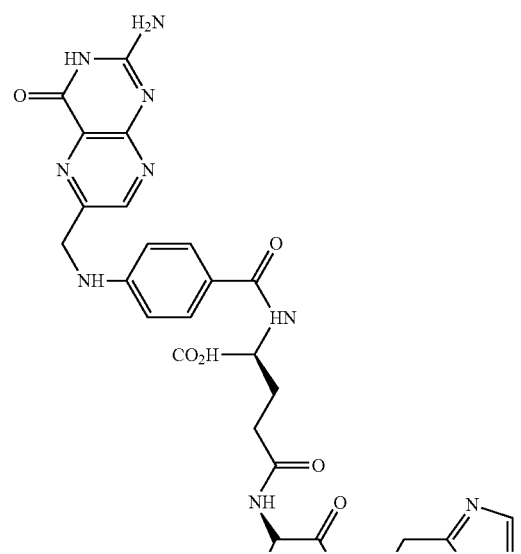

-continued
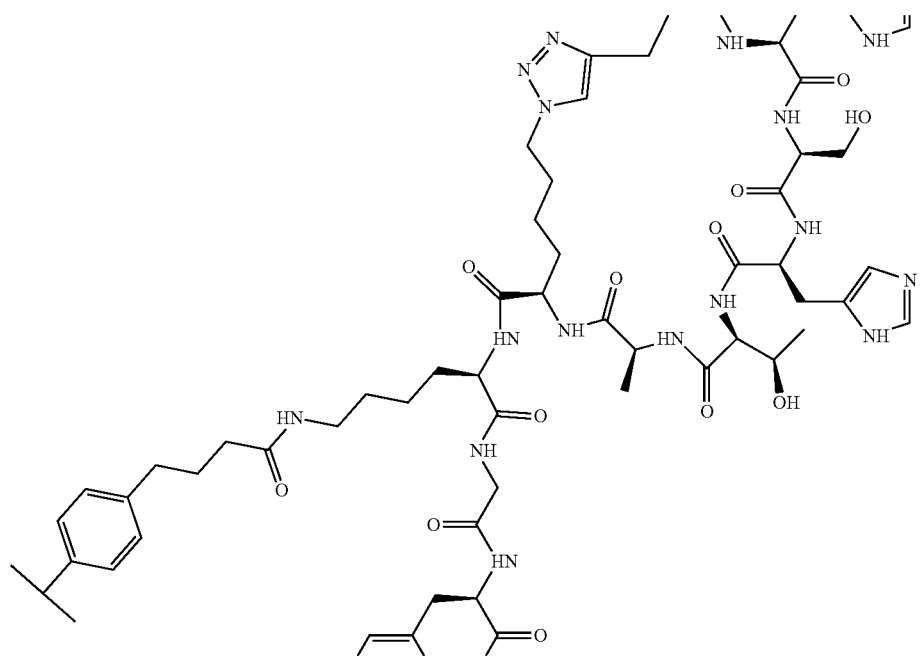
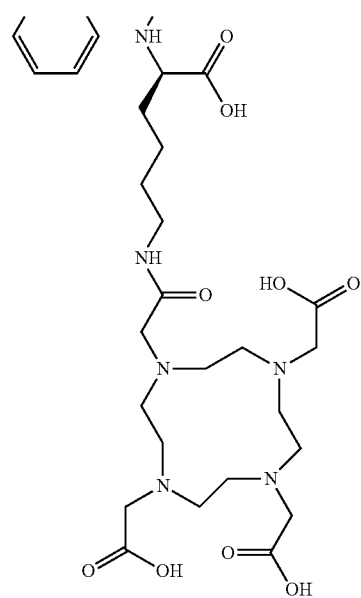
Folate-hshta-Lys(IPBA)-Gly-Phe-Lys(DOTA) (SEQ ID NO: 6)
Compound #1307

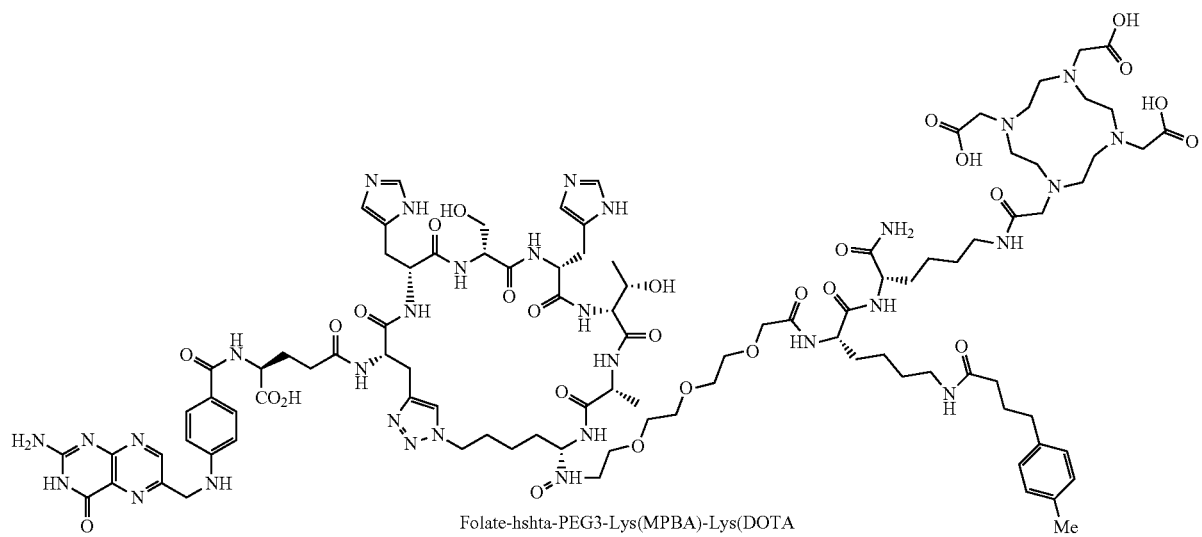
Folate-hshta-PEG3-Lys(MPBA)-Lys(DOTA
Folate-hshta-PEG3-Lys(MPBA)-Lys(DOTA) (SEQ ID NO: 6)
Compound #2809
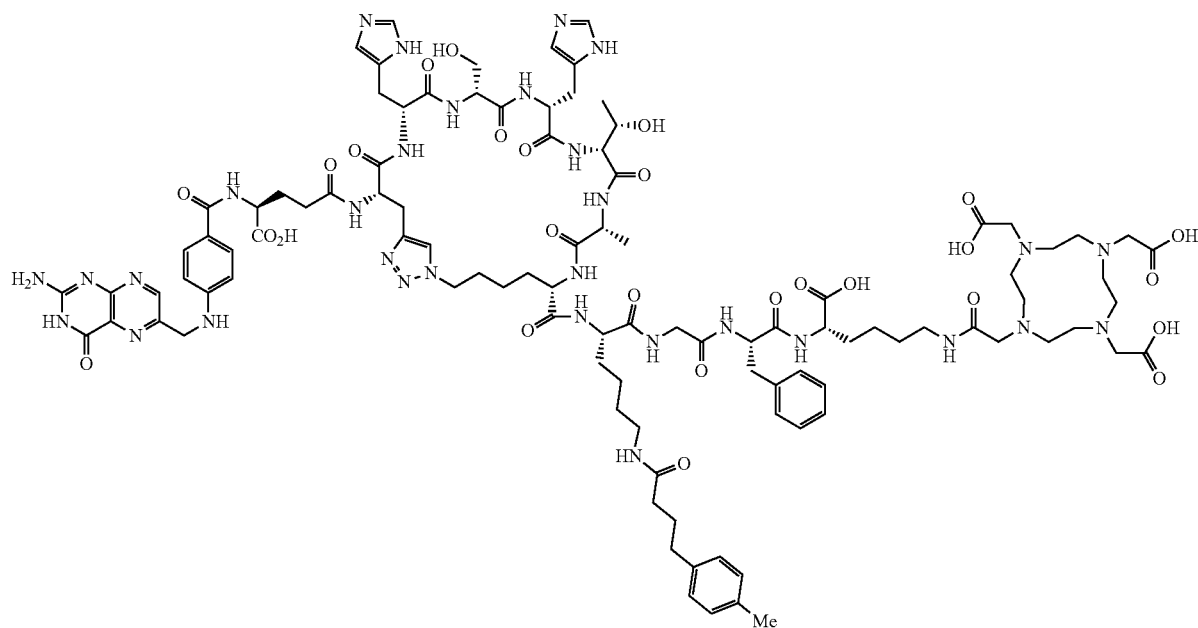
Folate-hshta-Lys(MPBA)-Gly-Phe-Lys(DOTA) (SEQ ID NO: 6)
Compound #6305

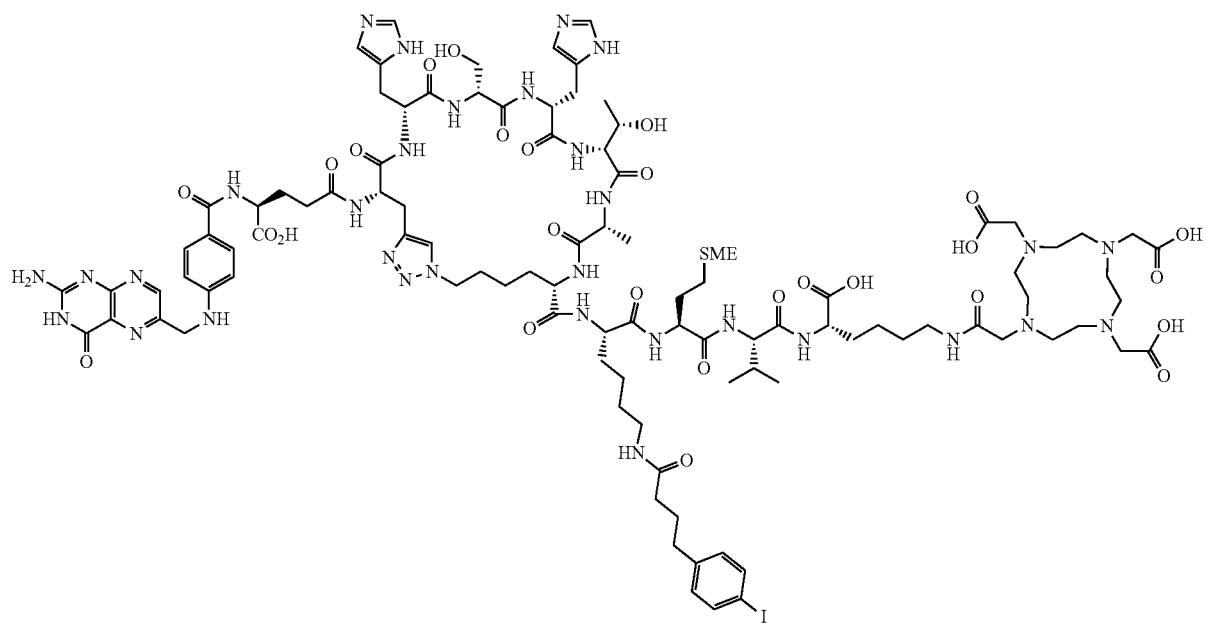
Folate-hshta-Lys(IPBA)-M-V-Lys(DOTA) (SEQ ID NO: 6)
Compound #1306
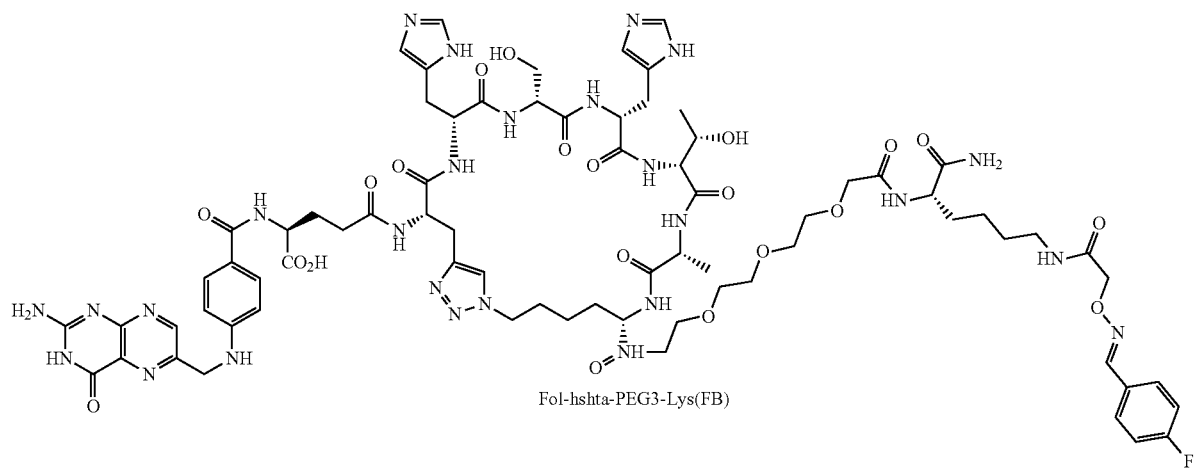
Folate-hshta-PEG3-Lys(FB) (SEQ ID NO: 6)
Compound #2

-continued
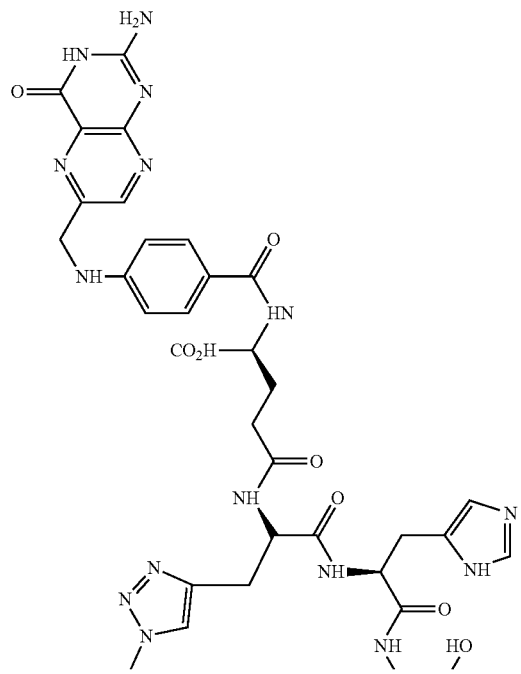
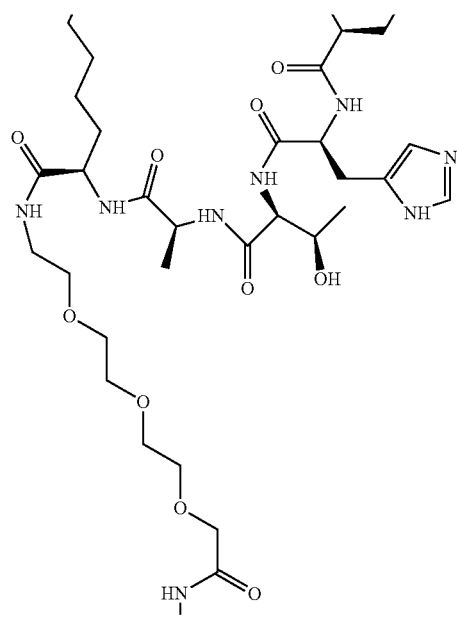

-continued
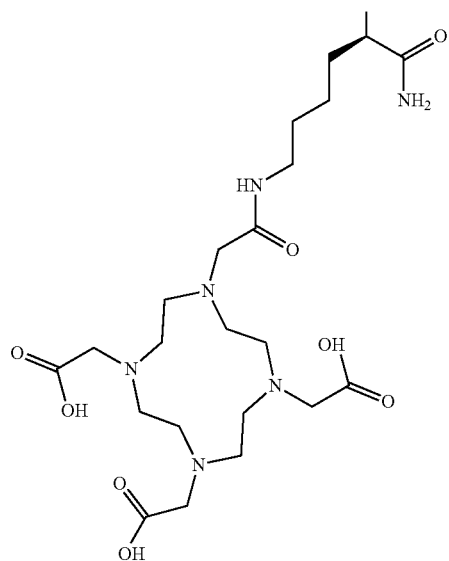
Fol-hshta-PEG3-Lys(DOTA) (SEQ ID NO: 6)
Compound #1189
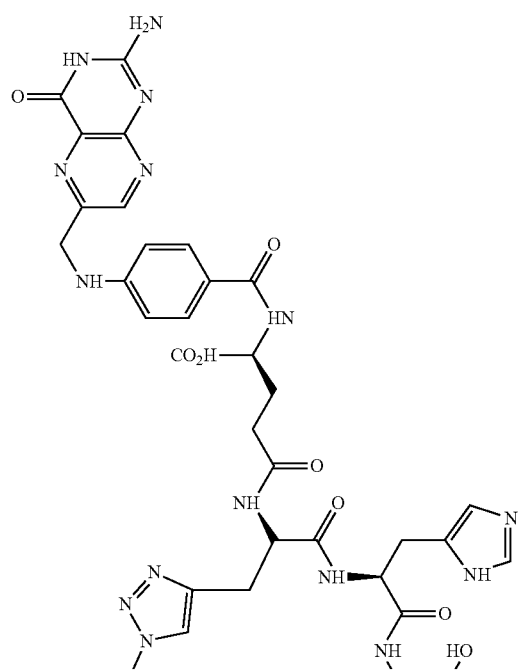

-continued
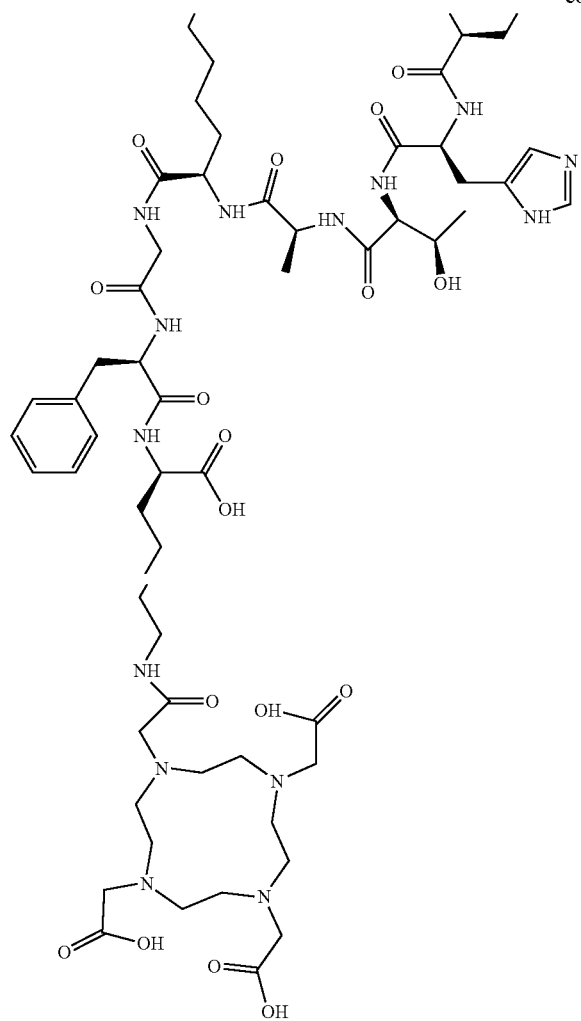
Fol-hshta-Gly-Phe-Lys(DOTA) (SEQ ID NO: 6)
Compound #7327
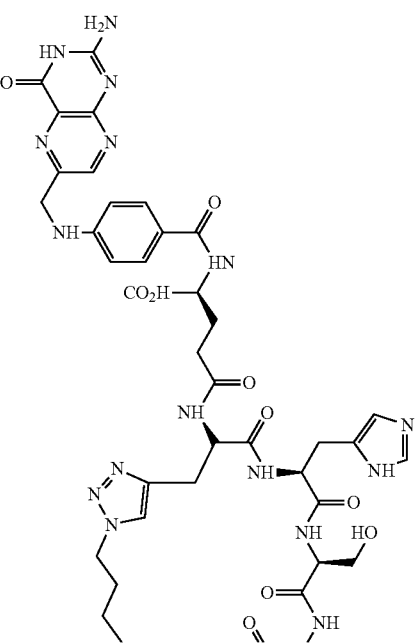

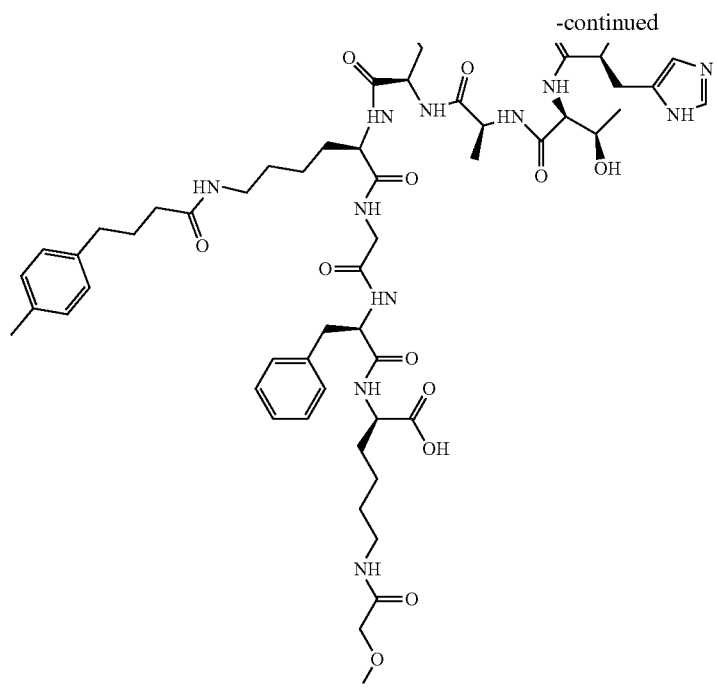
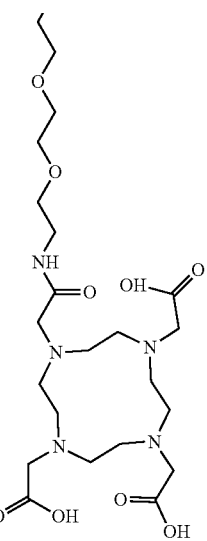
Fol-hshta-Lys(4-MPBA)-Gly-Phe-Lys(PEG3-DOTA) (SEQ ID NO: 6)
Compound #3302

-continued
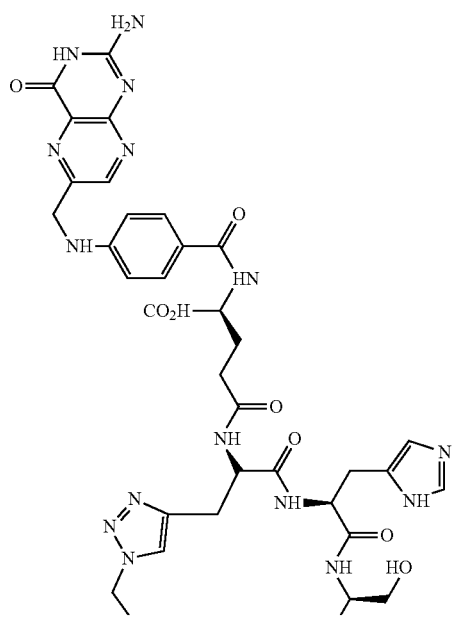
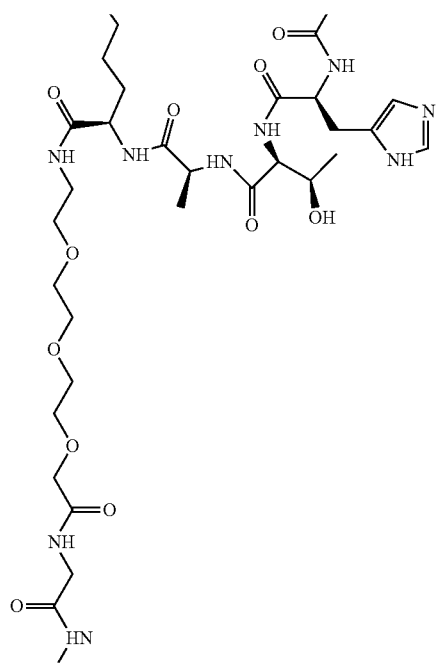

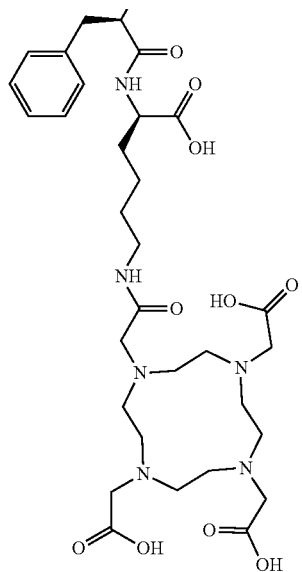

Fol-hshta-PEG3-Gly-Phe-Lys(DOTA) (SEQ ID NO: 6)

Compound #6307

To optimize the albumin binding potential of the heterobiligand, a plasma protein binding (PPB) experiment was performed. This experiment measured the amount of test article bound and free after equilibrating with plasma. Compound #6305 (folate-hshta-Lys(MPBA)-Gly-Phe-Lys(DOTA) (SEQ ID NO:6)), which contains the MPBA albumin binder, was 96.26% bound to mouse plasma and 98.34% bound to human plasma. Compound #1307 (folate-hshta-Lys(IPBA)-Gly-Phe-Lys(DOTA) (SEQ ID NO:6)), which is identical except for the use of IPBA instead of MPBA, demonstrated a significantly higher level of plasma binding. In mouse and human plasmas 99.6% and 99.5% was bound, respectively. The alternative brush border compound L-Met-L-Val-L-Lys (compound #1306; folate-hshta-Lys(IPBA)-M-V-Lys(DOTA) (SEQ ID NO:6)) was roughly 97% bound to plasma, demonstrating that the linker also plays a role in plasma affinity. The absence of an albumin binder (compound #7327; folate-hshta-Gly-Phe-Lys(DOTA) (SEQ ID NO:6)) demonstrated comparatively low binding in both mouse (40.87%) and human (40.29%) plasma. Plasma Protein Binding indicates that IPBA is a superior albumin binder than MPBA. Compound #1307 possesses the optimized Alb binder and neprilysin (NEP) cleavage linker and has been chosen for further in vivo study. The results are summarized in Table 2.

TABLE 2

Summary of FOLR1 Constructs

| # | Compound | Alb | BB | in vivo | % MeCN | Plasma % Bound (% Recovery) | in vitro Assay Data |
|---|---|---|---|---|---|---|---|
| 2809 | Fol-hshta-PEG3-Lys(4-MPBA)-Lys(DOTA) | MPBA | N/A | Rx/Dx | 29.6% | Hu: 83.28% (85.8% recovered) Mu: 92.09% (107.7% recovered) | Confirmed to be resistant to NEP cleavage. |
| 2 | Fol-hshta-PEG3-Lys(FB) | N/A | N/A | Dx | 17.45% | Hu: 43.01% (85.0% recovered) Mu: 20.22% (115.0% recovered) | |
| 1189 | Fol-hshta-PEG3-Lys(DOTA) | N/A | N/A | | 25.2% | Hu: 46.02% (102.5% recovered) Mu: 29.51% (97.4% recovered) | Confirmed to be resistant to NEP cleavage. |
| 7327 | Fol-hshta-Gly-Phe-Lys(DOTA) | N/A | GFK | | 23.8% | Hu: 40.29% (112.7% recovered) Mu: 40.87% (102.4% recovered) | Cleavage of -G-F-K- linker was confirmed in NEP assay. |
| 6305 | Fol-hshta-Lys(4-MPBA)-Gly-Phe-Lys(DOTA) | MPBA | GFK | Rx/Dx | 32.3% | Hu: 98.34% (86.2% recovered) Mu: 96.26% (107.1% recovered) | Cleavage of -G-F-K- linker was confirmed in NEP assay. |
| 1307 | Fol-hshta-Lys(4-IPBA)-Gly-Phe-Lys(DOTA) | IPBA | GFK | Rx/Dx | 34.1% | Hu: 99.50% (84.4% recovered) Mu: 99.60% (87.7% recovered) | Cleavage of -G-F-K- linker was confirmed in NEP assay. |

TABLE 2-continued

Summary of FOLR1 Constructs

| # | Compound | Alb | BB | in vivo | % MeCN | Plasma % Bound (% Recovery) | in vitro Assay Data |
|---|---|---|---|---|---|---|---|
| 1306 | Fol-hshta-Lys(4-IPBA)-Met-Val-Lys(DOTA) | IPBA | MVK | | 33.4% | Hu: 97.35% (84.8% recovered) Mu: 97.12% (82.7% recovered) | Cleavage of -M-V-K- linker was confirmed in NEP assay. |
| 3302 | Fol-hshta-Lys(4-MPBA)-Gly-Phe-Lys(PEG3-DOTA) | MPBA | GFK | Dx | 33.2% | Hu: 94.9% (88.1% recovered) Mu: 96.5% (102.8% recovered) | Cleavage of -G-F-K- linker was confirmed in NEP assay. |
| 6307 | Fol-hshta-PEG3-Gly-Phe-Lys(DOTA) | N/A | GFK | | 26.1% | Hu: 41.3% (81.6% recovered) Mu: 40.6% (68.9% recovered) | Cleavage of -G-F-K- linker was confirmed in NEP assay. |
| | Octreotide Acetate | | | | | Hu: 59.41% (84.3% recovered) Mu: 62.36% (84.5% recovered) | Control (Cyclic peptide) |

Alb: Albumin Binder;
BB: Brush Border Cleavable linker;
in vivo: compound has been dosed;
PPB: plasma protein binding assay (Human/CD-1 Mouse);
% MeCN: percent Acetonitrile that elutes the compound (HPLC).

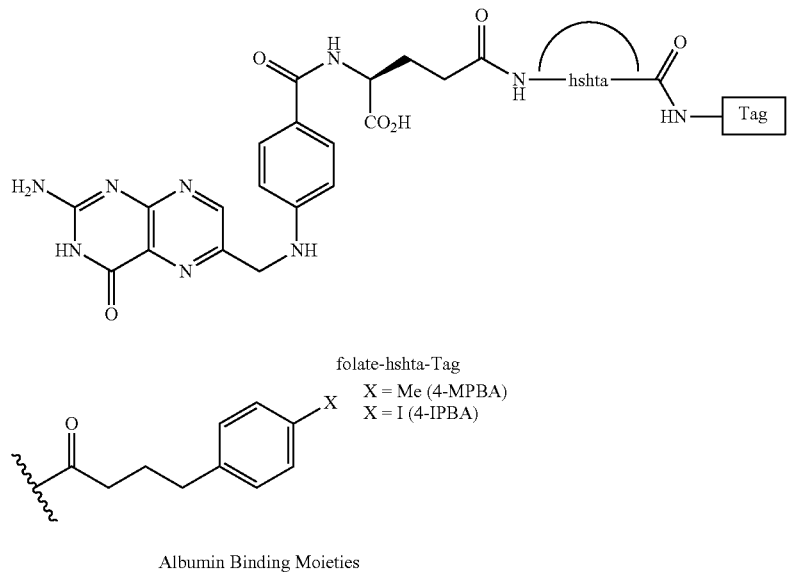

folate-hshta-Tag
X = Me (4-MPBA)
X = I (4-IPBA)

Albumin Binding Moieties

Figure 23:
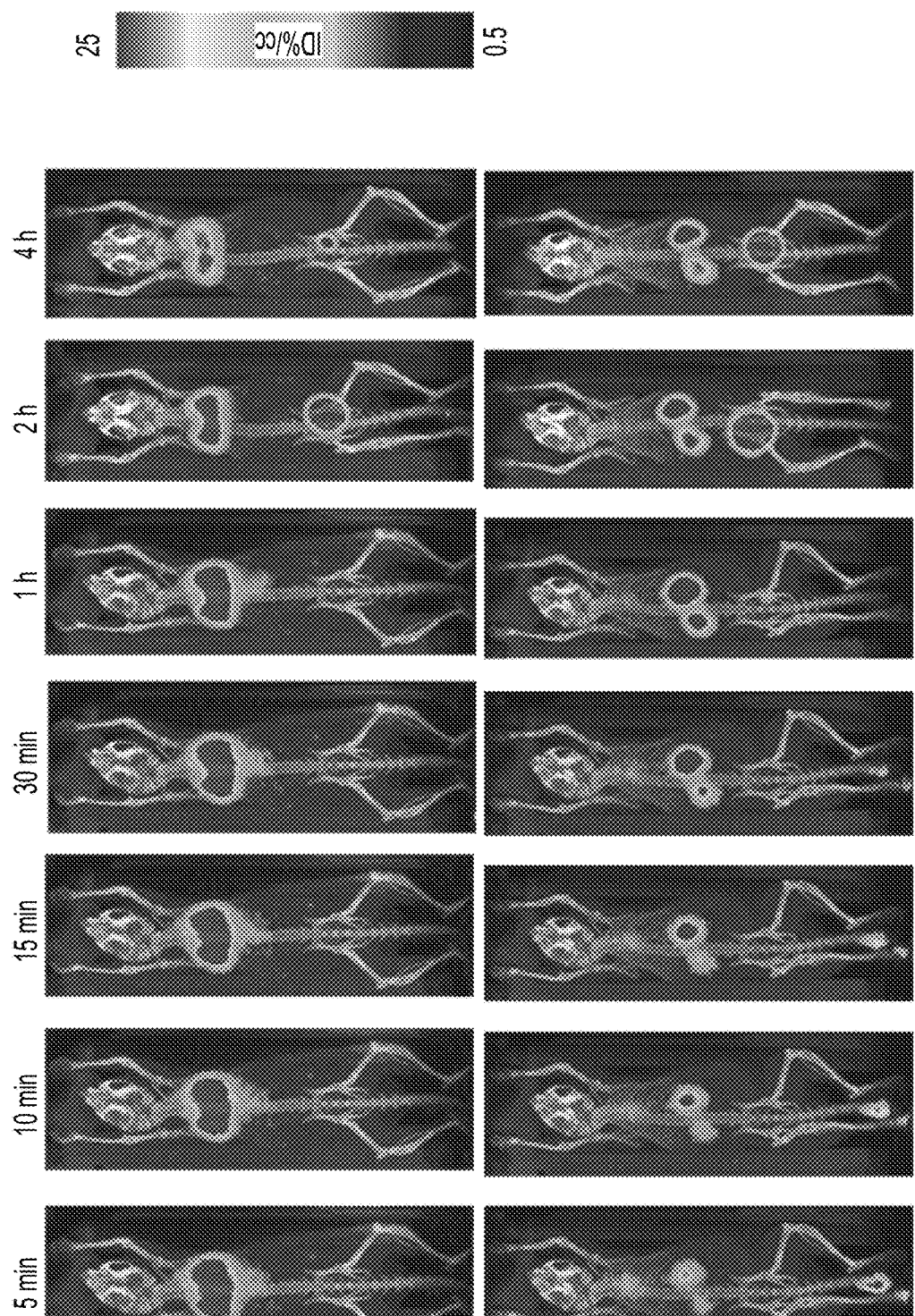
FIG. 23 are dorsal images of label detected in a mouse over time.
Figure 24:
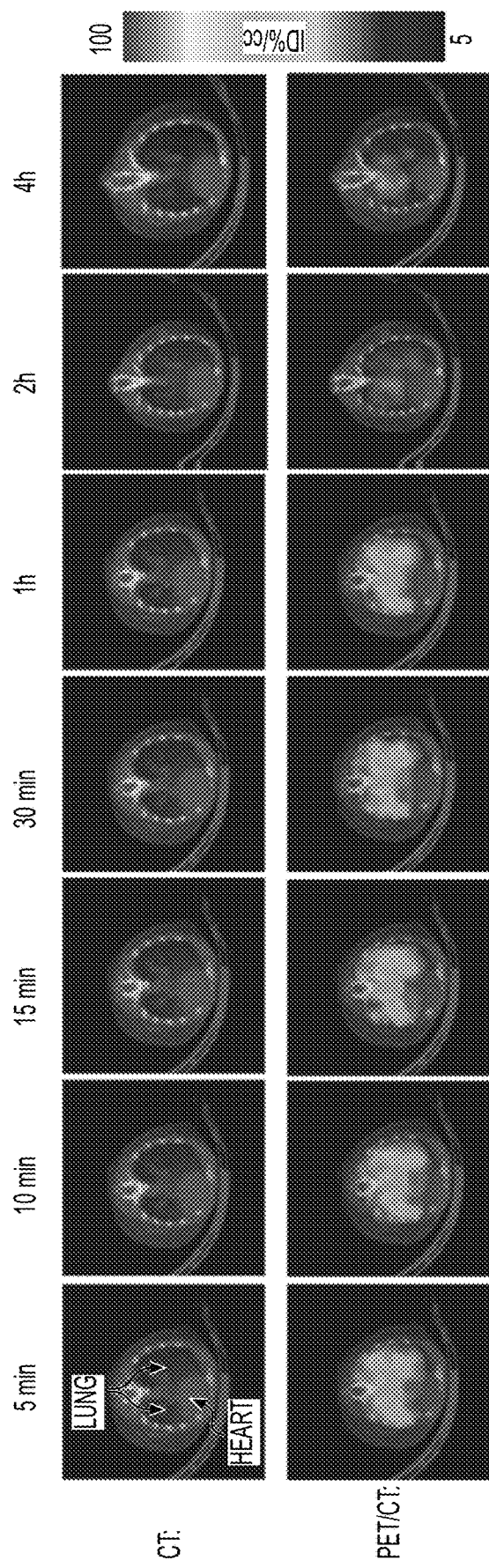
FIG. 24 are transverse slice images of label detected in a mouse over time.

Following the injection of four female NSG mice with the improved construct (compound #1307 chelated with $^{68}$Ga) the animals were imaged by PET/CT to profile the time-course biodistribution. Images were captured for compound #1307 at the time points 5 min, 10 min, 15 min, 30 min, 1 h, 2 h, and 4 h. PET/CT images were taken following the injection of 4 female NSG mice with $^{68}$Ga-chelated compound #2809. In contrast to compound #2809, compound #1307 demonstrated very low kidney absorption. Instead, this compound initially accumulates in the lung, a highly perfused organ that also expresses FOLR1. Images for mouse 4 are shown in FIG. 23 (Compounds #1307 and #2809) and FIG. 24 (Compound #1307).

The biodistribution of $^{68}$Ga-chelated compound #1307 was also calculated and compared to the biodistribution of $^{68}$Ga-chelated compound #2809 (FIG. 25). The kidney profile of compound #1307 demonstrates a seven-fold reduction in dose when compared to compound #2809 at the last time point (4 hours) (FIG. 25B). Both compounds demonstrate robust elimination through the bladder (FIG. 25D). Gratifyingly, the low kidney signal for compound #1307 did not result in an offsetting increase in liver clearance (FIG. 25E). This is in contrast with other FOLR1-targeted PET imaging agents.

Figure 25A:
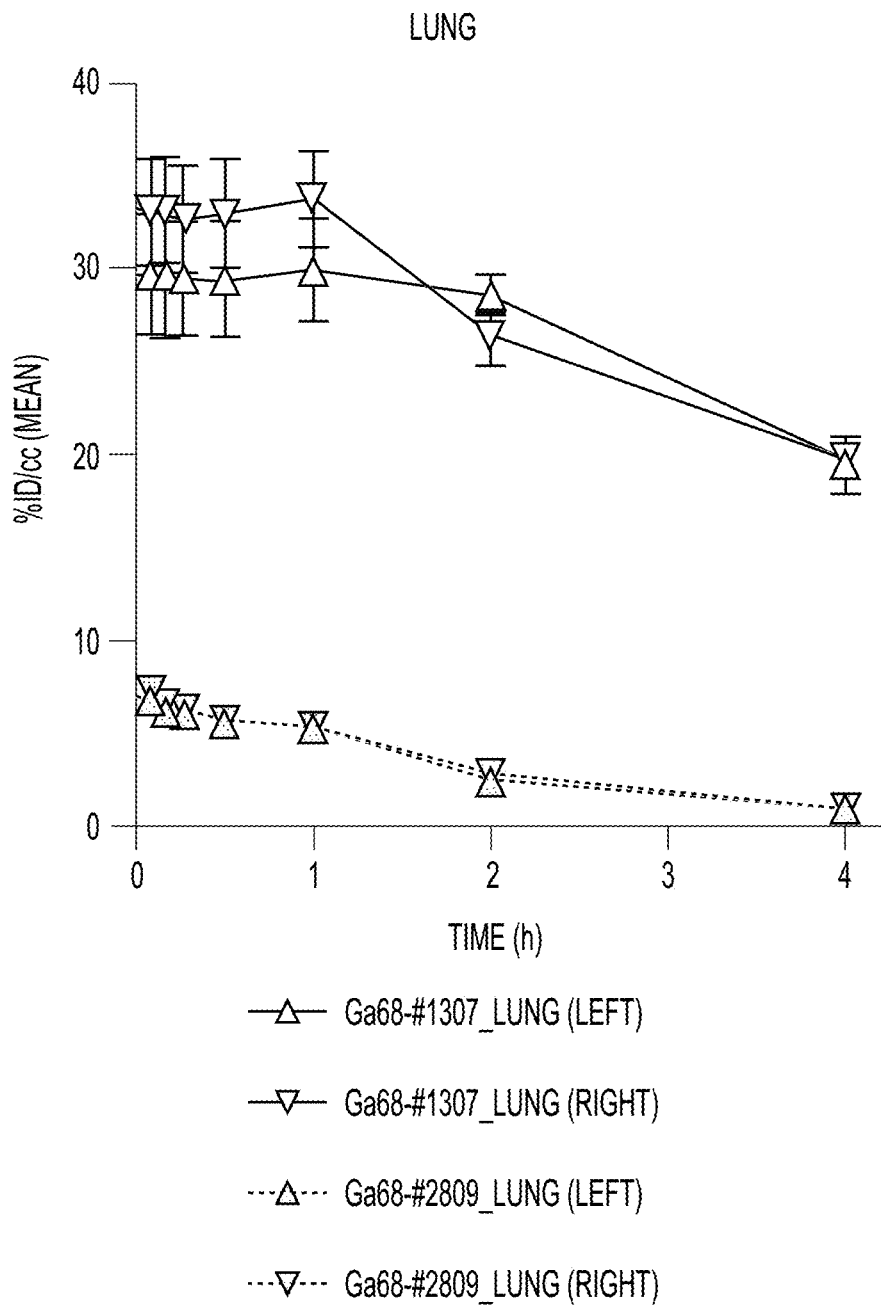
FIGS. 25A-25E are graphs of labeled compounds in lung (FIG. 25A), kidney (FIG. 25B), heart (FIG. 25C), bladder (FIG. 25D), and liver (FIG. 25E) over time.
Figure 25B:
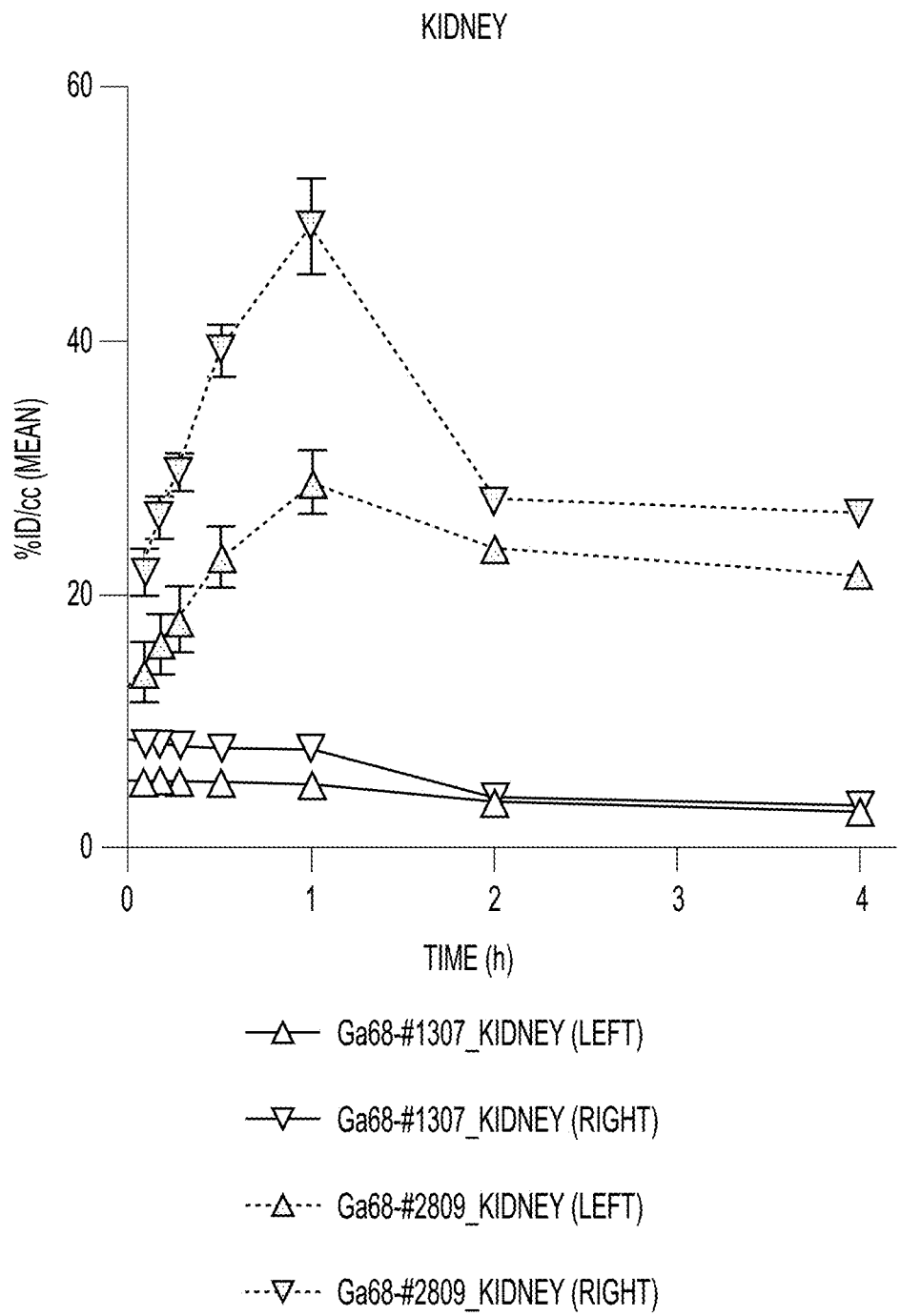
Figure 25C:
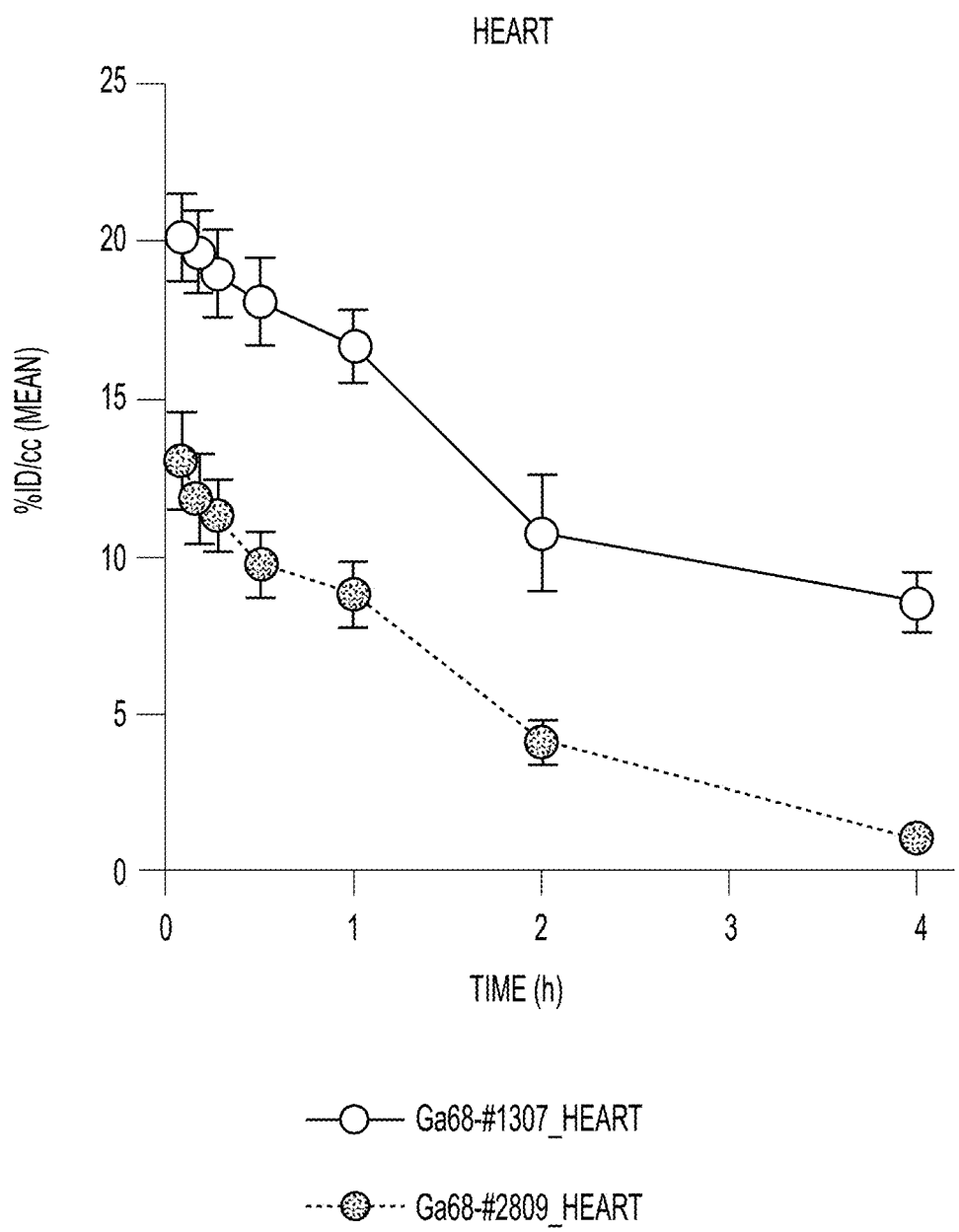
Figure 25D:
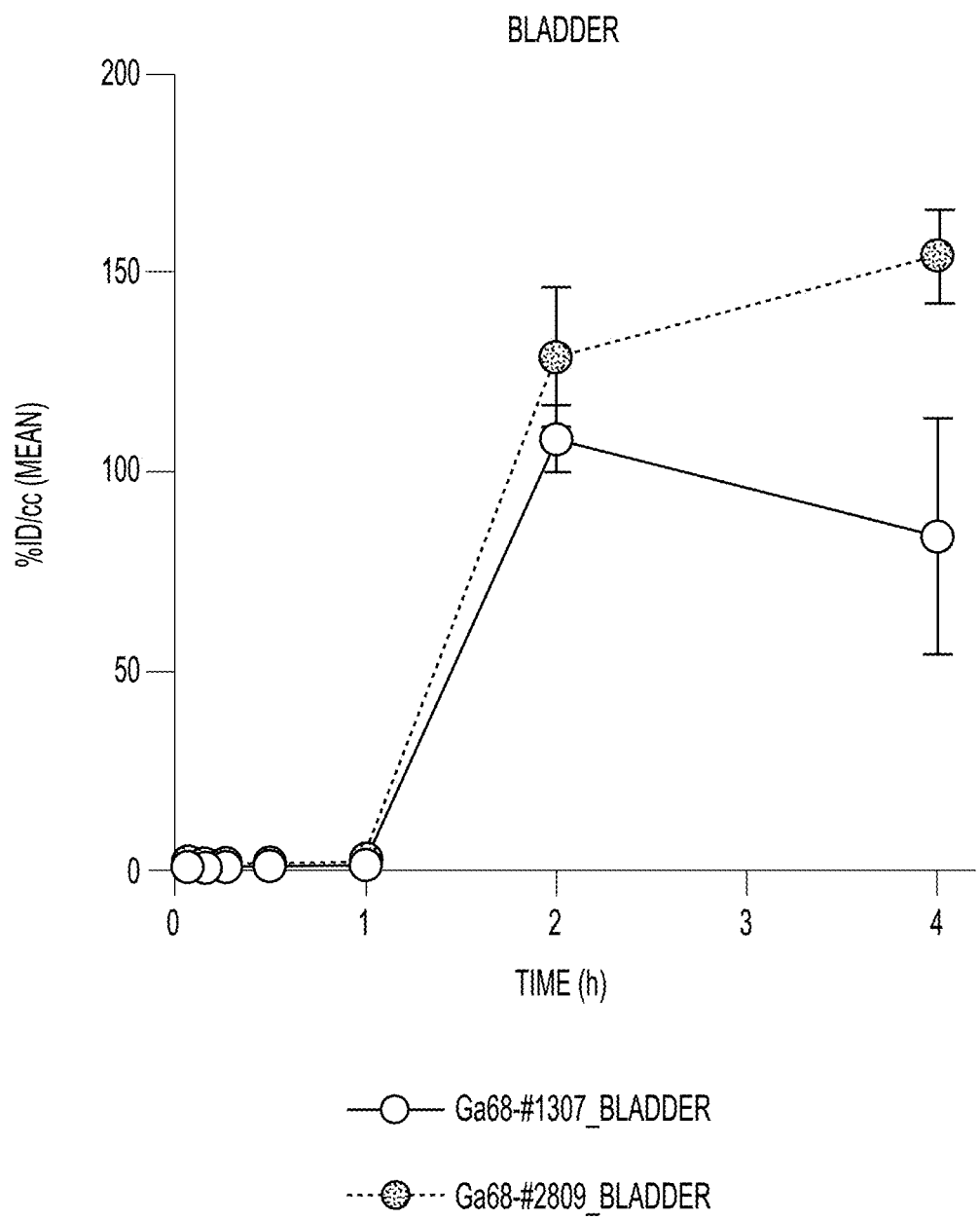
Figure 25E:
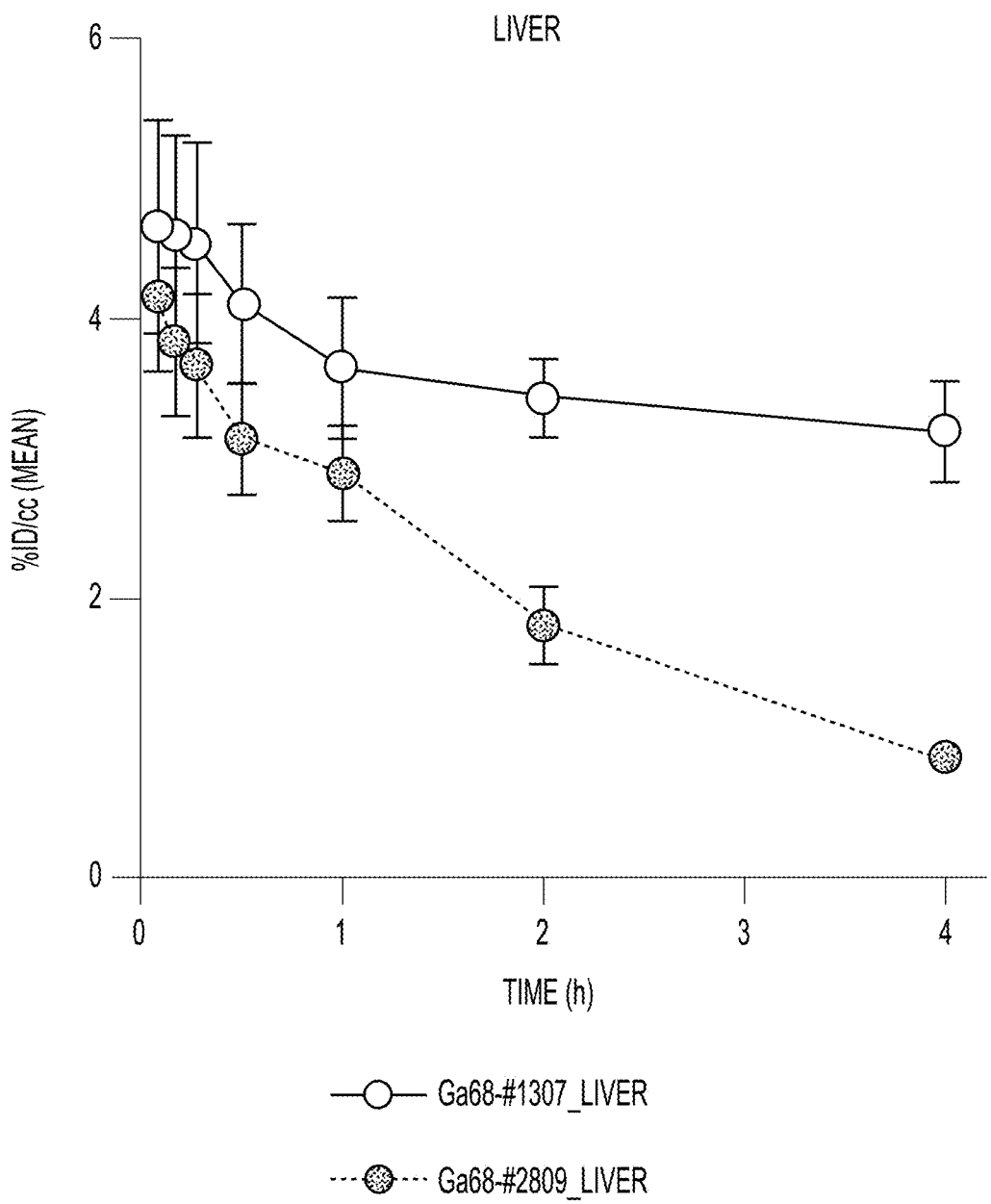

Higher accumulation of compound #1307 in the heart was also observed (FIG. 25C). The increased dose to this highly perfused organ is most likely due to the increased plasma binding contributed by the IPBA moiety. The lung also demonstrates increased accumulation of compound #1307 (FIG. 25A). The greater than three-fold increase in lung accumulation when compared to the less than two-fold increase in heart exposure suggests that this accumulation is the result of FOLR1-mediated accumulation.

Kidney retention of radiotracers is a source of nephrotoxicity that can hinder development of theranostic agents via radiation-mediated DNA damage. To reduce the radioactive dose to the kidney, compounds were constructed to incorporate a linker that is susceptible to cleavage by enzymes found predominately in the kidney's brush border.

identified by mass. 10 μM PCC containing the GFK linker was combined with varying amounts of NEP. At 10 nM NEP, complete consumption of the starting peptide was observed. At 1 nM and 0.1 nM NEP, partial cleavage was observed. Below 0.1 nM no cleavage was observed.

Folate-hshta-Lys(MPBA)-Gly-Phe-Lys(DOTA) (SEQ ID NO:6)

Molecular weight 2231.42

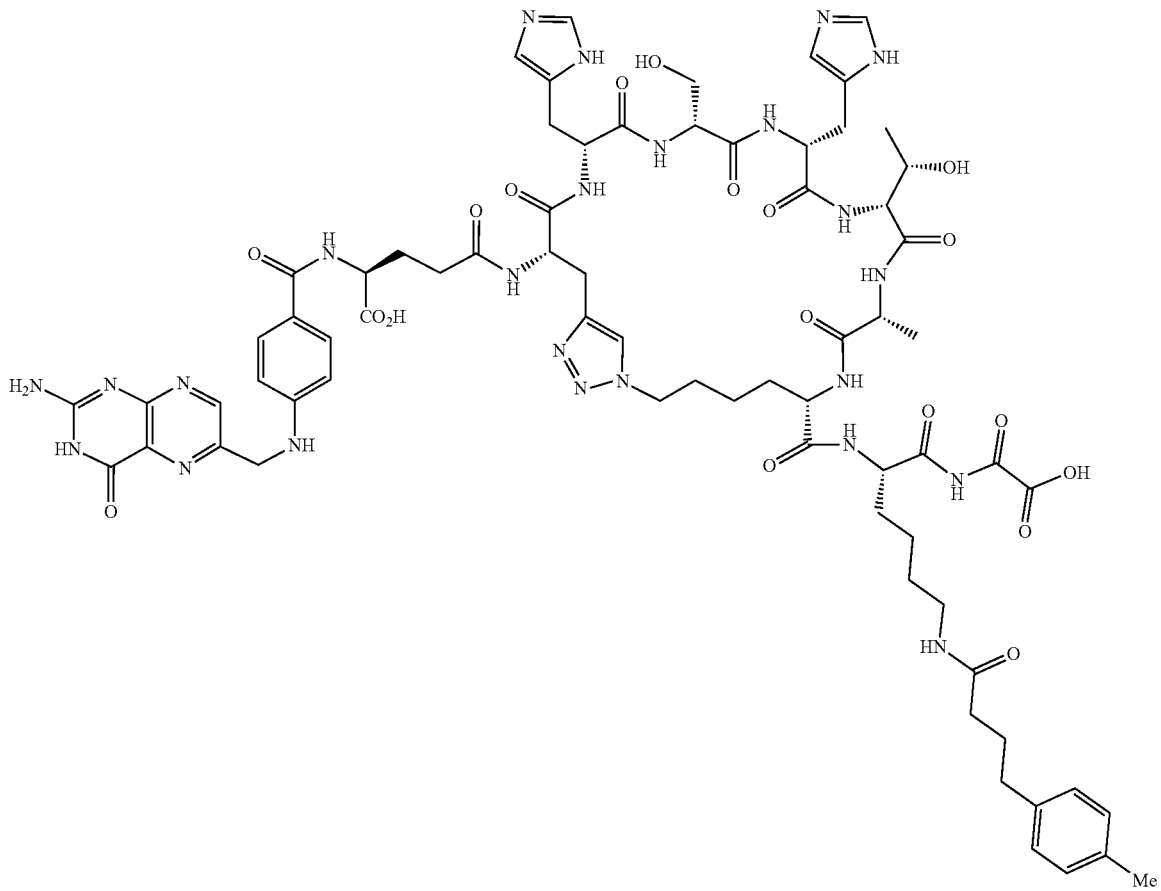

PCC Cleavage Fragment
Molecular Weight: 159.67
Folate-hshta-Lys(MPBA)-G-OH (SEQ ID NO: 6)

These enzymes cleave off the radionuclide-chelator complex, which is quickly eliminated by the kidney.

The zinc metalloprotease neprilysin (NEP) is expressed in a variety of tissue but has high abundance in the kidney. Two tripeptide sequences are recognized and cleaved by NEP: L-Met-L-Val-L-Lys and Gly-L-Phe-L-Lys. These sequences were used as cleavable linkers in the disclosed compounds.

In order to test the susceptibility of GFK and MVK linkers to NEP-mediated cleavage, the peptide (Folate-hshta-Lys (MPBA)-Gly-Phe-Lys(DOTA) (SEQ ID NO:6)) was incubated with human recombinant NEP and analyzed the solution for the presence of cleaved adducts. MALDI was utilized to monitor the cleavage of a PCC heterobiligand that contains a NEP protease recognizable sequence (G-F-K). The PCC concentration was constant and the NEP concentration was titrated down from 10 nM to 1 nM, 0.1 nM, 0.01 nM, and no NEP. The NEP-mediated cleaved adduct was The NEP-mediated cleavage was also monitored by HPLC. In agreement with the MALDI spectra, the HPLC chromatograms show depletion of the parent brush-border heterobiligand (retention time 17.1 minutes), dose-dependent on the amount of NEP spiked into the sample (10 nM, 1 nM, 0.1 nM, 0.01 nM, and no NEP). An appearance of a new peak (retention time 16.5 minutes) in concert with the depletion of the starting material is presumed to be the cleaved folate-containing peptide.

In order to test the specificity of NEP, a non-cleavable linker (PEG3) was also assayed. The NEP enzymatic cleavage assay was run using hshta-folate heterobiligands with and without the cleavable linker.

Folate-hshta-Lys(MPBA)-Gly-Phe-Lys(DOTA) (SEQ ID NO:6)

Molecular weight 2231.42

Folate-hshta-PEG3-Lys(MPBA)-Lys(DOTA) (SEQ ID NO:6)

Molecular weight 2215.42

In both MALDI and HPLC, the PEG3 compound was unchanged when incubated with NEP, while the GFK linker cleaved at the predicted site. In MALDI, the heterobiligand containing the -G-F-K- linker cleaved at the designed amide bond, producing an observable fragment with the predicted m/z (Folate-hshta-Lys(MPBA)-G-OH (SEQ ID NO:6); Molecular weight 1569.67). The heterobiligand containing a PEG3 in place of the -G-F-K-, however, did not cleave in the presence of NEP. In addition to confirming the selectivity of the NEP enzyme for the -G-F-K- peptide linker, it is also important to note that the remaining portions of the peptide were impervious to NEP.

The NEP-mediated cleavage was also monitored by HPLC. In agreement with the MALDI spectra, the HPLC chromatograms show depletion of the parent brush-border heterobiligand (retention time 17.1 minutes). The related non-cleavable analog remained unchanged (retention time 15.6 minutes). An appearance of a new peak (retention time 16.5 minutes) in concert with the depletion of the starting material is presumed to be the cleaved folate-containing peptide.

Two new heterobiligands were tested for NEP-mediated cleavage. One possesses an L-Met-L-Val-L-Lys linker, the other a Gly-L-Phe-L-Lys linker. Both are also appended with an improved albumin binder, 4-iodophenyl butyric acid (IPBA).

Folate-hshta-Lys(IPBA)-M-V-Lys(DOTA) (SEQ ID NO:6)
  Molecular weight 2369.39
Folate-hshta-Lys(IPBA)-Gly-Phe-Lys(DOTA) (SEQ ID NO:6)
  Molecular weight 2343.29

At 1 nM NEP, substantial (and in the case of GFK complete) cleavage of the test article was observed by MALDI-TOF MS. For the MVK linker, two species were identified, differing by mass of one methionine. This experiment confirms that both cleavable linkers are susceptible to NEP cleavage.

Folate-hshta-Lys(IPBA)-M-OH (SEQ ID NO:6)
  Molecular weight 1755.68
Folate-hshta-Lys(IPBA)-OH (SEQ ID NO:6)
  Molecular weight 1624.48
Folate-hshta-Lys(IPBA)-G-OH (SEQ ID NO:6)
  Molecular weight 1681.54

Key compounds were subjected to a plasma stability assay to determine the liability of the heterobiligand (and the NEP linker in particular) towards secreted peptidases found in mammalian plasma. Plasma stability of compounds #2809, 1307, 2 and 1306 and a propantheline bromide control were measured. Gratifyingly, we observed robust stability toward both rodent (CD-1 mouse) and human plasma for all compounds tested. This suggests that the PCCs with or without the L-amino acid NEP linker are stable in plasma. The results are shown in Table 3. All of the compounds showed stability in both human and mouse up to the limit of the assay (>289.1 min).

TABLE 3

Plasma Stability of Select Compounds

| # | Compound | Plasma Stability (t 1/2) |
|---|---|---|
| 2809 | Fol-hshta-PEG3-Lys(4-MPBA)-Lys(DOTA) | Hu: >289.1 min<br>Mu: >289.1 min |
| 2 | Fol-hshta-PEG3-Lys(FB) | Hu: >289.1 min<br>Mu: >289.1 min |

TABLE 3-continued

Plasma Stability of Select Compounds

| # | Compound | Plasma Stability (t 1/2) |
|---|---|---|
| 1307 | Fol-hshta-Lys(4-IPBA)-Gly-Phe-Lys(DOTA) | Hu: >289.1 min<br>Mu: >289.1 min |
| 1306 | Fol-hshta-Lys(4-IPBA)-Met-Val-Lys(DOTA) | Hu: >289.1 min<br>Mu: >289.1 min |
| 7327 | Fol-hshta-Gly-Phe-Lys(DOTA) | Hu: >6937.7 min<br>Mu: >6937.7 min |
| 6305 | Fol-hshta-Lys(4-MPBA)-Gly-Phe-Lys(DOTA) | Hu: >6937.7 min<br>Mu: >6937.7 min |
| 3303 | Fol-hshta-Gly-Phe-Lys(AO) | Hu: >6937.7 min<br>Mu: >6937.7 min (FB) |
| | Propantheline bromide (Control) | Hu: 11.6 min<br>Mu: 44.8 min |

The heterobiligand dosed in these studies is Folate-hshta-PEG3-Lys(MPBA)-Lys(DOTA) (Compound #2809; SEQ ID NO:6)) labeled with $^{177}$Lu. Plasma samples taken from tumor-bearing mice (at each dose) were assayed for biomarkers indicative of nephrotoxicity. These samples were compared to plasma taken from normal mice. Elevated urea levels in plasma could indicate kidney damage. Endogenous urea is converted to ammonia and carbon dioxide by the addition of urease. Berthelot's reagent reacts with the dissolved ammonia. The resulting green coloration can be used to back-calculate the amount of urea present in the original plasma sample.

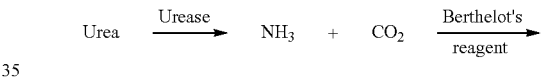

Mouse plasma samples (five mice each from the 0 MBq control group, 3.7 MBq group, and 9.25 MBq group) taken at endpoint and normal mouse plasma were evaluated in urea assays to gain information on renal function. Data show that the 9.25 MBq treated mice have 1.5 times elevated levels of blood urea nitrogen (BUN) level than the normal mice (Tables 4 and 5). The BUN value for normal mice has a range of 17-20 mg/dL, while mice with kidney injuries have 2x-4x higher BUN levels. Animals receiving either 0 or 3.7 MBq doses fell within nominal plasma urea levels. The highest dose, 9.25 MBq, yielded increased plasma urea levels.

TABLE 4

| $^{177}$Lu dose | [BUN] (mg/dL) |
|---|---|
| Normal Mice | 20.7 ± 4.3 |
| 0 MBq | 22.6 ± 2.7 |
| 3.7 MBq | 25.4 ± 4.3 |
| 9.25 MBq | 30.4 ± 7.8 |

TABLE 5

| Mice | [BUN] (mg/dL) |
|---|---|
| Normal C57BL/6[b] | 17 |
| Normal C57BL/6[b] | 20 |
| 2 day post Ischemia[b] | 51 |
| Normal DBA/2J[c] | 19 |
| 3 day post 5/6-nephrectomy[c] | 42 |

TABLE 5-continued

| Mice | [BUN] (mg/dL) |
|---|---|
| Normal C57BL/6[d] | 19 |
| 1 day post Renal Ischemia/Reperfusion[d] | 82 |

References:
[a]Rodrigues et. al., Biomed Res Int. 2014; 872827.
[b]Han et. al., Stem Cell Res Ther. 2013; 4(3) 74.
[c]Grindle et. al., Comp Med. 2006; 56(6) 482.
[d]Jouret et. al., PLoS One 2016; 11(9) e0163021.

Creatinine is another biomarker indicative of kidney stress. This compound is a byproduct of metabolism that is removed from circulation by the kidney. An elevated plasma creatinine level is indicative of poorly functioning kidneys. Mouse plasma samples (five mice each from the 0 MBq control group, 3.7 MBq group, and 9.25 MBq group) taken at endpoint and normal mouse plasma were evaluated in creatinine assays to gain information on renal function (Table 6). In the tumor therapeutic experiment, the animals dosed with 0 MBq and 3.7 MBq demonstrated elevated dissolved creatinine. Animals dosed with 9.25 MBq of the compound demonstrated substantially higher creatinine concentration.

TABLE 6

| $^{177}$Lu dose | [Creatinine] (μmol/L) |
|---|---|
| Normal Mice | 7.7 ± 3.6 |
| 0 MBq | 16.2 ± 12.0 |
| 3.7 MBq | 15.5 ± 6.1 |
| 9.25 MBq | 43.9 ± 27.0 |

Tumor growth, body weight, and gamma counting data were compiled at the endpoint of the $^{177}$Lu-#6305 therapy study of OVCAR3 xenografts. Tumor sizes at time of treatment were compared for the $^{177}$Lu-#6305 and previous therapy studies. The $^{68}$Ga and $^{177}$Lu labeling of heterobiligand #3302 is being tested. This heterobiligand is similar to compound #6305 but has a PEG3 spacer between the GFK linker and DOTA to improve the solubility and reactivity. Chelation of $^{175}$Lu proceeds more efficiently for #3302 than #6305, which indicates that this enhancement in labeling will translate to the $^{177}$Lu reaction.

Lu177-#6305 treatments were tested to determine the tolerated and most effective doses. Single dose treatments at 18.5 MBq/nmol specific activity. OVCAR3 mouse model was used. $10^7$ cell tumors were implanted in the mice one month before administration of $^{177}$Lu-#6305. Five mice each were administered Cold #6305, 9.25 MBq Lu177-#6305, and 14.8 MBq Lu177-#6305, and two mice were administered 29.6 MBq Lu177-#6305. Tumor growth and body weight were then monitored.

Figure 26:
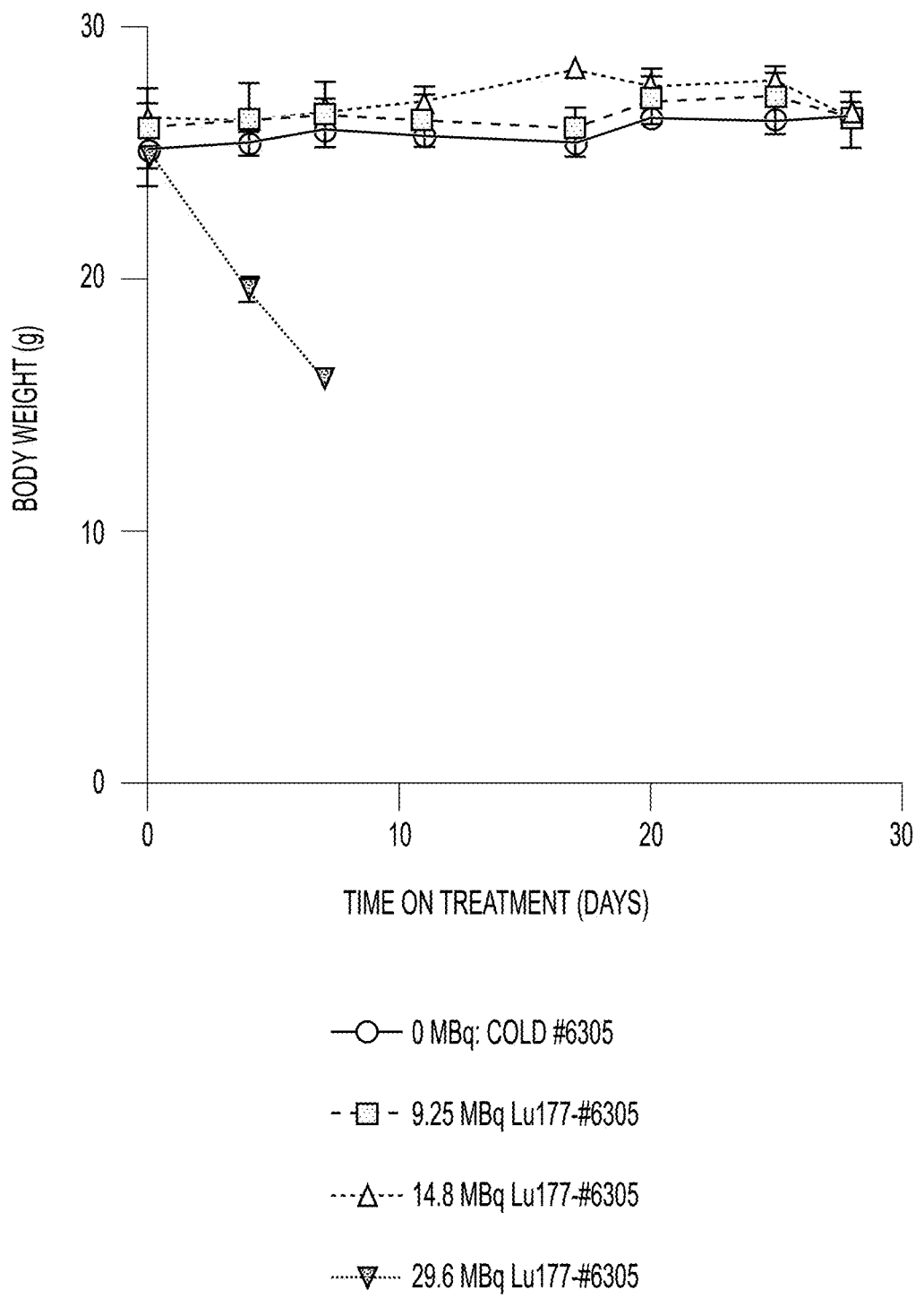
FIG. 26 is a graph of body weight change over days of treatment with Lu177-#6305.
Figure 27:
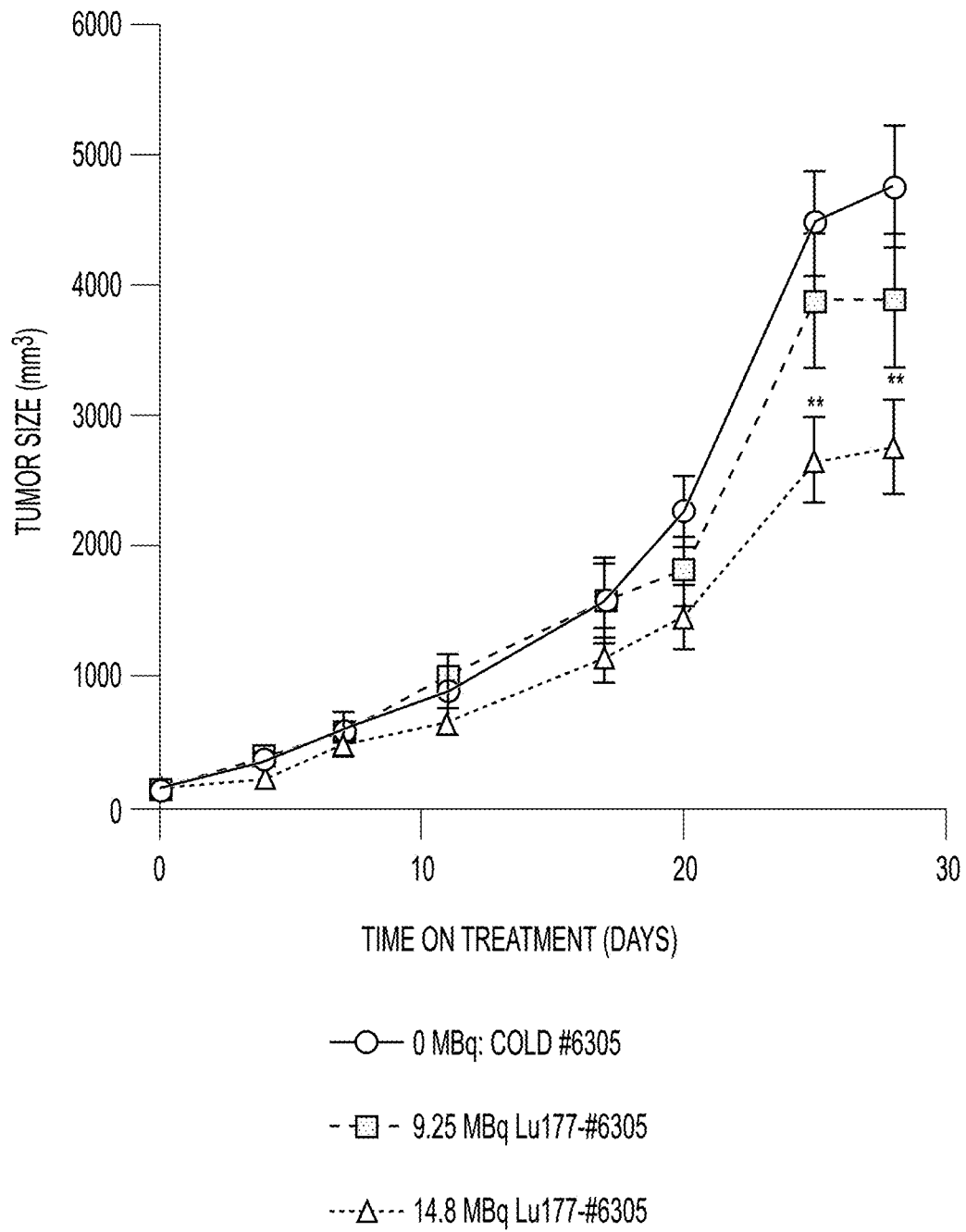
FIG. 27 is a graph of tumor size over days of treatment with Lu177-#6305 treatment.

No significant body weight change was detected in groups treated with 9.25 MBq and 14.8 MBq Lu177-#6305 (FIG. 26). The 29.6 MBq Lu177-#6305 treatment group showed substantial body weight decrease after injection (FIG. 26). 14.8 MBq Lu177-#6305 treatment significantly slowed down OVCAR3 tumor growth (FIG. 27).

Figure 28:
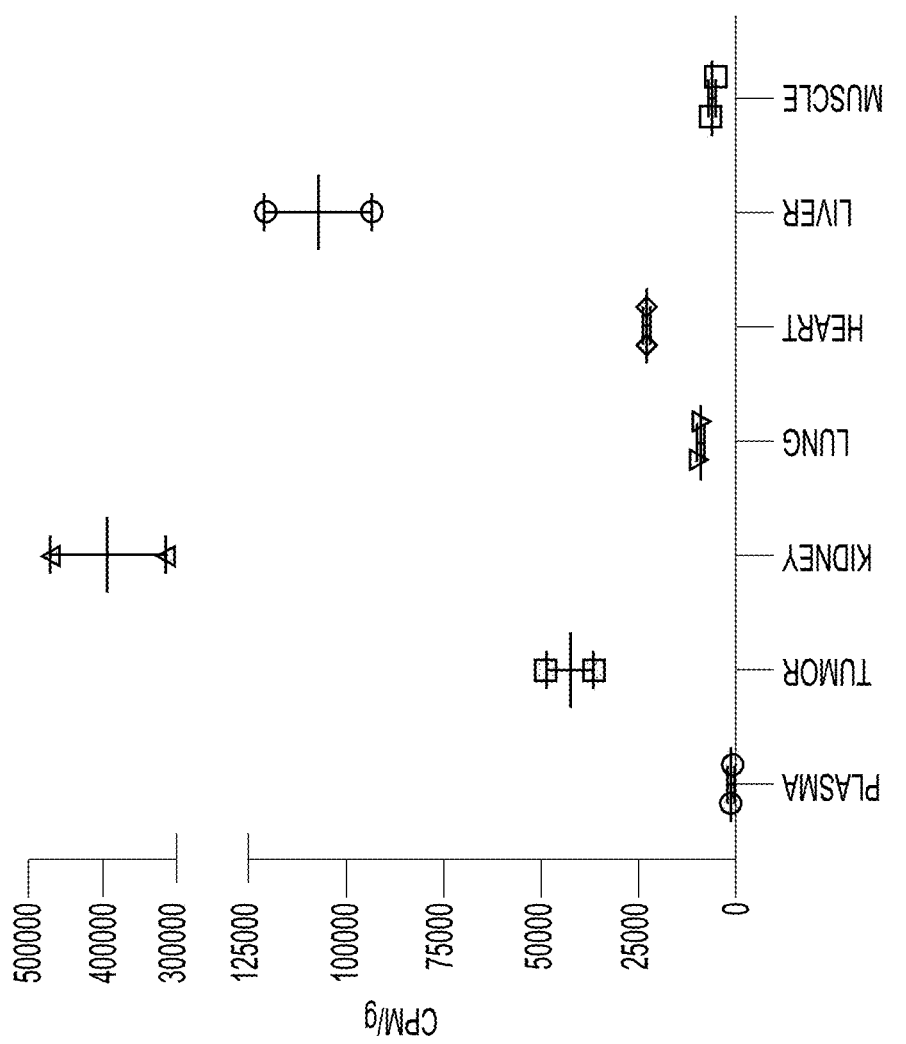
FIG. 28 is a graph of radioactivity (CPM/g) in various tissues 7 days after Lu177-#6305 injection.
Figure 29:
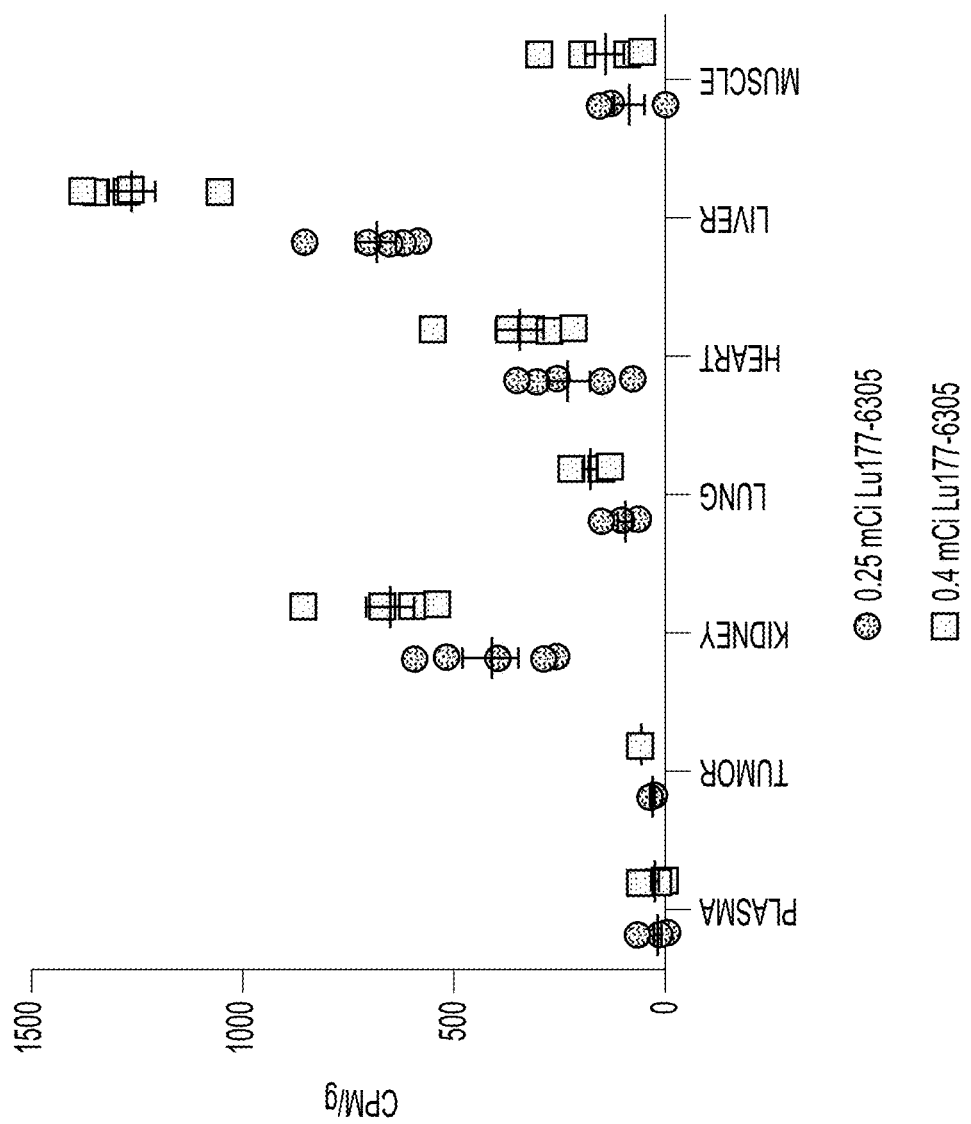
FIG. 29 is a graph of radioactivity (CPM/g) in various tissues at study endpoint (Day 28 post-injection) in various tissues.

7 days after Lu177-#6305 injection, the 29.6 MBq group lost 20% body weight. These mice were sacrificed. Tissues and plasma were collected for evaluation of radioactivity by gamma counting. The toxicity may have resulted from its accumulation in the kidneys and liver (FIG. 28). At study endpoint (Day 28 post-injection), plasma, tumors, kidneys, lungs, hearts, livers, and muscles from 9.25 MBq and 14.8 MBq treatment groups were collected for evaluation of radioactivity by gamma counting (FIG. 29).

Lu177-#6305 at 14.8 MBq significantly slowed down OVCAR3 xenograft tumor growth. Both 9.25 MBq and 14.8 MBq doses of Lu177-#6305 were tolerated without significant body weight change detected. The 29.6 MBq Lu177-#6305 dose caused substantial body weight decrease after injection. Based on the gamma counting data from the 29.6 MBq group on Day 7 post-injection, high radioactivity was detected in the kidney and the liver (394,834 CPM/g and 107,374 CPM/g, respectively). 42,674 CPM/g was detected in the tumor. Based on the gamma counting data from the groups of 9.25 MBq and 14.8 MBq on Day 28 post-injection, the liver radioactivity (685 CPM/g in the 9.25 MBq group and 1,264 CPM/g in the 14.8 MBq group) was higher than that in the kidney (414 CPM/g in the 9.25 MBq group and 653 CPM/g in the 14.8 MBq group). The tumor radioactivity was 33 CPM/g and 60 CPM/g, respectively, for the 9.25 MBq group and the 14.8 MBq group.

In the gamma counting data, the tumor/kidney ratio was 0.108 and 0.093 in the 29.6 MBq group and the 14.8 MBq group, which are quite comparable. There was a ~6-fold increase in tumor mass between Day 7 and Day 28, suggesting that the decrease in radioactivity in the tumor was slower than that in the kidney (the values were normalized to mass, CPM/g). There was a substantial increase in the liver/kidney radio from 0.27 to 1.94 (29.6 MBq group on Day 7 vs. 14.8 MBq group on Day 28).

Figure 30:
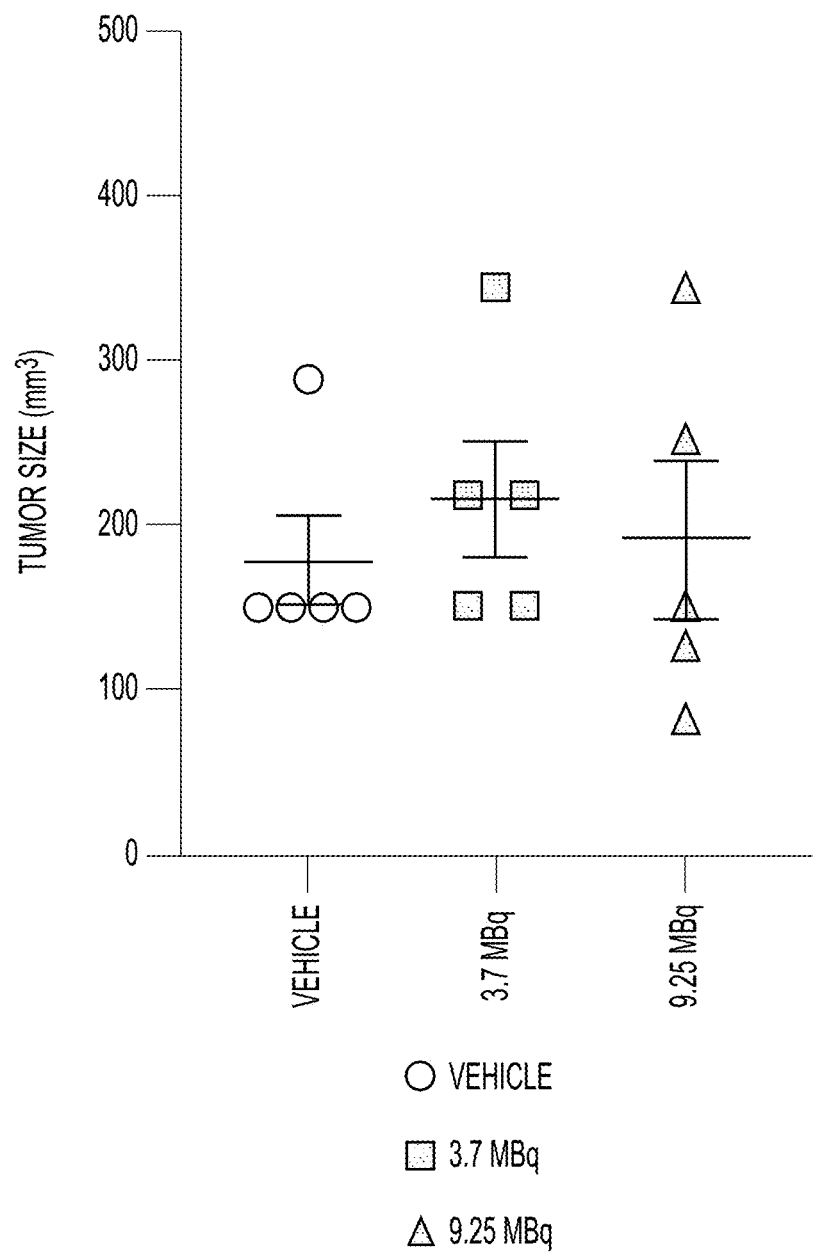
FIG. 30 is a graph of tumor size on day −2 for the $^{177}$Lu-#2809 treatment.

Tumor size on day -2 for the $^{177}$Lu-#2809 treatment is shown in FIG. 30. Heterobiligand #2809 has a PEG3 linker and MPBA albumin binder. A single dose at 81.4 MBq/nmol specific activity was used. Tumor size (avg.) at treatment was 203 mm$^3$. Significant tumor growth control at 9.25 MBq and partial response at 3.7 MBq was observed.

Figure 31:
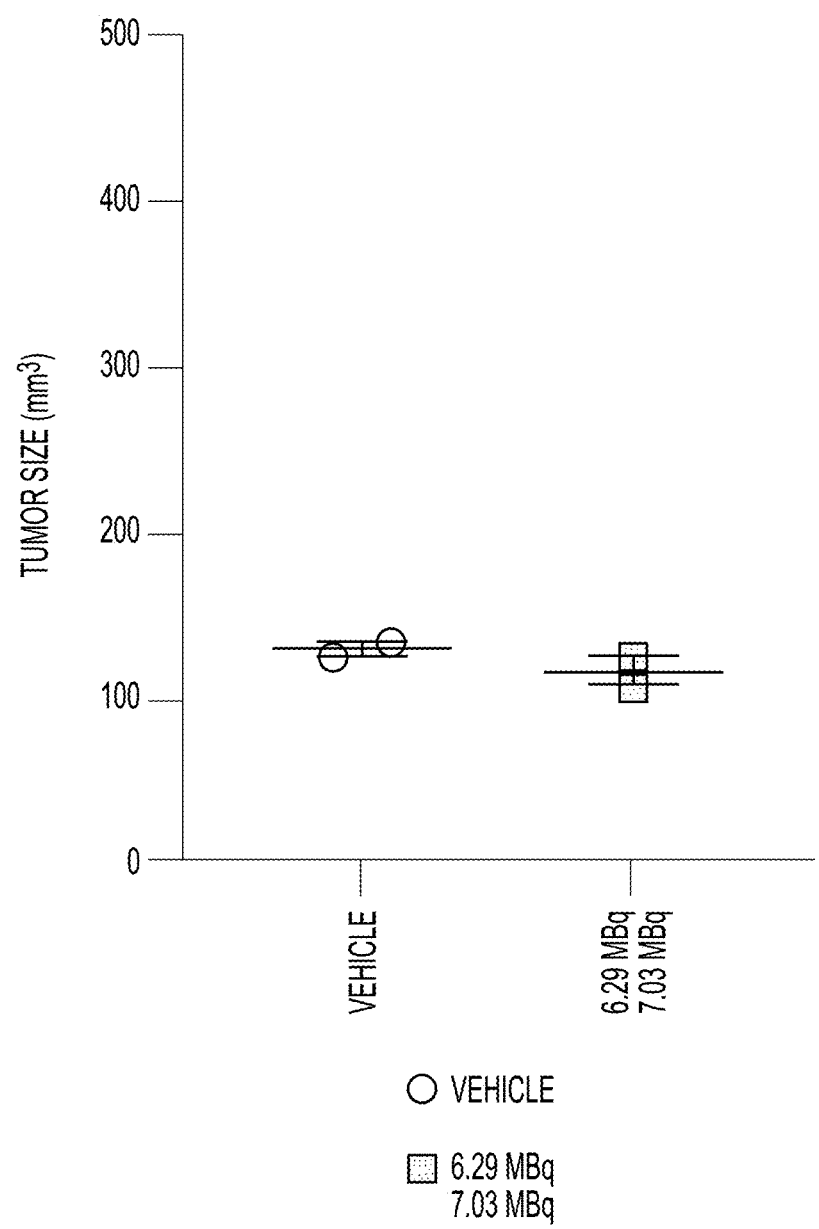
FIG. 31 is a graph of tumor size on day 0 for the $^{177}$Lu-#1307 treatment.

Tumor size on day 0 for the $^{177}$Lu-#1307 treatment is shown in FIG. 31. Heterobiligand #1307 has IPBA albumin binder and GFK linker (for kidney cleavage). A single dose at 1.73 MBq/nmol specific activity was used. Tumor size (avg.) at treatment was 117 mm$^3$. A partial response was observed at 6.29-7.03 MBq (small n).

Figure 32:
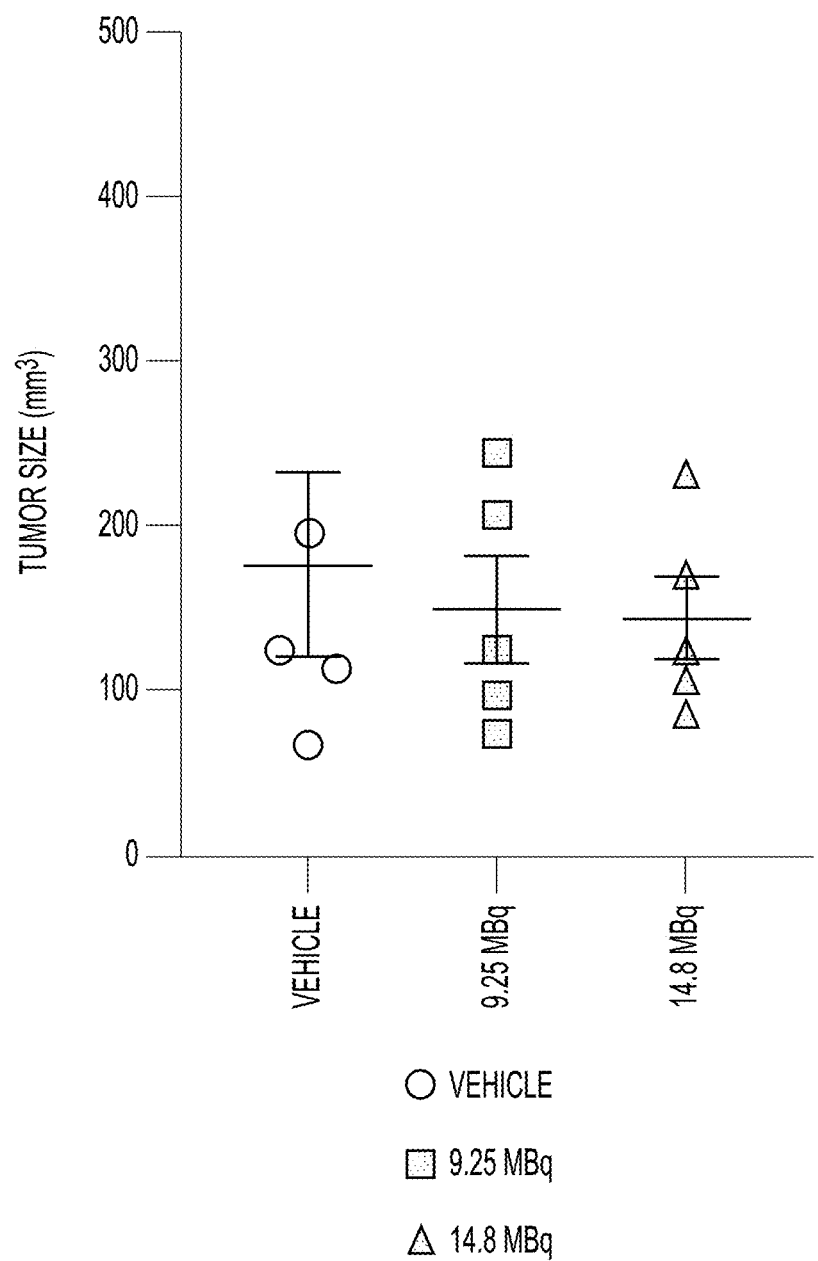
FIG. 32 is a graph of tumor size on day 0 for the $^{177}$Lu-#6305 treatment.

Tumor size on day 0 for the $^{177}$Lu-#6305 treatment is shown in FIG. 32. Heterobiligand #6305 has MPBA albumin binder and GFK linker (for kidney cleavage). A single dose at 18.5 MBq/nmol specific activity was used. Tumor size (avg.) at treatment was 148 mm$^3$. A partial response was observed at 14.8 MBq and nonresponse at 9.25 MBq.

The greatest tumor growth control was observed when treating at the highest $^{177}$Lu specific activity and largest tumor sizes. Also, the linkers attached to a given heterobiligand would have influenced its exposure to the tumor.

The heterobiligands can also be tested in in vivo therapy studies designed to investigate the specific activity of $^{177}$Lu labeling, tumor size at time of treatment, and protein binding contributions to therapy response. $^{18}$F-FBA PET imaging studies can also be used to profile the biodistribution and clearance with iteration of BB cleavable linker designs for reduction of renal uptake. SKOV3 can be employed as a second FOLR+ ovarian cancer xenograft model for PET imaging.

Figure 33A:
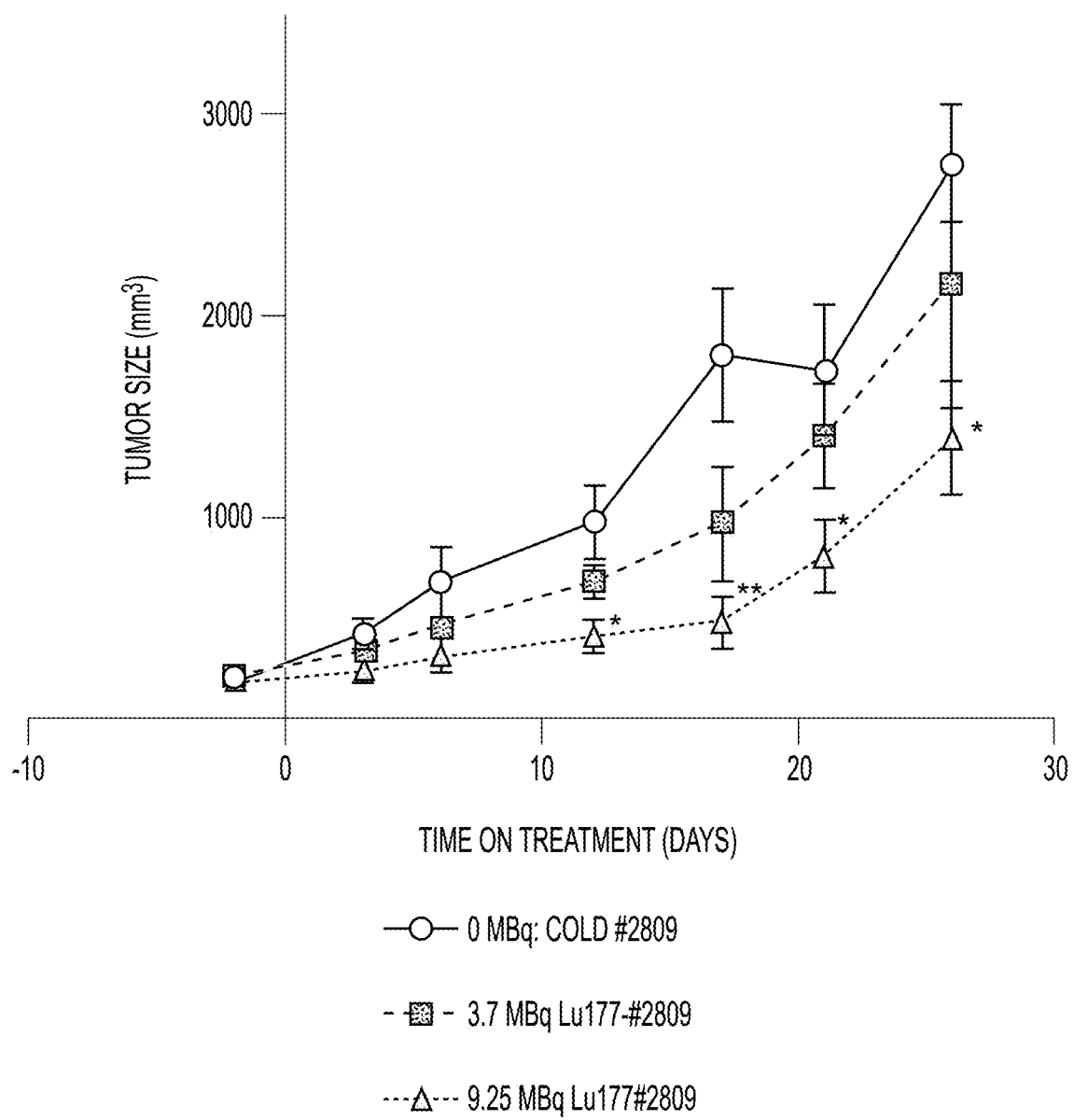
Figure 33C:
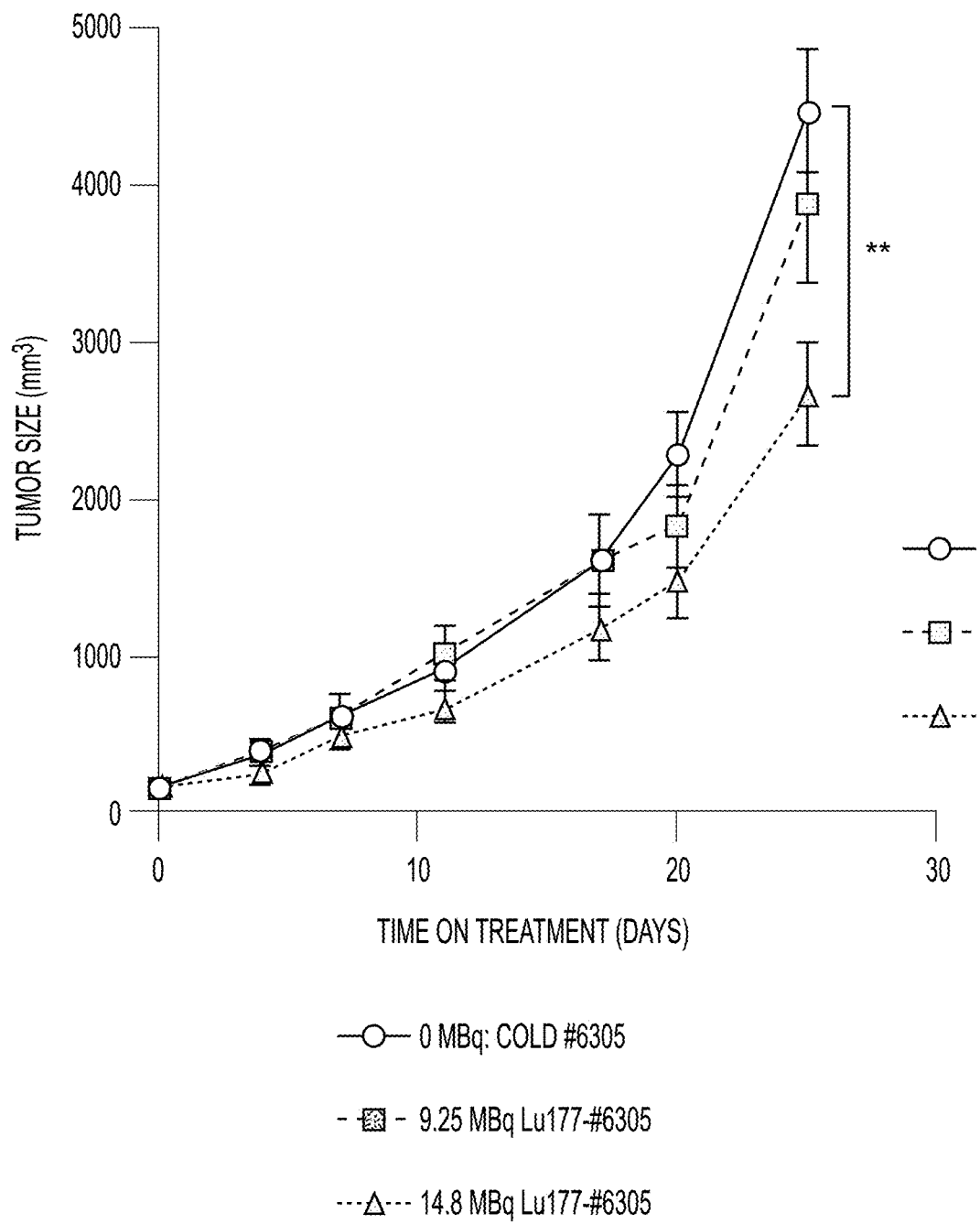

A summary of the results of in vivo response to heterobiligand treatment in OVCAR3 xenografts is shown in FIG. 33. FIG. 33A shows the results for OVCAR3 xenografts treated with Lu177-#2809 (SA=81.4 MBq/nmol). FIG. 33B shows results for OVCAR3 xenografts treated with Lu177-#1307 (SA=1.73 MBq/nmol). FIG. 33C shows results for OVCAR3 xenografts treated with Lu177-#6305 (SA=18.5 MBq/nmol).

Select FOLR constructs using AO instead of DOTA were tested. The results are summarized in Table 7.

TABLE 7

Summary of AO-containing FOLR1 Constructs

| # | Compound | Alb | BB | in vivo | % MeCN | Plasma % Bound (% Recovery) | in vitro Assay Data |
|---|---|---|---|---|---|---|---|
| 2808 | Fol-hshta-PEG3-Lys(4-MPBA)-Lys(AO) | MPBA | N/A | | — | | |
| 0328 | Fol-hshta-PEG3-Lys(AO) | N/A | N/A | Dx | 17.45% (FB) | Hu: 43.01% (85.0% recovered) Mu: 20.22% (115.0% recovered) (FB) | |
| 9416 | Fol-hshta-Lys(4-IPBA)-Gly-Phe-Lys(AO) | IPBA | GFK | | — | | |
| 3304 | Fol-hshta-Lys(4-MPBA)-Gly-Phe-Lys(AO) | MPBA | GFK | | 40.1% (FB) | | Cleavage of -G-F-K- linker was confirmed in NEP assay. |
| 3303 | Fol-hshta-Gly-Phe-Lys(AO) | N/A | GFK | Dx | 33.5% (FB) | Hu: 81.0% (80.6% recovered) Mu: 75.5% (77.7% recovered) (FB) | Cleavage of -G-F-K- linker was confirmed in NEP assay. |

Alb: Albumin Binder; BB: Brush Border Cleavable linker;
in vivo: compound has been dosed;
% MeCN: percent Acetonitrile that elutes the compound (HPLC).

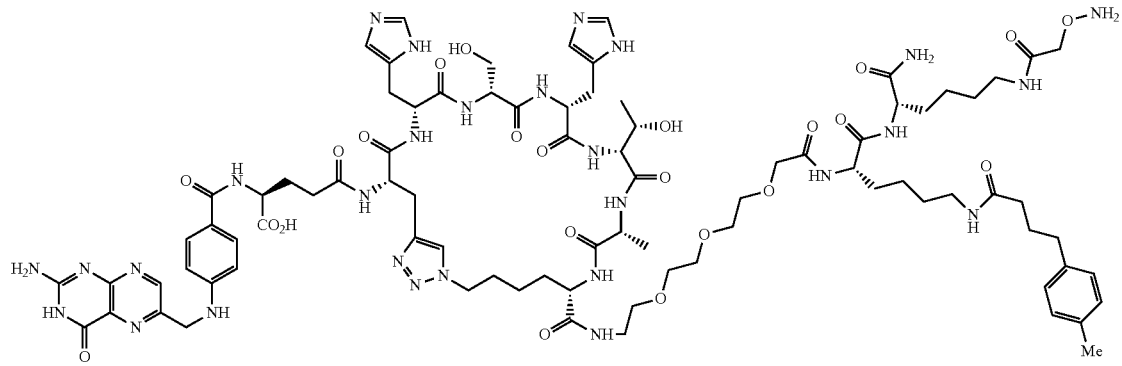

Fol-hshta-PEG3-Lys(4-MPBA)-Lys(AO) (SEQ ID NO: 6)
Compound #2808

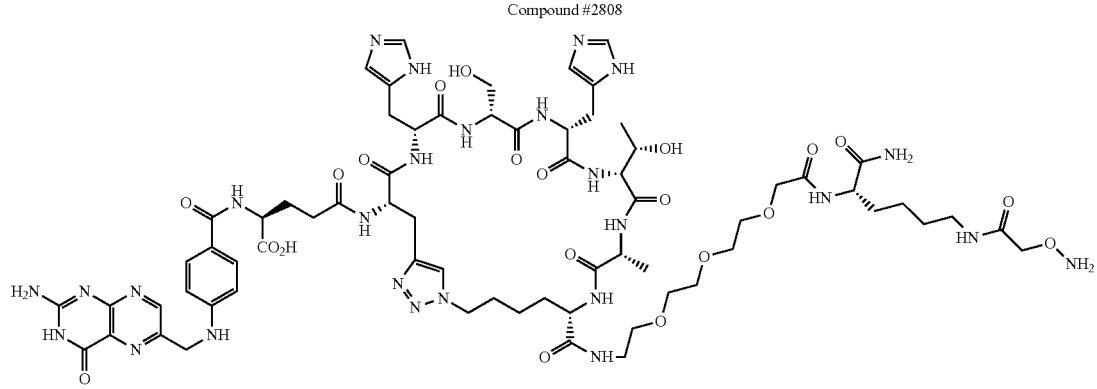

Fol-hshta-PEG3-Lys(AO) (SEQ ID NO: 6)
Compound #0328

TABLE 7-continued
Summary of AO-containing FOLR1 Constructs
| # | Compound | Alb BB | in vivo | % MeCN | Plasma % Bound (% Recovery) | in vitro Assay Data |
|---|----------|--------|---------|--------|------------------------------|---------------------|
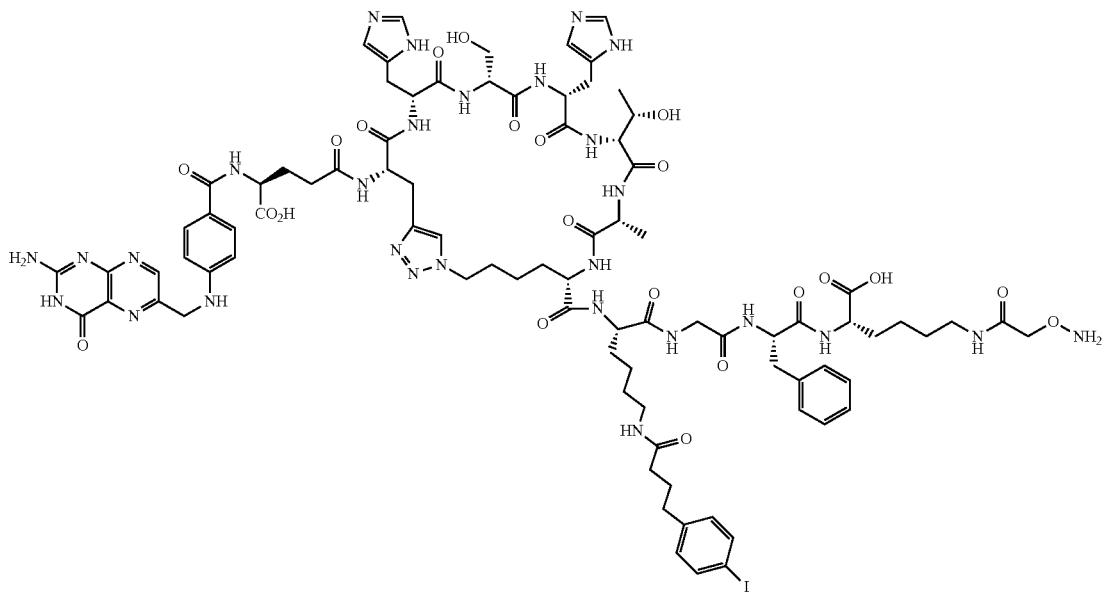
Fol-hshta-Lys(4-IPBA)-Gly-Phe-Lys(AO) (SEQ ID NO: 6)
Compound #9416
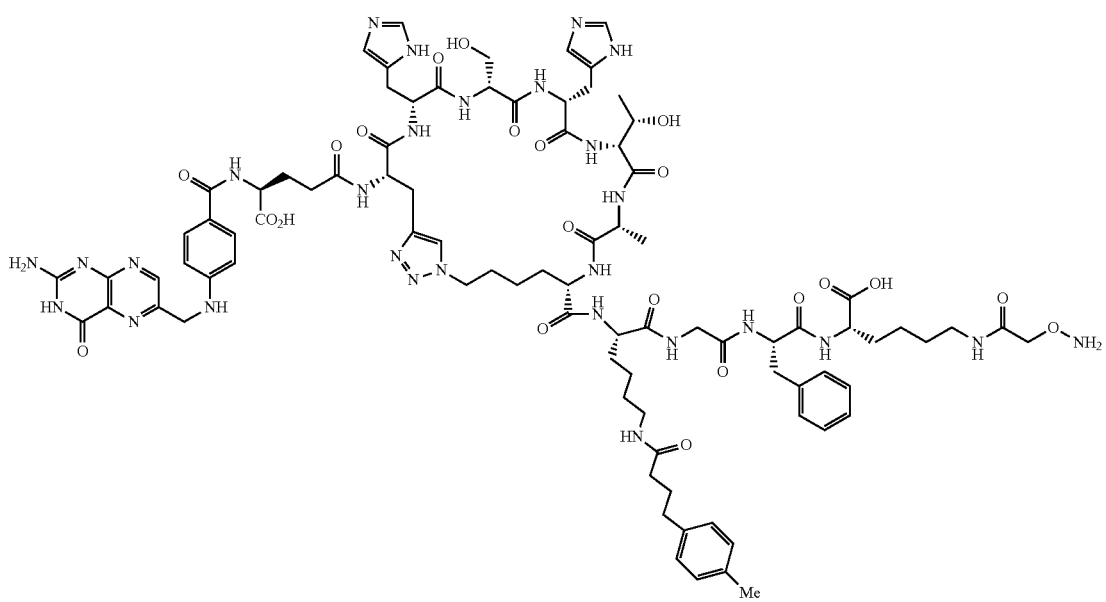
Fol-hshta-Lys(4-MPBA)-Gly-Phe-Lys(AO) (SEQ ID NO: 6)
Compound #3304

TABLE 7-continued

Summary of AO-containing FOLR1 Constructs

| # | Compound | Alb | BB | in vivo | % MeCN | Plasma % Bound (% Recovery) | in vitro Assay Data |
|---|----------|-----|----|---------|--------|-----------------------------|---------------------|

Fol-hshta-Gly-Phe-Lys(AO) (SEQ ID NO: 6)

Example 2: In Vivo Studies of Heterobiligand Compounds

Figure 34:
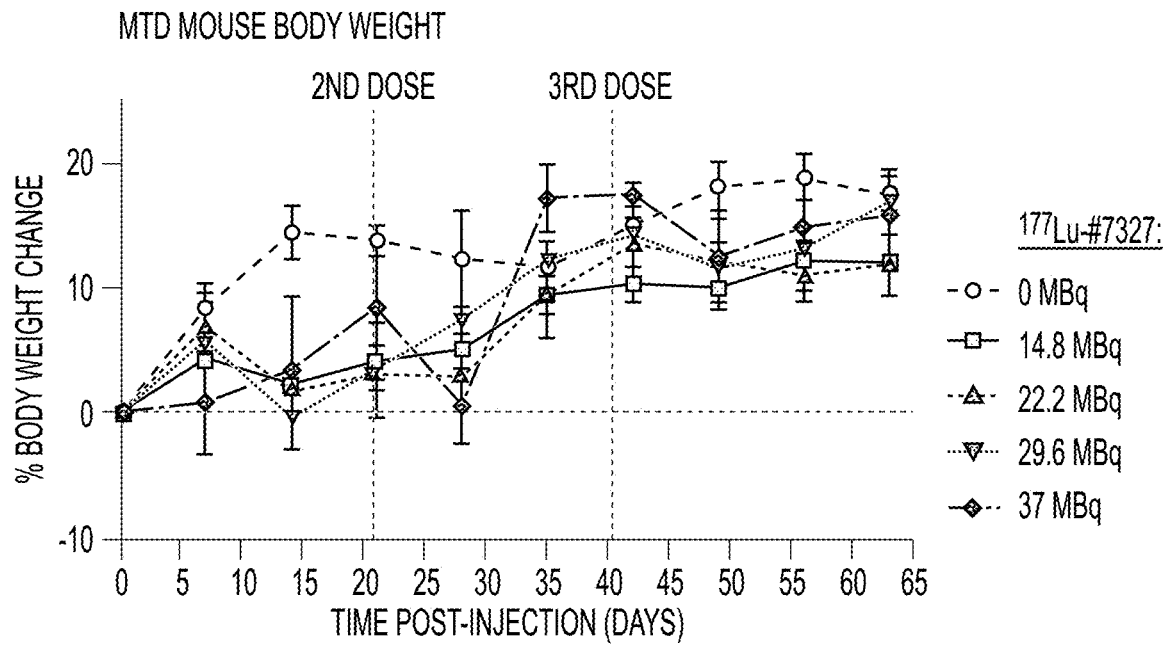
FIG. 34 is a graph of percent body weight change versus time (in days) post-injection of different radioactivity doses of $^{177}$Lu-7327.
Figure 35:
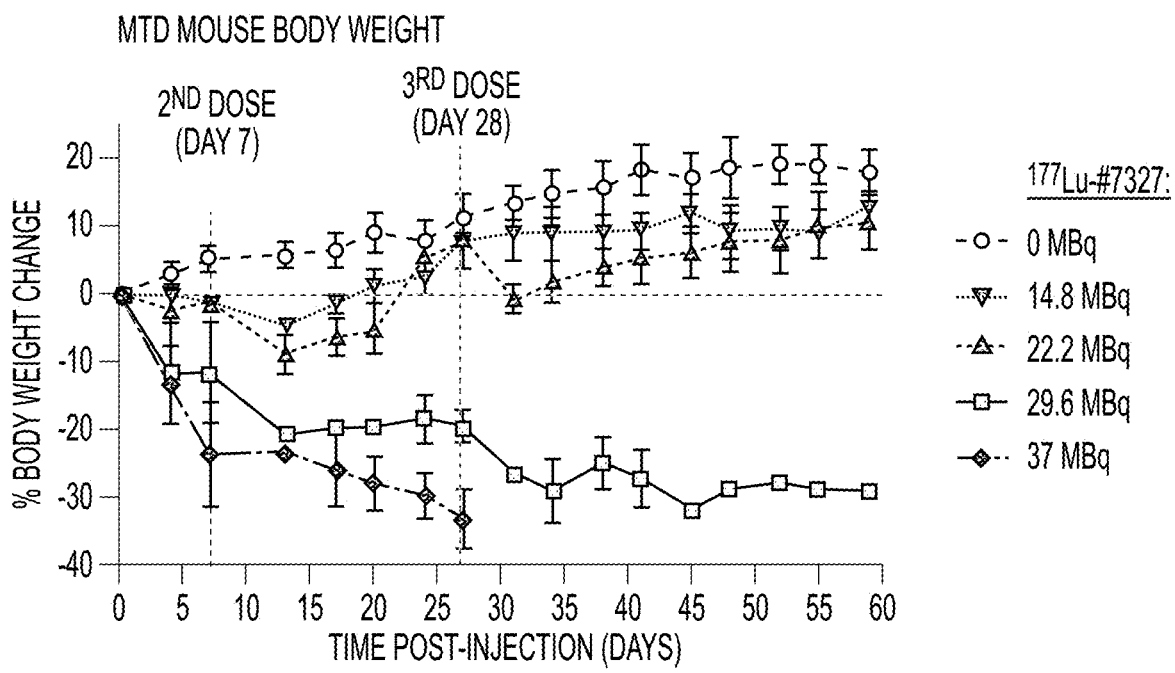
FIG. 35 is a graph of percent body weight change versus time (in days) post-injection of different radioactivity doses of $^{177}$Lu-7327.

In order to establish a maximum tolerated dose (MTD), a tolerability study was undertaken testing increasing amounts of the 177-Lu heterobiligand 7327 (folate-hshta-Gly-Phe-Lys(DOTA)). Animals were monitored for signs of toxicity and weighed twice weekly. Repeated doses of 14.8 MBq, 22.2 MBq, 29.6 MBq, and 37 MBq were well tolerated (FIGS. 34 and 35). The second and third doses were administered 21 days following the previous dose. Doses of 111 MBq and 185 MBq were not tolerated (FIG. 35). At these high doses, animals lost substantial body weight following the first dose, which worsened following the second and third doses. This experiment established an MTD for 177-Lu 7327 of between 37 and 111 MBq. The tolerance of the 0 MBq arm suggests that the radionuclide drives the toxicity profile and not the peptide alone.

Figure 36A:
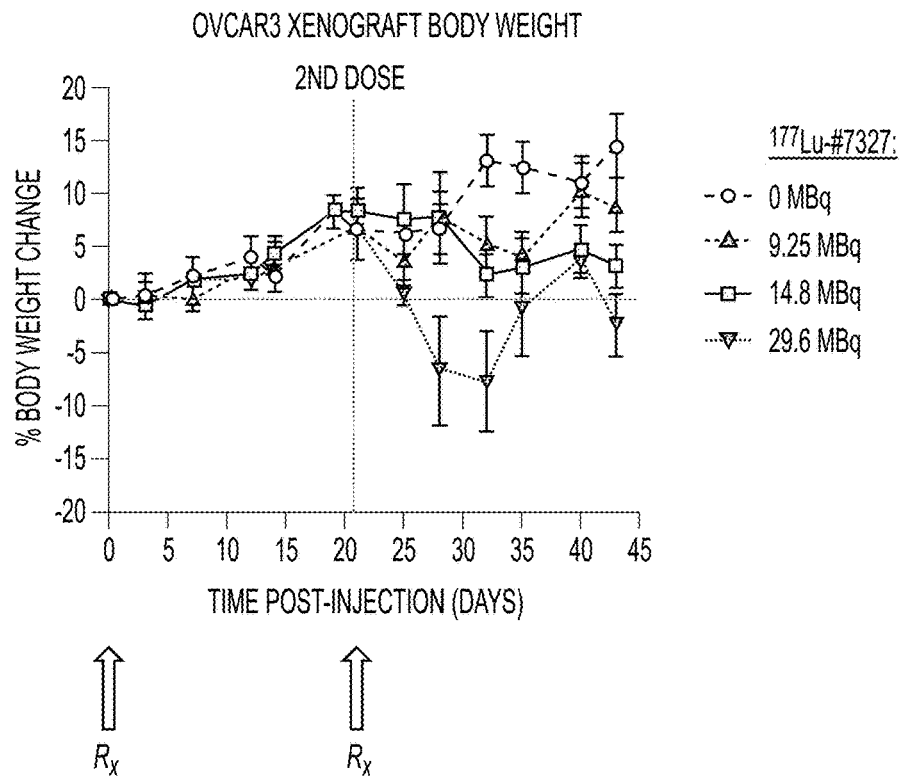
FIG. 36A is a graph of percent body weight change versus time (in days) post-injection of different radioactivity doses of $^{177}$Lu-7327.

Female NSG mice were implanted subcutaneously with OVCAR3 cells. Once tumors reached volumes of 200 mm$^3$, the animals were treated with 177-Lu 7327. Three treatment arms of 9.25 MBq, 14.8 MBq, and 29.6 MBq were studied. The first dose was well tolerated and the animals displayed no visible signs of radiotoxicity. Climbing body weights of all animals also suggest each dosing arm was well tolerated (FIG. 36A).

Figure 36B:
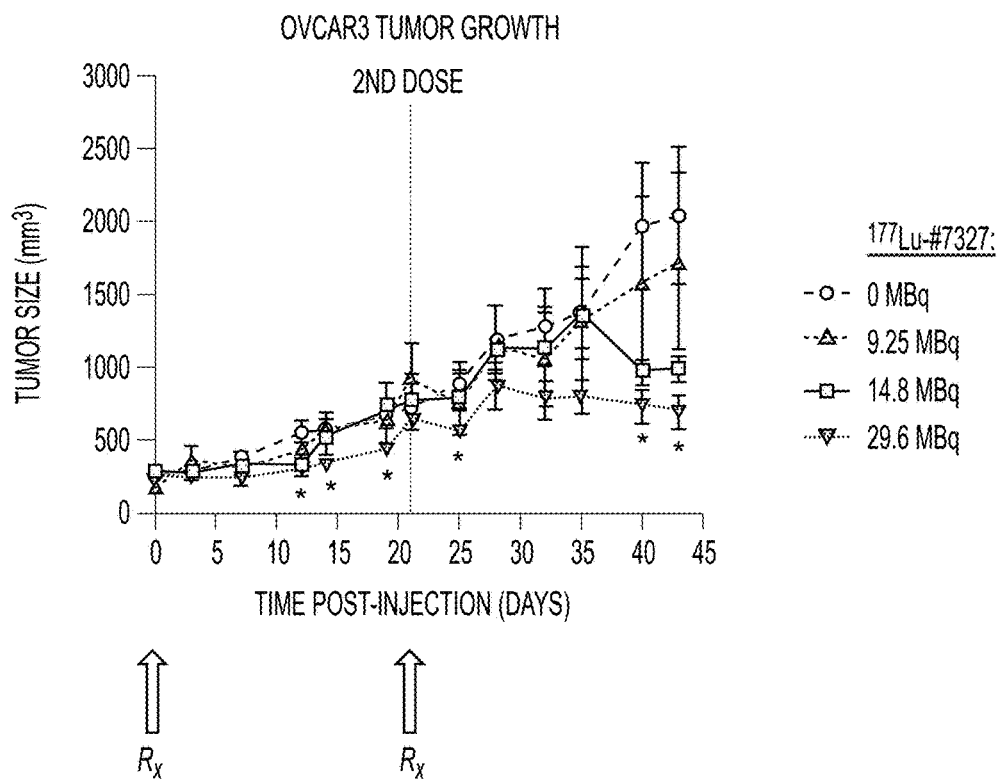
FIG. 36B is a graph of tumor size versus time (in days) post-injection of different radioactivity doses of $^{177}$Lu-7327.
Figure 37A:
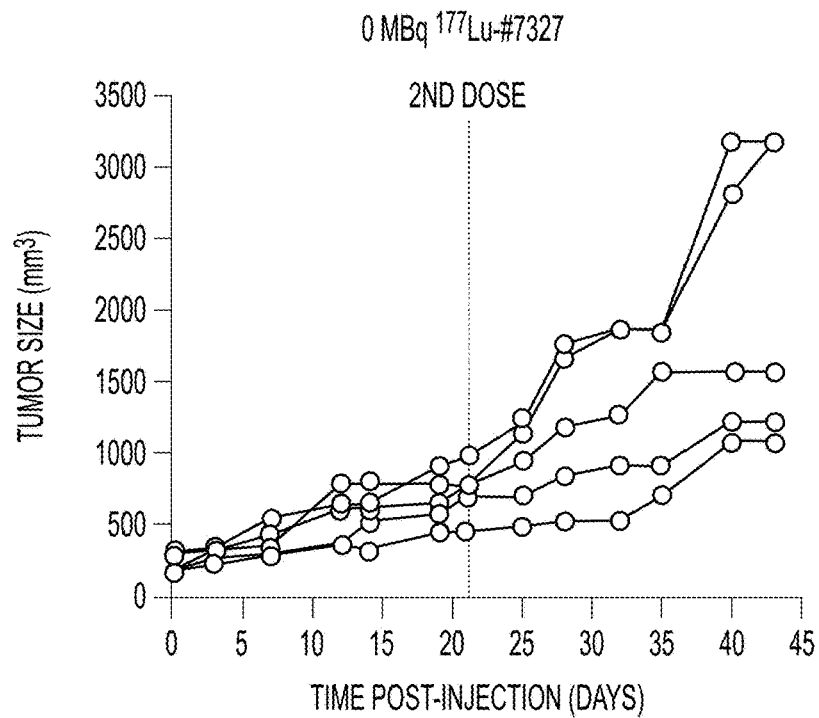
FIGS. 37A-37D are graphs of tumor size versus time (in days) post-injection of different radioactivity doses of $^{177}$Lu-7327 in different mice.
Figure 37B:
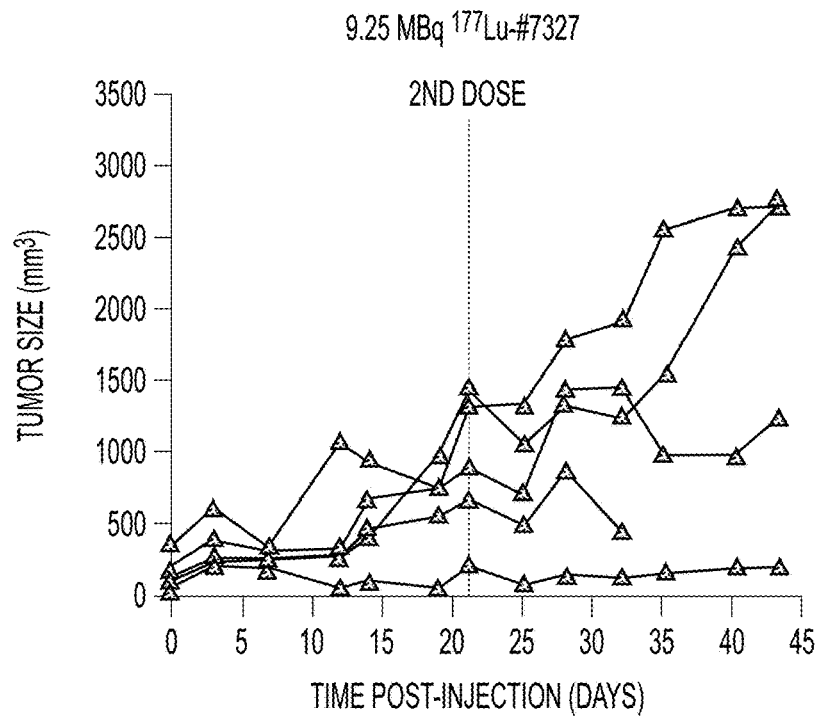
Figure 37C:
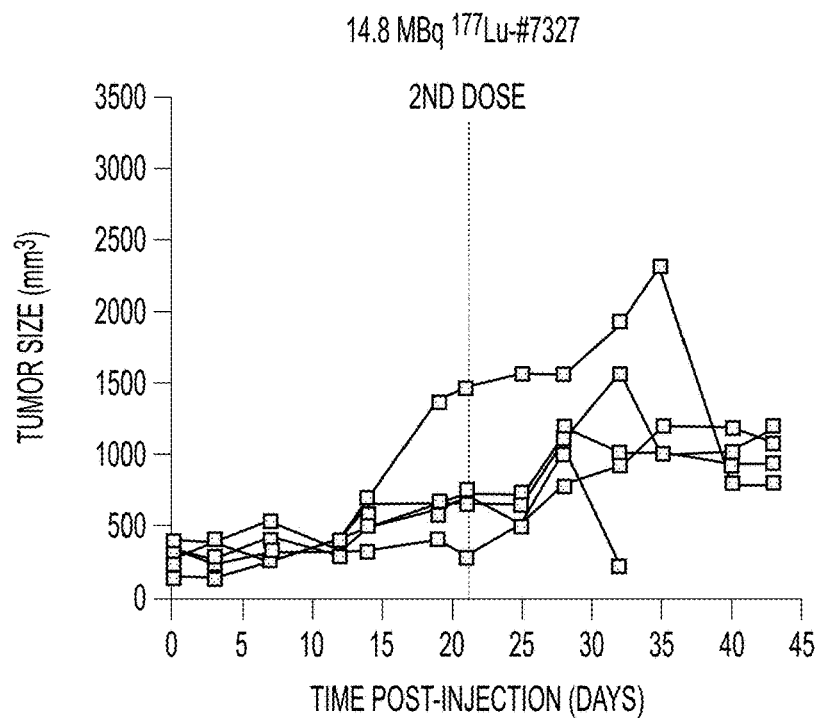
Figure 37D:
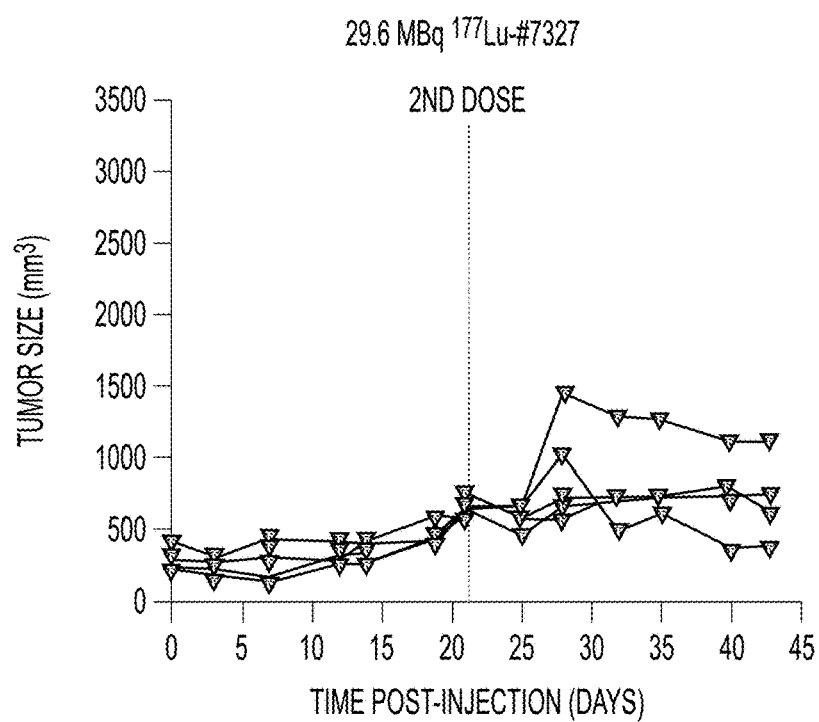

A second dose was administered 21 days following the first dose. Body weight loss of animals within the 9.25 MBq and 14.8 MBq arms was minimal (FIG. 36A). Animals receiving the highest dose exhibited modest loss of body weight that stabilized and then rebounded 10 days following the second dose. Caliper-measured tumor volume stabilized and then fell following the second dose of the highest arm (FIGS. 36B and 37). Statistically significant differential between treated and untreated was reached 12 days post injection for the 29.6 MBq arm (* for p≤0.05). P values were determined by ordinary one-way ANOVA with Tukey's multiple comparisons test.

Figure 38A:
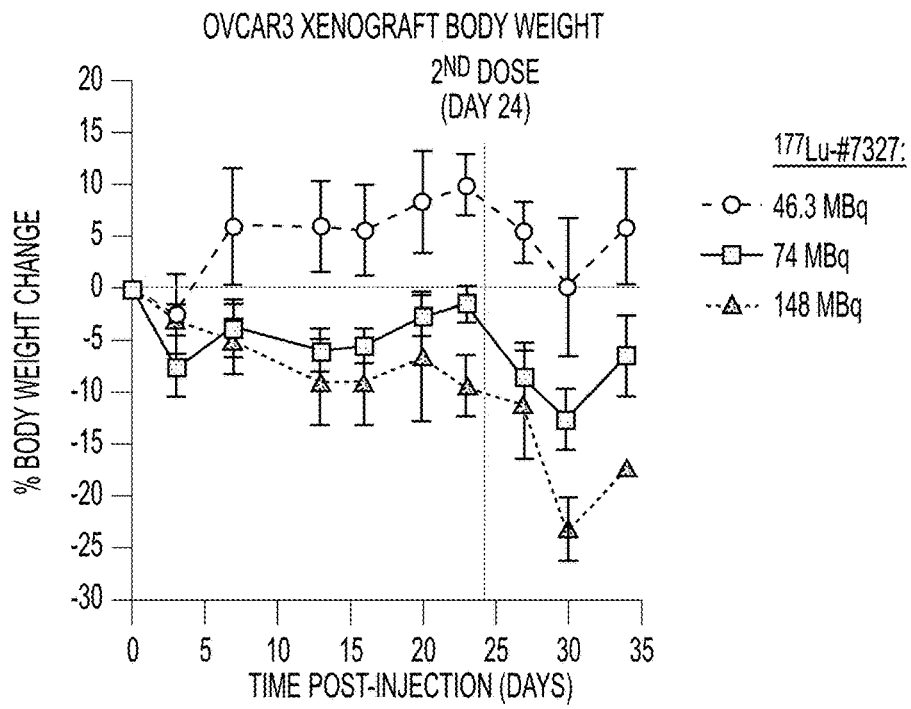
FIG. 38A is a graph of percent body weight change versus time (in days) post-injection of different radioactivity doses of $^{177}$Lu-7327.
Figure 38B:
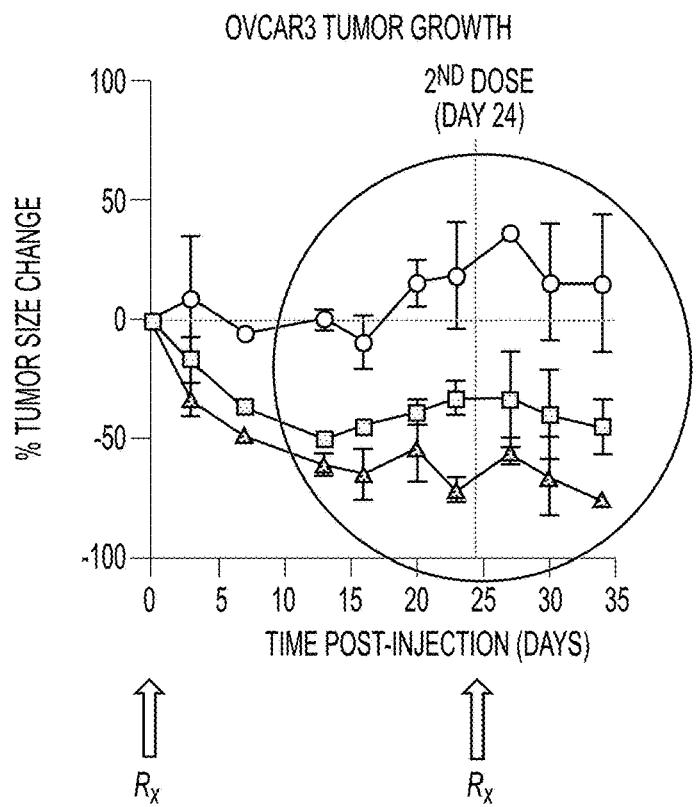
FIG. 38B is a graph of percent tumor size change versus time (in days) post-injection of different radioactivity doses of $^{177}$Lu-7327.

At 45 days post injection, the animals bearing the smallest tumors were randomized and given elevated doses of 177-Lu 7327. Animals received 46.3 MBq, 74 MBq, or 148 MBq doses. The first dose was well tolerated for all groups (FIG. 38A). The two highest doses, 74 MBq and 148 MBq, caused modest body weight loss (FIG. 38A). Tumor volumes for these doses decreased on average 50% following this single therapeutic dose (FIG. 38B). Animals in the 46.3 MBq group experienced weight gain and stable tumor volumes (FIG. 38B). On day 24, each arm received an additional treatment. Animals in all three groups exhibited shrinking tumor sizes (FIG. 38B). This data suggests that 177-Lu 7327 can stabilize and in some cases reverse highly aggressive FOLR1 expressing tumors.

In order to understand the toxicity-limiting tissues and organs, plasma was collected from the therapy studies and analyzed for blood urea nitrogen (BUN) and creatinine. BUN is often utilized in a series of tests to assess kidney function. Elevated BUN levels are an indication of reduced kidney function. Creatinine is another important kidney biomarker. Elevated creatinine is a sign of poor renal function.

Normal BUN levels were observed in mice receiving doses at or below 29.6 MBq (Table 9). Those receiving doses of 46.3 MBq and 74 MBq exhibited slightly elevated BUN levels (Table 9). Mice that received the highest dose of 148 MBq had elevated BUN levels (74.1 mg/dL) (Table 9).

TABLE 9

Assessment of Blood Urea Nitrogen (BUN) After Therapy

| $^{177}$Lu-#7327 dose | [BUN] (mg/dL) |
|----------------------|---------------|
| 0 MBq | 27.3 ± 2.4 |
| 9.25 MBq | 27.5 ± 2.6 |
| 14.8 MBq | 30.6 ± 3.6 |
| 29.6 MBq | 30.3 ± 2.1 |
| 46.3 MBq | 32.4 ± 1.3 |
| 74 MBq | 34.6 ± 1.0 |
| 148 MBq | 74.1 ± 21.3 |

The creatinine trends largely recapitulate the healthy renal functions uncovered in the BUN assay. Animals receiving up to 29.6 MBq had normal creatinine levels (Table 10). One mouse in the 46.3 MBq and 74 MBq groups had elevated creatinine plasma concentrations. As a group, animals receiving 148 MBq had elevated creatinine levels (Table 10).

TABLE 10

Assessment of Creatinine After Therapy

| $^{177}$Lu-#7327 dose | [Creatinine] (μmol/L) |
|---|---|
| 0 MBq | 12.2 ± 2.0 |
| 9.25 MBq | 15.3 ± 2.7 |
| 14.8 MBq | 16.4 ± 1.9 (Mouse #1) |
| | 41.6 ± 2.8 (Mouse #2) |
| 29.6 MBq | 12.4 ± 0.3 |
| 46.3 MBq | 13.9 ± 1.7 |
| 74 MBq | 11.8 ± 3.3 (Mice #1 & 2) |
| | 37.6 ± 2.6 (Mouse #3) |
| 148 MBq | 19.0 ± 1.6 |

Figure 39:
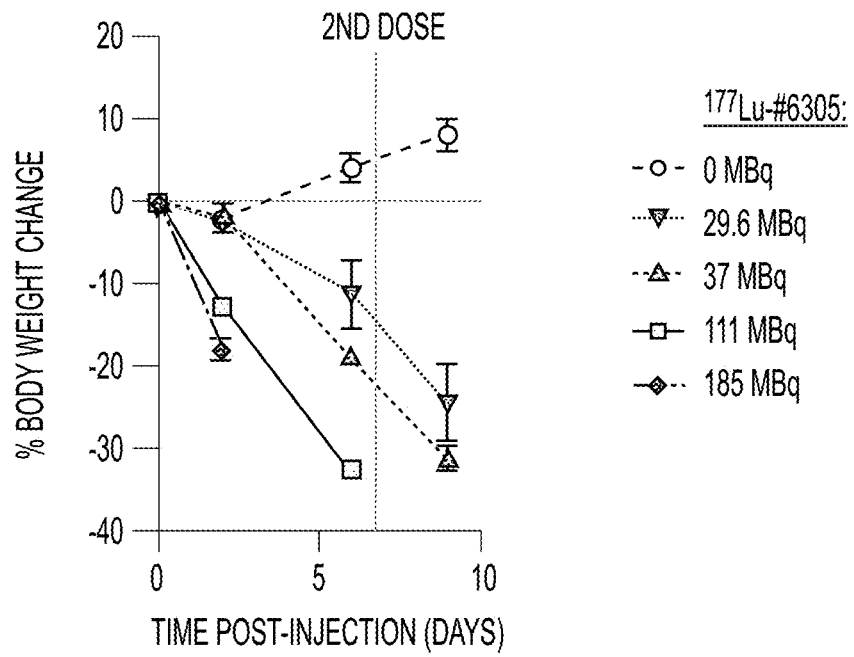
FIG. 39 is a graph of percent body weight change versus time (in days) post-injection of different radioactivity doses of $^{177}$Lu-6305.
Figure 40:
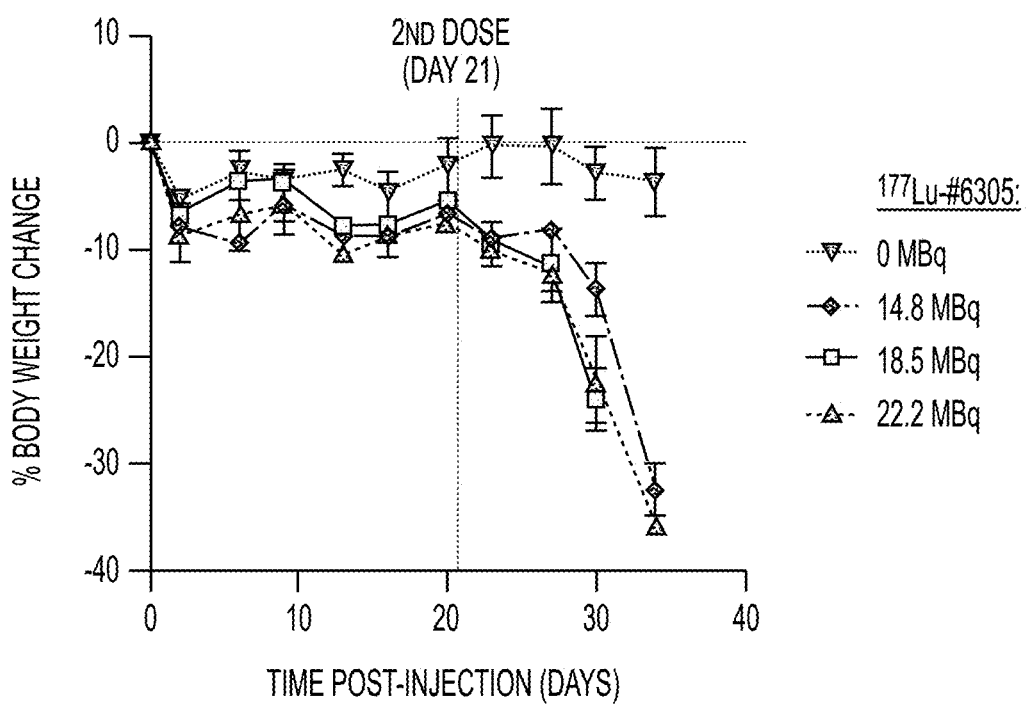
FIG. 40 is a graph of percent body weight change versus time (in days) post-injection of different radioactivity doses of $^{177}$Lu-6305.

Efforts were undertaken to evaluate 177-Lu 6305 (folate-hshta-Lys(MPBA)-Gly-Phe-Lys(DOTA)), a compound with a brush border cleavable linker in addition to an albumin binder. The albumin binding moiety increases the circulation time of the compound by shielding it from renal proteases and elimination. Two separate MTD experiments were undertaken. Animals receiving doses of 29.6 MBq, 37 MBq, 111 MBq, and 185 MBq began to experience weight loss after the first dose (FIG. 39). A second dose 7 days after the first was not tolerated (FIG. 39). A second experiment interrogated lower doses. Animals receiving a single dose of 14.8 MBq, 18.5 MBq, and 22.2 MBq exhibited only minimal loss in body weight that quickly stabilized (FIG. 40). A second dose administered 21 days was not tolerated (FIG. 40). The tolerance of the 0 MBq arm indicates that the radionuclide drives the toxicity profile and not the peptide alone (FIG. 40).

Example 3: Analysis of Heterobiligands for Therapeutic Use

Introduction

Folate receptor is highly overexpressed in ovarian cancer and presents an attractive target to specifically deliver therapeutic radiation. Indi $^{177}$Lu-7327 is a low molecular weight (~2100 Da), water soluble, ultra-high affinity synthetic peptide-folate conjugate targeting the folate receptor alpha (FOLR). This construct is internalized into ovarian cancer cells by the cell's folate receptor, outcompeting native folate for receptor binding by approximately 500-fold. FOLR-targeted drugs can present significant renal toxicity unless rapidly cleared. Since FOLR is highly expressed in the kidney, the kidney exposure of Indi $^{177}$Lu-7327 is mitigated by inclusion of a 3-amino acid linker that is enzymatically cleaved at the renal brush border membrane. Upon cleavage, the intact $^{177}$Lu-DOTA fragment is released from the primary drug conjugate and passed to the bladder for excretion. The drug is highly stable in human plasma and due to the use of d-amino acids and its low molecular weight, it is unlikely to be immunogenic.

Indi $^{177}$Lu-7327 is a radiolabeled peptide-folate conjugate is especially useful in the treatment of patients with epithelial ovarian, primary peritoneal or fallopian tube cancers that are platinum resistant and FOLR positive. FOLR is a folate-binding protein located on cellular membranes that contributes to folate uptake by cells. It is an attractive anticancer drug target owing to its overexpression in a range of solid tumors, including ovarian, lung, and breast cancers (Scaranti et al., Nature Reviews Clinical Oncology. 2020; 17(6):349-359). PCC technology is a powerful screening strategy to rapidly discover high-avidity, synthetic peptide ligands to judiciously selected epitopes of proteins (Agnew et al., Chemical Reviews. 2019; 119(17):9950-9970). Heterobiligands designed for multivalent interactions with human FOLR were developed by conjugating folate ligand to macrocyclic peptide ligands selected by our PCC platform. The close proximity of targeted FOLR epitopes to the active site and chemical linker optimization were leveraged in generating ultra-high affinity binding that outcompetes the native folate ligand.

The FOLR targeting ligand in Indi $^{177}$Lu-7327 is chemically attached via a DOTA chelator to lutetium-177 ($^{177}$Lu), a therapeutic radioactive atom which releases an energetic beta particle to precisely deliver cell killing radiation to the tumor. To reduce treatment related kidney exposure, the chemically attached G-F-K linker is susceptible to enzymatic cleavage at the renal brush border membrane. When Indi $^{177}$Lu-7327 enters the renal brush border cells, enzymatic cleavage results in liberation of the intact $^{177}$Lu-DOTA fragment and excretion in the urine.

Ovarian cancer can only be definitively diagnosed with a tissue biopsy. Ovarian cancer is suspected when there are certain findings on a clinical pelvic exam, symptoms that may be concerning for a malignancy, or abnormalities that may be seen incidentally on imaging studies for other purposes. Once suspected, bloodwork, such as cancer antigen CA-125, is conducted in combination with imaging which is often ultrasound (US) followed by computed tomography (CT) or magnetic resonance imaging (MRI). When possible, positron emission tomography combined with CT (PET-CT) can be used to further quantify the likelihood of an ovarian tumor. The role of imaging in ovarian cancer involves detection, characterization, and staging. Imaging plays an important role in characterization of ovarian masses, as the number of benign ovarian masses greatly exceeds the number of malignant masses (Balachandran and Iyer, Applied Radiology. 2005; 34(9):19-29). If someone is considered at elevated risk for having an ovarian tumor, risk-based protocols that combine surgery, sometimes with neoadjuvant chemotherapy, are used to both stage and treat the patient.

Women who have completed initial treatment for advanced stage ovarian carcinoma are monitored closely for evidence of recurrence. Follow up consists of physical exams, CA-125 blood level monitoring, and imaging (CT or PET-CT being the most common modalities). Typically, if CA-125 levels are obtained and an elevation from post-treatment baseline is seen, this would determine the need for radiologic imaging to try and identify location of tumor recurrence. Some women have interval debulking procedures scheduled either during or immediately following completion of first-line treatment. Women can also have interval debulking procedures as part of the initial treatment for recurrent or suspected recurrent ovarian cancer.

PET-CT is used to diagnose recurrence of ovarian cancer. A meta-analysis comparing techniques for detection of recurrence determined that PET-CT performed better than CT or MRI with sensitivities of 95% vs 79% and 75%, respectively, and specificities of 88% vs 84% and 78%, respectively (Gu et al., European Journal of Radiology. 2009; 71(1):164-174).

If epithelial ovarian cancer is diagnosed early (Stage I or Localized), the 5-year survival rate is 92%. Stage II or Regional 5-year survival rate is approximately 76%. Stage III/IV or Distant 5-year survival rate is around 30%.

Approximately 66-80% of women with epithelial ovarian cancer are diagnosed at Stage III or higher (American Cancer Society).

All ovarian cancer patients, except those going immediately to palliative care, require surgery, with most women having surgery soon after the diagnosis is suspected or confirmed. For premenopausal women with early stage (Stage I) disease, an individualized approach that includes fertility preserving options is sometimes possible. When fertility is not a concern in younger women, or in women who are no longer of reproductive age, surgery for early-stage disease (Stage I-II) most commonly removes the uterus, cervix, both fallopian tubes, and both ovaries. Pelvic washings are always done prior to any surgical manipulation to determine the presence of cancer cells in the peritoneal fluid. Additional biopsies and/or lymph node dissections may also be performed if the intraoperative findings differ from the preoperative imaging studies.

For later stage cancers, Stage women may be given the option of clinical trials in addition to traditional therapy. Most Stage III cancer is managed initially with a debulking cytoreductive surgery with the goal being to reduce the tumor burden as much as possible allowing the patient the most optimal outcome from chemotherapy. The debulking surgery includes removing as many diseased organs as possibly including the uterus, cervix, tubes, and ovaries along with any diseased organs or tissue including pelvic lymph nodes, the peritoneal lining, part of the diaphragm, bowel, spleen, and portions of the liver. Optimal surgical debulking is defined as removing the tumor and leaving residual implants that are <1 cm in greatest diameter. Optimal surgical debulking has been shown to improve survival outcomes.

The most common chemotherapeutic agents used to treat epithelial ovarian cancer after initial surgery are cisplatin or carboplatin plus paclitaxel or docetaxel. These two drugs are most commonly given IV three to four weeks apart for a total of six treatments (Matulonis et al., *Nature Reviews Disease Primers.* 2016; 2(1):16061). Approximately 70-80% of women with epithelial ovarian cancer will relapse after initial therapy is completed (Lorusso et al., *International Journal of Surgical Oncology.* 2012; 2012:613980). Once a woman has relapsed with ovarian cancer, she also has a high likelihood of her cancer becoming platinum resistant. A woman who has relapsed with epithelial ovarian cancer is not considered curable. This fact drives second-line therapy research toward non-platinum-based drugs that could extend median survival times beyond the ~12-months post recurrence generally observed (Davis et al., *Gynecologic Oncology.* 2014; 133(3):624-631).

Often, a woman with recurrent epithelial ovarian cancer will have subsequent surgeries done for further cytoreduction, commonly called interval debulking, or for complications commonly seen with metastatic ovarian cancer including most commonly bowel obstructions.

Materials and Methods

Folate-hshta-Lys(MPBA)-Gly-Phe-Lys(DOTA)

Folate-hshta-G-F-K($^{177}$Lu-DOTA)-OH has four components: Folate-hshta is the targeting vector (where h=d-histidine, s=d-serine, t=d-threonine, and a=d-alanine), G-F-K (Glycine-Phenylalanine-Lysine) is a L-amino acid linker that is susceptible to enzymatic cleavage at the renal brush border membrane for kidney protection, DOTA (1,4,7,10-tetraazacyclododecane-1,4,7,10-tetraacetic acid) is a radiometal chelator, and $^{177}$Lu is the beta emitter that upon internalization delivers radiation to the nucleus of tumor cells to cause DNA damage. The targeting vector utilizes folate conjugated to hshta, a d-amino-acid-containing cyclic peptide, resulting in high affinity for the folate receptor alpha (FOLR).

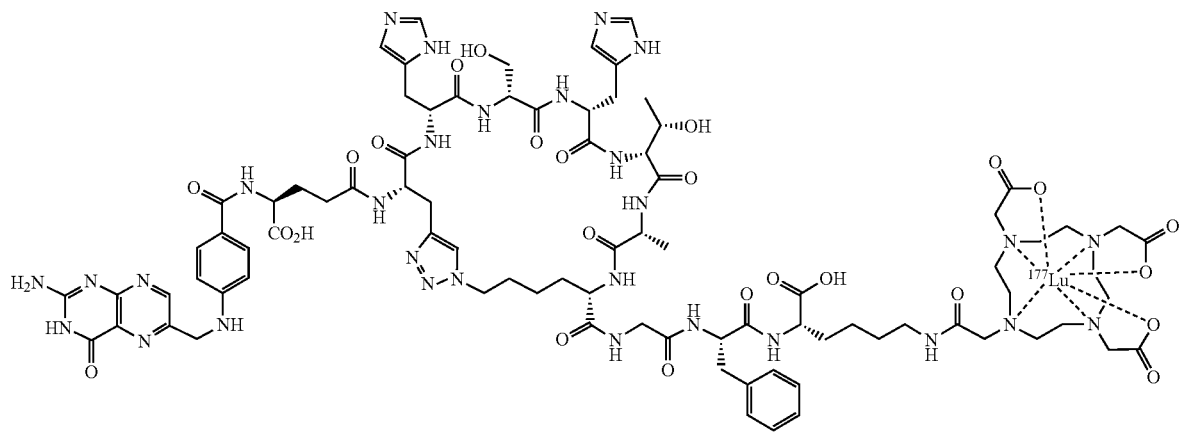

Chemical Formula: $C_{85}H_{112}{}^{177}LuN_{29}O_{25}$
Molecular Weight: 2116.95

Indi 7327 Precursor Synthesis

Standard solid-phase peptide synthesis (SPPS) coupling conditions using fluorenylmethoxycarbonyl (Fmoc)-protected amino acids and chlorotrityl chloride (CTC) resin were employed to synthesize the linear compound (Table 11, Scheme 1). The click macrocyclization reaction was catalyzed by copper iodide on resin. The C-terminus lysine was selectively deprotected to reveal a free amine, which was used to conjugate the DOTA chelating moiety. Finally, the peptide was cleaved from the resin and deprotected in one step. All components (amino acids, pteroic acid, and DOTA) were obtained from commercial sources.

TABLE 11

Solid Phase Peptide Synthesis (SPPS) Steps

| Step Number | Materials | Coupling Reagents |
|---|---|---|
| 1 | Fmoc-Lys(Dde)-OH (1.00 eq) | DIEA (4.00 eq) |
| 2 | Fmoc-Phe-OH (3.00 eq) | HBTU (2.85 eq) and DIEA (6.00 eq) |
| 3 | Fmoc-Gly-OH (3.00 eq) | HBTU (2.85 eq) and DIEA (6.00 eq) |
| 4 | Fmoc-Lys(N₃)-OH (2.00 eq) | HATU (1.90 eq) and DIEA (4.00 eq) |
| 5 | Fmoc-D-Ala-OH (3.00 eq) | HBTU (2.85 eq) and DIEA (6.00 eq) |
| 6 | Fmoc-D-Thr(tBu)-OH (3.00) | HBTU (2.85 eq) and DIEA (6.00 eq) |
| 7 | Fmoc-D-His(Trt)-OH (3.00 eq) | HBTU (2.85 eq) and DIEA (6.00 eq) |
| 8 | Fmoc-D-Ser(tBu)-OH (3.00 eq) | HATU (2.85 eq) and DIEA (6.00 eq) |
| 9 | Fmoc-D-His(Trt)-OH (3.00 eq) | HATU (2.85 eq) and DIEA (6.00 eq) |
| 10 | Fmoc-Pra-OH (2.00 eq) | HATU (1.90 eq) and DIEA (4.00 eq) |
| 11 | Fmoc-Glu-OtBu (3.00 eq) | HBTU (2.85 eq) and DIEA (6.00 eq) |

TABLE 11-continued

Solid Phase Peptide Synthesis (SPPS) Steps

| Step Number | Materials | Coupling Reagents |
|---|---|---|
| 12 | PTEROIC ACID (CAS: 119-24-4) (1.50 eq) (dissolve in DMSO 6 mg/mL) | EDCI (1.5 eq), HOBT (1.5 eq), and DIEA (4.00 eq), 36 hours |
| 13 | Click Reaction | CuI (0.75 eq), L-Ascorbic Acid (5.0 eq), piperidine (6 mL) in NMP (30 mL), |
| 14 | De-Dde | 10 hours 2% NH₂NH₂ in DMF |
| 15 | DOTA(3tBu)(CAS: 137076-54-1)(2.00 eq) | HBTU (1.90 eq) and DIEA (4.00 eq) |

CuI: copper (I) iodide;
DIEA: N,N-diisopropylethylamine;
DMF: dimethylformamide;
EDCI: 1-ethyl-3-(3-dimethylaminopropyl)carbodiimide;
HATU: 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium;
HBTU: 2-(1H-benzotriazol-1-yl)-1,1,3,3-tetramethyluronium hexafluorophosphate, Hexafluorophosphate Benzotriazole Tetramethyl Uronium;
HOBT: 1-Hydroxybenzotriazole hydrate;
NMP: N-methylpyrrolidone;
SPPS: solid phase peptide synthesis.

Scheme 1. Indi 7327 Synthesis

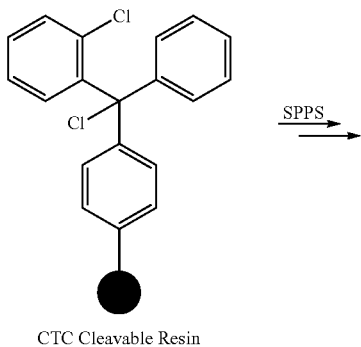

CTC Cleavable Resin

SPPS →

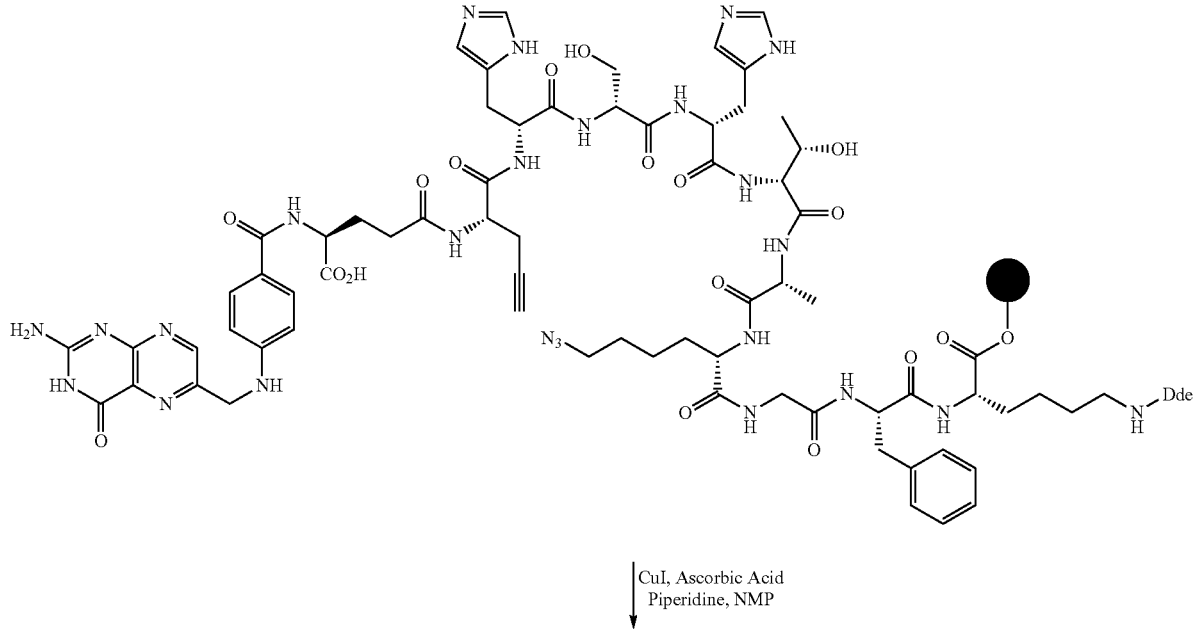

CuI, Ascorbic Acid
Piperidine, NMP

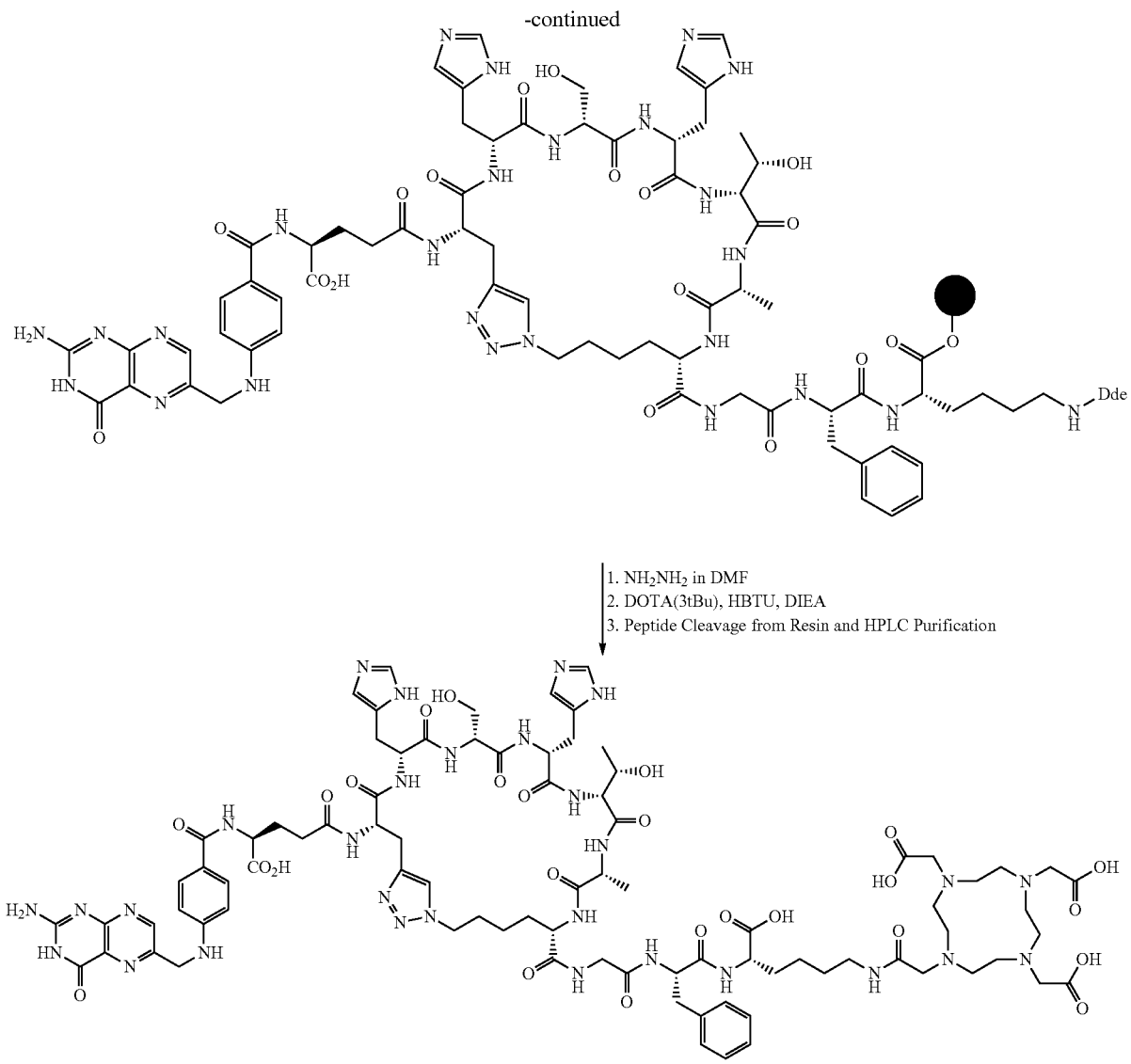

Folate-{propargylglycine}-{D-H}-{D-S}-{D-H}-{D-T}-{D-A}-{Lys(N3)}-{G}-{L-F}-{L-Lys(DOTA)-OH}, {propargylglycine} is cyclized with {Lys(N3)}

Indi 7327 Precursor Purification and Analytical Testing

The crude material was purified using reverse phase high-performance liquid chromatography (HPLC) purification. HPLC analysis of the purified material reveals high isolated purity of Indi 7327. This method estimates purity to be 97%.

Purity and identity were determined by analytical HPLC and liquid chromatography coupled with mass spectrometry (LC/MS) analysis. LC/MS analysis of the purified fractions exhibits polycationic species consistent with Indi 7327. The most abundant ion is 648.6, corresponding to a $[M+3H]^{3+}$ molecular species. Other identifiable charged species include 972.4, $[M+2H]^{2+}$ and 486.7, $[M+4H]^{4+}$.

$^{177}$Lu Labeling Procedures $^{177}$Lu chloride (in 0.05 M HCl solution) was ordered from the National Isotope Development Center (NIDC). The material is produced weekly from the University of Missouri Research Reactor Center (MURR). Buffered gentisic acid (260-330 µL) is added to the desired quantity of $^{177}$Lu chloride (typically 814-1665 MBq of activity which corresponds to 10-20 µL of the solution as received) in a metal-free Eppendorf. The gentisic acid solution is prepared by diluting gentisic acid to a concentration of 10 mg/mL in 0.4 M NaOAc (pH=4.5). Gentisic acid is utilized to minimize radiolysis of the peptide. A volume of peptide solution is added to the reaction corresponding to the desired specific activity (typically 60-120 µL). After all additions are complete, a final pH measurement is taken. The measured reaction pH has consistently fallen within the acceptable pH of 4.5-4.8 and has never required adjustment. The reaction is aged for 15 minutes at 95° C. Labeling efficiency and yield of the $^{177}$Lu chelation reaction are determined by reverse phase HPLC coupled to an in-line radio detector. The $^{177}$Lu labeling of Indi 7327 occurs in near quantitative yield. No un-chelated $^{177}$Lu is present.

Results

Nonclinical studies were first conducted with Folate-hshta-PEG$_{10}$-PEG$_{10}$-K(Biotin), where Folate-hshta is the targeting heterobiligand, PEG$_{10}$ is a deca(ethylene glycol) linker, and K(Biotin) is the detection label. This peptide-folate heterobiligand showed low picomolar affinity ($EC_{50}$=65 pM) in enzyme-linked immunosorbent assay (ELISA), enhanced binding to human FOLR protein compared to folate alone, and selective binding in human OVCAR3 (FOLR+) epithelial ovarian cancer cells (FIG. 6). Tested alone, the macrocyclic peptide ligand hshta demonstrated low micromolar affinity for recombinant human FOLR protein in ELISA. Conjugation of hshta to folate ligand yielded a highly potent heterobiligand with ~30-fold greater affinity than folate itself. This heterobiligand was resilient to displacement by exogenous folate in a competitive ELISA. Cross reactivity with the murine folate receptor was also observed. Dose-dependent binding to human OVCAR3 (FOLR+) ovarian cancer cells and low non-specific binding to PC3 (FOLR−) cells were demonstrated0 by flow cytometry. Selective internalization into OVCAR3 (FOLR+) cells and limited uptake into PC3 (FOLR−) cells were demonstrated by live cell imaging of DyLight650-labeled peptide-folate heterobiligand on a confocal microscope. In the merged image, purple puncta were observed indicating co-localization of internalized heterobiligand with early endosomes (Rab5a+ vesicles) in OVCAR3 cells. An acid wash (pH 3.0) assay (Kamen et al., *Journal of Biological Chemistry*. 1988; 263(27):13602-13609) analyzed by flow cytometry provided further evidence that a high percentage of DyLight650-labeled peptide-folate heterobiligand was internalized in the OVCAR3 cell line.

To reduce treatment-related kidney exposure, the heterobiligand was chemically modified with a 3-amino acid (Gly-Phe-Lys) linker that is susceptible to cleavage by neprilysin, an abundant endopeptidase on the renal brush border membrane. In vitro cleavage studies of Indi 7327 (Folate-hshta-G-F-K(DOTA)-OH) confirmed that the G-F-K sequence is selectively recognized by neprilysin and cleaved at the amide bond between Gly and Phe, thus releasing the DOTA chelator fragment containing Lys. In vitro bioanalysis studies showed that Indi 7327 is stable in both human and mouse plasma ($T_{1/2}$>6900 min), 40.87% bound to mouse plasma proteins, and 40.29% bound to human plasma proteins. In vivo positron emission tomography (PET) imaging of Indi $^{68}$Ga-7327 showed a significant reduction in kidney uptake with rapid drainage to the bladder in human OVCAR3 (FOLR+) tumor implanted female NOD scid gamma (NSG) mice. This is consistent with the mechanism that cleavage in the renal brush border membrane liberates the intact radionuclide-chelator complex, which is then excreted in the urine. Similar tumor uptake of Indi $^{68}$Ga-7327 was observed when compared to constructs that lack the renal brush border cleavage site.

A series of in vivo studies examining the tolerated doses and anti-tumor activity of Indi $^{177}$Lu-7327 were conducted using IV administration. Healthy, non-tumor bearing female NSG mice tolerated three treatments of Indi $^{177}$Lu-7327 at radioactive doses up to 111 MBq. In OVCAR3 tumor implanted female NSG mice, two treatments of Indi $^{177}$Lu-7327 at a radioactive dose of 29.6 MBq resulted in tumor stasis. Tumor stasis was also observed in OVCAR3 tumor implanted female NSG mice that received two treatments of Indi $^{177}$Lu-7327 at a radioactive dose of 74 MBq. Tumor regression was then observed in OVCAR3 tumor implanted female NSG mice that received two treatments of Indi $^{177}$Lu-7327 at 29.6 MBq followed by a third treatment at 74 MBq. Kidney injury biomarker levels in mouse plasma collected at study endpoints were determined to be largely in the normal range. Indi $^{177}$Lu-7327 treated mice demonstrated normal body weights (+/−10%) and behavior (no observable change).

Biodistribution was initially evaluated by PET imaging, as the time frame for a significant portion of clearance is roughly similar to the time frame of PET imaging experiments. Indi $^{68}$Ga-7327 was injected via the tail vein into OVCAR3 (FOLR+) tumor implanted female NSG mice once the tumor size reached 200 mm$^3$, and microPET/CT scans were acquired at 5 min, 10 min, 15 min, 30 min, 1 h, 2 h, and 4 h post-injection. PET images were corrected for CT-based photon attenuation, detector normalization and radioisotope decay and converted to units of percent injected dose per cc (% ID/cc). The imaging study revealed that the biodistribution of Indi $^{68}$Ga-7327 is based in the tumor and clearance organs (kidney, bladder). Rapid accumulation of Indi $^{68}$Ga-7327 was observed in the tumor, with 1.55% ID/cc at 4 h post-injection. Radiation that has found the tumor folate receptor is internalized and no longer subject to clearance mechanisms. Indi $^{68}$Ga-7327 clears via the kidneys to the bladder for excretion in the urine.

Figure 41:
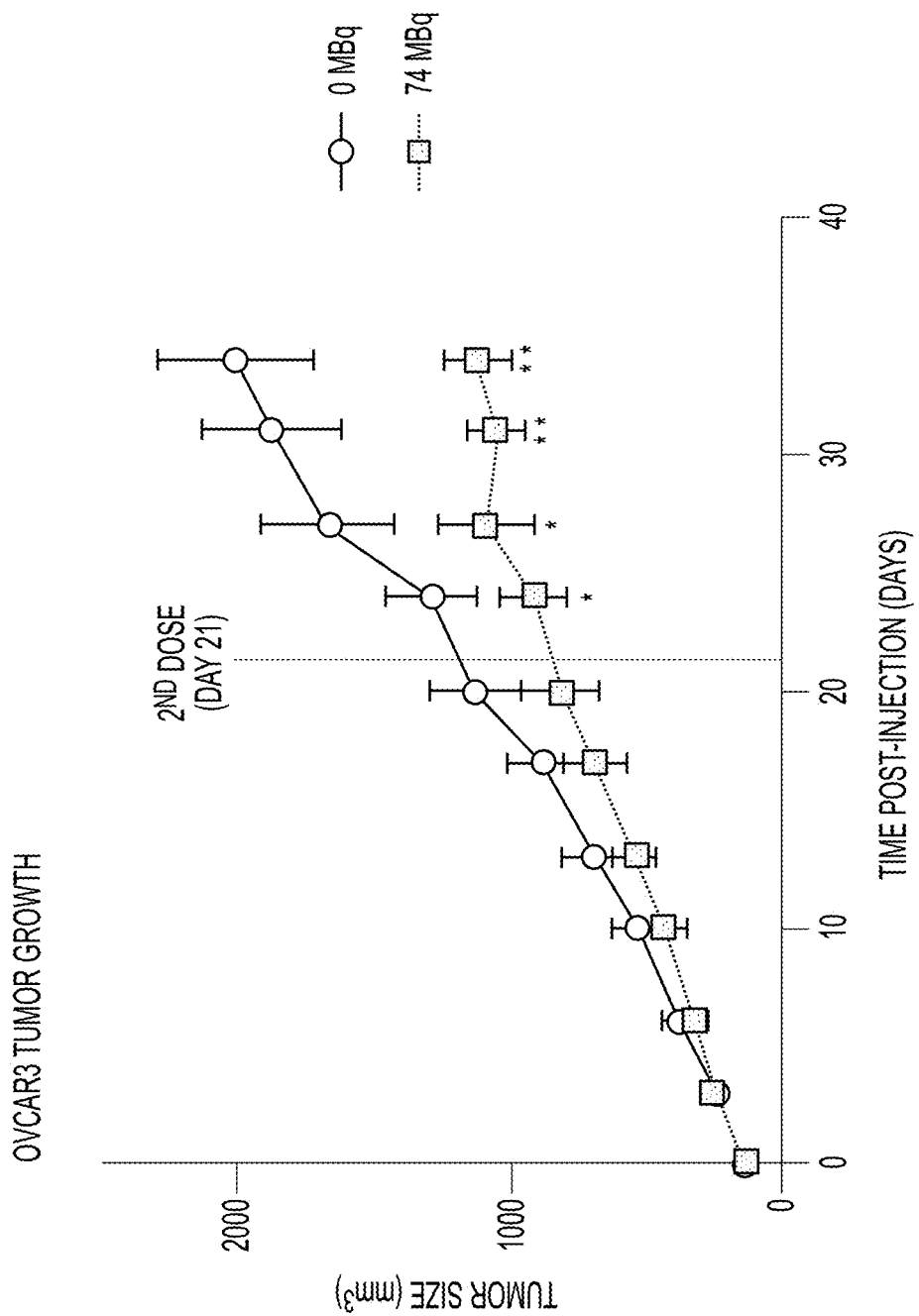
FIG. 41 is a graph of tumor size versus time (in days) post-injection of 0 MBq and 74 MBq of $^{177}$Lu-7327.

Therapy response based on Indi $^{177}$Lu-7327 has been demonstrated in a number of tumor stasis or regression studies using IV administration. Female NSG mice were implanted subcutaneously with human OVCAR3 (FOLR+) ovarian cancer cells. Once tumors reached volumes of 200 mm$^3$, the animals were treated with Indi $^{177}$Lu-7327. One treatment arm of 74 MBq and a control group of 0 MBq were studied (FIGS. 41 and 38A). Following two doses of Indi $^{177}$Lu-7327 at 74 MBq, there was a decrease in tumor volume. The second dose was administered 21 days following the first dose. Statistically significant differential between treated and control was reached 24 days post-injection (three days following the second dose) for the 74 MBq arm. P values (* for p≤0.05, ** for p≤0.01) were determined by ordinary one-way ANOVA with Tukey's multiple comparisons test. Normal body weights and behavior (no observable change) indicated that the treatments were well tolerated.

Another therapy response study in OVCAR3 tumor-bearing NSG mice evaluated three treatment arms of 9.25, 14.8, and 29.6 MBq and a control group of 0 MBq (FIGS. 36 and 37). Following two doses of Indi $^{177}$Lu-7327, there was a dose dependent decrease in tumor volume. The second dose was administered 21 days following the first dose. Animals receiving the 29.6 MBq dose of Indi $^{177}$Lu-7327 exhibited modest (5-10%) loss of body weight that stabilized and then recovered 10 days following the second dose. Normal body weights and behavior (no observable change) indicated that the treatments were well tolerated.

Statistically significant differential between treated and control was reached 12 days post-injection for the 29.6 MBq arm. P values (* for p≤0.05) were determined by ordinary one-way ANOVA with Tukey's multiple comparisons test. At 45 days post-injection, the animals bearing the smallest tumors were re-randomized and given elevated doses of Indi $^{177}$Lu-7327. Three treatment arms of 46.3, 74, and 148 MBq were studied (FIG. 38A). Tumor volumes for the 74 and 148 MBq arms decreased by 50%, on average, following this single elevated therapeutic dose. On day 24, the mice received an additional treatment that maintained the therapy response. These data show that Indi $^{177}$Lu-7327 can stabilize and, at augmented doses, reverse the growth of FOLR-expressing tumors.

We have been using mouse body weight, mouse behavior, and kidney injury biomarkers (at end of study) to assess toxicology. Weight loss provides information on longer time horizons for doses at or below the maximum tolerated dose (MTD). In order to establish a MTD, dose range finding studies were undertaken testing increasing amounts of Indi $^{177}$Lu-7327 in healthy, non-tumor bearing female NSG mice using IV administration (FIGS. 34 and 35). Mouse body weight and behavior were monitored. Multiple dose administration of 14.8, 22.2, 29.6, and 37 MBq were well tolerated. The second and third doses were administered 21 days following the previous dose. At the high doses of 111 and 185 MBq, animals lost substantial body weight following the first dose, which worsened following the second and third doses. These studies established an MTD for Indi $^{177}$Lu-7327 that lies between 37 and 111 MBq. The high tolerability observed in the 0 MBq group (treated with Indi 7327) indicates that the radionuclide drives the toxicity profile and not the peptide alone.

Figure 42:
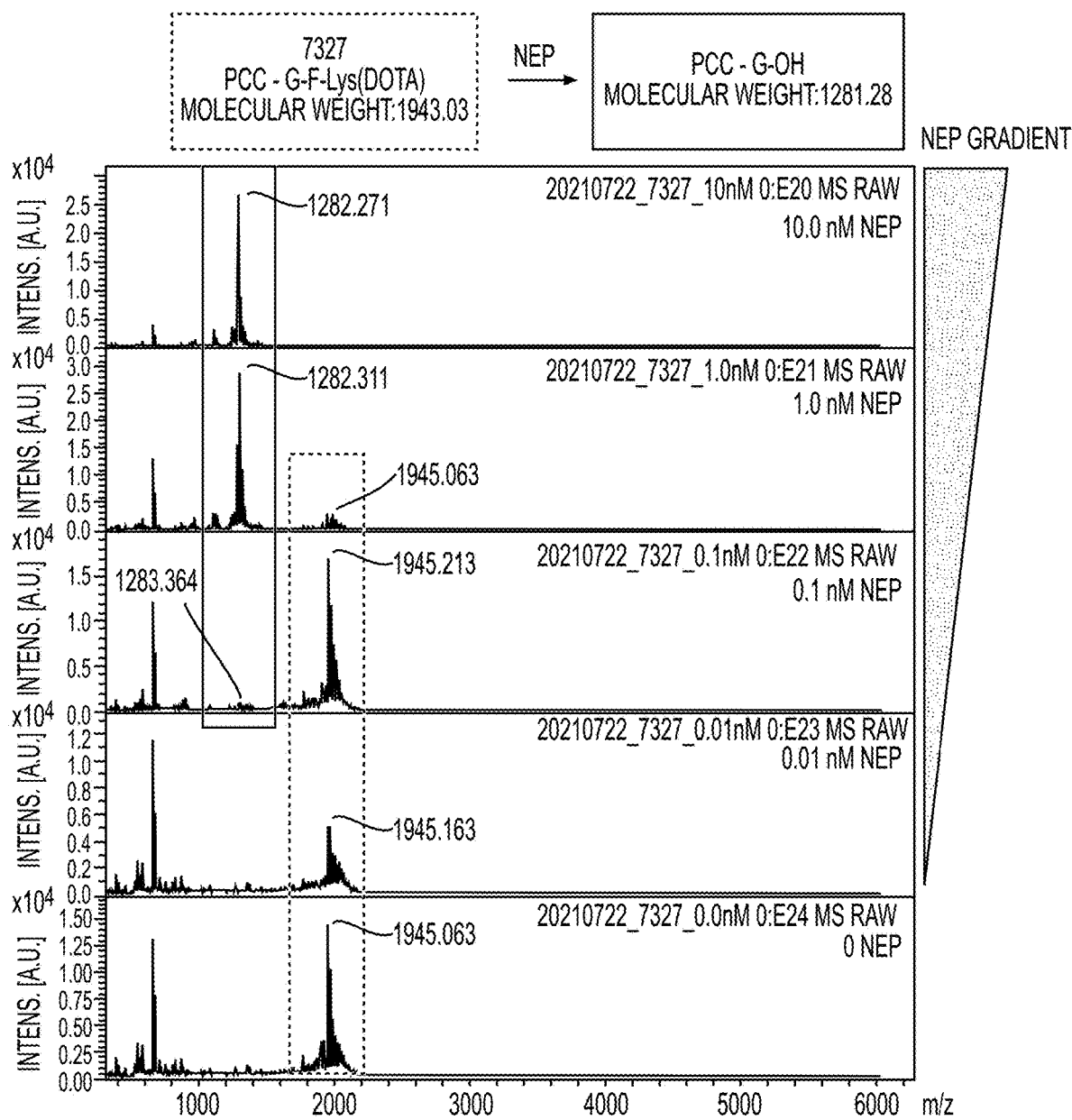
FIG. 42 is a diagram of the compound species resulting from incubation of compound #7327 (folate-hshta-Gly-Phe-Lys(DOTA)) with different concentration of NEP and shows that compound #7327 is progressively cleaved by increasing NEP into a single predominant species corresponding to cleavage of the G-F-K peptide linker in compound #7327.

To reduce the radioactive dose to the kidney, Indi $^{177}$Lu-7327 was constructed to incorporate a GFK linker that is susceptible to cleavage by enzymes found predominately in the kidney's brush border. These enzymes cleave off the radionuclide-chelator complex, which is quickly eliminated by the kidney for excretion in the urine. The zinc metalloprotease neprilysin (NEP) is expressed with high abundance in the kidney. Preclinical studies by Suzuki et al. showed that the tripeptide GFK sequence is recognized as a substrate and cleaved by NEP on the renal brush border membrane (Suzuk et al., *Journal of Medicinal Chemistry.* 2018; 61(12):5257-5268). To confirm NEP-mediated cleavage of the GFK linker in Indi 7327, the peptide was incubated with recombinant human NEP at 37° C. for 1 h and analyzed by matrix-assisted laser desorption/ionization mass spectrometry (MALDI-MS) for the evolution of cleaved adducts (FIG. 42). Titration of NEP (10.0 to 0 nM) resulted in partial to complete cleavage of Indi 7327. The expected cleaved adduct (mass: 1283.16 m/z) appears in the samples containing 10, 1.0, and 0.1 nM NEP. At 10 nM NEP, no intact Indi 7327 remains indicating complete consumption of the peptide. At 1.0 and 0.1 nM NEP, partial cleavage was observed. Below 0.1 nM NEP, no cleavage was observed. In addition to confirming the selectivity of NEP for the GFK linker, it is also important to note that the remaining portions of the Indi 7327 were impervious to the enzyme.

In vitro bioanalysis studies showed that Indi 7327 is stable in plasma ($T_{1/2}$>6900 min), 40.87% bound to mouse plasma proteins, and 40.29% bound to human plasma proteins (Table 2).

Kidney injury biomarkers were evaluated from mouse plasma collected at the end of the therapy response studies of Indi $^{177}$Lu-7327. The blood urea nitrogen (BUN) and creatinine levels were evaluated to gain information on renal function. After Indi $^{177}$Lu-7327 therapy, mouse plasma from the treatment arms of 9.25, 14.8, and 29.6 MBq and the control group of 0 MBq showed normal BUN (Table 9) and creatinine levels (Table 10). After augmenting the dose of Indi $^{177}$Lu-7327, BUN and creatinine levels were normal in the treatment arms of 46.3 and 74 MBq and elevated at the highest dosing (148 MBq) (Tables 9 and 10).

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, sub-group, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise. Thus, for example, reference to "a ligand" includes a plurality of such ligands, reference to "the ligand" is a reference to one or more ligands and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different ligands does not indicate that the listed ligands are obvious one to the other, nor is it an admission of equivalence or obviousness.

Every compound disclosed herein is intended to be and should be considered to be specifically disclosed herein. Further, every subgroup that can be identified within this disclosure is intended to be and should be considered to be specifically disclosed herein. As a result, it is specifically contemplated that any compound, or subgroup of compounds can be either specifically included for or excluded from use or included in or excluded from a list of compounds.

Those skilled in the art will recognize, or be able to ascertain using no more than routine experimentation, many equivalents to the specific embodiments of the method and compositions described herein. Such equivalents are intended to be encompassed by the following claims.

We claim:

1. A heterobiligand comprising a first ligand having affinity for an epitope on folate receptor 1 (FOLR1), a linker, and a second ligand, wherein the second ligand comprises a folate, wherein the linker links the first ligand and the second ligand, wherein the heterobiligand specifically binds FOLR1, wherein the first ligand comprises a 3-10 amino acid sequence of D-amino acids, artificial amino acids, or combinations thereof, and wherein the folate binds the FOLR1 active site.

2. The heterobiligand of claim 1, wherein the folate binds the FOLR1 active site.

3. The heterobiligand of claim 1, wherein the folate is

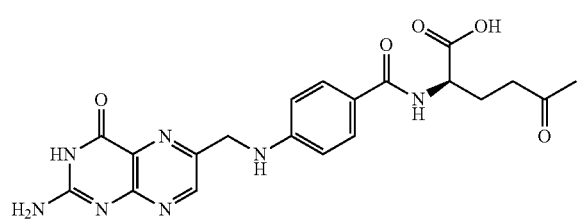

4. The heterobiligand of claim 1, wherein the first ligand comprises 5 to 9 amino acids.

5. The heterobiligand of claim 1, wherein the epitope comprises the amino acid sequence HHKEKPGPEDKLHE (SEQ ID NO:3), GPWIQQVDQSWRKERVLN (SEQ ID NO:4), or RCIQMWFDPAQGNPNEEVAR (SEQ ID NO:5).

6. The heterobiligand of claim 1, wherein the epitope comprises the amino acid sequence HHKEKPGPEDKLHE (SEQ ID NO:3).

7. The heterobiligand of claim 1, wherein the first ligand comprises an amino acid sequence selected from the group consisting of hshta (SEQ ID NO:6), kyeet (SEQ ID NO:9), deryt (SEQ ID NO:20), Ghwef (SEQ ID NO:8), ltdwh (SEQ ID NO:10), hepff (SEQ ID NO:11), wGlhk (SEQ ID NO:12), wwprG (SEQ ID NO:13), nnyl (SEQ ID NO:14), twsw (SEQ ID NO:15), yfytw (SEQ ID NO:16), wkhef (SEQ ID NO:17), tyGeh (SEQ ID NO:18), and anGel (SEQ ID NO:19).

8. The heterobiligand of claim 1, wherein the first ligand comprises an amino acid sequence hshta (SEQ ID NO:6), kyeet (SEQ ID NO:9), and deryt (SEQ ID NO:20).

9. The heterobiligand of claim 1, wherein the first ligand comprises an amino acid sequence hshta (SEQ ID NO:6).

10. The heterobiligand of claim 1, wherein the first ligand comprises a 1,4-substituted-1,2,3-triazole residue (Tz4) or a 1,5-substituted-1,2,3-triazole residue (Tz5).

11. The heterobiligand of claim 1, wherein the linker is an amide bond, $PEG_3$, $PEG_3$-Tz, $PEG_3$-Lys, or peptide.

12. The heterobiligand of claim 1, wherein the heterobiligand further comprises a reporter moiety.

13. The heterobiligand of claim 12, wherein the reporter moiety is selected from the group consisting of biotin, copper-DOTA, biotin-$PEG_3$, aminooxyacetate, $^{19}$FB, $^{18}$FB, and FITC-$PEG_3$.

14. The heterobiligand of claim 12, wherein the reporter moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

15. The heterobiligand of claim 1, wherein the heterobiligand further comprises a therapeutic moiety.

16. The heterobiligand of claim 15, wherein the therapeutic moiety is selected from the group consisting of radionuclide-DOTA and radionuclide-NOTA.

17. The heterobiligand of claim 15, wherein the therapeutic moiety is $^{177}$Lu-DOTA, $^{177}$Lu-NOTA, $^{225}$Ac-DOTA, or $^{225}$Ac-NOTA.

18. The heterobiligand of claim 1 further comprising an albumin binding moiety.

19. The heterobiligand of claim 18, wherein the albumin binding moiety is 4-methylphenyl butyrate (MPBA) or 4-iodophenyl butyrate (IPBA).

20. The heterobiligand of claim 1, wherein the heterobiligand further comprises a reporter moiety, whereby the heterobiligand is an imaging agent.

21. The heterobiligand of claim 20, wherein the heterobiligand further comprises a therapeutic moiety.

22. A composition comprising the heterobiligand of claim 1.

23. A method of detecting a tumor expressing folate receptors in a subject, the method comprising:
   administering to the subject a composition comprising a first ligand having affinity for an epitope on folate receptor 1 (FOLR1), a linker, and a second ligand, wherein the second ligand comprises a folate, wherein the linker links the first ligand and the second ligand, wherein the heterobiligand specifically binds FOLR1, wherein the first ligand comprises a 3-10 amino acid sequence of D-amino acids, artificial amino acids, or combinations thereof, and wherein the folate binds the FOLR1 active site,
   wherein the heterobiligand further comprises a reporter moiety, and
   wherein detection of the reporter moiety in the subject indicates that the heterobiligand binds to FOLR1 on the tumor.

24. The method of claim 23, wherein the reporter moiety is an imaging agent.

25. The method of claim 24, wherein the heterobiligand further comprises a therapeutic moiety.

26. The method of claim 25, wherein the heterobiligand binds to the tumor and provides a therapeutic effect, thereby decreasing the size of the tumor.

27. The method of claim 25, wherein the therapeutic moiety is linked to the first ligand via a neprilysin (NEP) cleavage site, wherein cleavage of the heterobiligand in the presence of NEP releases the therapeutic moiety from the heterobiligand.

28. The method of claim 27, wherein the cleaved heterobiligand is protective to an organ.

29. The method of claim 28, wherein the organ is the kidney.

30. A method of treating a subject with cancer, the method comprising administering to the subject a composition comprising a first ligand having affinity for an epitope on folate receptor 1 (FOLR1), a linker, and a second ligand, wherein the second ligand comprises a folate, wherein the linker links the first ligand and the second ligand, wherein the heterobiligand specifically binds FOLR1, wherein the first ligand comprises a 3-10 amino acid sequence of D-amino acids, artificial amino acids, or combinations thereof, and wherein the folate binds the FOLR1 active site, wherein the heterobiligand further comprises a therapeutic moiety, wherein the subject has cancer cells expressing FOLR1.

* * * * *